United States Patent
Sugimoto et al.

(10) Patent No.: US 9,399,635 B2
(45) Date of Patent: Jul. 26, 2016

(54) PYRAZOLE DERIVATIVE

(75) Inventors: Hachiro Sugimoto, Kyoto (JP); Michiaki Okuda, Kyoto (JP); Takashi Takahashi, Tokyo (JP); Ichiro Hijikuro, Tokyo (JP); Hidetaka Suzuki, Tokyo (JP); Shinichi Nakayama, Kyoto (JP)

(73) Assignee: GREEN TECH CO., LTD., Mie (JP)

( * ) Notice: Subject to any disclaimer, the term of this patent is extended or adjusted under 35 U.S.C. 154(b) by 22 days.

(21) Appl. No.: 14/110,188

(22) PCT Filed: Apr. 11, 2012

(86) PCT No.: PCT/JP2012/059944
§ 371 (c)(1),
(2), (4) Date: Dec. 16, 2013

(87) PCT Pub. No.: WO2012/141228
PCT Pub. Date: Oct. 18, 2012

(65) Prior Publication Data
US 2014/0088029 A1 Mar. 27, 2014

(30) Foreign Application Priority Data

Apr. 11, 2011 (JP) ................................. 2011-087040

(51) Int. Cl.
| | |
|---|---|
| C07D 401/14 | (2006.01) |
| C07D 403/10 | (2006.01) |
| C07D 405/14 | (2006.01) |
| C07D 209/12 | (2006.01) |
| C07D 401/12 | (2006.01) |
| C07D 403/06 | (2006.01) |
| C07D 405/12 | (2006.01) |
| C07D 409/12 | (2006.01) |
| C07D 409/14 | (2006.01) |
| C07D 417/12 | (2006.01) |
| C07D 417/14 | (2006.01) |
| C07H 15/203 | (2006.01) |
| C07D 403/14 | (2006.01) |
| C07H 15/26 | (2006.01) |

(52) U.S. Cl.
CPC ............ *C07D 401/14* (2013.01); *C07D 209/12* (2013.01); *C07D 401/12* (2013.01); *C07D 403/06* (2013.01); *C07D 403/10* (2013.01); *C07D 403/14* (2013.01); *C07D 405/12* (2013.01); *C07D 405/14* (2013.01); *C07D 409/12* (2013.01); *C07D 409/14* (2013.01); *C07D 417/12* (2013.01); *C07D 417/14* (2013.01); *C07H 15/203* (2013.01); *C07H 15/26* (2013.01)

(58) Field of Classification Search
None
See application file for complete search history.

(56) References Cited

U.S. PATENT DOCUMENTS

| | | | |
|---|---|---|---|
| 4,877,881 A | 10/1989 | Belliotti et al. | |
| 7,355,081 B2 * | 4/2008 | Lee ........................ | C07C 49/248 560/53 |
| 7,531,669 B2 * | 5/2009 | Schubert ............... | C07C 243/22 548/375.1 |
| 7,709,535 B2 * | 5/2010 | Lee ........................ | C07C 49/248 514/679 |
| 2006/0160812 A1 | 7/2006 | Schubert et al. | |
| 2007/0293507 A1 | 12/2007 | Baik et al. | |
| 2010/0048901 A1 | 2/2010 | Takahashi et al. | |
| 2010/0190803 A1 | 7/2010 | Shin et al. | |
| 2010/0197784 A1 | 8/2010 | Lee et al. | |
| 2010/0216859 A1 | 8/2010 | Chen | |
| 2011/0082295 A1 | 4/2011 | Sugimoto et al. | |

FOREIGN PATENT DOCUMENTS

| | | |
|---|---|---|
| CN | 101570512 A | 11/2009 |
| IN | 1568/MUM/2008 | 1/2010 |
| JP | 63-22079 | 1/1988 |
| JP | 2005534626 A | 11/2005 |
| JP | 2008513464 A | 5/2008 |
| JP | 2008129132 A | 6/2008 |
| JP | 2008137914 A | 6/2008 |
| JP | 2010168344 A | 8/2010 |
| JP | 2012229208 A | 11/2012 |
| WO | WO-02083614 A1 | 10/2002 |
| WO | WO-03105751 A2 | 12/2003 |
| WO | WO-2005006945 A2 | 1/2005 |
| WO | WO-2008030072 A1 | 3/2008 |
| WO | WO-2008066151 A1 | 6/2008 |
| WO | WO-2009145219 A1 | 12/2009 |

(Continued)

OTHER PUBLICATIONS

Yang et al., "Curcumin Inhibits Formation of Amyloid β Oligomers and Fibrils, Binds Plaques, and Reduces Amyloid in Vivo", *J. Biol. Chem.*, pp. 5892-5901 (2005).

(Continued)

*Primary Examiner* — Kamal Saeed
(74) *Attorney, Agent, or Firm* — Marshall, Gerstein & Borun LLP

(57) ABSTRACT

Provided is a novel therapeutic means for Alzheimer's disease. In particular, provided is a compound represented by the following general formula (I):

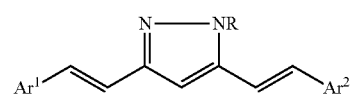

[wherein $Ar^1$ represents 2-methoxy-4-(2-pyridylmethoxy) phenyl etc. and $Ar^2$ represents a 1H-indol-6-yl group etc.] or a salt thereof.

17 Claims, 2 Drawing Sheets

(56) References Cited

FOREIGN PATENT DOCUMENTS

| WO | WO-2010045395 A2 | 4/2010 |
|---|---|---|
| WO | WO-2012141228 A1 | 10/2012 |

OTHER PUBLICATIONS

Li, Q. et al., "Styryl-based compounds as potential in vivo imaging agents for β-amyloid plaques", *ChemBioChem*, pp. 1679-1687 (2007).

Narlawar et al., "Curcumin-Derived Pyrazoles and Isoxazoles: Swiss Army Knives or Blunt Tools for Alzheimer's Disease?", *ChemMedChem*, pp. 165-172 (2008).

Written Opinion in corresponding PCT/JP2012/059944 mailed Apr. 27, 2012.

International Search Report in corresponding PCT/JP2012/059944 mailed Apr. 27, 2012.

International Search Report and Written Opinion in PCT/JP2013/074998 dated Oct. 22, 2013.

Kong et al., "Protectors of Oxidative Stress Inhibit Aβ(1-42) Aggregation in vitro", Bull. Korean Chem. Soc., vol. 23, No. 12, pp. 1773-1777 (2002).

Yang et al., "Protein Structure and Folding: Curcumin Inhibits Formation of Amyloid β Oligomers and Fibrils, Binds Plaques, and Reduces Amyloid in Vivo," J. Biol. Chem., 280 (7), pp. 5892-5901 (2005).

Lohith et al., "Glycosides and Amino Acyl Esters of Carbohydrates as Potent Inhibitors of Angiotensin Converting Enzyme", European Journal of Medicinal Chem., pp. 1059-1072 (2016).

Lohith et al., "Glycosides and Amino Acyl Esters of Carbohydrates as Potent Inhibitors of Angiotensin Converting Enzyme", European Journal of Medicinal Chem., pp. 1059-1072 (2006).

\* cited by examiner

PYRAZOLE DERIVATIVE

TECHNICAL FIELD

The present invention relates to a novel compound; a tau aggregation inhibitor, a β-secretase inhibitor, and an amyloid β-protein aggregation inhibitor using the same; and a pharmaceutical composition using the same for the prevention or treatment of diseases such as dementia and Alzheimer's disease.

BACKGROUND ART

Senile dementia has become a serious medical and social problem along with the rapid aging of society in recent years and the development of effective anti-dementia drugs has been greatly desired. There are already very many studies on Alzheimer's disease but the cause of the disease has not been clearly defined. An Alzheimer's disease drug, Aricept, is based on its acetylcholinesterase inhibitory activity. This drug is very useful as symptomatic therapy but is not a drug for fundamental therapy.

Alzheimer's disease is considered to be caused by aggregation of amyloid β-protein (hereinafter also referred to as Aβ), aggregation of tau, and the like. Hence, a substance that can inhibit aggregation of these proteins is a potential candidate for a fundamental therapeutic agent for Alzheimer's disease.

Yang et al. have reported that curcumin has an Aβ aggregation inhibitory activity, a disaggregation activity on Aβ aggregate, and the like (Non Patent Literature 1). The inventors of the present invention have revealed that curcumin and its derivatives have an inhibitory activity against secretase, which is involved in the generation of Aβ (Patent Literature 1 and 2). Narlawar et al. have synthesized curcumin derivatives by replacing the 1,3-dicarbonyl moiety with a pyrazole ring and reported that these compounds have a tau aggregation inhibitory activity (Non Patent Literature 2).

CITATION LIST

Patent Literature

Patent Literature 1: WO 2008/066151
Patent Literature 2: WO 2009/145219

Non Patent Literature

Non Patent Literature 1:
Fusheng Yang et al., J. Biol. Chem. 2005, Feb. 18; 280 (7) 5892-5901
Non Patent Literature 2:
Rajeshwar Narlawar et al., ChemMedChem 2008, 3, 165-172

SUMMARY OF INVENTION

Technical Problem

As described in the above literature, a curcumin derivative can be a promising candidate for a fundamental therapeutic agent for Alzheimer's disease. Under this technical background, an object of the present invention is thus to provide a novel therapeutic means for Alzheimer's disease.

Solution to Problem

The inventors succeeded in creating a novel compound that is distinct from known compounds and found that the compound has an excellent pharmacological activity. The inventors further conducted extensive studies to complete the present invention.

As a result of the extensive investigations to solve the above problems, the inventors synthesized a curcumin derivative by replacing the 1,3-dicarbonyl moiety of curcumin with a pyrazole ring and replacing at least one of the 4-hydroxy-3-methoxyphenyl groups at both ends with a substituent and found that the curcumin derivative has a potent tau aggregation inhibitory activity. The inventors also found that this derivative has a high brain penetration and also possesses a β-secretase inhibitory activity and an Aβ aggregation inhibitory activity.

A curcumin derivative in which the 1,3-dicarbonyl moiety of curcumin is replaced with a pyrazole ring is described in Non Patent Literature 2 etc. A curcumin derivative in which one of the 4-hydroxy-3-methoxyphenyl groups at both ends of curcumin is replaced with a substituent is described in Patent Literature 1 and 2, etc. However, a curcumin derivative which has a pyrazole ring and in which at least one of the 4-hydroxy-3-methoxyphenyl groups at both ends is replaced with a substituent is a novel compound that has not been disclosed in known literature.

The tau aggregation inhibitory activity of a curcumin derivative is described in Non Patent Literature 2. In this literature, the nitrogen atom at position 1 of the pyrazole ring is replaced with various groups, and the tau aggregation inhibitory activities of the derivatives significantly vary with the groups introduced into the ring. However, no modification was made to the benzene rings at both ends and thus all the synthesized derivatives have the 4-hydroxy-3-methoxyphenyl groups as curcumin does. Therefore, the person skilled in the art who has read Non Patent Literature 2 is expected to consider that the group introduced into the pyrazole ring plays an important role for the tau aggregation inhibitory activity and that the 4-hydroxy-3-methoxyphenyl groups at both ends are irrelevant to the tau aggregation inhibitory activity. Thus the person skilled in the art would not attempt to replace the 4-hydroxy-3-methoxyphenyl groups with a substituent.

The present invention has been completed based on the above findings.

That is, the present invention relates to the following.

[1] A compound represented by the following general formula (I):

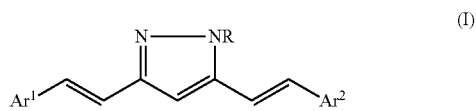

[wherein R represents hydrogen, a chain or cyclic hydrocarbon group optionally having a substituent, or a heterocyclic group optionally having a substituent; and
$Ar^1$ and $Ar^2$ are the same or different and each represent a homocyclic or heterocyclic group optionally having a substituent;
with the exception of the case where R is hydrogen and $Ar^1$ and $Ar^2$ each represent a 4-hydroxy-3-methoxyphenyl group] or a salt thereof.

[2] The compound or a salt thereof according to the above [1], wherein R in the general formula (I) is hydrogen.

[3] The compound or a salt thereof according to the above [1] or [2], wherein $Ar^1$ in the general formula (I) is a phenyl group optionally having a substituent.

[4] The compound or a salt thereof according to the above [1] or [2], wherein Ar¹ in the general formula (I) is a phenyl group having a $C_{1-3}$ alkyloxy group optionally having a substituent.

[5] The compound or a salt thereof according to the above [1] or [2], wherein Ar¹ in the general formula (I) is a phenyl group having a $C_{1-3}$ alkyloxy group substituted with a heterocycloalkyl group optionally having a substituent, a phenyl group having a $C_{1-3}$ alkyloxy group substituted with a cycloalkyl group optionally having a substituent, a phenyl group having a $C_{1-3}$ alkyloxy group substituted with a heteroaryl group optionally having a substituent, a phenyl group having a $C_{1-3}$ alkyloxy group substituted with an aryl group optionally having a substituent, a phenyl group having a $C_{1-3}$ alkyloxy group substituted with a dialkylamino group optionally having a substituent, a phenyl group having a $C_{1-3}$ alkyloxy group substituted with an alkyloxy group optionally having a substituent, or a phenyl group having a $C_{1-3}$ alkyloxy group substituted with an alkyl group optionally having a substituent.

[6] The compound or a salt thereof according to the above [1] or [2], wherein Ar¹ in the general formula (I) is a phenyl group having a tetrahydrofuran-3-ylmethoxy group, a tetrahydrofuran-2-ylmethoxy group, a 2-(piperidin-1-yl)ethoxy group, a 2-(4-methylpiperazino)ethoxy group, a 2-(4-benzylpiperazino)ethoxy group, a 2-morpholinoethoxy group, a 2-pyrrolidinoethoxy group, a β-D-glucopyranosyloxy group, a 2-[4-(tert-butoxycarbonyl)piperazin-1-yl]ethoxy group, a 2-[4-(methylsulfonyl)piperazin-1-yl]ethoxy group, or a 2-[4-(2-hydroxyethyl)piperazin-1-yl]ethoxy group.

[7] The compound or a salt thereof according to the above [1] or [2], wherein Ar¹ in the general formula (I) is a 2-methoxy-4-(tetrahydrofuran-3-ylmethoxy)phenyl group, a 2-methoxy-4-(tetrahydrofuran-2-ylmethoxy)phenyl group, a 2-methoxy-4-[2-(piperidin-1-yl)ethoxy]phenyl group, a 2-methoxy-4-[2-(4-methylpiperazino)ethoxy]phenyl group, a 2-methoxy-4-(2-morpholinoethoxy)phenyl group, a 4-(β-D-glucopyranosyl)oxy-2-methoxyphenyl group, a 4-(tetrahydrofuran-3-ylmethoxy)phenyl group, a 4-(tetrahydrofuran-2-ylmethoxy)phenyl group, a 3-methoxy-4-(tetrahydrofuran-3-ylmethoxy)phenyl group, a 3-methoxy-4-(tetrahydrofuran-2-ylmethoxy)phenyl group, a 2-[2-(4-benzylpiperazino)ethoxy]-4-methoxyphenyl group, a 4-diethylamino-2-(2-morpholinoethoxy) phenyl group, a 4-dimethylamino-2-(2-morpholinoethoxy)phenyl group, a 4-diethylamino-2-(2-morpholinoethoxy)phenyl group, a 4-diethylamino-2-(2-pyrrolidinoethoxy)phenyl group, or a 4-diethylamino-2-[2-(piperidin-1-yl)ethoxy]phenyl group.

[8] The compound or a salt thereof according to the above [1] or [2], wherein Ar¹ in the general formula (I) is a phenyl group having a pyridin-2-ylmethoxy group, a pyridin-3-ylmethoxy group, a pyridin-4-ylmethoxy group, or a 1-pyrrolylmethoxy group.

[9] The compound or a salt thereof according to the above [1] or [2], wherein Ar¹ in the general formula (I) is a 4-(pyridin-2-ylmethoxy)phenyl group, a 2-methoxy-4-(pyridin-2-ylmethoxy)phenyl group, a 2-[2-(piperidin-1-yl)ethoxy]-4-(pyridin-2-ylmethoxy)phenyl group, a 2-(2-morpholinoethoxy)-4-(pyridin-2-ylmethoxy)phenyl group, a 2-(2-pyrrolidinoethoxy)-4-(pyridin-2-ylmethoxy)phenyl group, a 2-[2-(4-methylpiperazino)ethoxy]-4-(pyridin-2-ylmethoxy) phenyl group, a 3-methoxy-4-(pyridin-2-ylmethoxy)phenyl group, a 2-hydroxy-4-(pyridin-2-ylmethoxy)phenyl group, a 3-(pyridin-2-ylmethoxy)phenyl group, a 2-methoxy-3-(pyridin-2-ylmethoxy)phenyl group, a 4-methoxy-3-(pyridin-2-ylmethoxy)phenyl group, a 3-methoxy-5-(pyridin-2-ylmethoxy)phenyl group, a 2-methoxy-5-(pyridin-2-ylmethoxy)phenyl group, a 2-(pyridin-2-ylmethoxy)phenyl group, a 4-methoxy-2-(pyridin-2-ylmethoxy)phenyl group, a 5-methoxy-2-(pyridin-2-ylmethoxy)phenyl group, a 2-nitro-5-(pyridin-3-ylmethoxy)phenyl group, a 4-diethylamino-2-(pyridin-3-ylmethoxy)phenyl group, or a 2-methoxy-2-(1-pyrrolylmethoxy)phenyl group.

[10] The compound or a salt thereof according to any one of the above [1] to [9], wherein Ar² in the general formula (I) is a bicyclic homocyclic or heterocyclic group optionally having a substituent.

[11] The compound or a salt thereof according to any one of the above [1] to [9], wherein Ar² in the general formula (I) is a bicyclic heterocyclic group optionally having a substituent.

[12] The compound or a salt thereof according to the above [11], wherein Ar² in the general formula (I) is an indol-2-yl group, an indol-3-yl group, an indol-4-yl group, an indol-5-yl group, an indol-6-yl group, an indol-7-yl group, a benzotriazol-5-yl group, a benzimidazol-5-yl group, a quinoxalin-6-yl group, a benzofuran-2-yl group, a benzothiophen-2-yl group, a 1H-indazol-5-yl group, a 7-azaindol-3-yl group, a quinolin-2-yl group, a quinolin-5-yl group, a quinolin-8-yl group, a 1,4-benzodioxan-6-yl group, a 1,3-benzodioxol-5-yl group, a chromon-3-yl group, a coumarin-6-yl group, a 7-methoxycoumarin-4-yl group, or a 4-methoxycoumarin-6-yl group.

[13] The compound or a salt thereof according to the above [11], wherein Ar² in the general formula (I) is a bicyclic heterocyclic group having a methyl group, an ethyl group, a benzyl group, an acetyl group, a benzoyl group, a tert-butoxycarbonyl group, a methylsulfonyl group, a p-toluenesulfonyl group, a hydroxy group, or a nitro group.

[14] The compound or a salt thereof according to the above [11], wherein Ar² in the general formula (I) is a 1-methylindol-6-yl group, a 1-methylindol-2-yl group, a 1-methylindol-3-yl group, a 1-ethylindol-6-yl group, a 1-benzylindol-3-yl group, a 1-benzylindol-6-yl group, a 1-acetylindol-3-yl group, a 1-acetylindol-6-yl group, a 1-benzoylindol-3-yl group, a 1-tert-butoxycarbonylindol-5-yl group, a 1-methylsulfonylindol-3-yl group, a 1-methylsulfonylindol-6-yl group, a 1-p-toluenesulfonylindol-3-yl group, a 1-p-toluenesulfonylindol-6-yl group, a 4-hydroxyindol-3-yl group, or a 4-nitroindol-3-yl group.

[15] A tau aggregation inhibitor comprising the compound or a salt thereof according to any one of the above [1] to [14] as an active ingredient.

[16] A β-secretase inhibitor comprising the compound or a salt thereof according to any one of the above [1] to [14] as an active ingredient.

[17] An amyloid β-protein aggregation inhibitor comprising the compound or a salt thereof according to any one of the above [1] to [14] as an active ingredient.

[18] A pharmaceutical composition comprising the compound or a salt thereof according to any one of the above [1] to [14] as an active ingredient.

[19] The pharmaceutical composition according to the above [18] for use in the prevention or treatment of a disease in which tau, β-secretase, or amyloid β-protein is involved.

[20] The pharmaceutical composition according to the above [18] for use in the prevention or treatment of Alzheimer's disease.

[21] An oral or parenteral preparation comprising the compound or a salt thereof according to any one of the above [1] to [14] and one or more pharmacologically acceptable carriers.

[22] A compound represented by the following general formula (II):

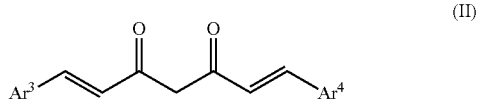

(II)

[wherein Ar$^3$ and Ar$^4$ are the same or different and each represent a homocyclic or heterocyclic group optionally having a substituent
(with the exception of the case where (i) Ar$^3$ is an aryl or heteroaryl group optionally having a substituent and Ar$^4$ is a phenyl group optionally having a substituent located at position 2 and having an electron withdrawing group, a 1H-indol-2-yl group optionally having a substituent, a 1H-indol-3-yl group optionally having a substituent, a 1H-indol-4-yl group optionally having a substituent, a 1H-indol-5-yl group optionally having a substituent, a 1H-indol-6-yl group optionally having a substituent, or a 1H-indol-7-yl group optionally having a substituent, and where (ii) Ar$^3$ is a phenyl group optionally substituted with a hydroxy group, a methoxy group, or an acetoxy group and Ar$^4$ is a phenyl group, a 4-chlorophenyl group, a 2-methoxyphenyl group, a 3-methoxyphenyl group, a 4-methoxyphenyl group, a 3-hydroxyphenyl group, a 4-acetylaminophenyl group, a 3,4-difluorophenyl group, a 2,4-dichlorophenyl group, a 2,3-dimethoxyphenyl group, a 2,4-dimethoxyphenyl group, a 2,6-dimethoxyphenyl group, a 3,5-dimethoxyphenyl group, a 3,4-dihydroxyphenyl group, a 3-fluoro-4-hydroxyphenyl group, a 2-hydroxy-5-methoxyphenyl group, a 3-hydroxy-4-methoxyphenyl group, a 3-hydroxy-5-methoxyphenyl group, a 3-methoxy-4-nitrophenyl group, a 4-acetoxy-3-methoxyphenyl group, a 4-dimethylamino-3-methoxyphenyl group, a 4-hydroxy-3-nitrophenyl group, a 2-methoxynaphthalen-1-yl group, a 6-methoxynaphthalen-2-yl group, a 1H-pyrrol-2-yl group, a pyridin-2-yl group, a 1H-imidazol-2-yl group, a 1-methyl-1H-pyrrol-2-yl group, a 9-ethyl-9H-carbazol-3-yl group, a 1-methyl-1H-indol-3-yl group, a 1H-indol-3-yl group, a 1H-indol-5-yl group, or a 1H-indol-6-yl group)]
or a salt thereof.

Advantageous Effects of Invention

The compound of the present invention has a tau aggregation inhibitory activity, a β-secretase inhibitory activity, an Aβ aggregation inhibitory activity, and the like, as well as high brain penetration, and is thus useful as a therapeutic agent for Alzheimer's disease and the like.

DESCRIPTION OF EMBODIMENTS

Figure 1:
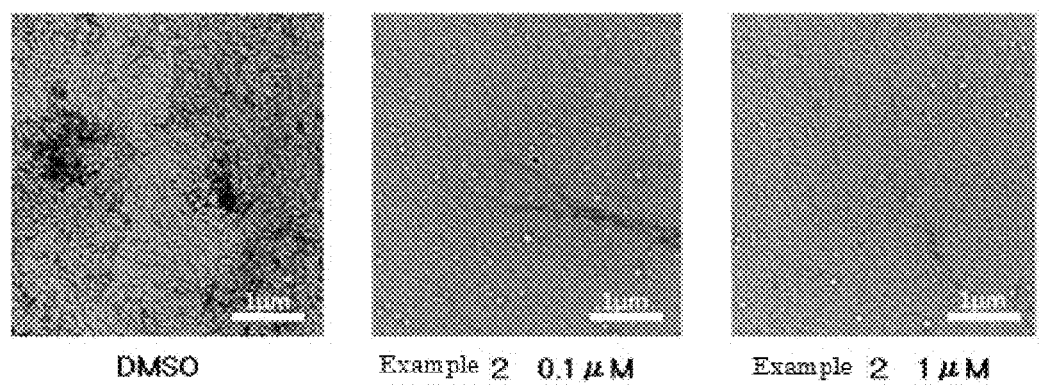
FIG. 1 shows the electron micrographs of the thioflavin S sample prepared in Pharmacological test example 1. The left figure shows the result obtained in the case where only DMSO was added, the middle figure shows the result obtained in the case where the compound of Example 2 at 0.1 μM was added, and the right figure shows the result obtained in the case where the compound of Example 2 at 1 μM was added.

The present invention will be described in detail below.

R in the general formula (I) represents hydrogen, a chain or cyclic hydrocarbon group optionally having a substituent, or a heterocyclic group optionally having a substituent, and preferably represents hydrogen. The chain or cyclic hydrocarbon group is not particularly limited as long as it does not impair the effects of the present invention, and examples thereof include (preferably $C_{1-6}$) alkyl groups such as a methyl group, an ethyl group, a propyl group, and an isopropyl group; (preferably $C_{1-6}$) alkenyl groups such as a vinyl group; (preferably $C_{6-12}$) aryl groups such as a phenyl group and a naphthyl group; etc. The heterocyclic group is not particularly limited as long as it does not impair the effects of the present invention. Examples thereof include heterocyclic groups containing 1 to 3 oxygen atoms, sulfur atoms, and/or nitrogen atoms, and specific examples thereof include a pyrrolyl group, a pyrrolinyl group, an imidazolyl group, a pyrazolyl group, a pyridyl group, a furyl group, a thienyl group, an oxazolyl group, etc. The substituent is not particularly limited as long as it does not impair the effects of the present invention, and examples thereof include (preferably $C_{1-6}$) alkyl groups such as a methyl group and an ethyl group; (preferably $C_{7-10}$) aralkyl groups such as a benzyl group; (preferably $C_{2-7}$) acyl groups such as an acetyl group and a benzoyl group; (preferably $C_{2-7}$) alkylcarbonyl groups such as a tert-butoxycarbonyl group; (preferably $C_{1-6}$) alkylsulfonyl groups such as a methylsulfonyl group and a p-toluenesulfonyl group; a hydroxy group; a nitro group; etc.

Ar$^1$ and Ar$^2$ in the general formula (I) are the same or different and each represent a homocyclic or heterocyclic group optionally having a substituent. The "homocyclic group" is not particularly limited as long as it does not impair the effects of the present invention, and examples thereof include a vinyl group, a phenyl group, a naphthyl group, etc. The "heterocyclic group" is not particularly limited as long as it does not impair the effects of the present invention, and examples thereof include a pyrrolyl group, a pyrrolinyl group, an imidazolyl group, a pyrazolyl group, a pyridyl group, a furyl group, a thienyl group, an oxazolyl group, etc. The "bicyclic homocyclic group" is not particularly limited as long as it does not impair the effects of the present invention, and examples thereof include a naphthyl group etc. The substituent is not particularly limited as long as it does not impair the effects of the present invention, and examples thereof include (preferably $C_{1-6}$) alkyl groups such as a methyl group and an ethyl group; (preferably $C_{7-10}$) aralkyl groups such as a benzyl group; (preferably $C_{2-7}$) acyl groups such as an acetyl group and a benzoyl group; (preferably $C_{2-7}$) alkylcarbonyl groups such as a tert-butoxycarbonyl group; (preferably $C_{1-6}$) alkylsulfonyl groups such as a methylsulfonyl group and a p-toluenesulfonyl group; a hydroxy group; a nitro group; etc.

Preferably, $Ar^1$ represents a phenyl group optionally having a substituent. The substituent on the phenyl group is not particularly limited as long as it does not impair the effects of the present invention, and preferred examples thereof include
(1) a $C_{1-3}$ alkyloxy group optionally having a substituent,
(2) an aryloxy group optionally having a substituent,
(3) a disubstituted amino group (in which the two substituents may join together to form a ring),
(4) an aryl group optionally having a substituent or a heteroaryl group optionally having a substituent,
(5) a bromine atom,
(6) an alkyl group optionally having a substituent, an alkenyl group optionally having a substituent, or an alkynyl group optionally having a substituent,
(7) a nitro group,
(8) an acyl group,
(9) an alkylcarbonylamino group, a sulfonyl group, a sulfinyl group, or a sulfonyloxy group, etc.

(1) $C_{1-3}$ Alkyloxy Group Optionally having a Substituent

Examples of the "$C_{1-3}$ alkyloxy group optionally having a substituent" include
(1a) a $C_{1-3}$ alkyloxy group substituted with a heterocycloalkyl group optionally having a substituent,
(1b) a $C_{1-3}$ alkyloxy group substituted with a cycloalkyl group optionally having a substituent,
(1c) a $C_{1-3}$ alkyloxy group substituted with a heteroaryl group optionally having a substituent,
(1d) a $C_{1-3}$ alkyloxy group substituted with an aryl group optionally having a substituent,
(1e) a $C_{1-3}$ alkyloxy group substituted with a dialkylamino group optionally having a substituent,
(1f) a $C_{1-3}$ alkyloxy group substituted with an alkyloxy group optionally having a substituent,
(1g) a $C_{1-3}$ alkyloxy group substituted with an alkyl group optionally having a substituent, etc.

(1a) $C_{1-3}$ Alkyloxy Group Substituted with a Heterocycloalkyl group optionally having a substituent Examples of the "$C_{1-3}$ alkyloxy group substituted with a heterocycloalkyl group optionally having a substituent" include a tetrahydrofuran-3-ylmethoxy group, a tetrahydrofuran-2-ylmethoxy group, a 2-(piperidin-1-yl)ethoxy group, a 2-(4-methylpiperazino)ethoxy group, a 2-(4-benzylpiperazino)ethoxy group, a 2-morpholinoethoxy group, a 2-pyrrolidinoethoxy group, a β-D-glucopyranosyloxy group, a 2-[4-(tert-butoxycarbonyl)piperazin-1-yl]ethoxy group, a 2-[4-(methylsulfonyl)piperazin-1-yl]ethoxy group, a 2-[4-(2-hydroxyethyl)piperazin-1-yl]ethoxy group, etc.

Examples of the "phenyl group having a $C_{1-3}$ alkyloxy group substituted with a heterocycloalkyl group optionally having a substituent" include a 2-methoxy-4-(tetrahydrofuran-3-ylmethoxy)phenyl group, a 2-methoxy-4-(tetrahydrofuran-2-ylmethoxy)phenyl group, a 2-methoxy-4-[2-(piperidin-1-yl)ethoxy]phenyl group, a 2-methoxy-4-[2-(4-methylpiperazino)ethoxy]phenyl group, a 2-methoxy-4-(2-morpholinoethoxy)phenyl group, a 4-(β-D-glucopyranosyl)oxy-2-methoxyphenyl group, a 4-(tetrahydrofuran-3-ylmethoxy)phenyl group, a 4-(tetrahydrofuran-2-ylmethoxy)phenyl group, a 3-methoxy-4-(tetrahydrofuran-3-ylmethoxy)phenyl group, a 3-methoxy-4-(tetrahydrofuran-2-ylmethoxy)phenyl group, a 2-[2-(4-benzylpiperazino)ethoxy]-4-methoxyphenyl group, a 4-diethylamino-2-(2-morpholinoethoxy)phenyl group, a 4-dimethylamino-2-(2-morpholinoethoxy)phenyl group, a 4-diethylamino-2-(2-morpholinoethoxy)phenyl group, a 4-diethylamino-2-(2-pyrrolidinoethoxy)phenyl group, a 4-diethylamino-2-[2-(piperidin-1-yl)ethoxy]phenyl group, etc.

(1b) $C_{1-3}$ Alkyloxy Group Substituted with a Cycloalkyl Group Optionally having a Substituent Examples of the "$C_{1-3}$ alkyloxy group substituted with a cycloalkyl group optionally having a substituent" include a cyclohexylmethoxy group etc.

Examples of the "phenyl group having a $C_{1-3}$ alkyloxy group substituted with a cycloalkyl group optionally having a substituent" include a 4-cyclohexylmethoxy-2-methoxyphenyl group, a 2-cyclohexylmethoxy-4-hydroxyphenyl group, a 2-cyclohexylmethoxy-3-fluorophenyl group, a 2-cyclohexylmethoxy-5-fluorophenyl group, a 5-chloro-2-cyclohexylmethoxyphenyl group, a 2,4-di(cyclohexylmethoxy)phenyl group, etc.

(1c) $C_{1-3}$ Alkyloxy Group Substituted with a Heteroaryl Group Optionally having a Substituent Examples of the "$C_{1-3}$ alkyloxy group substituted with a heteroaryl group optionally having a substituent" include a pyridin-2-ylmethoxy group, a pyridin-3-ylmethoxy group, a pyridin-4-ylmethoxy group, a 1-pyrrolylmethoxy group, etc.

Examples of the "phenyl group having a $C_{1-3}$ alkyloxy group substituted with a heteroaryl group optionally having a substituent" include a 4-(pyridin-2-ylmethoxy)phenyl group, a 2-methoxy-4-(pyridin-2-ylmethoxy)phenyl group, a 2-[2-(piperidin-1-yl)ethoxy]-4-(pyridin-2-ylmethoxy)phenyl group, a 2-(2-morpholinoethoxy)-4-(pyridin-2-ylmethoxy)phenyl group, a 2-(2-pyrrolidinoethoxy)-4-(pyridin-2-ylmethoxy)phenyl group, a 2-[2-(4-methylpiperazino)ethoxy]-4-(pyridin-2-ylmethoxy) phenyl group, a 3-methoxy-4-(pyridin-2-ylmethoxy)phenyl group, a 2-hydroxy-4-(pyridin-2-ylmethoxy)phenyl group, a 3-(pyridin-2-ylmethoxy)phenyl group, a 2-methoxy-3-(pyridin-2-ylmethoxy)phenyl group, a 4-methoxy-3-(pyridin-2-ylmethoxy)phenyl group, a 3-methoxy-5-(pyridin-2-ylmethoxy)phenyl group, a 2-methoxy-5-(pyridin-2-ylmethoxy)phenyl group, a 2-(pyridin-2-ylmethoxy)phenyl group, a 4-methoxy-2-(pyridin-2-ylmethoxy)phenyl group, a 5-methoxy-2-(pyridin-2-ylmethoxy)phenyl group, a 2-nitro-5-(pyridin-3-ylmethoxy)phenyl group, a 4-diethylamino-2-(pyridin-3-ylmethoxy)phenyl group, a 2-methoxy-2-(1-pyrrolylmethoxy)phenyl group, etc.

(1d) $C_{1-3}$ Alkyloxy Group Substituted with an Aryl Group Optionally having a Substituent Examples of the "$C_{1-3}$ alkyloxy group substituted with an aryl group optionally having a substituent" include a phenethyloxy group, a benzyloxy group, a 1-naphthylmethoxy group, a diphenylmethoxy group, a 4-methoxybenzyloxy group, a 2-chloro-6-fluorobenzyloxy group, a 2,4-dichlorobenzyloxy group, a 4-tert-butylbenzyloxy group, etc.

Examples of the "phenyl group having a $C_{1-3}$ alkyloxy group substituted with an aryl group optionally having a substituent" include a 2-methoxy-4-phenethyloxyphenyl group, a 4-benzyloxy-2-methoxyphenyl group, a 4-(1-naphthylmethoxy)-2-methoxyphenyl group, a 4-diphenylmethoxy-2-methoxyphenyl group, a 2-benzyloxy-4-hydroxyphenyl group, a 2-benzyloxy-4-chlorophenyl group, a 2-benzyloxy-3-fluorophenyl group, a 2-benzyloxy-3,5-dichlorophenyl group, a 5-benzyloxy-2-nitrophenyl group, a 5-(4-methoxybenzyloxy)-2-nitrophenyl group, a 5-(2-chloro-6-fluorobenzyloxy)-2-nitrophenyl group, a 5-(2,4-dichlorobenzyloxy)-2-nitrophenyl group, a 5-(4-tert-butylbenzyloxy)-2-nitrophenyl group, a 4-benzyloxy-2-bromophenyl group, a 4-benzyloxy-2-phenylphenyl group, a 2-benzyloxy-5-bromophenyl group, a 2-benzyloxy-5-phenylphenyl group, a 2-benzyloxy-5-(indol-6-yl)phenyl group, a 2-benzyloxy-4-dimethylaminophenyl group, a 2-benzyloxy-4-diethylaminophenyl group, a 4-diethylamino-2-(4-methoxybenzyloxy)phenyl group, a 4-diethylamino-2-(2- chloro-6-fluorobenzyloxy)phenyl group, a 4-diethylamino-2-(2,4-dichlorobenzyloxy)phenyl group, a 4-diethylamino-2-(4-tert-butylbenzyloxy)phenyl group, etc.

(1e) $C_{1-3}$ Alkyloxy Group Substituted with a Dialkylamino Group Optionally having a Substituent Examples of the "$C_{1-3}$ alkyloxy group substituted with a dialkylamino group optionally having a substituent" include a 2-dimethylaminoethoxy group, a 3-dimethylaminopropoxy group, a 2-dimethylamino-1-methylethoxy group, a 2-dimethylamino-1-methylethoxy group, etc.

Examples of the "phenyl group having a $C_{1-3}$ alkyloxy group substituted with a dialkylamino group optionally having a substituent" include a 4-(3-dimethylaminopropoxy)phenyl group, a 2-chloro-4-(3-dimethylaminoethoxy)phenyl group, a 2-bromo-5-(3-dimethylaminoethoxy)phenyl group, a 2-(2-dimethylaminoethoxy)-4-methoxyphenyl group, a 4-diethylamino-2-(2-dimethylamino-1-methylethoxy)phenyl group, etc.

(1f) $C_{1-3}$ Alkyloxy Group Substituted with an Alkyloxy Group Optionally having a Substituent Examples of the "$C_{1-3}$ alkyloxy group substituted with an alkyloxy group optionally having a substituent" include a methoxyethoxy group, a benzyloxy ethoxy group, etc.

Examples of the "phenyl group having a $C_{1-3}$ alkyloxy group substituted with an alkyloxy group optionally having a substituent" include a 2-methoxy-4-methoxyethoxyphenyl group, a 2-benzyloxyethoxy-4-methoxyphenyl group, etc.

(1g) $C_{1-3}$ Alkyloxy Group Substituted with an Alkyl Group Optionally having a Substituent Examples of the "$C_{1-3}$ alkyloxy group substituted with an alkyl group optionally having a substituent" include an isopropoxy group, a 2-methylpropoxy group, a 3-methyl-2-butenyloxy group, etc.

Examples of the "phenyl group having a $C_{1-3}$ alkyloxy group substituted with an alkyl group optionally having a substituent" include a 4-hydroxy-2-isopropoxyphenyl group, a 4-isopropoxy-2-methoxyphenyl group, a 2-methoxy-4-(2-methylpropoxy)phenyl group, a 3-fluoro-2-(2-methylpropoxy)phenyl group, a 2,5-di(2-methylpropoxy)phenyl group, a 2,4-di(2-methylpropoxy)phenyl group, a 4-diethylamino-2-isopropoxyphenyl group, a 4-diethylamino-2-(3-methyl-2-butenyloxy)phenyl group, etc.

(2) Aryloxy Group Optionally having a Substituent

Examples of the "aryloxy group optionally having a substituent" include a phenoxy group etc.

Examples of the "phenyl group having an aryloxy group optionally having a substituent" include a 2-phenoxyphenyl group, a 3-phenoxyphenyl group, a 4-phenoxyphenyl group, etc.

(3) Disubstituted Amino Group

Examples of the "disubstituted amino group" include a dimethylamino group, a diethylamino group, etc. Examples of the "disubstituted amino group" in which the two substituents join together to form a ring include an imidazol-1-yl group, a pyrazol-1-yl group, a triazol-2-yl group, a pyrrolidin-1-yl group, a piperidin-1-yl group, a 4-benzylpiperidin-1-yl group, a morpholin-4-yl group, a piperazin-1-yl group, a 4-methylpiperazin-1-yl group, a 4-benzylpiperazin-1-yl group, a 4-phenylpiperazin-1-yl group, a 4-(tert-butoxycarbonyl)piperazin-1-yl group, a 4-(methylsulfonyl)piperazin-1-yl group, a 4-(2-hydroxyethyl)piperazin-1-yl group, a 1,4-diazepan-1-yl group, a 4-methyl-1,4-diazepan-1-yl group, a 4-benzyl-1,4-diazepan-1-yl group, a 4-(tert-butoxycarbonyl)-1,4-diazepan-1-yl group, etc.

Examples of the "phenyl group having a disubstituted amino group (in which the two substituents may join together to form a ring)" include a 4-dimethylaminophenyl group, a 4-dimethylamino-2-methoxyphenyl group, a 4-diethylamino-2-hydroxyphenyl group, a 4-diethylamino-2-methoxyphenyl group, a 2-dimethylaminophenyl group, a 4-bromo-2-dimethylaminophenyl group, a 5-bromo-2-dimethylaminophenyl group, a 2-dimethylamino-5-trifluoromethylphenyl group, a 2-dimethylamino-4-phenylphenyl group, a 2-dimethylamino-5-phenylphenyl group, a 4-dimethylamino-3-methoxyphenyl group, a 4-dimethylamino-2-nitrophenyl group, a 4-dimethylamino-2-chlorophenyl group, a 4-dimethylamino-2-methoxymethoxyphenyl group, a 4-dimethylamino-2-trifluoromethylphenyl group, a 5-dimethylamino-2-nitrophenyl group, a 2-benzoyloxy-4-diethylaminophenyl group, a 4-diethylamino-2-ethoxycarbonyloxyphenyl group, a 4-diethylamino-2-ethylaminocarbonyloxyphenyl group, a 4-diethylamino-2-(2-hydroxyethoxy)phenyl group, a 4-(imidazol-1-yl)phenyl group, a 4-(pyrazol-1-yl)phenyl group, a 4-(triazol-2-yl)phenyl group, a 4-(pyrrolidin-1-yl)phenyl group, a 4-(piperidin-1-yl)phenyl group, a 4-(morpholin-4-yl)phenyl group, a 4-(piperazin-1-yl)phenyl group, a 4-(4-methylpiperazin-1-yl)phenyl group, a 4-(4-benzylpiperazin-1-yl)phenyl group, a 2-(pyrrolidin-1-yl)phenyl group, a 2-(piperidin-1-yl)phenyl group, a 2-(morpholin-4-yl)phenyl group, a 2-[4-(tert-butoxycarbonyl)piperazin-1-yl]phenyl group, a 2-[4-(methylsulfonyl)piperazin-1-yl]phenyl group, a 2-[4-(2-hydroxyethyl)piperazin-1-yl]phenyl group, a 2-bromo-4-(piperidin-1-yl)phenyl group, a 2-bromo-4-(4-benzylpiperidin-1-yl)phenyl group, a 2-bromo-4-(morpholin-4-yl)phenyl group, a 2-bromo-4-(4-methylpiperazin-1-yl)phenyl group, a 2-bromo-4-(4-benzylpiperazin-1-yl)phenyl group, a 2-bromo-4-(4-phenylpiperazin-1-yl)phenyl group, a 2-bromo-4-(pyrrolidin-1-yl)phenyl group, a 2-bromo-4-[4-(tert-butoxycarbonyl)piperazin-1-yl]phenyl group, a 2-bromo-4-(piperazin-1-yl)phenyl group, a 2-bromo-4-[4-(methylsulfonyl)piperazin-1-yl]phenyl group, a 2-bromo-4-[4-(2-hydroxyethyl)piperazin-1-yl]phenyl group, a 4-(1,4-diazepan-1-yl)phenyl group, a 4-(4-methyl-1,4-diazepan-1-yl)phenyl group, a 4-(4-benzyl-1,4-diazepan-1-yl)phenyl group, a 4-[4-(tert-butoxycarbonyl)-1,4-diazepan-1-yl]phenyl group, a 2-bromo-4-(1,4-diazepan-1-yl)phenyl group, a 2-bromo-4-(4-methyl-1,4-diazepan-1-yl)phenyl group, a 2-bromo-4-(4-benzyl-1,4-diazepan-1-yl)phenyl group, a 2-bromo-4-[4-(tert-butoxycarbonyl)-1,4-diazepan-1-yl]phenyl group, a 5-hydroxy-2-(pyrrolidin-1-yl)phenyl group, a 5-hydroxy-2-(piperidin-1-yl)phenyl group, a 5-hydroxy-2-(morpholin-4-yl)phenyl group, a 2-(4-benzylpiperidin-1-yl)-5-hydroxyphenyl group, a 5-hydroxy-2-[4-(2-hydroxyethyl)piperazin-1-yl]phenyl group, a 5-hydroxy-2-(piperazin-1-yl)phenyl group, a 2-[4-(tert-butoxycarbonyl)piperazin-1-yl]-5-hydroxyphenyl group, a 5-hydroxy-2-(4-phenylpiperazin-1-yl)phenyl group, a 5-hydroxy-2-(4-methylpiperazin-1-yl)phenyl group, a 2-(1,4-diazepan-1-yl)-5-hydroxyphenyl group, a 5-hydroxyphenyl-2-(4-methyl-1,4-diazepan-1-yl) group, a 2-(4-benzyl-1,4-diazepan-1-yl)-5-hydroxyphenyl group, a 2-[4-(tert-butoxycarbonyl)-1,4-diazepan-1-yl]-5-hydroxyphenyl group, a 5-bromo-2-[4-(2-hydroxyethyl)piperazin-1-yl]phenyl group, etc.

(4) Aryl Group Optionally having a Substituent or Heteroaryl Group Optionally having a Substituent Examples of the "aryl group optionally having a substituent" include a phenyl group, a 2-methylphenyl group, a 2-ethoxyphenyl group, a 1-naphthyl group, a 2-naphthyl group, etc. Examples of the "heteroaryl group optionally having a substituent" include a 2-pyridyl group, a 3-pyridyl group, a 4-pyridyl group, an imidazol-1-yl group, a 1H-1,2,4-triazol-1-yl group, a 4-ethoxycarbonyl-1H-1,2,3-triazol-1-yl group, a 5-ethoxycarbonyl-1H-1,2,3-triazol-1-yl group, a 1-benzyl-1H-1,2,3-triazol-4-yl group, a 1-benzyl-1H-1,2,3-triazol-5-yl group, a 1-ethoxycarbonylmethyl-1H-1,2,3-triazol-4-yl group, a 1-ethoxycarbonylmethyl-1H-1,2,3-triazol-5-yl group, a 1H-benzimidazol-1-yl group, a 1H-tetrazol-5-yl group, a 1-benzyl-1H-tetrazol-5-yl group, a 1-ethoxycarbonylmethyl-1H-tetrazol-5-yl group, etc.

Examples of the "phenyl group having an aryl group optionally having a substituent or the phenyl group having a heteroaryl group optionally having a substituent" include a 2-phenylphenyl group, a 3-phenylphenyl group, a 4-phenylphenyl group, a 5-hydroxy-2-phenylphenyl group, a 5-fluoro-2-phenylphenyl group, a 5-chloro-2-phenylphenyl group, a 5-hydroxy-2-(2-methylphenyl)phenyl group, a 2-(2-ethoxyphenyl)-5-hydroxyphenyl group, a 2-(1-naphthyl)phenyl group, a 2-(2-naphthyl)phenyl group, a 5-hydroxy-2-(1-naphthyl)phenyl group, a 2-(2-pyridyl)phenyl group, a 2-(3-pyridyl)phenyl group, a 2-(4-pyridyl)phenyl group, a 4-(2-pyridyl)phenyl group, a 4-(imidazol-1-yl)phenyl group, a 4-(1H-benzimidazol-1-yl)phenyl group, a 2-(1H-1,2,4-triazol-1-yl)phenyl group, a 2-(4-ethoxycarbonyl-1H-1,2,3-triazol-1-yl)phenyl group, a 2-(5-ethoxycarbonyl-1H-1,2,3-triazol-1-yl)phenyl group, a 2-(1-benzyl-1H-1,2,3-triazol-4-yl)phenyl group, a 2-(1-benzyl-1H-1,2,3-triazol-5-yl)phenyl group, a 2-(1-ethoxycarbonylmethyl-1H-1,2,3-triazol-4-yl)phenyl group, a 2-(1-ethoxycarbonylmethyl-1H-1,2,3-triazol-5-yl)phenyl group, a 2-(1H-tetrazol-5-yl)phenyl group, a 2-(1-benzyl-1H-tetrazol-5-yl)phenyl group, a 2-(1-ethoxycarbonylmethyl-1H-tetrazol-5-yl)phenyl group, etc.

(5) Bromine Atom

Examples of the "phenyl group having a bromine atom" include a 2-bromophenyl group, a 3-bromophenyl group, a 4-bromophenyl group, a 2-bromo-3-hydroxyphenyl group, a 2-bromo-4-hydroxyphenyl group, a 2-bromo-5-hydroxyphenyl group, a 2-bromo-5-methoxyphenyl group, a 2-bromo-5-methoxymethoxyphenyl group, a 4-bromo-2-fluorophenyl group, a 5-bromo-2-fluorophenyl group, a 2-bromo-4-hydroxy-5-methoxyphenyl group, a 2-bromo-5-hydroxy-4-methoxyphenyl group, a 2,4-dibromo-5-hydroxyphenyl group, a 2,3-dibromo-4-hydroxy-5-methoxyphenyl group, etc.

(6) Alkyl Group Optionally having a Substituent, Alkenyl Group Optionally having a Substituent, or Alkynyl Group Optionally having a substituent Examples of the "alkyl group optionally having a substituent, the alkenyl group optionally having a substituent, or the alkynyl group optionally having a substituent" include an isopropyl group, a hydroxymethyl group, a n-propyl group, a 2-cyclopropylethyl group, a 2-(methoxymethyl)ethyl group, a 2-(dimethylaminomethyl)ethyl group, a 2-(diethylaminomethyl)ethyl group, a phenethyl group, a 2-(pyridin-2-yl)ethyl group, a 2-(pyridin-3-yl)ethyl group, 2-(pyridin-4-yl)ethyl group, a 2-methylethenyl group, a 2-cyclopropylethenyl group, a 2-(methoxymethyl)ethenyl group, a 2-(dimethylaminomethyl)ethenyl group, a 2-(diethylaminomethyl)ethenyl group, a styryl group, a 2-(pyridin-2-yl)ethenyl group, a 2-(pyridin-3-yl)ethenyl group, a 2-(pyridin-4-yl)ethenyl group, a 1-propynyl group, a cyclopropylethynyl group, a methoxymethylethynyl group, a 2-(dimethylaminomethyl)ethynyl group, a 2-(diethylaminomethyl)ethynyl group, a phenylethynyl group, a pyridin-2-ylethynyl group, a pyridin-3-ylethynyl group, a pyridin-4-ylethynyl group, etc.

Examples of the "phenyl group having an alkyl group optionally having a substituent, the phenyl group having an alkenyl group optionally having a substituent, or the phenyl group having an alkynyl group optionally having a substituent" include a 4-isopropylphenyl group, a 2-(hydroxymethyl)phenyl group, a 2-methoxy-4-(n-propyl)phenyl group, a 4-(2-cyclopropylethyl)-2-methoxyphenyl group, a 2-methoxy-4-[2-(methoxymethyl)ethyl]phenyl group, a 4-[2-(dimethylaminomethyl)ethyl]-2-methoxyphenyl group, a 4-[2-(diethylaminomethyl)ethyl]-2-methoxyphenyl group, a 2-methoxy-4-phenethylphenyl group, a 2-methoxy-4-[2-(pyridin-2-yl)ethyl]phenyl group, a 2-methoxy-4-[2-(pyridin-3-yl)ethyl]phenyl group, a 2-methoxy-4-[2-(pyridin-4-yl)ethyl]phenyl group, a 2-styrylphenyl group, a 2-methoxy-4-(2-methylethenyl)phenyl group, a 4-(2-cyclopropylethenyl)-2-methoxyphenyl group, a 2-methoxy-4-[2-(methoxymethyl)ethenyl]phenyl group, a 4-[2-(dimethylaminomethyl)ethenyl]-2-methoxyphenyl group, a 4-[2-(diethylaminomethyl)ethenyl]-2-methoxyphenyl group, a 2-methoxy-4-styrylphenyl group, a 2-methoxy-4-[2-(pyridin-2-yl)ethenyl]phenyl group, a 2-methoxy-4-[2-(pyridin-3-yl)ethenyl]phenyl group, a 2-methoxy-4-[2-(pyridin-4-yl)ethenyl]phenyl group, a 2-methoxy-4-(1-propynyl)phenyl group, a 4-(2-cyclopropylethynyl)-2-methoxyphenyl group, a 2-methoxy-4-[2-(methoxymethyl)ethynyl]phenyl group, a 4-[2-(dimethylaminomethyl)ethynyl]-2-methoxyphenyl group, a 4-[2-(diethylaminomethyl)ethynyl]-2-methoxyphenyl group, a 2-methoxy-4-(phenylethynyl)phenyl group, a 2-methoxy-4-[2-(pyridin-2-yl)ethynyl]phenyl group, a 2-methoxy-4-[2-(pyridin-3-yl)ethynyl]phenyl group, a 2-methoxy-4-[2-(pyridin-4-yl)ethynyl]phenyl group, etc.

(7) Nitro Group

Examples of the "phenyl group having a nitro group" include a 2-nitrophenyl group, a 4-hydroxy-3-nitrophenyl group, a 3-methoxy-4-nitrophenyl group, a 5-methoxy-2-nitrophenyl group, a 5-methoxymethoxy-2-nitrophenyl group, a 5-fluoro-2-nitrophenyl group, a 5-hydroxy-2-nitrophenyl group, a 5-chloro-2-nitrophenyl group, a 2-chloro-5-nitrophenyl group, a 4,5-dimethoxy-2-nitrophenyl group, etc.

(8) Acyl Group

Examples of the "phenyl group having an acyl group" include a 2-hydroxycarbonylphenyl group, a 3-hydroxycarbonylphenyl group, a 2-methoxycarbonylphenyl group, a 3-methoxycarbonylphenyl group, a 4-methoxycarbonylphenyl group, a 2-dimethylaminocarbonylphenyl group, a 3-(di-n-propylaminocarbonyl)phenyl group, etc.

(9) Alkylcarbonylamino Group and Other Groups

The "phenyl group optionally having a substituent" also includes a phenyl group having an alkylcarbonylamino group, a sulfonyl group, a sulfinyl group, or a sulfonyloxy group.

The number of the substituents (1) to (9) introduced into the phenyl group is not particularly limited and a plurality of the same or different substituents may be introduced. Preferably, the number of the substituents introduced into the phenyl group is only one. The position of the substituents (1) to (9) on the phenyl group is also not particularly limited and the substituents may be introduced into the ortho, meta, and/or para positions. Preferably, the substituent is introduced into the para position. The phenyl group represented by $Ar^1$ may have a substituent not included in the above substituents (1) to (9), namely, a hydroxy group, a methoxy group, and a halogen atom other than a bromine atom, etc.

$Ar^2$ in the general formula (I) preferably represents a homocyclic or heterocyclic group optionally having a substituent, more preferably a bicyclic homocyclic or heterocyclic group optionally having a substituent, most preferably a bicyclic heterocyclic group optionally having a substituent.

The "bicyclic heterocyclic group" is not particularly limited as long as it does not impair the effects of the present invention. Preferred examples thereof include an indol-2-yl group, an indol-3-yl group, an indol-4-yl group, an indol-5-yl group, an indol-6-yl group, an indol-7-yl group, a benzotriazol-5-yl group, a benzimidazol-5-yl group, a quinoxalin-6-yl group, a benzofuran-2-yl group, a benzothiophen-2-yl group, a 1H-indazol-5-yl group, a 7-azaindol-3-yl group, a quinolin-2-yl group, a quinolin-5-yl group, a quinolin-8-yl group, a 1,4-benzodioxan-6-yl group, a 1,3-benzodioxol-5-yl group, a chromon-3-yl group, a coumarin-6-yl group, a 7-methoxycoumarin-4-yl group, a 4-methoxycoumarin-6-yl group, etc. Examples of a substituent on the bicyclic heterocyclic group include a methyl group, an ethyl group, a benzyl group, an acetyl group, a benzoyl group, a tert-butoxycarbonyl group, a methylsulfonyl group, a p-toluenesulfonyl group, a hydroxy group, a nitro group, etc.

The "bicyclic heterocyclic group optionally having a substituent" is not particularly limited as long as it does not impair the effects of the present invention. Preferred examples thereof include a nonsubstituted bicyclic heterocyclic group; a 1-methyl-indol-6-yl group, a 1-methylindol-2-yl group, a 1-methylindol-3-yl group, a 1-ethylindol-6-yl group, a 1-benzylindol-3-yl group, a 1-benzylindol-6-yl group, a 1-acetylindol-3-yl group, a 1-acetylindol-6-yl group, a 1-benzoylindol-3-yl group, a 1-tert-butoxycarbonylindol-5-yl group, a 1-methylsulfonylindol-3-yl group, a 1-methylsulfonylindol-6-yl group, a 1-p-toluenesulfonylindol-3-yl group, a 1-p-toluenesulfonylindol-6-yl group, a 4-hydroxyindol-3-yl group, a 4-nitroindol-3-yl group, etc.; a bicyclic heterocyclic group substituted with an alkyl group (for example, a $C_{1-6}$ alkyl group), an aralkyl group (for example, a $C_{7-10}$ aralkyl group), an acyl group (for example, a $C_{2-10}$ acyl group), a hydroxyl group, a nitro group, or the like; etc.

In view of the tau aggregation inhibitory activity etc., preferred structure of the compound represented by the general formula (I) is as follows.

$Ar^1$ in the general formula (I) is particularly preferably a phenyl group having the above substituent (1), more preferably a phenyl group having the above substituent (1a) or (1c), furthermore preferably a 2-methoxy-4-(pyridin-2-ylmethoxy)phenyl group.

$Ar^2$ in the general formula (I) is particularly preferably an indol-2-yl group optionally having a substituent, an indol-3-yl group optionally having a substituent, an indol-4-yl group optionally having a substituent, an indol-5-yl group optionally having a substituent, an indol-6-yl group optionally having a substituent, an indol-7-yl group optionally having a substituent, a benzotriazol-5-yl group optionally having a substituent, a benzimidazol-5-yl group optionally having a substituent, a quinoxalin-6-yl group optionally having a substituent, a benzofuran-2-yl group optionally having a substituent, or a benzothiophen-2-yl group optionally having a substituent; more preferably an indol-2-yl group, an indol-3-yl group, an indol-6-yl group, a 1-methyl-indol-6-yl group, a benzotriazol-5-yl group, a benzimidazol-5-yl group, a quinoxalin-6-yl group, a benzofuran-2-yl group, or a benzothiophen-2-yl group; further more preferably an indol-6-yl group.

A salt of the compound represented by the general formula (I) is also encompassed in the present invention. The salt is preferably a pharmacologically acceptable salt and examples thereof include hydrohalic acid salts such as hydrofluoride, hydrochloride, hydrobromide, and hydroiodide; inorganic acid salts such as sulfate, nitrate, perchlorate, phosphate, carbonate, and bicarbonate; organic carboxylic acid salts such as acetate, oxalate, maleate, tartrate, and fumarate; organic sulfonic acid salts such as methanesulfonate, trifluoromethanesulfonate, ethanesulfonate, benzenesulfonate, toluenesulfonate, and camphorsulfonate; amino acid salts such as aspartate and glutamate; amine salts such as trimethylamine salt, triethylamine salt, procaine salt, pyridine salt, and phenethylbenzylamine salt; alkali metal salts such as sodium salt and potassium salt; alkaline earth metal salts such as magnesium salt and calcium salt; etc. Preferred are hydrochloride and oxalate.

The compound represented by the general formula (I) can be produced with reference to the method described in, for example, Rajeshwar Narlawar et al., ChemMedChem 2008, 3, 165-172, WO 2008/066151, WO 2009/145219, or the like, or any combination of the methods described in these literature. Specifically, the compound can be produced by the following Steps 1 and 2.

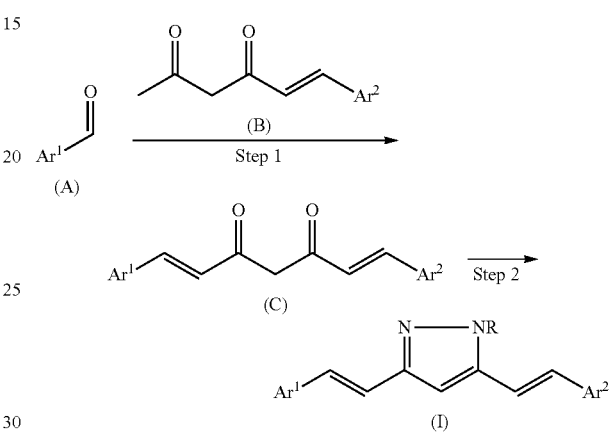

In the above formula, $Ar^1$ and $Ar^2$ are as defined above.

In Step 1, an aldehyde represented by the general formula (A) is allowed to react with a compound represented by the general formula (B) in the presence of a solvent and a catalyst to give a diketone represented by the general formula (C). The diketone represented by the general formula (C) or a salt thereof is also encompassed in the present invention. In the above formula, the aldehyde represented by the general formula (A) has $Ar^1$ and the compound represented by the general formula (B) has $Ar^2$. However, an aldehyde corresponding to the aldehyde of the general formula (A) may have $Ar^2$ and a compound corresponding to the compound of the general formula (B) may have $Ar^1$, and the diketone of the general formula (C) may be obtained by the reaction of the aldehyde having $Ar^2$ and the compound having $Ar^1$.

The solvent used in the reaction is not particularly limited as long as it does not inhibit the reaction, and examples thereof include ethyl acetate, N, N-dimethylacetamide, N,N-dimethylformamide, N-methyl pyrrolidinone, dimethylsulfoxide, tetrahydrofuran, acetonitrile, etc. These solvents may be used alone or in combination of two or more kinds thereof in an appropriate mixing ratio.

The catalyst used in the reaction is also not particularly limited. Examples thereof include bases such as a primary amine and a secondary amine, and specific examples thereof include n-butylamine, ethanolamine, piperidine, morpholine, etc.

A water scavenger may be added in order to capture the water produced by the reaction. Examples of the water scavenger include an alkyl borate, an alkyl phosphate, an orthoester, etc., and specific examples thereof include trimethyl orthoformate and tri-n-butyl borate.

The quantitative ratio of the aldehyde represented by the general formula (A) and the compound represented by the general formula (B) is not particularly limited, but preferably the amount of the compound used is 0.5 to 10 mol, more preferably 0.5 to 2 mol, relative to 1 mol of the aldehyde.

The reaction temperature is not particularly limited, but is preferably 0 to 200° C., more preferably 50 to 100° C.

The reaction duration is not particularly limited, but is preferably 0.5 to 48 hours, more preferably 1 to 24 hours.

The aldehyde represented by the general formula (A) and the compound represented by the general formula (B) that are used in Step 1 may be commercially available products or those synthesized by a known method (for example, the method described in WO 2008/066151 or WO 2009/145219).

In Step 2, a diketone represented by the general formula (C) is allowed to react with a hydrazine or its derivative in the presence of a solvent to give a compound represented by the general formula (I). In accordance with a compound of interest, Step 2 may have the step of adding a substituent to the compound of the general formula (C) obtained by allowing the diketone to react with the hydrazine or its derivative (a compound represented by $H_2N$—NHR, a salt thereof, or the like).

The hydrazine used in the reaction is not particularly limited and examples thereof include hydrazine monohydrate, hydrazine aqueous solution, anhydrous hydrazine, hydrazine acetate, hydrazine monohydrochloride, a derivative thereof, etc.

The solvent used in the reaction is not particularly limited as long as it does not inhibit the reaction and examples thereof include protic solvents such as acetic acid, methanol, ethanol, and water; non-protic solvents such as ethyl acetate, toluene, tetrahydrofuran, methylene chloride, chloroform, etc. These solvents may be used alone or in combination of two or more kinds thereof in an appropriate mixing ratio.

The quantitative ratio of the diketone represented by the general formula (C) and the hydrazine is not particularly limited, but preferably the amount of the hydrazine used is 1 to 50 mol, more preferably 2 to 10 mol, relative to 1 mol of the diketone.

The reaction temperature is not particularly limited, but is preferably 20 to 120° C., more preferably 50 to 80° C.

The reaction duration is not particularly limited, but is preferably 1 to 24 hours, more preferably 1 to 6 hours.

The compounds of the present invention may be administered alone or in combination with one or more of the compounds of the present invention or with one or more compounds other than the compounds of the present invention. The compound of the present invention may be administered as a formulation comprising one or more pharmacologically acceptable carriers. The effective dosage and frequency of administration may vary with the dosage form, the age, body weight, symptoms, etc. of the patient, and the like, but the daily dosage is usually about 0.01 to 100 mg/kg, more preferably about 1 to 50 mg/kg.

The dosage form of an agent comprising the compound of the present invention as an active ingredient is not particularly limited and the agent may be orally or parenterally administered by a usual method. The compound can be formulated and administered as oral or parenteral preparations, such as tablets, powders, granules, capsules, solutions, emulsions, elixirs, suspensions, syrups, troches, inhalations, suppositories, injections, ointments, ophthalmic ointments, ophthalmic preparations, nasal preparations, ear preparations, cataplasms/gel patches, lotions, etc. The dosage of a medicine of the present invention can be determined as appropriate in accordance with the severity of the symptom, the age, sex, body weight of the patient, the dosage form, the type of the salt, the specific disease, etc.

Since the compound of the present invention has a tau aggregation inhibitory activity, a β-secretase inhibitory activity, and an Aβ aggregation inhibitory activity, the compound of the present invention is effective in preventing and treating diseases in which tau, β-secretase, or Aβ is involved, such as Alzheimer's disease (familial Alzheimer's disease and sporadic Alzheimer's disease), senile dementia, Down syndrome, Parkinson's disease, Creutzfeldt-Jakob disease, amyotrophic lateral sclerosis, diabetic neuropathy, Huntington's chorea, multiple sclerosis, etc. Among these nervous diseases, the compound of the present invention is especially effective in preventing and treating Alzheimer's disease.

The compound of the present invention can be formulated by a commonly used method into a dosage form such as a tablet, a powder, a fine granule, a granule, a coated tablet, a capsule, a solution, an emulsion, an elixir, a suspension, a syrup, a troche, an inhalation, a suppository, an injection, an ointment, an ophthalmic ointment, an ophthalmic preparation, a nasal preparation, an ear preparation, a cataplasm/gel patch, a lotion, etc. For the formulation into such a dosage form, an excipient, a binder, a lubricant, a colorant and a flavor modifier that are usually used for the formulation of a medicine can be used, and as needed a stabilizer, an emulsifier, an absorption enhancer, a surfactant, a pH adjuster, a preservative, an antioxidant, and/or the like can also be used. Thus, ingredients that are usually used as raw materials of a pharmaceutical formulation may be mixed with the compound and formulated into a dosage form by a conventional method. For example, in the production of an oral preparation, a crystalline or amorphous compound of the present invention is mixed with an excipient, and as needed with a binder, a disintegrator, a lubricant, a colorant, a flavor modifier, etc., and formed into a powder, a fine granule, a granule, a tablet, a coated tablet, a capsule, etc. by a conventional method. Examples of the ingredient include animal and vegetable fats and oils such as soybean oil, beef tallow, and synthetic glyceride; hydrocarbons such as liquid paraffin, squalane, and hard paraffin; ester oils such as octyldodecyl myristate and isopropyl myristate; higher alcohols such as cetostearyl alcohol and behenyl alcohol; silicone resins; silicone oils; surfactants such as polyoxyethylene fatty acid ester, sorbitan fatty acid ester, glycerin fatty acid ester, polyoxyethylene sorbitan fatty acid ester, polyoxyethylene hardened castor oil, and polyoxyethylene-polyoxypropylene block copolymer; water soluble polymers such as hydroxyethyl cellulose, hydroxypropyl methylcellulose, hydroxypropyl methylcellulose phthalate, polyacrylate, carboxy vinyl polymer, polyethylene glycol, polyvinylpyrrolidone, and methylcellulose; lower alcohols such as ethanol and isopropanol; polyalcohols such as glycerin, propylene glycol, dipropylene glycol, and sorbitol; sugars such as glucose and sucrose; inorganic powders such as anhydrous silicic acid, magnesium aluminum silicate, and aluminium silicate; purified water; etc. Examples of the excipient include lactose, corn starch, saccharose, glucose, mannitol, sorbitol, crystalline cellulose, silicon dioxide, etc. Examples of the binder include polyvinyl alcohol, polyvinyl ether, methylcellulose, ethylcellulose, gum arabic, tragacanth, gelatin, shellac, hydroxypropyl methylcellulose, hydroxypropyl cellulose, polyvinylpyrrolidone, polypropylene glycol-polyoxyethylene block polymer, meglumine, etc. Examples of the disintegrator include starch, agar, gelatin powder, crystalline cellulose, calcium carbonate, sodium bicarbonate, calcium citrate, dextrin, pectin, carboxymethyl cellulose calcium, etc. Examples of the lubricant include magnesium stearate, talc, polyethylene glycol, silica, hydrogenated vegetable oil, etc. Examples of the colorant include a colorant that is approved as an additive to a medicine, etc. Examples of the flavor modifier include cocoa powder, menthol, aromatic powder, mentha oil, borneol, cinnamon powder, etc. Needless to say, the obtained tablets and granules may be coated with a sugar or the like as needed. In the production of a solution such as a syrup, an emulsion, an elixir, a suspension, and an injection, the compound of the present invention is mixed as needed with a pH adjuster, a solubilizer, an emulsifier, a dispersant, an isotonic agent, a solubilization assisting agent, a stabilizer, or the like, and formed into such a solution by a conventional method. In the production of an external medicine, the production method is not limited and the production can be carried out by a conventional method. That is, for the formulation of an external medicine, various types of raw materials that are usually used for medicines, quasi drugs, cosmetics, or the like can be used as a base ingredient. Specific examples of the base ingredient to be used include animal and vegetable oils, mineral oils, ester oils, waxes, higher alcohols, fatty acids, silicone oils, surfactants, phospholipids, alcohols, polyalcohols, water soluble polymers, clay minerals, purified water, etc. Further, a pH adjuster, an antioxidant, a chelating agent, an antibacterial and antifungal agent, a colorant, a flavor, and/or the like can be added as needed. The base ingredient of the external medicine of the present invention is not limited to the above ingredients. As needed, other ingredients can be added and examples thereof include an ingredient having a differentiation inducing activity, a blood flow increasing agent, a bactericide, an anti-inflammatory, a cell activator, a vitamin, an amino acid, a moisturizer, a keratolytic agent, etc. The amount of the base ingredient to be added is determined so that the concentration will be a usual base ingredient concentration in the production of an external medicine.

The compound of the present invention can be used for a therapeutic method for a disease in which tau, β-secretase, or Aβ is involved. Specific examples of the method include the following (a) to (c):

(a) a therapeutic method for a disease in which tau is involved, the method comprising the step of administering a compound represented by the general formula (I) or a salt thereof to a patient with a disease in which tau is involved;
(b) a therapeutic method for a disease in which β-secretase is involved, the method comprising the step of administering a compound represented by the general formula (I) or a salt thereof to a patient with a disease in which β-secretase is involved; and
(c) a therapeutic method for a disease in which Aβ is involved, the method comprising the step of administering a compound represented by the general formula (I) or a salt thereof to a patient with a disease in which Aβ is involved.

The compound of the present invention can also be used for a method for inhibiting tau aggregation, a method for inhibiting β-secretase, and a method for inhibiting Aβ aggregation. Specific examples of the method include the following (d) to (i):

(d) a method for inhibiting tau aggregation, the method comprising the step of administering a compound represented by the general formula (I) or a salt thereof to a human, thereby inhibiting tau aggregation in the living human body;
(e) a method for inhibiting tau aggregation, the method comprising the step of bringing a compound represented by the general formula (I) or a salt thereof in contact with tau;
(f) a method for inhibiting β-secretase, the method comprising the step of administering a compound represented by the general formula (I) or a salt thereof to a human, thereby inhibiting β-secretase in the living human body;
(g) a method for inhibiting β-secretase, the method comprising the step of bringing a compound represented by the general formula (I) or a salt thereof in contact with β-secretase;
(h) a method for inhibiting Aβ aggregation, the method comprising the step of administering a compound represented by the general formula (I) or a salt thereof to a human, thereby inhibiting Aβ aggregation in the living human body; and
(i) a method for inhibiting Aβ aggregation, the method comprising the step of bringing a compound represented by the general formula (I) or a salt thereof in contact with Aβ.

The salt in the above methods may be a pharmacologically acceptable salt.

EXAMPLES

The present invention will be described in further detail with reference to Examples etc., but the present invention is not limited thereto. Various modifications of the present invention can be made by a person who has common knowledge in the art, without departing from the scope of the technical idea of the present invention.

In Examples, synthetic compounds having a structure represented by the general formula (I) in which R is a hydrogen atom are detected as a mixture of two tautomers represented by the general formulas (I) and (I') as shown below, depending on the measurement condition of $^1$H NMR. The tautomers represented by the general formulas (I) and (I') are the same substance. Therefore, the synthetic compounds in Examples can be named based on either the general formula (I) or the general formula (I').

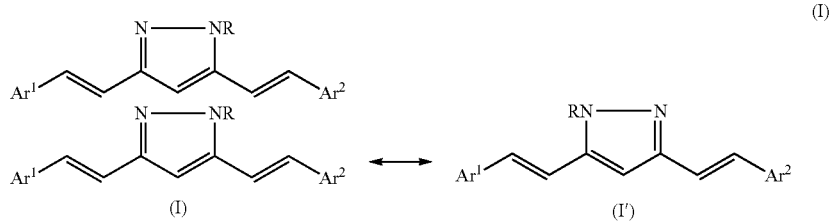

A compound represented by the following general formula (II) corresponds to a compound represented by the above general formula (C) and is a synthetic intermediate that is encompassed in the present invention. The compound represented by the general formula (II) can exist in tautomeric forms including a keto form and an enol form, and these tautomeric forms are the same substance. Therefore, such a synthetic intermediate can be named based on any of the general formula (II), the general formula (II'), and the general formula (II"). The melting points may differ from the values shown in Examples depending on the crystal system and/or the degree of contamination with impurities.

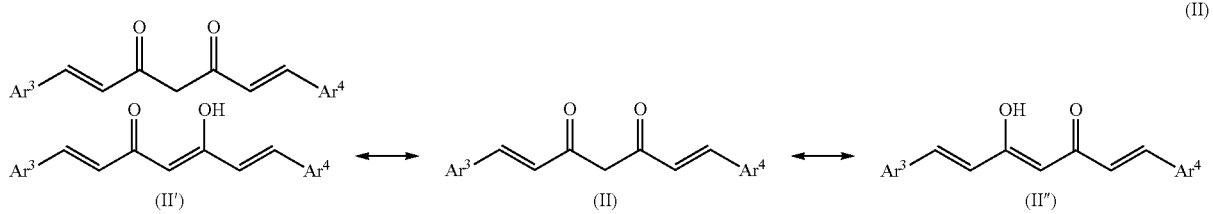

Example 1

Synthesis of 3-[(1E)-2-(1H-indol-6-yl)ethenyl]-5-[(1E)-2-[2-methoxy-4-(2-tetrahydrofuranylmethoxy)phenyl]ethenyl]-1H-pyrazole

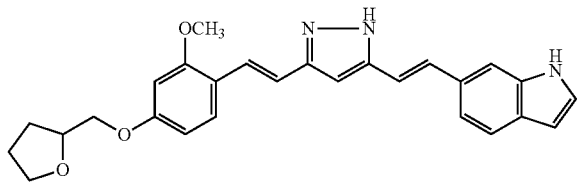 [SMILES: COc1cc(OCC2CCCO2)ccc1/C=C/c1cc(/C=C/c2ccc3cc[nH]c3c2)[nH]n1]

(1) Synthesis of 2-methoxy-4-(2-tetrahydrofuranylmethoxy)benzaldehyde

In 160 mL of N-methylpyrrolidone was dissolved 24.5 g (161 mmol) of 4-hydroxy-2-methoxybenzaldehyde. To this solution were added 63 g (0.19 mol) of cesium carbonate and 40 g (0.24 mol) of tetrahydrofurfuryl bromide at room temperature and the mixture was stirred at 80° C. for 22 hours. Water (800 mL) was added to the resulting reaction mixture under ice-cooling, and extraction with diethyl ether (500 mL×3 times) was performed. The combined organic layer was washed with water and then with saturated brine and dried over anhydrous sodium sulfate. After filtration, the solvent was evaporated under reduced pressure. The resulting crude product was purified on basic alumina (hexane/ethyl acetate=50/50 to 0/100) to give 23.7 g (62% yield) of the title compound as a light yellow powder with the following properties.

$^1$H NMR (δ, acetone-$d_6$): 1.7-2.0 (m, 4H), 3.74 (m, 1H), 3.84 (m, 1H), 3.97 (s, 3H), 4.10 (m, 2H), 4.21 (m, 1H), 6.64 (ddd, J=0.8, 2.2, 8.5 Hz, 1H), 6.71 (d, J=2.2 Hz, 1H), 7.71 (d, J=8.5 Hz, 1H), 10.27 (d, J=0.8 Hz, 1H). melting point 73.3° C.

(2) Synthesis of (1E,6E)-1-(1H-indol-6-yl)-7-[2-methoxy-4-(2-tetrahydrofuranylmethoxy)phenyl]hepta-1,6-diene-3,5-dione In a 20 mL reaction vessel were placed 19.3 mg (85.0 μmol) of 6-(1H-indol-6-yl)hex-5-ene-2,4-dione and 22 mg (0.32 mol) of boron oxide and they were dissolved in 0.4 mL of ethyl acetate. To the mixture under stirring at 70° C., 20 mg (85 μmol) of 2-methoxy-4-(2-tetrahydrofuranylmethoxy)benzaldehyde and 32 μL (0.14 mmol) of triisopropyl borate were sequentially added. After the mixture was stirred at the same temperature for 1 hour, 18 μL (0.18 mmol) of piperidine was added and the mixture was further stirred for 1 hour. To the reaction mixture was added a 1:1 solution (2 mL) of 1 N hydrochloric acid and saturated brine at room temperature and the mixture was stirred for 5 minutes to 1 hour (further, the mixture was neutralized with a saturated sodium bicarbonate aqueous solution as needed). The resulting organic phase was directly subjected to purification by silica gel column chromatography (hexane/ethyl acetate or methylene chloride/methanol) to give 10.2 mg (27% yield) of the title compound as an orange powder with the following properties.

$^1$H NMR (δ, acetone-$d_6$): 1.7-2.0 (m, 4H), 3.74 (m, 1H), 3.84 (m, 1H), 3.95 (s, 3H), 4.05 (m, 2H), 4.21 (m, 1H), 6.00 (s, 1H), 6.53 (br d, J=3 Hz, 1H), 6.62 (dd, J=2.2, 8.5 Hz, 1H), 6.67 (d, J=2.2 Hz, 1H), 6.78 (d, J=16 Hz, 1H), 6.82 (d, J=16 Hz, 1H), 7.44 (dd, J=1.7, 8.5 Hz, 1H), 7.47 (m, 1H), 7.63 (d, J=8.3 Hz, 1H), 7.64 (d, J=8.5 Hz, 1H), 7.74 (br s, 1H), 7.78 (d, J=16 Hz, 1H), 7.93 (d, J=16 Hz, 1H), 10.5 (br s, NH). melting point 159-161° C., MS (ESI+) m/z 446.3 (M+1).

(3) Synthesis of 3-[(1E)-2-(1H-indol-6-yl)ethenyl]-5-[(1E)-2-[2-methoxy-4-(2-tetrahydrofuranylmethoxy)phenyl]ethenyl]-1H-pyrazole In 4.5 mL of acetic acid was dissolved 400 mg (0.898 mmol) of (1E,6E)-1-(1H-indol-6-yl)-7-[2-methoxy-4-(2-tetrahydrofuranylmethoxy)phenyl]hepta-1,6-diene-3,5-dione. To this solution was added 0.45 g (9.0 mmol) of hydrazine monohydrate at room temperature and the mixture was stirred at 60° C. for 3 hours. The resulting reaction mixture was diluted with ethyl acetate, washed with a saturated sodium bicarbonate aqueous solution and then with saturated brine, and dried over magnesium sulfate. After filtration, the solvent was evaporated under reduced pressure. The residue was purified by silica gel column chromatography (hexane/ethyl acetate or methylene chloride/methanol). The resulting solid was washed with an organic solvent to give 298 mg (75% yield) of the title compound as a pale yellowish white powder with the following properties.

$^1$H NMR (δ, acetone-$d_6$): 1.7-2.0 (m, 4H), 3.74 (m, 1H), 3.84 (m, 1H), 3.92 (s, 3H), 4.01 (d, J=5.0 Hz, 1H), 4.21 (m, 1H), 6.47 (br d, J=3 Hz, 1H), 6.58 (dd, J=2.2, 8.5 Hz, 1H), 6.62 (d, J=2.2 Hz, 1H), 6.70 (s, 1H), 7.06 (d, J=17 Hz, 1H), 7.10 (d, J=17 Hz, 1H), 7.32 (d, J=17 Hz, 1H), 7.34 (dd, J=1.7, 8.5 Hz, 1H), 7.35 (m, 1H), 7.39 (d, J=17 Hz, 1H), 7.52 (d, J=8.5 Hz, 1H), 7.57 (d, J=8.5 Hz, 1H), 7.59 (br s, 1H), 10.3 (br s, NH). melting point 218-220° C., MS (ESI+) m/z 442.2 (M+1).

Example 2

Synthesis of 3-[(1E)-2-(1H-indol-6-yl)ethenyl]-5-[(1E)-2-[2-methoxy-4-(2-pyridylmethoxy)phenyl]ethenyl]-1H-pyrazole

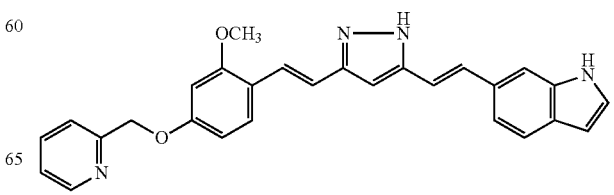

(1) Synthesis of 2-methoxy-4-(2-pyridylmethoxy)benzaldehyde

In 53 mL of N,N-dimethylformamide were dissolved 8.00 g (52.6 mmol) of 4-hydroxy-2-methoxybenzaldehyde, 14.5 g (105 mmol) of potassium carbonate, and 9.06 g (55.2 mmol) of 2-chloromethylpyridine hydrochloride and the solution was stirred at 50° C. for 4 hours. To the reaction mixture, 260 mL of water was added at room temperature and the precipitated crystal was separated by filtration. The crystal was washed with water and dried under reduced pressure to give 11.5 g (82% yield) of the title compound as a pale grey-brown powder with the following properties.

$^1$H NMR (δ, acetone-$d_6$): 3.97 (s, 3H), 5.31 (s, 2H), 6.74 (ddd, J=0.8, 2.2, 8.5 Hz, 1H), 6.84 (d, J=2.2 Hz, 1H), 7.34 (m, 1H), 7.58 (d, J=8.0 Hz, 1H), 7.73 (d, J=8.5 Hz, 1H), 7.84 (dt, J=1.9, 7.7 Hz, 1H), 8.60 (br d, J=5 Hz, 1H), 10.28 (d, J=0.8 Hz, 1H). melting point 93.6° C.

(2) Synthesis of (1E,6E)-1-(1H-indol-6-yl)-7-[2-methoxy-4-(2-pyridylmethoxy) phenyl]hepta-1,6-diene-3,5-dione Synthesis was performed in the same manner as in Example 1 (2) except that 21 mg (85 μmol) of 2-methoxy-4-(2-pyridylmethoxy)benzaldehyde was used instead of 20 mg (85 μmol) of 2-methoxy-4-(2-tetrahydrofuranylmethoxy)benzaldehyde to give 12.4 mg (32% yield) of the title compound as an orange powder with the following properties.

$^1$H NMR (δ, acetone-$d_6$): 3.95 (s, 3H), 5.27 (s, 2H), 6.00 (s, 1H), 6.53 (br d, J=3 Hz, 1H), 6.71 (dd, J=2.2, 8.5 Hz, 1H), 6.78 (d, J=16 Hz, 1H), 6.79 (d, J=2.2 Hz, 1H), 6.82 (d, J=16 Hz, 1H), 7.33 (m, 1H), 7.44 (dd, J=1.7, 8.5 Hz, 1H), 7.47 (m, 1H), 7.58 (d, J=8.0 Hz, 1H), 7.63 (d, J=8.3 Hz, 1H), 7.64 (d, J=8.5 Hz, 1H), 7.74 (br s, 1H), 7.78 (d, J=16 Hz, 1H), 7.84 (dt, J=1.7, 7.7 Hz, 1H), 7.93 (d, J=16 Hz, 1H), 8.60 (br d, J=5 Hz, 1H), 10.5 (br s, NH). melting point 165-168° C., MS (ESI+) m/z 453.2 (M+1).

(3) Synthesis of 3-[(1E)-2-(1H-indol-6-yl)ethenyl]-5-[(1E)-2-[2-methoxy-4-(2-pyridylmethoxy)phenyl]ethenyl]-1H-pyrazole Synthesis was performed in the same manner as in Example 1 (3) except that 400 mg (0.884 mmol) of (1E,6E)-1-(1H-indol-6-yl)-7-[2-methoxy-4-(2-pyridylmethoxy) phenyl]hepta-1,6-diene-3,5-dione was used instead of 400 mg (0.898 mmol) of (1E,6E)-1-(1H-indol-6-yl)-7-[2-methoxy-4-(2-tetrahydrofuranylmethoxy)phenyl]hepta-1,6-diene-3,5-dione to give 239 mg (60% yield) of the title compound as a pale yellowish white powder with the following properties.

$^1$H NMR (δ, acetone-$d_6$): 3.92 (s, 3H), 5.24 (s, 2H), 6.47 (br d, J=3 Hz, 1H), 6.67 (dd, J=2.2, 8.5 Hz, 1H), 6.70 (s, 1H), 6.75 (d, J=2.2 Hz, 1H), 7.07 (d, J=17 Hz, 1H), 7.11 (d, J=17 Hz, 1H), 7.32 (d, J=17 Hz, 1H), 7.30-7.38 (m, 3H), 7.39 (d, J=17 Hz, 1H), 7.54 (d, J=8.3 Hz, 1H), 7.55-7.59 (m, 2H), 7.59 (br s, 1H), 7.84 (dt, J=1.7, 7.7 Hz, 1H), 8.60 (br d, J=5 Hz, 1H), 10.3 (br s, NH). melting point 237-239° C., MS (ESI+) m/z 449.2 (M+1).

Example 3

Synthesis of 3-[(1E)-2-(1H-indol-6-yl)ethenyl]-5-[(1E)-2-[2-hydroxy-4-(2-pyridylmethoxy)phenyl]ethenyl]-1H-pyrazole

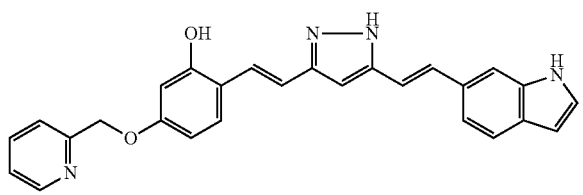 [SMILES: Oc1cc(OCc2ccccn2)ccc1/C=C/c1cc(/C=C/c2ccc3cc[nH]c3c2)[nH]n1]

(1) Synthesis of 2-hydroxy-4-(2-pyridylmethoxy)benzaldehyde

In 50 mL of water was dissolved 16.4 g (100 mmol) of 2-chloromethylpyridine hydrochloride. To this solution was added 50 mL of chloroform. The solution was neutralized by adding a saturated sodium bicarbonate aqueous solution at room temperature. The organic layer was dried over magnesium sulfate. The solvent was evaporated under reduced pressure and 250 mL of acetonitrile was added to the residue to give a solution of 2-chloromethylpyridine in acetonitrile.

Separately, 13.8 g (100 mmol) of 2,4-dihydroxybenzaldehyde was dissolved in 250 mL of acetonitrile and 32.5 g (100 mmol) of cesium carbonate was added at room temperature. To this solution, the solution of 2-chloromethylpyridine in acetonitrile prepared in advance was added dropwise at 50° C. over 4 hours and the mixture was stirred for 11 hours. After filtration, the solvent was evaporated under reduced pressure. The residue was purified by silica gel column chromatography (hexane/ethyl acetate=80/20 to 50/50) to give 6.10 g (27% yield) of the title compound as a white solid.

$^1$H NMR (δ, chloroform-d): 5.25 (s, 2H), 6.53 (d, J=2.5 Hz, 1H), 6.65 (dd, J=2.6, 8.1 Hz, 1H), 7.25 (m, 1H), 7.45 (m, 2H), 7.73 (dt, J=1.9, 7.7 Hz, 1H), 8.61 (d, J=4.8 Hz, 1H), 9.73 (s, 1H), 11.4 (s, 1H). melting point 89.2-89.7° C., MS (EI) m/z 229 (M$^+$).

(2) Synthesis of (1E,6E)-1-(1H-indol-6-yl)-7-[2-hydroxy-4-(2-pyridylmethoxy) phenyl]hepta-1,6-diene-3,5-dione Synthesis was performed using the same materials in the same relative quantities as in Example 1 (2) except that 908 mg (3.96 mmol) of 3-hydroxy-4-(2-pyridylmethoxy)benzaldehyde was used instead of 20 mg (85 μmol) of 2-methoxy-4-(2-tetrahydrofuranylmethoxy)benzaldehyde to give 356 mg (21% yield) of the title compound as an orange powder with the following properties.

$^1$H NMR (δ, DMSO-$d_6$): 5.19 (s, 2H), 6.08 (s, 1H), 6.48 (m, 1H), 6.55-6.59 (m, 2H), 6.79 (d, J=16 Hz, 1H), 6.86 (d, J=16 Hz, 1H), 7.35-7.37 (m, 1H), 7.41-7.43 (m, 1H), 7.47-7.50 (m, 2H), 7.58-7.60 (m, 2H), 7.70 (s, 1H), 7.74 (d, J=16 Hz, 1H), 7.81 (d, J=16 Hz, 1H), 3.14 (dt, J=2.0, 7.7 Hz, 1H), 8.59 (m, 1H), 10.4 (s, 1H), 11.4 (s, 1H), 16.4 (br s, 1H). melting point 187.6-189.5° C.

(3) Synthesis of 3-[(1E)-2-(1H-indol-6-yl)ethenyl]-5-[(1E)-2-[2-hydroxy-4-(2-pyridylmethoxy)phenyl]ethenyl]-1H-pyrazole Synthesis was performed using the same materials in the same relative quantities as in Example 1 (3) except that 700 mg (1.61 mmol) of (1E,6E)-1-(1H-indol-6-yl)-7-[2-hydroxy-4-(2-pyridylmethoxy)phenyl]hepta-1,6-diene-3,5-dione was used instead of 400 mg (0.898 mmol) of (1E,6E)-1-(1H-indol-6-yl)-7-[2-methoxy-4-(2-tetrahydrofuranylmethoxy)phenyl]hepta-1,6-diene-3,5-dione to give 226 mg (32% yield) of the title compound as a pale yellowish white powder with the following properties.

$^1$H NMR (δ, acetone-$d_6$): 5.17 (s, 2H), 6.46 (m, 1H), 6.58-6.60 (m, 1H), 6.60 (s, 1H), 6.68 (s, 1H), 7.09 (d, J=16 Hz, 1H), 7.10 (d, J=17 Hz, 1H), 7.29-7.34 (m, 3H), 7.30 (d, J=17 Hz, 1H), 7.40 (d, J=16 Hz, 1H), 7.48 (d, J=8.1 Hz, 1H), 7.52 (d, J=8.1 Hz, 1H), 7.56 (d, J=8.1 Hz, 1H), 7.58 (s, 1H), 7.81 (dt, J=1.8, 7.7 Hz, 1H), 8.58 (m, 1H), 10.2 (br s, 1H). melting point 202.5-203.5° C., MS (EI) m/z 434 (M+). EI-HRMS m/z calcd for $C_{27}H_{22}N_4O_2$ (M+) 434.1743, found 434.1740.

Example 4

Synthesis of 3-[(1E)-2-(1H-indol-5-yl)ethenyl]-5-[(1E)-2-[4-(2-pyridylmethoxy)phenyl]ethenyl]-1H-pyrazole

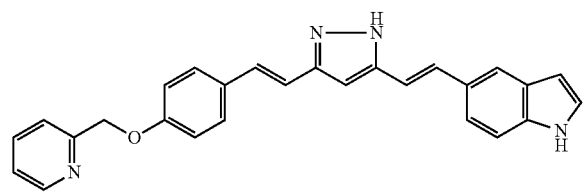 [SMILES: C(=C\c1cc(/C=C/c2ccc3[nH]ccc3c2)[nH]n1)/c1ccc(OCc2ccccn2)cc1]

(1) Synthesis of 4-(2-pyridylmethoxy)benzaldehyde

In 5.0 mL of N,N-dimethylformamide was dissolved 611 mg (5.00 mmol) of 4-hydroxybenzaldehyde. To this solution were added 3.26 g (10.0 mol) of cesium carbonate and 0.98 g (6.0 mmol) of 2-chloromethylpyridine hydrochloride at room temperature and the mixture was stirred at 50° C. overnight. The resulting reaction mixture was diluted with ethyl acetate (100 mL), washed with water and then with saturated brine (each in an amount of 30 mL), and dried over magnesium sulfate. After filtration, the solvent was evaporated under reduced pressure. The residue was purified by silica gel column chromatography (hexane/ethyl acetate=80/20 to 50/50) to give 821 mg (77% yield) of the title compound as a light green crystal.

(2) Synthesis of 6-(1H-indol-5-yl)hex-5-ene-2,4-dione

In a 300 mL pear-shaped evaporating flask equipped with a cooling tube were placed 15.5 mL of ethyl acetate, 15.9 mL (155 mmol) of 2,4-pentanedione, and 3.24 g (46.5 mmol) of boron oxide. To the mixture under stirring at 70° C., 4.50 g (31.0 mmol) of 1H-indole-5-carboxaldehyde and a solution of 7.2 mL (31 mmol) of triisopropyl borate in ethyl acetate (31 mL) were added dropwise. The mixture was stirred at 70° C. for 30 minutes and a solution of 3.68 mL (37.2 mmol) of n-butylamine in ethyl acetate (9.3 mL) was added dropwise. After being stirred at 85° C. for 1 hour, the mixture was cooled down to 50° C., and 3 N hydrochloric acid (22 mL) was added thereto. The mixture was stirred at the same temperature for 10 minutes and neutralized with a saturated sodium bicarbonate solution. The resulting solution was diluted with ethyl acetate, washed twice with saturated brine, and dried over magnesium sulfate. After filtration, the solvent was evaporated under reduced pressure. The residue was purified by silica gel column chromatography (hexane/ethyl acetate=90/10 to 70/30) and crystallization (ethyl acetate/hexane) to give 3.46 g (49% yield) of the title compound as a yellow powder with the following properties.

$^1$H NMR (δ, acetone-$d_6$): 2.11 (s, 3H), 5.81 (s, 1H), 6.53 (d, J=3.1 Hz, 1H), 6.63 (d, J=16 Hz, 1H), 7.38 (m, 1H), 7.47 (m, 2H), 7.73 (d, J=16 Hz, 1H), 7.87 (s, 1H), 10.49 (br s, NH). melting point 136-137° C.

(3) Synthesis of (1E,6E)-1-(1H-indol-5-yl)-7-[4-(2-pyridylmethoxy)phenyl]hepta-1,6-diene-3,5-dione In a 20 mL reaction vessel were placed 31.0 mg (136 μmol) of 6-(1H-indol-5-yl)hex-5-ene-2,4-dione and 13.2 mg (0.190 mmol) of boron oxide and they were dissolved in 0.88 mL of ethyl acetate. To the mixture under stirring at 70° C., 29 mg (0.14 mmol) of 4-(2-pyridylmethoxy)benzaldehyde and 62 μL (0.27 mmol) of triisopropyl borate were sequentially added. After the mixture was stirred at the same temperature for 1 hour, a solution of 2.7 μL (27 μmol) of piperidine in ethyl acetate (0.135 mL) was added and the mixture was further stirred for 1 hour. To the reaction mixture was added a 1:1 solution (0.4 mL) of 1 N hydrochloric acid and saturated brine at room temperature and the mixture was stirred for 5 minutes to 1 hour (further, the mixture was neutralized with a saturated sodium bicarbonate aqueous solution as needed). The resulting organic phase was directly subjected to purification by silica gel column chromatography (hexane/ethyl acetate or methylene chloride/methanol) to give 37.1 mg (65% yield) of the title compound as a yellow powder.

(4) Synthesis of 3-[(1E)-2-(1H-indol-5-yl)ethenyl]-5-[(1E)-2-[4-(2-pyridylmethoxy)phenyl]ethenyl]-1H-pyrazole In 0.34 mL of acetic acid was dissolved 15 mg (35 μmol) of (1E,6E)-1-(1H-indol-5-yl)-7-[4-(2-pyridylmethoxy)phenyl]hepta-1,6-diene-3,5-dione. To this solution was added 34 μL (0.70 mmol) of hydrazine monohydrate at room temperature and the mixture was stirred at 60° C. for 3 hours. The reaction mixture was neutralized with a saturated sodium bicarbonate aqueous solution and extraction with ethyl acetate was performed. The resulting organic layer was washed with saturated brine and dried over magnesium sulfate. After filtration, the solvent was evaporated under reduced pressure. The residue was purified by silica gel column chromatography (hexane/ethyl acetate or methylene chloride/methanol). The resulting solid was washed with an organic solvent to give 3.5 mg (24% yield) of the title compound as a pale yellowish white powder with the following properties.

$^1$H NMR (δ, acetone-$d_6$): 5.22 (s, 2H), 6.48 (d, J=3.1 Hz, 1H), 6.70 (s, 1H), 7.03 (d, J=17 Hz, 1H), 7.04 (d, J=8.8 Hz, 2H), 7.05 (d, J=17 Hz, 1H), 7.16 (d, J=17 Hz, 1H), 7.30 (d, J=17 Hz, 1H), 7.26-7.35 (m, 2H), 7.41 (dd, J=1.5, 8.7 Hz, 1H), 7.43 (d, J=8.7 Hz, 1H), 7.52 (d, J=8.8 Hz, 2H), 7.55 (br d, J=7.7 Hz, 1H), 7.72 (br s, 1H), 7.82 (dt, J=1.8, 7.7 Hz, 1H), 8.58 (br d, J=5 Hz, 1H), 10.3 (br s, NH). melting point 95-102° C., MS (ESI+) m/z 419.4 (M+1).

Example 5

Synthesis of 3-[(1E)-2-(1H-indol-5-yl)ethenyl]-5-[(1E)-2-[3-methoxy-4-(2-pyridylmethoxy)phenyl]ethenyl]-1H-pyrazole

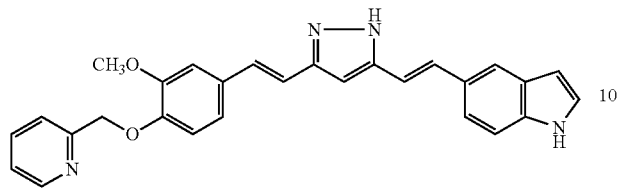

(1) Synthesis of 3-methoxy-4-(2-pyridylmethoxy)benzaldehyde

Synthesis was performed in the same manner as in Example 4 (1) except that 761 mg (5.00 mmol) of 4-hydroxy-3-methoxybenzaldehyde was used instead of 611 mg (5.00 mmol) of 4-hydroxybenzaldehyde to give 1.016 g (84% yield) of the title compound as a light green crystal.

(2) Synthesis of (1E,6E)-1-(1H-indol-5-yl)-7-[3-methoxy-4-(2-pyridylmethoxy) phenyl]hepta-1,6-diene-3,5-dione Synthesis was performed in the same manner as in Example 4 (3) except that 33 mg (0.14 mmol) of 3-methoxy-4-(2-pyridylmethoxy)benzaldehyde was used instead of 29 mg (0.14 mmol) of 4-(2-pyridylmethoxy)benzaldehyde to give 42.3 mg (69% yield) of the title compound as an orange powder.

(3) Synthesis of 3-[(1E)-2-(1H-indol-5-yl)ethenyl]-5-[(1E)-2-[3-methoxy-4-(2-pyridylmethoxy)phenyl]ethenyl]-1H-pyrazole Synthesis was performed in the same manner as in Example 4 (4) except that 15 mg (33 μmol) of (1E,6E)-1-(1H-indol-5-yl)-7-[3-methoxy-4-(2-pyridylmethoxy) phenyl]hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 5.0 mg (34% yield) of the title compound as a yellowish white powder with the following properties.
$^1$H NMR (δ, acetone-$d_6$): 3.93 (s, 3H), 5.20 (s, 2H), 6.48 (d, J=3.2 Hz, 1H), 6.70 (s, 1H), 6.99-7.09 (m, 4H), 7.15 (d, J=17 Hz, 1H), 7.25-7.36 (m, 4H), 7.40 (dd, J=1.4, 8.5 Hz, 1H), 7.43 (d, J=8.5 Hz, 1H), 7.60 (br d, J=7.7 Hz, 1H), 7.71 (br s, 1H), 7.82 (dt, J=1.8, 7.7 Hz, 1H), 8.57 (br d, J=5 Hz, 1H), 10.3 (br s, NH). melting point 96-101° C., MS (ESI+) m/z 449.4 (M+1).

Example 6

Synthesis of 3-[(1E)-2-(1H-indol-5-yl)ethenyl]-5-[(1E)-2-[4-methoxy-3-(2-pyridylmethoxy)phenyl]ethenyl]-1H-pyrazole

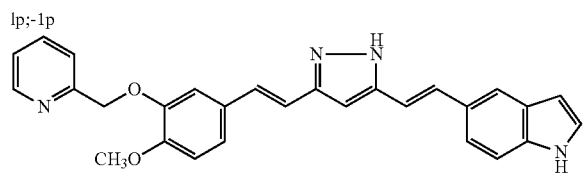

(1) Synthesis of 4-methoxy-3-(2-pyridylmethoxy)benzaldehyde

Synthesis was performed in the same manner as in Example 4 (1) except that 761 mg (5.00 mmol) of 3-hydroxy-4-methoxybenzaldehyde was used instead of 611 mg (5.00 mmol) of 4-hydroxybenzaldehyde to give 989 mg (81% yield) of the title compound as a light green crystal.

(2) Synthesis of (1E,6E)-1-(1H-indol-5-yl)-7-[4-methoxy-3-(2-pyridylmethoxy) phenyl]hepta-1,6-diene-3,5-dione Synthesis was performed in the same manner as in Example 4 (3) except that 33 mg (0.14 mmol) of 4-methoxy-3-(2-pyridylmethoxy)benzaldehyde was used instead of 29 mg (0.14 mmol) of 4-(2-pyridylmethoxy)benzaldehyde to give 38.9 mg (63% yield) of the title compound as a yellow powder.

(3) Synthesis of 3-[(1E)-2-(1H-indol-5-yl)ethenyl]-5-[(1E)-2-[4-methoxy-3-(2-pyridylmethoxy)phenyl]ethenyl]-1H-pyrazole Synthesis was performed in the same manner as in Example 4 (4) except that 15 mg (33 μmol) of (1E,6E)-1-(1H-indol-5-yl)-7-[4-methoxy-3-(2-pyridylmethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 3.8 mg (26% yield) of the title compound as a pale yellowish white powder with the following properties.
$^1$H NMR (δ, acetone-$d_6$): 3.87 (s, 3H), 5.26 (s, 2H), 6.49 (d, J=2.9 Hz, 1H), 6.75 (s, 1H), 7.00 (d, J=8.3 Hz, 1H), 7.02 (d, J=17 Hz, 1H), 7.05 (d, J=17 Hz, 1H), 7.11 (dd, J=2.0, 8 Hz, 1H), 7.13 (d, J=17 Hz, 1H), 7.30 (d, J=17 Hz, 1H), 7.27-7.36 (m, 3H), 7.41 (dd, J=1.4, 8.3 Hz, 1H), 7.43 (d, J=8.3 Hz, 1H), 7.64 (br d, J=7.9 Hz, 1H), 7.71 (br s, 1H), 7.83 (dt, J=1.8, 7.7 Hz, 1H), 8.59 (br d, J=5 Hz, 1H), 10.3 (br s, NH). melting point 109-118° C., MS (ESI+) m/z 449.3 (M+1).

Example 7

Synthesis of 3-[(1E)-2-(1H-indol-5-yl)ethenyl]-5-[(1E)-2-[3-(2-pyridylmethoxy)phenyl]ethenyl]-1H-pyrazole

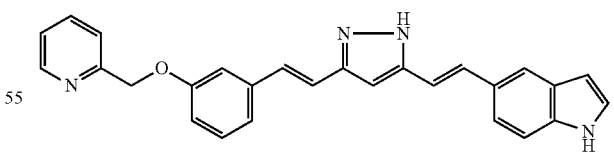

(1) Synthesis of 3-(2-pyridylmethoxy)benzaldehyde

Synthesis was performed in the same manner as in Example 4 (1) except that 611 mg (5.00 mmol) of 3-hydroxybenzaldehyde was used instead of 611 mg (5.00 mmol) of 4-hydroxybenzaldehyde to give 772 mg (72% yield) of the title compound as a white powder.

(2) Synthesis of (1E,6E)-1-(1H-indol-5-yl)-7-[3-(2-pyridylmethoxy)phenyl]hepta-1,6-diene-3,5-dione Synthesis was performed in the same manner as in Example 4 (3) except that 29 mg (0.14 mmol) of 3-(2-pyridylmethoxy)benzaldehyde was used instead of 29 mg (0.14 mmol) of 4-(2-pyridylmethoxy)benzaldehyde to give 24.9 mg (43% yield) of the title compound as an orange powder.

(3) Synthesis of 3-[(1E)-2-(1H-indol-5-yl)ethenyl]-5-[(1E)-2-[3-(2-pyridylmethoxy)phenyl]ethenyl]-1H-pyrazole Synthesis was performed in the same manner as in Example 4 (4) except that 15 mg (35 μmol) of (1E,6E)-1-(1H-indol-5-yl)-7-[3-(2-pyridylmethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 9.4 mg (63% yield) of the title compound as a pale yellowish white powder with the following properties.
$^1$H NMR (δ, acetone-$d_6$): 5.25 (s, 2H), 6.49 (d, J=2.9 Hz, 1H), 6.75 (s, 1H), 6.95 (ddd, J=1, 2.5, 8.1 Hz, 1H), 7.07 (d, J=17 Hz, 1H), 7.17 (br d, J=8 Hz, 1H), 7.18 (m, 2H), 7.25-7.36 (m, 5H), 7.41 (dd, J=1.5, 8.5 Hz, 1H), 7.43 (d, J=8.5 Hz, 1H), 7.58 (br d, J=7.9 Hz, 1H), 7.72 (br s, 1H), 7.82 (dt, J=1.8, 7.7 Hz, 1H), 8.59 (br d, J=5 Hz, 1H), 10.3 (br s, NH). melting point 183-186° C., MS (ESI+) m/z 419.3 (M+1).

Example 8

Synthesis of 3-[(1E)-2-(1H-indol-5-yl)ethenyl]-5-[(1E)-2-[2-(2-pyridylmethoxy)phenyl]ethenyl]-1H-pyrazole

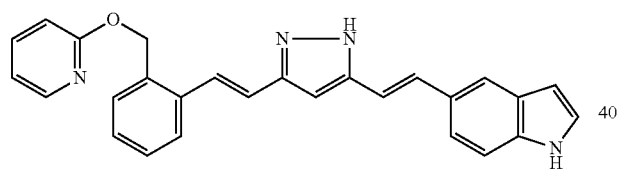

(1) Synthesis of 2-(2-pyridylmethoxy)benzaldehyde

Synthesis was performed in the same manner as in Example 4 (1) except that 611 mg (5.00 mmol) of 2-hydroxybenzaldehyde was used instead of 611 mg (5.00 mmol) of 4-hydroxybenzaldehyde to give 882 mg (83% yield) of the title compound as a pale brown powder.

(2) Synthesis of (1E,6E)-1-(1H-indol-5-yl)-7-[2-(2-pyridylmethoxy)phenyl]hepta-1,6-diene-3,5-dione Synthesis was performed in the same manner as in Example 4 (3) except that 29 mg (0.14 mmol) of 2-(2-pyridylmethoxy)benzaldehyde was used instead of 29 mg (0.14 mmol) of 4-(2-pyridylmethoxy)benzaldehyde to give 36.3 mg (63% yield) of the title compound as an orange powder.

(3) Synthesis of 3-[(1E)-2-(1H-indol-5-yl)ethenyl]-5-[(1E)-2-[2-(2-pyridylmethoxy)phenyl]ethenyl]-1H-pyrazole Synthesis was performed in the same manner as in Example 4 (4) except that 15 mg (35 μmol) of (1E,6E)-1-(1H-indol-5-yl)-7-[2-(2-pyridylmethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 9.9 mg (67% yield) of the title compound as a yellowish white powder with the following properties.
$^1$H NMR (δ, DMSO-$d_6$): 5.30 (s, 2H), 6.44 (br s, 1H), 6.69 (s, 1H), 6.9-7.4 (m, 10H), 7.49 (d, J=17 Hz, 1H), 7.58 (br d, J=7.9 Hz, 1H), 7.64 (br d, J=8 Hz, 1H), 7.66 (br s, 1H), 7.88 (br t, J=7.7 Hz, 1H), 8.60 (br d, J=5 Hz, 1H), 11.2 (br s, NH). melting point 220-223° C., MS (ESI+) m/z 419.3 (M+1).

Example 9

Synthesis of 3-[(1E)-2-(1H-indol-5-yl)ethenyl]-5-[(1E)-2-[2-methoxy-5-(2-pyridylmethoxy)phenyl]ethenyl]-1H-pyrazole

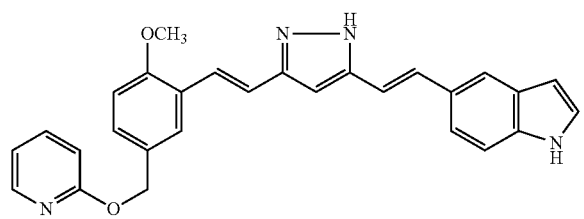 [SMILES: COc1ccc(COc2ccccn2)cc1/C=C/c1cc(/C=C/c2ccc3[nH]ccc3c2)[nH]n1]

(1) Synthesis of 2-methoxy-5-(2-pyridylmethoxy)benzaldehyde

Synthesis was performed in the same manner as in Example 4 (1) except that 761 mg (5.00 mmol) of 5-hydroxy-2-methoxybenzaldehyde was used instead of 611 mg (5.00 mmol) of 4-hydroxybenzaldehyde to give 1.018 g (84% yield) of the title compound as a white amorphous solid.

(2) Synthesis of (1E,6E)-1-(1H-indol-5-yl)-7-[2-methoxy-5-(2-pyridylmethoxy) phenyl]hepta-1,6-diene-3,5-dione Synthesis was performed in the same manner as in Example 4 (3) except that 33 mg (0.14 mmol) of 2-methoxy-5-(2-pyridylmethoxy)benzaldehyde was used instead of 29 mg (0.14 mmol) of 4-(2-pyridylmethoxy)benzaldehyde to give 30.6 mg (50% yield) of the title compound as an orange powder.

(3) Synthesis of 3-[(1E)-2-(1H-indol-5-yl)ethenyl]-5-[(1E)-2-[2-methoxy-5-(2-pyridylmethoxy)phenyl]ethenyl]-1H-pyrazole Synthesis was performed in the same manner as in Example 4 (4) except that 15 mg (33 μmol) of (1E,6E)-1-(1H-indol-5-yl)-7-[2-methoxy-5-(2-pyridylmethoxy) phenyl]hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 9.2 mg (62% yield) of the title compound as a pale yellowish white powder with the following properties.
$^1$H NMR (δ, acetone-$d_6$): 3.85 (s, 3H), 5.20 (s, 2H), 6.49 (d, J=3.1 Hz, 1H), 6.73 (s, 1H), 6.94 (dd, J=2.6, 9.0 Hz, 1H), 6.96 (d, J=9.0 Hz, 1H), 7.06 (d, J=17 Hz, 1H), 7.19 (d, J=17 Hz, 1H), 7.33 (d, J=17 Hz, 1H), 7.26-7.36 (m, 3H), 7.41 (dd, J=1.5, 8.5 Hz, 1H), 7.43 (d, J=8.5 Hz, 1H), 7.45 (d, J=17 Hz, 1H), 7.58 (br d, J=7.7 Hz, 1H), 7.73 (br s, 1H), 7.81 (dt, J=1.8, 7.7 Hz, 1H), 8.58 (br d, J=5 Hz, 1H), 10.3 (br s, NH). melting point 116-122° C., MS (ESI+) m/z 449.3 (M+1).

Example 10

Synthesis of 3-[(1E)-2-(1H-indol-3-yl)ethenyl]-5-[(1E)-2-[4-(2-pyridylmethoxy)phenyl]ethenyl]-1H-pyrazole

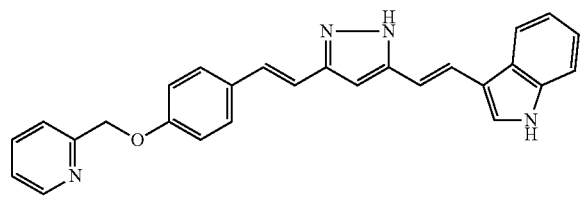 [SMILES: C(=C\c1cc(/C=C/c2c[nH]c3ccccc23)[nH]n1)/c1ccc(OCc2ccccn2)cc1]

(1) Synthesis of 6-(1H-indol-3-yl)hex-5-ene-2,4-dione

Synthesis was performed in the same manner as in Example 4 (2) except that 4.50 g (31.0 mmol) of 1H-indole-3-carboxaldehyde was used instead of 4.50 g (31.0 mmol) of 1H-indole-5-carboxaldehyde to give 2.14 g (30% yield) of the title compound as a yellow powder.
$^1$H NMR (δ, acetone-$d_6$): 2.08 (s, 3H), 5.81 (s, 1H), 6.66 (d, J=16 Hz, 1H), 7.1-7.3 (m, 2H), 7.51 (m, 1H), 7.85 (s, 1H), 7.89 (d, J=16 Hz, 1H), 8.00 (m, 1H). melting point 155-158° C.

(2) Synthesis of (1E,6E)-1-(1H-indol-3-yl)-7-[4-(2-pyridylmethoxy)phenyl]hepta-1,6-diene-3,5-dione In a 20 mL reaction vessel were placed 31.0 mg (136 μmol) of 6-(1H-indol-3-yl)hex-5-ene-2,4-dione and 13.2 mg (0.190 mmol) of boron oxide and they were dissolved in 0.88 mL of ethyl acetate. To the mixture under stirring at 70° C., 29 mg (0.14 mmol) of 4-(2-pyridylmethoxy)benzaldehyde and 62 μL (0.27 mmol) of triisopropyl borate were sequentially added. After the mixture was stirred at the same temperature for 1 hour, a solution of 2.7 μL (27 μmol) of piperidine in ethyl acetate (0.135 mL) was added and the mixture was further stirred for 1 hour. To the reaction mixture was added a 1:1 solution (0.4 mL) of 1 N hydrochloric acid and saturated brine at room temperature and the mixture was stirred for 5 minutes to 1 hour (further, the mixture was neutralized with a saturated sodium bicarbonate aqueous solution as needed). The resulting organic phase was directly subjected to purification by silica gel column chromatography (hexane/ethyl acetate or methylene chloride/methanol) to give 25.7 mg (45% yield) of the title compound as an orange powder.

(3) Synthesis of 3-[(1E)-2-(1H-indol-3-yl)ethenyl]-5-[(1E)-2-[4-(2-pyridylmethoxy)phenyl]ethenyl]-1H-pyrazole Synthesis was performed in the same manner as in Example 4 (4) except that 15 mg (35 μmol) of (1E,6E)-1-(1H-indol-3-yl)-7-[4-(2-pyridylmethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 5.8 mg (39% yield) of the title compound as a yellowish white powder with the following properties.
$^1$H NMR (δ, acetone-$d_6$): 5.21 (s, 2H), 6.46 (dd, J=1, 3.0 Hz, 1H), 6.69 (s, 1H), 7.02 (d, J=17 Hz, 1H), 7.05 (d, J=8.8 Hz, 2H), 7.09 (d, J=17 Hz, 1H), 7.15 (d, J=17 Hz, 1H), 7.1-7.2 (m, 2H), 7.32 (m, 1H), 7.43 (d, J=17 Hz, 1H), 7.46 (m, 1H), 7.52 (d, J=8.8 Hz, 2H), 7.53-7.60 (m, 2H), 7.82 (dt, J=1.8, 7.7 Hz, 1H), 7.96 (m, 1H), 8.58 (br d, J=5 Hz, 1H), 10.5 (br s, NH). melting point 196-199° C., MS (ESI+) m/z 419.3 (M+1).

Example 11

Synthesis of 3-[(1E)-2-(1H-indol-3-yl)ethenyl]-5-[(1E)-2-[3-methoxy-4-(2-pyridylmethoxy)phenyl]ethenyl]-1H-pyrazole

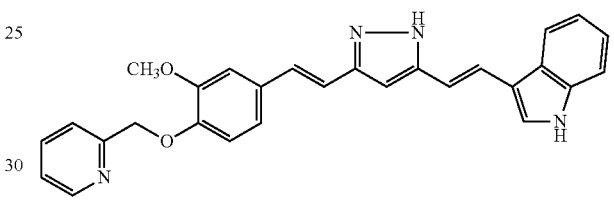

(1) Synthesis of (1E,6E)-1-(1H-indol-3-yl)-7-[3-methoxy-4-(2-pyridylmethoxy) phenyl]hepta-1,6-diene-3,5-dione Synthesis was performed in the same manner as in Example 10 (2) except that 33 mg (0.14 mmol) of 3-methoxy-4-(2-pyridylmethoxy)benzaldehyde was used instead of 29 mg (0.14 mmol) of 4-(2-pyridylmethoxy)benzaldehyde to give 29.2 mg (47% yield) of the title compound as an orange powder.

(2) Synthesis of 3-[(1E)-2-(1H-indol-3-yl)ethenyl]-5-[(1E)-2-[3-methoxy-4-(2-pyridylmethoxy)phenyl]ethenyl]-1H-pyrazole Synthesis was performed in the same manner as in Example 4 (4) except that 15 mg (33 μmol) of (1E,6E)-1-(1H-indol-3-yl)-7-[3-methoxy-4-(2-pyridylmethoxy) phenyl]hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 8.4 mg (57% yield) of the title compound as a pale yellowish white powder with the following properties.
$^1$H NMR (δ, acetone-$d_6$): 3.93 (s, 3H), 5.20 (s, 2H), 6.69 (s, 1H), 7.0-7.13 (m, 5H), 7.1-7.2 (m, 2H), 7.27 (d, J=2 Hz, 1H), 7.30 (m, 1H), 7.43 (d, J=17 Hz, 1H), 7.47 (m, 1H), 7.60 (s, 1H), 7.61 (d, J=7 Hz, 1H), 7.82 (dt, J=1.7, 7.7 Hz, 1H), 7.96 (m, 1H), 8.56 (br d, J=5 Hz, 1H), 10.5 (br s, NH). melting point 120-130° C., MS (ESI+) m/z 449.3 (M+1).

Example 12

Synthesis of 3-[(1E)-2-(1H-indol-3-yl)ethenyl]-5-[(1E)-2-[4-methoxy-3-(2-pyridylmethoxy)phenyl]ethenyl]-1H-pyrazole

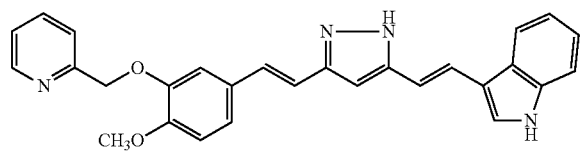

(1) Synthesis of (1E,6E)-1-(1H-indol-3-yl)-7-[4-methoxy-3-(2-pyridylmethoxy) phenyl]hepta-1,6-diene-3,5-dione Synthesis was performed in the same manner as in Example 10 (2) except that 33 mg (0.14 mmol) of 4-methoxy-3-(2-pyridylmethoxy)benzaldehyde was used instead of 29 mg (0.14 mmol) of 4-(2-pyridylmethoxy)benzaldehyde to give 26.3 mg (43% yield) of the title compound as a yellow powder.

(2) Synthesis of 3-[(1E)-2-(1H-indol-3-yl)ethenyl]-5-[(1E)-2-[4-methoxy-3-(2-pyridylmethoxy)phenyl]ethenyl]-1H-pyrazole Synthesis was performed in the same manner as in Example 4 (4) except that 15 mg (33 µmol) of (1E,6E)-1-(1H-indol-3-yl)-7-[4-methoxy-3-(2-pyridylmethoxy) phenyl]hepta-1,6-diene-3,5-dione was used instead of 15 mg (35 µmol) of (1E,6E)-1-(1H-indol-5-yl)-7-[4-(2-pyridylmethoxy) phenyl]hepta-1,6-diene-3,5-dione to give 5.9 mg (40% yield) of the title compound as a pale yellowish white powder with the following properties.

$^1$H NMR (δ, DMSO-d$_6$): 3.80 (s, 3H), 5.23 (s, 2H), 6.64 (s, 1H), 6.94 (d, J=17 Hz, 1H), 6.9-7.2 (m, 6H), 7.30 (br s, 1H), 7.32 (d, J=17 Hz, 1H), 7.35 (m, 1H), 7.42 (br d, J=7.4 Hz, 1H), 7.56 (br d, J=7.6 Hz, 1H), 7.63 (br s, 1H), 7.88 (br t, J=7.7 Hz, 1H), 7.87 (br d, J=8 Hz, 1H), 8.59 (br d, J=5 Hz, 1H), 11.4 (br s, NH). melting point 232-243° C., MS (ESI+) m/z 449.3 (M+1).

Example 13

Synthesis of 3-[(1E)-2-(1H-indol-3-yl)ethenyl]-5-[(1E)-2-[3-(2-pyridylmethoxy)phenyl]ethenyl]-1H-pyrazole

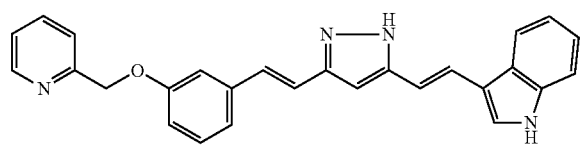 [SMILES: C(=C\c1cc(/C=C/c2c[nH]c3ccccc23)[nH]n1)/c1cccc(OCc2ccccn2)c1]

(1) Synthesis of (1E,6E)-1-(1H-indol-3-yl)-7-[3-(2-pyridylmethoxy)phenyl]hepta-1,6-diene-3,5-dione Synthesis was performed in the same manner as in Example 10 (2) except that 29 mg (0.14 mmol) of 3-(2-pyridylmethoxy)benzaldehyde was used instead of 29 mg (0.14 mmol) of 4-(2-pyridylmethoxy)benzaldehyde to give 15.7 mg (27% yield) of the title compound as an orange powder.

(2) Synthesis of 3-[(1E)-2-(1H-indol-3-yl)ethenyl]-5-[(1E)-2-[3-(2-pyridylmethoxy)phenyl]ethenyl]-1H-pyrazole Synthesis was performed in the same manner as in Example 4 (4) except that 15 mg (35 µmol) of (1E,6E)-1-(1H-indol-3-yl)-7-[3-(2-pyridylmethoxy)phenyl]hepta-1,6-diene-3,5-dione was used instead of 15 mg (35 µmol) of (1E,6E)-1-(1H-indol-5-yl)-7-[4-(2-pyridylmethoxy)phenyl]hepta-1,6-diene-3,5-dione to give 5.7 mg (38% yield) of the title compound as a pale yellowish white powder with the following properties.

$^1$H NMR (δ, acetone-d$_6$): 5.25 (s, 2H), 6.73 (s, 1H), 6.94 (ddd, J=1, 2.6, 8.2 Hz, 1H), 7.10 (d, J=17 Hz, 1H), 7.11-7.21 (m, 5H), 7.25-7.30 (m, 2H), 7.33 (m, 1H), 7.44 (d, J=17 Hz, 1H), 7.46 (m, 1H), 7.56-7.62 (m, 2H), 7.82 (dt, J=1.8, 7.7 Hz, 1H), 7.96 (m, 1H), 8.59 (br d, J=5 Hz, 1H), 10.5 (br s, NH). melting point 198-201° C., MS (ESI+) m/z 419.4 (M+1).

Example 14

Synthesis of 3-[(1E)-2-(1H-indol-3-yl)ethenyl]-5-[(1E)-2-[2-(2-pyridylmethoxy)phenyl]ethenyl]-1H-pyrazole

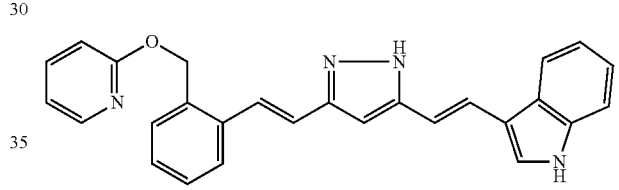

(1) Synthesis of (1E,6E)-1-(1H-indol-3-yl)-7-[2-(2-pyridylmethoxy)phenyl]hepta-1,6-diene-3,5-dione Synthesis was performed in the same manner as in Example 10 (2) except that 29 mg (0.14 mmol) of 2-(2-pyridylmethoxy)benzaldehyde was used instead of 29 mg (0.14 mmol) of 4-(2-pyridylmethoxy)benzaldehyde to give 34.6 mg (60% yield) of the title compound as an orange powder.

(2) Synthesis of 3-[(1E)-2-(1H-indol-3-yl)ethenyl]-5-[(1E)-2-[2-(2-pyridylmethoxy)phenyl]ethenyl]-1H-pyrazole Synthesis was performed in the same manner as in Example 4 (4) except that 15 mg (35 µmol) of (1E,6E)-1-(1H-indol-3-yl)-7-[2-(2-pyridylmethoxy)phenyl]hepta-1,6-diene-3,5-dione was used instead of 15 mg (35 µmol) of (1E,6E)-1-(1H-indol-5-yl)-7-[4-(2-pyridylmethoxy)phenyl]hepta-1,6-diene-3,5-dione to give 7.8 mg (53% yield) of the title compound as a pale yellowish white powder with the following properties.

$^1$H NMR (δ, acetone-d$_6$): 5.31 (s, 2H), 6.71 (s, 1H), 6.99 (dd, J=7, 7 Hz, 1H), 7.08 (d, J=7.5 Hz, 1H), 7.10 (d, J=17 Hz, 1H), 7.1-7.2 (m, 2H), 7.23 (d, J=17 Hz, 1H), 7.25 (m, 1H), 7.32 (m, 1H), 7.44 (d, J=17 Hz, 1H), 7.46 (m, 1H), 7.57-7.65 (m, 3H), 7.67 (dd, J=1.4, 7.8 Hz, 1H), 7.85 (dt, J=1.8, 7.7 Hz, 1H), 7.97 (m, 1H), 8.60 (br d, J=5 Hz, 1H), 10.5 (br s, NH). melting point 114-125° C., MS (ESI+) m/z 419.4 (M+1).

Example 15

Synthesis of 3-[(1E)-2-(1H-indol-3-yl)ethenyl]-5-[(1E)-2-[2-methoxy-5-(2-pyridylmethoxy)phenyl]ethenyl]-1H-pyrazole

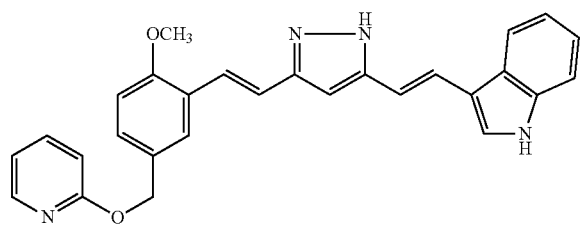 [SMILES: COc1ccc(COc2ccccn2)cc1/C=C/c1cc(/C=C/c2c[nH]c3ccccc23)[nH]n1]

(1) Synthesis of (1E,6E)-1-(1H-indol-3-yl)-7-[2-methoxy-5-(2-pyridylmethoxy) phenyl]hepta-1,6-diene-3,5-dione Synthesis was performed in the same manner as in Example 10 (2) except that 33 mg (0.14 mmol) of 2-methoxy-5-(2-pyridylmethoxy)benzaldehyde was used instead of 29 mg (0.14 mmol) of 4-(2-pyridylmethoxy)benzaldehyde to give 38.0 mg (62% yield) of the title compound as an orange powder.

(2) Synthesis of 3-[(1E)-2-(1H-indol-3-yl)ethenyl]-5-[(1E)-2-[2-methoxy-5-(2-pyridylmethoxy)phenyl]ethenyl]-1H-pyrazole Synthesis was performed in the same manner as in Example 4 (4) except that 15 mg (33 µmol) of (1E,6E)-1-(1H-indol-3-yl)-7-[2-methoxy-5-(2-pyridylmethoxy) phenyl]hepta-1,6-diene-3,5-dione was used instead of 15 mg (35 µmol) of (1E,6E)-1-(1H-indol-5-yl)-7-[4-(2-pyridylmethoxy) phenyl]hepta-1,6-diene-3,5-dione to give 7.3 mg (49% yield) of the title compound as a pale yellowish white powder with the following properties.

$^1$H NMR (δ, acetone-$d_6$): 3.85 (s, 3H), 5.20 (s, 2H), 6.71 (s, 1H), 6.93 (dd, J=2.6, 8.9 Hz, 1H), 6.96 (d, J=8.9 Hz, 1H), 7.10 (d, J=17 Hz, 1H), 7.1-7.2 (m, 2H), 7.19 (d, J=17 Hz, 1H), 7.31 (m, 1H), 7.34 (d, J=2.6 Hz, 1H), 7.44 (d, J=17 Hz, 1H), 7.46 (d, J=17 Hz, 1H), 7.46 (m, 1H), 7.56-7.62 (m, 2H), 7.82 (dt, J=1.8, 7.7 Hz, 1H), 7.97 (m, 1H), 8.58 (br d, J=5 Hz, 1H), 10.5 (br s, NH). melting point 233-238° C., MS (ESI+) m/z 449.3 (M+1).

Example 16

Synthesis of 3-[(1E)-2-(1H-indol-6-yl)ethenyl]-5-[(1E)-2-[4-(2-pyridylmethoxy)phenyl]ethenyl]-1H-pyrazole

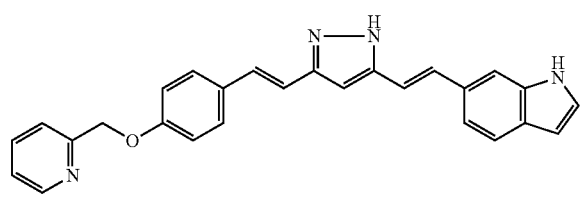 [SMILES: C(=C\c1cc(/C=C/c2ccc3cc[nH]c3c2)[nH]n1)/c1ccc(OCc2ccccn2)cc1]

(1) Synthesis of (1E,6E)-1-(1H-indol-6-yl)-7-[4-(2-pyridylmethoxy)phenyl]hepta-1,6-diene-3,5-dione In a 20 mL reaction vessel were placed 31.0 mg (136 µmol) of 6-(1H-indol-6-yl)hex-5-ene-2,4-dione and 13.2 mg (0.190 mmol) of boron oxide and they were dissolved in 0.88 mL of ethyl acetate. To the mixture under stirring at 70° C., 29 mg (0.14 mmol) of 4-(2-pyridylmethoxy)benzaldehyde and 62 µL (0.27 mmol) of triisopropyl borate were sequentially added. After the mixture was stirred at the same temperature for 1 hour, a solution of 2.7 µL (27 µmol) of piperidine in ethyl acetate (0.135 mL) was added and the mixture was further stirred for 1 hour. To the reaction mixture was added a 1:1 solution (0.4 mL) of 1 N hydrochloric acid and saturated brine at room temperature and the mixture was stirred for 5 minutes to 1 hour (further, the mixture was neutralized with a saturated sodium bicarbonate aqueous solution as needed). The resulting organic phase was directly subjected to purification by silica gel column chromatography (hexane/ethyl acetate or methylene chloride/methanol) to give 41.3 mg (72% yield) of the title compound as a yellow powder.

(2) Synthesis of 3-[(1E)-2-(1H-indol-6-yl)ethenyl]-5-[(1E)-2-[4-(2-pyridylmethoxy)phenyl]ethenyl]-1H-pyrazole Synthesis was performed in the same manner as in Example (4) except that 15 mg (35 µmol) of (1E,6E)-1-(1H-indol-6-yl)-7-[4-(2-pyridylmethoxy)phenyl]hepta-1,6-diene-3,5-dione was used instead of 15 mg (35 µmol) of (1E,6E)-1-(1H-indol-5-yl)-7-[4-(2-pyridylmethoxy)phenyl]hepta-1,6-diene-3,5-dione to give 5.2 mg (35% yield) of the title compound as a pale yellowish white powder with the following properties.

$^1$H NMR (δ, acetone-$d_6$): 5.21 (s, 2H), 6.46 (dd, J=1, 3.0 Hz, 1H), 6.71 (s, 1H), 7.03 (d, J=17 Hz, 1H), 7.05 (d, J=8.8 Hz, 2H), 7.09 (d, J=17 Hz, 1H), 7.16 (d, J=17 Hz, 1H), 7.26-7.36 (m, 4H), 7.52 (d, J=8.8 Hz, 2H), 7.53-7.6 (m, 3H), 7.82 (dt, J=1.8, 7.7 Hz, 1H), 8.58 (br d, J=5 Hz, 1H), 10.3 (br s, NH). melting point 211-214° C., MS (ESI+) m/z 419.3 (M+1).

Example 17

Synthesis of 3-[(1E)-2-(1H-indol-6-yl)ethenyl]-5-[(1E)-2-[3-methoxy-4-(2-pyridylmethoxy)phenyl]ethenyl]-1H-pyrazole

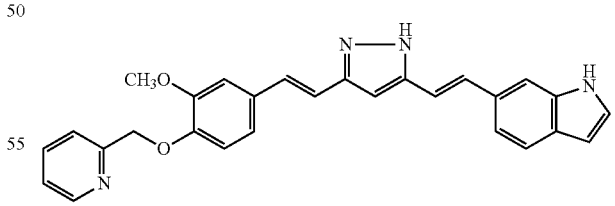

(1) Synthesis of (1E,6E)-1-(1H-indol-6-yl)-7-[3-methoxy-4-(2-pyridylmethoxy) phenyl]hepta-1,6-diene-3,5-dione Synthesis was performed in the same manner as in Example 16 (1) except that 33 mg (0.14 mmol) of 3-methoxy-4-(2-pyridylmethoxy)benzaldehyde was used instead of 29 mg (0.14 mmol) of 4-(2-pyridylmethoxy)benzaldehyde to give 29.7 mg (48% yield) of the title compound as an orange powder.

(2) Synthesis of 3-[(1E)-2-(1H-indol-6-yl)ethenyl]-5-[(1E)-2-[3-methoxy-4-(2-pyridylmethoxy)phenyl]ethenyl]-1H-pyrazole Synthesis was performed in the same manner as in Example 4 (4) except that 15 mg (33 μmol) of (1E,6E)-1-(1H-indol-6-yl)-7-[3-methoxy-4-(2-pyridylmethoxy) phenyl] hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 9.3 mg (63% yield) of the title compound as a pale yellowish white powder with the following properties.

$^1$H NMR (δ, DMSO-$d_6$): 3.86 (s, 3H), 5.17 (s, 2H), 6.41 (br s, 1H), 6.70 (s, 1H), 6.94-7.1 (m, 5H), 7.17-7.30 (m, 3H), 7.31-7.38 (m, 2H), 7.47-7.55 (m, 3H), 7.84 (br d, J=8 Hz, 1H), 8.57 (br d, J=4 Hz, 1H), 11.2 (br s, NH). melting point 236-243° C., MS (ESI+) m/z 449.3 (M+1).

Example 18

Synthesis of 3-[(1E)-2-(1H-indol-6-yl)ethenyl]-5-[(1E)-2-[4-methoxy-3-(2-pyridylmethoxy)phenyl]ethenyl]-1H-pyrazole

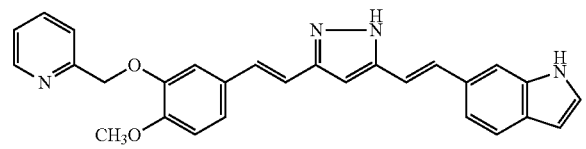

(1) Synthesis of (1E,6E)-1-(1H-indol-6-yl)-7-[4-methoxy-3-(2-pyridylmethoxy) phenyl]hepta-1,6-diene-3,5-dione Synthesis was performed in the same manner as in Example 16(1) except that 33 mg (0.14 mmol) of 4-methoxy-3-(2-pyridylmethoxy)benzaldehyde was used instead of 29 mg (0.14 mmol) of 4-(2-pyridylmethoxy)benzaldehyde to give 32.0 mg (52% yield) of the title compound as an orange powder.

(2) Synthesis of 3-[(1E)-2-(1H-indol-6-yl)ethenyl]-5-[(1E)-2-[4-methoxy-3-(2-pyridylmethoxy)phenyl]ethenyl]-1H-pyrazole Synthesis was performed in the same manner as in Example 4 (4) except that 15 mg (33 μmol) of (1E,6E)-1-(1H-indol-6-yl)-7-[4-methoxy-3-(2-pyridylmethoxy) phenyl] hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 9.9 mg (67% yield) of the title compound as a pale yellowish white powder with the following properties.

$^1$H NMR (δ, acetone-$d_6$): 3.87 (s, 3H), 5.26 (s, 2H), 6.46 (dd, J=0.8, 3.2 Hz, 1H), 6.70 (s, 1H), 7.00 (d, J=8.3 Hz, 1H), 7.02 (d, J=17 Hz, 1H), 7.09 (d, J=17 Hz, 1H), 7.11 (m, 1H), 7.13 (d, J=17 Hz, 1H), 7.25-7.38 (m, 5H), 7.53-7.58 (m, 2H), 7.64 (d, J=7.9 Hz, 1H), 7.83 (dt, J=1.7, 7.7 Hz, 1H), 8.58 (br d, J=5 Hz, 1H), 10.3 (br s, NH). melting point 110-117° C., MS (ESI+) m/z 449.3 (M+1).

Example 19

Synthesis of 3-[(1E)-2-(1H-indol-6-yl)ethenyl]-5-[(1E)-2-[3-(2-pyridylmethoxy)phenyl]ethenyl]-1H-pyrazole

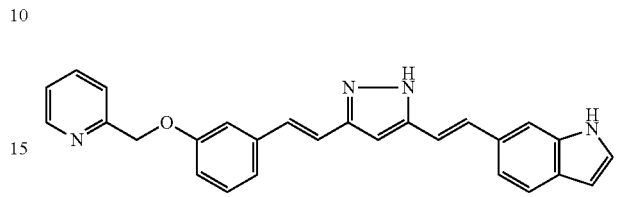

(1) Synthesis of (1E,6E)-1-(1H-indol-6-yl)-7-[3-(2-pyridylmethoxy)phenyl]hepta-1,6-diene-3,5-dione Synthesis was performed in the same manner as in Example 16 (1) except that 29 mg (0.14 mmol) of 3-(2-pyridylmethoxy)benzaldehyde was used instead of 29 mg (0.14 mmol) of 4-(2-pyridylmethoxy)benzaldehyde to give 23.4 mg (41% yield) of the title compound as an orange powder.

(2) Synthesis of 3-[(1E)-2-(1H-indol-6-yl)ethenyl]-5-[(1E)-2-[3-(2-pyridylmethoxy)phenyl]ethenyl]-1H-pyrazole Synthesis was performed in the same manner as in Example 4 (4) except that 15 mg (35 μmol) of (1E,6E)-1-(1H-indol-6-yl)-7-[3-(2-pyridylmethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 10.7 mg (72% yield) of the title compound as a yellowish white powder with the following properties.

$^1$H NMR (δ, acetone-$d_6$): 5.25 (s, 2H), 6.46 (dd, J=0.8, 3.2 Hz, 1H), 6.76 (s, 1H), 6.95 (ddd, J=1, 2.6, 8.1 Hz, 1H), 7.10 (d, J=17 Hz, 1H), 7.17 (br d, J=8 Hz, 1H), 7.18 (m, 2H), 7.23-7.38 (m, 6H), 7.53-7.62 (m, 3H), 7.82 (dt, J=1.8, 7.7 Hz, 1H), 8.59 (br d, J=5 Hz, 1H), 10.3 (br s, NH). melting point 193-195° C., MS (ESI+) m/z 419.4 (M+1).

Example 20

Synthesis of 3-[(1E)-2-(1H-indol-6-yl)ethenyl]-5-[(1E)-2-[2-(2-pyridylmethoxy)phenyl]ethenyl]-1H-pyrazole

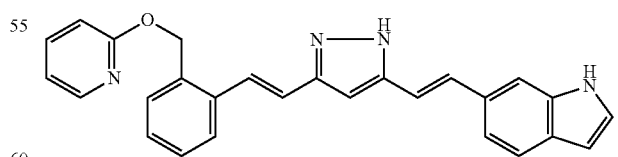

(1) Synthesis of (1E,6E)-1-(1H-indol-6-yl)-7-[2-(2-pyridylmethoxy)phenyl]hepta-1,6-diene-3,5-dione Synthesis was performed in the same manner as in Example 16 (1) except that 29 mg (0.14 mmol) of 2-(2- pyridylmethoxy)benzaldehyde was used instead of 29 mg (0.14 mmol) of 4-(2-pyridylmethoxy)benzaldehyde to give 37.0 mg (64% yield) of the title compound as a yellow powder.

(2) Synthesis of 3-[(1E)-2-(1H-indol-6-yl)ethenyl]-5-[(1E)-2-[2-(2-pyridylmethoxy)phenyl]ethenyl]-1H-pyrazole Synthesis was performed in the same manner as in Example 4 (4) except that 15 mg (35 µmol) of (1E,6E)-1-(1H-indol-6-yl)-7-[2-(2-pyridylmethoxy)phenyl]hepta-1,6-diene-3,5-dione was used instead of 15 mg (35 µmol) of (1E,6E)-1-(1H-indol-5-yl)-7-[4-(2-pyridylmethoxy)phenyl]hepta-1,6-diene-3,5-dione to give 9.7 mg (65% yield) of the title compound as a yellowish white powder with the following properties.

$^1$H NMR (δ, acetone-$d_6$): 5.31 (s, 2H), 6.46 (dd, J=0.9, 3.1 Hz, 1H), 6.74 (s, 1H), 6.99 (dd, J=7.4, 7.4 Hz, 1H), 7.08 (dd, J=0.9, 8.2 Hz, 1H), 7.10 (d, J=17 Hz, 1H), 7.22 (m, 1H), 7.23 (d, J=17 Hz, 1H), 7.28-7.36 (m, 4H), 7.54-7.59 (m, 2H), 7.62 (d, J=17 Hz, 1H), 7.63 (d, J=7.9 Hz, 1H), 7.67 (dd, J=1.7, 7.8 Hz, 1H), 7.85 (dt, J=1.8, 7.7 Hz, 1H), 8.60 (br d, J=5 Hz, 1H), 10.3 (br s, NH). melting point 113-120° C., MS (ESI+) m/z 419.3 (M+1).

Example 21

Synthesis of 3-[(1E)-2-(1H-indol-6-yl)ethenyl]-5-[(1E)-2-[2-methoxy-5-(2-pyridylmethoxy)phenyl]ethenyl]-1H-pyrazole

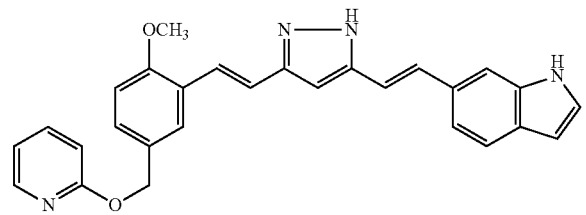 [SMILES: COc1ccc(COc2ccccn2)cc1/C=C/c1cc(/C=C/c2ccc3cc[nH]c3c2)[nH]n1]

(1) Synthesis of (1E,6E)-1-(1H-indol-6-yl)-7-[2-methoxy-5-(2-pyridylmethoxy) phenyl]hepta-1,6-diene-3,5-dione Synthesis was performed in the same manner as in Example 16 (1) except that 33 mg (0.14 mmol) of 2-methoxy-5-(2-pyridylmethoxy)benzaldehyde was used instead of 29 mg (0.14 mmol) of 4-(2-pyridylmethoxy)benzaldehyde to give 42.1 mg (68% yield) of the title compound as an orange powder.

(2) Synthesis of 3-[(1E)-2-(1H-indol-6-yl)ethenyl]-5-[(1E)-2-[2-methoxy-5-(2-pyridylmethoxy)phenyl]ethenyl]-1H-pyrazole Synthesis was performed in the same manner as in Example 4 (4) except that 15 mg (33 µmol) of (1E,6E)-1-(1H-indol-6-yl)-7-[2-methoxy-5-(2-pyridylmethoxy) phenyl]hepta-1,6-diene-3,5-dione was used instead of (1E,6E)-1-(1H-indol-5-yl)-7-[4-(2-pyridylmethoxy) phenyl]hepta-1,6-diene-3,5-dione to give 11.6 mg (78% yield) of the title compound as a pale yellowish white powder with the following properties.

$^1$H NMR (δ, acetone-$d_6$): 3.85 (s, 3H), 5.19 (s, 2H), 6.46 (dd, J=0.8, 3.1 Hz, 1H), 6.73 (s, 1H), 6.94 (dd, J=2.6, 9.0 Hz, 1H), 6.96 (d, J=9.0 Hz, 1H), 7.10 (d, J=17 Hz, 1H), 7.19 (d, J=17 Hz, 1H), 7.27-7.38 (m, 5H), 7.45 (d, J=17 Hz, 1H), 7.53-7.62 (m, 3H), 7.81 (dt, J=1.8, 7.7 Hz, 1H), 8.58 (br d, J=5 Hz, 1H), 10.3 (br s, NH). melting point 111-120° C., MS (ESI+) m/z 449.4 (M+1).

Example 22

Synthesis of 3-[(1E)-2-(1H-indol-6-yl)ethenyl]-5-[(1E)-2-[2-methoxy-3-(2-pyridylmethoxy)phenyl]ethenyl]-1H-pyrazole

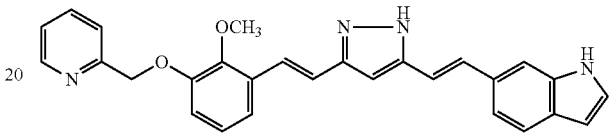

(1) Synthesis of 2-methoxy-3-(2-pyridylmethoxy)benzaldehyde

Synthesis was performed using the same materials in the same relative quantities as in Example 4 (1) except that 100 mg (0.657 mmol) of 3-hydroxy-2-methoxybenzaldehyde was used instead of 611 mg (5.00 mmol) of 4-hydroxybenzaldehyde to give 66.8 mg (42% yield) of the title compound as a white powder.

(2) Synthesis of (1E,6E)-1-(1H-indol-6-yl)-7-[2-methoxy-3-(2-pyridylmethoxy) phenyl]hepta-1,6-diene-3,5-dione Synthesis was performed in the same manner as in Example 16 (1) except that 33 mg (0.14 mmol) of 2-methoxy-3-(2-pyridylmethoxy)benzaldehyde was used instead of 29 mg (0.14 mmol) of 4-(2-pyridylmethoxy)benzaldehyde to give 40.6 mg (66% yield) of the title compound as an orange powder.

(3) Synthesis of 3-[(1E)-2-(1H-indol-6-yl)ethenyl]-5-[(1E)-2-[2-methoxy-3-(2-pyridylmethoxy)phenyl]ethenyl]-1H-pyrazole Synthesis was performed in the same manner as in Example 4 (4) except that 15 mg (33 µmol) of (1E,6E)-1-(1H-indol-6-yl)-7-[2-methoxy-3-(2-pyridylmethoxy) phenyl]hepta-1,6-diene-3,5-dione was used instead of 15 mg (35 µmol) of (1E,6E)-1-(1H-indol-5-yl)-7-[4-(2-pyridylmethoxy) phenyl]hepta-1,6-diene-3,5-dione to give 8.4 mg (57% yield) of the title compound as a yellowish white powder with the following properties.

$^1$H NMR (δ, acetone-$d_6$): 3.91 (s, 3H), 5.25 (s, 2H), 6.46 (dd, J=0.8, 3.2 Hz, 1H), 6.78 (s, 1H), 7.0-7.06 (m, 2H), 7.11 (d, J=17 Hz, 1H), 7.19 (d, J=17 Hz, 1H), 7.27-7.38 (m, 5H), 7.50 (d, J=17 Hz, 1H), 7.54-7.60 (m, 2H), 7.64 (d, J=7.9 Hz, 1H), 7.84 (dt, J=1.8, 7.7 Hz, 1H), 8.58 (br d, J=5 Hz, 1H), 10.3 (br s, NH). melting point 109-114° C., MS (ESI+) m/z 449.3 (M+1).

Example 23

Synthesis of 3-[(1E)-2-(1H-indol-6-yl)ethenyl]-5-[(1E)-2-[4-methoxy-2-(2-pyridylmethoxy)phenyl]ethenyl]-1H-pyrazole

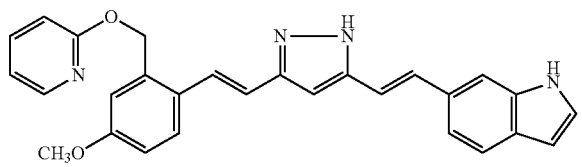

(1) Synthesis of 4-methoxy-2-(2-pyridylmethoxy)benzaldehyde

Synthesis was performed using the same materials in the same relative quantities as in Example 4 (1) except that 100 mg (0.657 mmol) of 2-hydroxy-4-methoxybenzaldehyde was used instead of 611 mg (5.00 mmol) of 4-hydroxybenzaldehyde to give 69.3 mg (43% yield) of the title compound as a white powder.

(2) Synthesis of (1E,6E)-1-(1H-indol-6-yl)-7-[4-methoxy-2-(2-pyridylmethoxy) phenyl]hepta-1,6-diene-3,5-dione Synthesis was performed in the same manner as in Example 16 (1) except that 33 mg (0.14 mmol) of 4-methoxy-2-(2-pyridylmethoxy)benzaldehyde was used instead of 29 mg (0.14 mmol) of 4-(2-pyridylmethoxy)benzaldehyde to give 42.7 mg (69% yield) of the title compound as an orange powder.

(3) Synthesis of 3-[(1E)-2-(1H-indol-6-yl)ethenyl]-5-[(1E)-2-[4-methoxy-2-(2-pyridylmethoxy)phenyl]ethenyl]-1H-pyrazole Synthesis was performed in the same manner as in Example 4 (4) except that 15 mg (33 µmol) of (1E,6E)-1-(1H-indol-6-yl)-7-[4-methoxy-2-(2-pyridylmethoxy) phenyl]hepta-1,6-diene-3,5-dione was used instead of 15 mg (35 µmol) of (1E,6E)-1-(1H-indol-5-yl)-7-[4-(2-pyridylmethoxy) phenyl]hepta-1,6-diene-3,5-dione to give 7.5 mg (50% yield) of the title compound as a yellowish white powder with the following properties.

$^1$H NMR (δ, acetone-$d_6$): 3.79 (s, 3H), 5.30 (s, 2H), 6.46 (br d, J=3 Hz, 1H), 6.59 (dd, J=2, 8.6 Hz, 1H), 6.67 (d, J=2 Hz, 1H), 6.68 (s, 1H), 7.09 (d, J=17 Hz, 1H), 7.10 (d, J=17 Hz, 1H), 7.29 (d, J=17 Hz, 1H), 7.29-7.36 (m, 3H), 7.52 (d, J=17 Hz, 1H), 7.53-7.58 (m, 2H), 7.57 (d, J=8.6 Hz, 1H), 7.63 (d, J=7.8 Hz, 1H), 7.85 (br t, J=7.7 Hz, 1H), 8.60 (br d, J=5 Hz, 1H), 10.3 (br s, NH). melting point 107-115° C., MS (ESI+) m/z 449.4 (M+1).

Example 24

Synthesis of 3-[(1E)-2-(1H-indol-6-yl)ethenyl]-5-[(1E)-2-[5-methoxy-2-(2-pyridylmethoxy)phenyl]ethenyl]-1H-pyrazole

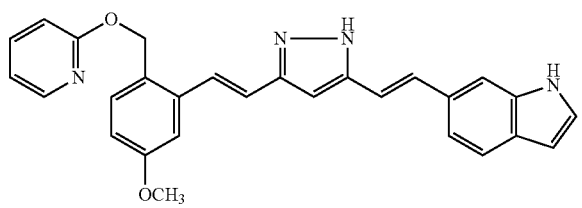 [SMILES: COc1ccc(COc2ccccn2)c(/C=C/c2cc(/C=C/c3ccc4cc[nH]c4c3)[nH]n2)c1]

(1) Synthesis of 5-methoxy-2-(2-pyridylmethoxy)benzaldehyde

Synthesis was performed using the same materials in the same relative quantities as in Example 4 (1) except that 100 mg (0.657 mmol) of 2-hydroxy-5-methoxybenzaldehyde was used instead of 611 mg (5.00 mmol) of 4-hydroxybenzaldehyde to give 77.3 mg (48% yield) of the title compound as a white powder.

(2) Synthesis of (1E,6E)-1-(1H-indol-6-yl)-7-[5-methoxy-2-(2-pyridylmethoxy) phenyl]hepta-1,6-diene-3,5-dione Synthesis was performed in the same manner as in Example 16 (1) except that 33 mg (0.14 mmol) of 5-methoxy-2-(2-pyridylmethoxy)benzaldehyde was used instead of 29 mg (0.14 mmol) of 4-(2-pyridylmethoxy)benzaldehyde to give 29.4 mg (48% yield) of the title compound as an orange powder.

(3) Synthesis of 3-[(1E)-2-(1H-indol-6-yl)ethenyl]-5-[(1E)-2-[5-methoxy-2-(2-pyridylmethoxy)phenyl]ethenyl]-1H-pyrazole Synthesis was performed in the same manner as in Example 4 (4) except that 15 mg (33 µmol) of (1E,6E)-1-(1H-indol-6-yl)-7-[5-methoxy-2-(2-pyridylmethoxy) phenyl]hepta-1,6-diene-3,5-dione was used instead of 15 mg (35 µmol) of (1E,6E)-1-(1H-indol-5-yl)-7-[4-(2-pyridylmethoxy) phenyl]hepta-1,6-diene-3,5-dione to give 7.0 mg (47% yield) of the title compound as a pale yellowish white powder with the following properties.

$^1$H NMR (δ, DMSO-$d_6$): 3.75 (s, 3H), 5.22 (s, 2H), 6.41 (br s, 1H), 6.71 (s, 1H), 6.81 (br d, J=9 Hz, 1H), 7.01 (d, J=9 Hz, 1H), 7.01 (d, J=17 Hz, 1H), 7.18 (d, J=17 Hz, 1H), 7.17-7.6 (m, 9H), 7.87 (dd, J=1.6, 7.7 Hz, 1H), 8.59 (br d, J=5 Hz, 1H), 11.2 (br s, NH). melting point 119-124° C., MS (ESI+) m/z 449.4 (M+1).

Example 25

Synthesis of 3-[(1E)-2-(1H-indol-6-yl)ethenyl]-5-[(1E)-2-[3-methoxy-5-(2-pyridylmethoxy)phenyl]ethenyl]-1H-pyrazole

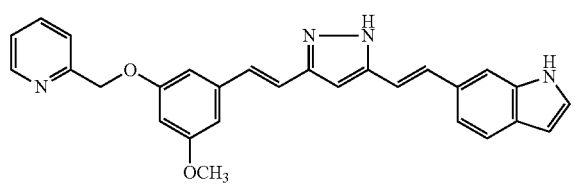 [SMILES: COc1cc(/C=C/c2cc(/C=C/c3ccc4cc[nH]c4c3)[nH]n2)cc(OCc2ccccn2)c1]

(1) Synthesis of 3-methoxy-5-(2-pyridylmethoxy)benzaldehyde

Synthesis was performed using the same materials in the same relative quantities as in Example 4 (1) except that 100 mg (0.657 mmol) of 3-hydroxy-5-methoxybenzaldehyde was used instead of 611 mg (5.00 mmol) of 4-hydroxybenzaldehyde to give 85.6 mg (54% yield) of the title compound as a white powder.

(2) Synthesis of (1E,6E)-1-(1H-indol-6-yl)-7-[3-methoxy-5-(2-pyridylmethoxy) phenyl]hepta-1,6-diene-3,5-dione Synthesis was performed in the same manner as in Example 16 (1) except that 33 mg (0.14 mmol) of 3-methoxy-5-(2-pyridylmethoxy)benzaldehyde was used instead of 29 mg (0.14 mmol) of 4-(2-pyridylmethoxy)benzaldehyde to give 22.8 mg (37% yield) of the title compound as an orange powder.

(3) Synthesis of 3-[(1E)-2-(1H-indol-6-yl)ethenyl]-5-[(1E)-2-[3-methoxy-5-(2-pyridylmethoxy)phenyl]ethenyl]-1H-pyrazole Synthesis was performed in the same manner as in Example 4 (4) except that 15 mg (33 μmol) of (1E,6E)-1-(1H-indol-6-yl)-7-[3-methoxy-5-(2-pyridylmethoxy) phenyl]hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 8.5 mg (57% yield) of the title compound as a yellowish white powder with the following properties.
$^1$H NMR (δ, acetone-d$_6$): 3.82 (s, 3H), 5.23 (s, 2H), 6.46 (br d, J=3 Hz, 1H), 6.54 (dd, J=2.2, 2.2 Hz, 1H), 6.75 (s, 1H), 6.76 (br s, 1H), 6.86 (br s, 1H), 7.10 (d, J=17 Hz, 1H), 7.13 (d, J=17 Hz, 1H), 7.18 (d, J=17 Hz, 1H), 7.27-7.38 (m, 4H), 7.51-7.60 (m, 3H), 7.85 (dt, J=1.8, 7.7 Hz, 1H), 8.58 (br d, J=5 Hz, 1H), 10.3 (br s, NH). melting point 88-93° C., MS (ESI+) m/z 449.4 (M+1).

Example 26

Synthesis of 3-[(1E)-2-(1H-indol-6-yl)ethenyl]-5-[(1E)-2-[2-methoxy-4-(2-piperidinoethoxy)phenyl]ethenyl]-1H-pyrazole

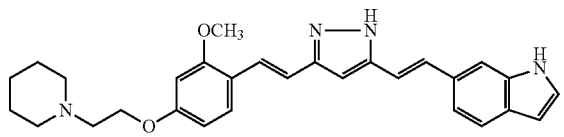 [SMILES: COc1cc(OCCN2CCCCC2)ccc1/C=C/c1cc(/C=C/c2ccc3cc[nH]c3c2)[nH]n1]

(1) Synthesis of 2-methoxy-4-(2-piperidinoethoxy)benzaldehyde

In 2.0 mL of N,N-dimethylformamide were dissolved 304 mg (2.00 mmol) of 4-hydroxy-2-methoxybenzaldehyde, 0.55 g (4.0 mmol) of potassium carbonate, and 64 mg (0.20 mmol) of tetrabutylammonium bromide. To this solution was added 0.74 g (4.0 mmol) of 1-(2-chloroethyl)piperidine hydrochloride and the mixture was stirred at 100° C. overnight. The resulting reaction mixture was diluted with ethyl acetate (100 mL), washed with water and then with saturated brine (each in an amount of 20 mL), and dried over magnesium sulfate. After filtration, the solvent was evaporated under reduced pressure. The residue was purified by silica gel column chromatography (ethyl acetate/methanol=100/0 to 90/10) to give 88.9 mg (16% yield) of the title compound as a brown viscous matter.

(2) Synthesis of (1E,6E)-1-(1H-indol-6-yl)-7-[2-methoxy-4-(2-piperidinoethoxy)phenyl]hepta-1,6-diene-3,5-dione Synthesis was performed in the same manner as in Example 16 (1) except that 36 mg (0.14 mmol) of 2-methoxy-4-(2-piperidinoethoxy)benzaldehyde was used instead of 29 mg (0.14 mmol) of 4-(2-pyridylmethoxy)benzaldehyde to give 46.3 mg (75% yield) of the title compound as an orange powder.

(3) Synthesis of 3-[(1E)-2-(1H-indol-6-yl)ethenyl]-5-[(1E)-2-[2-methoxy-4-(2-piperidinoethoxy)phenyl]ethenyl]-1H-pyrazole Synthesis was performed in the same manner as in Example 4 (4) except that 15 mg (32 μmol) of (1E,6E)-1-(1H-indol-6-yl)-7-[2-methoxy-4-(2-piperidinoethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 7.7 mg (52% yield) of the title compound as a pale yellowish white powder with the following properties.
$^1$H NMR (δ, acetone-d$_6$): 1.41 (m, 2H), 1.54 (m, 4H), 2.47 (m, 4H), 2.69 (t, J=6.0 Hz, 2H), 3.90 (s, 3H), 4.12 (t, J=6.0 Hz, 2H), 6.46 (dd, J=0.8, 3.1 Hz, 1H), 6.56 (d, J=2.4, 8.4 Hz, 1H), 6.59 (d, J=2.4 Hz, 1H), 6.68 (s, 1H), 7.04 (d, J=17 Hz, 1H), 7.08 (d, J=17 Hz, 1H), 7.30 (d, J=17 Hz, 1H), 7.3-7.38 (m, 2H), 7.38 (d, J=17 Hz, 1H), 7.51 (d, J=8.4 Hz, 1H), 7.54-7.60 (m, 2H), 10.3 (br s, NH). melting point 150-155° C., MS (ESI+) m/z 469.4 (M+1).

Example 27

Synthesis of 3-[(1E)-2-(1H-indol-6-yl)ethenyl]-5-[(1E)-2-[2-methoxy-4-(2-morpholinoethoxy)phenyl]ethenyl]-1H-pyrazole

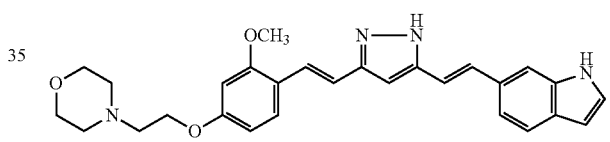

(1) Synthesis of 2-methoxy-4-(2-morpholinoethoxy)benzaldehyde

Synthesis was performed in the same manner as in Example 26 (1) except that 0.74 g (4.0 mmol) of 4-(2-chloroethyl)morpholine hydrochloride was used instead of 0.74 g (4.0 mmol) of 1-(2-chloroethyl)piperidine hydrochloride to give 302 mg (56% yield) of the title compound as a brown viscous matter.

(2) Synthesis of (1E,6E)-1-(1H-indol-6-yl)-7-[2-methoxy-4-(2-morpholinoethoxy)phenyl]hepta-1,6-diene-3,5-dione Synthesis was performed in the same manner as in Example 16 (1) except that 36 mg (0.14 mmol) of 2-methoxy-4-(2-morpholinoethoxy)benzaldehyde was used instead of 29 mg (0.14 mmol) of 4-(2-pyridylmethoxy)benzaldehyde to give 50.1 mg (82% yield) of the title compound as an orange powder.

(3) Synthesis of 3-[(1E)-2-(1H-indol-6-yl)ethenyl]-5-[(1E)-2-[2-methoxy-4-(2-morpholinoethoxy)phenyl]ethenyl]-1H-pyrazole Synthesis was performed in the same manner as in Example 4 (4) except that 15 mg (32 μmol) of (1E,6E)-1-(1H- indol-6-yl)-7-[2-methoxy-4-(2-morpholinoethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 9.2 mg (62% yield) of the title compound as a pale yellowish white powder with the following properties.

$^1$H NMR (δ, acetone-$d_6$): 2.52 (t, J=4.6 Hz, 4H), 2.74 (t, J=5.8 Hz, 2H), 3.61 (t, J=4.6 Hz, 4H), 3.90 (s, 3H), 4.16 (t, J=5.8 Hz, 2H), 6.46 (dd, J=1, 3.1 Hz, 1H), 6.57 (dd, J=2.4, 8.4 Hz, 1H), 6.60 (d, J=2.4 Hz, 1H), 6.68 (s, 1H), 7.04 (d, J=17 Hz, 1H), 7.09 (d, J=17 Hz, 1H), 7.30 (d, J=17 Hz, 1H), 7.30-7.36 (m, 2H), 7.37 (d, J=17 Hz, 1H), 7.51 (d, J=8.4 Hz, 1H), 7.53-7.60 (m, 2H), 10.3 (br s, NH). melting point 113-122° C., MS (ESI+) m/z 471.4 (M+1).

Example 28

Synthesis of 3-[(1E)-2-(1H-indol-6-yl)ethenyl]-5-[(1E)-2-[2-methoxy-4-[2-(4-methylpiperazino)ethoxy]phenyl]ethenyl]-1H-pyrazole

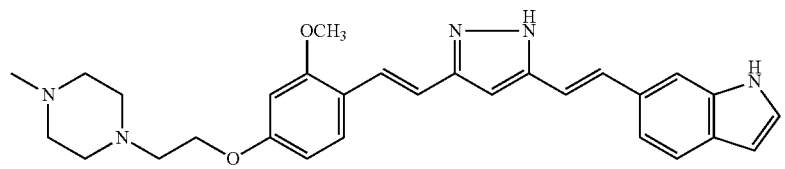 [SMILES: COc1cc(OCCN2CCN(C)CC2)ccc1/C=C/c1cc(/C=C/c2ccc3cc[nH]c3c2)[nH]n1]

(1) Synthesis of 2-methoxy-4-[2-(4-methylpiperazino)ethoxy]benzaldehyde

To a solution of 304 mg (2.00 mmol) of 4-hydroxy-2-methoxybenzaldehyde in N,N-dimethylformamide (4.0 mL) was added 105 mg (55%, 2.40 mmol) of sodium hydride at room temperature. The mixture was stirred at room temperature for 30 minutes, and 0.69 mL (8.0 mmol) of ethylene dibromide was added thereto. The mixture was stirred at 80° C. for 7 hours, and 2.2 mL (20 mmol) of 1-methylpiperazine was added thereto. The mixture was stirred at 80° C. overnight. Water was added to the reaction mixture under ice-cooling and extraction with ethyl acetate was performed. The resulting organic layer was washed with saturated sodium bicarbonate solution and then with saturated brine and dried over magnesium sulfate. After filtration, the solvent was evaporated under reduced pressure. The residue was purified by silica gel column chromatography (ethyl acetate/methanol=100/0 to 40/60) to give 115 mg (20% yield) of the title compound as a brown viscous matter.

(2) Synthesis of (1E,6E)-1-(1H-indol-6-yl)-7-[2-methoxy-4-[2-(4-methylpiperazino)ethoxy]phenyl]hepta-1,6-diene-3,5-dione Synthesis was performed in the same manner as in Example 16 (1) except that 38 mg (0.14 mmol) of 2-methoxy-4-[2-(4-methylpiperazino)ethoxy]benzaldehyde was used instead of 29 mg (0.14 mmol) of 4-(2-pyridylmethoxy)benzaldehyde to give 40.9 mg (65% yield) of the title compound as an orange powder.

(3) Synthesis of 3-[(1E)-2-(1H-indol-6-yl)ethenyl]-5-[(1E)-2-[2-methoxy-4-[2-(4-methylpiperazino)ethoxy]phenyl]ethenyl]-1H-pyrazole Synthesis was performed in the same manner as in Example 4 (4) except that 15 mg (31 μmol) of (1E,6E)-1-(1H-indol-6-yl)-7-[2-methoxy-4-[2-(4-methylpiperazino)ethoxy]phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 8.8 mg (59% yield) of the title compound as a yellowish white powder with the following properties.

$^1$H NMR (δ, acetone-$d_6$): 2.18 (s, 3H), 2.37 (br s, 4H), 2.55 (br s, 4H), 2.74 (t, J=5.9 Hz, 2H), 3.90 (s, 3H), 4.13 (t, J=5.9 Hz, 2H), 6.46 (br d, J=3.1 Hz, 1H), 6.56 (dd, J=2.3, 8.4 Hz, 1H), 6.59 (d, J=2.3 Hz, 1H), 6.68 (s, 1H), 7.04 (d, J=17 Hz, 1H), 7.09 (d, J=17 Hz, 1H), 7.31 (d, J=17 Hz, 1H), 7.30-7.36 (m, 2H), 7.37 (d, J=17 Hz, 1H), 7.51 (d, J=8.4 Hz, 1H), 7.53-7.59 (m, 2H), 10.3 (br s, NH). melting point 134-142° C., MS (ESI+) m/z 484.4 (M+1).

Example 29

Synthesis of 3-[(1E)-2-(1H-indol-6-yl)ethenyl]-5-[(1E)-2-[4-[(β-D-glucopyranosyl)oxy]-2-methoxyphenyl]ethenyl]-1H-pyrazole

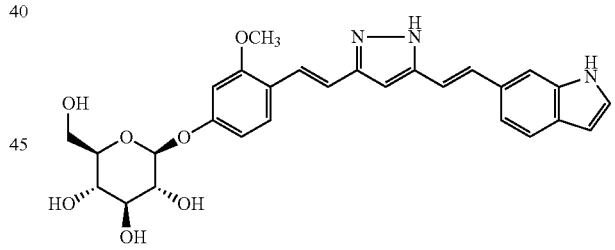

(1) Synthesis of 2-methoxy-4-[(2,3,4,6-tetra-O-acetyl-β-D-glucopyranosyl)oxy]benzaldehyde A 1N sodium hydroxide aqueous solution (10.4 mL) was added to a solution of 666 mg (4.38 mmol) of 4-hydroxy-2-methoxybenzaldehyde, 1.50 g (3.65 mmol) of 2,3,4,6-tetra-O-acetyl-α-D-glucopyranosyl bromide, and 1.18 g (3.66 mmol) of tetrabutylammonium bromide in chloroform (11 mL) at room temperature, and the mixture was vigorously stirred for 1 hour. The reaction mixture was subjected to extraction with ethyl acetate. After washing with a saturated sodium bicarbonate solution and then with saturated brine, drying over magnesium sulfate was performed. After filtration, the solvent was evaporated under reduced pressure. The residue was purified by silica gel column chromatography (hexane/ethyl acetate=75/25 to 60/40) to give 606 mg (40% yield) of 2-methoxy-4-[(2,3,4,6-tetra-O-acetyl-β-D-glucopyranosyl) oxy]benzaldehyde as a white powder.

(2) Synthesis of (1E,6E)-1-(1H-indol-6-yl)-7-[2-methoxy-4-[(2,3,4,6-tetra-O-acetyl-β-D-glucopyranosyl)oxy]phenyl]hepta-1,6-diene-3,5-dione Synthesis was performed in the same manner as in Example 16 (1) except that 65 mg (0.14 mmol) of 2-methoxy-4-[(2,3,4,6-tetra-O-acetyl-β-D-glucopyranosyl)oxy]benzaldehyde was used instead of 29 mg (0.14 mmol) of 4-(2-pyridylmethoxy)benzaldehyde to give 83.0 mg (92% yield) of the title compound as an orange powder.

(3) Synthesis of 3-[(1E)-2-(1H-indol-6-yl)ethenyl]-5-[(1E)-2-[4-[(β-D-glucopyranosyl)oxy]-2-methoxyphenyl]ethenyl]-1H-pyrazole Synthesis was performed in the same manner as in Example 4 (4) except that 15 mg (22 μmol) of (1E,6E)-1-(1H-indol-6-yl)-7-[2-methoxy-4-[(2,3,4,6-tetra-O-acetyl-β-D-glucopyranosyl)oxy]phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 14.7 mg of a crude product, 3-[(1E)-2-(1H-indol-6-yl)ethenyl]-5-[(1E)-2-[4-[(2,3,4,6-tetra-O-acetyl-β-D-glucopyranosyl)oxy]-2-methoxyphenyl]ethenyl]-1H-pyrazole.

In 1.0 mL of tetrahydrofuran, 14.7 mg of the above compound was dissolved and a solution of 5.4 mg (0.10 mmol) of sodium methoxide in methanol (1.0 mL) was added at room temperature. The mixture was stirred at the same temperature for 1 hour and neutralized with 100 μL of 1 N hydrochloric acid (0.10 mmol). The solvent was evaporated under reduced pressure. The residue was purified by silica gel column chromatography (methylene chloride/methanol=95/5 to 70/30) to give 5.9 mg (53% 2-step yield) of the title compound as a pale yellowish white powder with the following properties.

$^1$H NMR (δ, DMSO-d$_6$): 3.84 (s, 3H), 4.64 (m, 1H), 4.90 (m, 1H), 5.07 (m, 1H), 5.14 (m, 1H), 5.34 (m, 1H), 6.41 (br s, 1H), 6.65 (br d, J=9 Hz, 1H), 6.69 (s, 1H), 6.72 (d, J=2.4 Hz, 1H), 6.99 (br d, J=17 Hz, 2H), 7.20-7.40 (m, 4H), 7.47-7.60 (m, 3H), 11.2 (br s, NH). melting point 194-199° C., MS (ESI+) m/z 520.3 (M+1).

Example 30

Synthesis of 3-[(1E)-2-(1H-benzotriazol-5-yl)ethenyl]-5-[(1E)-2-[2-methoxy-4-(2-pyridylmethoxy)phenyl]ethenyl]-1H-pyrazole

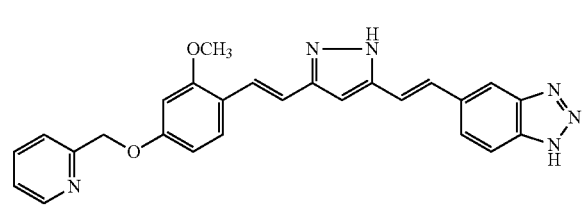 [SMILES: COc1cc(OCc2ccccn2)ccc1/C=C/c1cc(/C=C/c2ccc3[nH]nnc3c2)[nH]n1]

(1) Synthesis of 6-[2-methoxy-4-(2-pyridylmethoxy)phenyl]hex-5-ene-2,4-dione Synthesis was performed using the same materials in the same relative quantities as in Example 4 (2) except that 10.0 g (41.1 mmol) of 2-methoxy-4-(2-pyridylmethoxy)benzaldehyde was used instead of 4.50 g (31.0 mmol) of 1H-indole-5-carboxaldehyde to give 5.65 g (42% yield) of the title compound as a yellowish white powder with the following properties.

$^1$H NMR (δ, acetone-d$_6$): 2.10 (s, 3H), 3.92 (s, 3H), 5.25 (s, 2H), 5.75 (s, 1H), 6.63 (d, J=16 Hz, 1H), 6.67 (dd, J=2.4, 8.6 Hz, 1H), 6.76 (d, J=2.4 Hz, 1H), 7.32 (m, 1H), 7.56 (d, J=7.8 Hz, 1H), 7.60 (d, J=8.6 Hz, 1H), 7.82 (dt, J=1.8, 7.8 Hz, 1H), 7.85 (d, J=16 Hz, 1H), 8.58 (m, 1H). melting point 81-82° C., MS (ESI+) m/z 326.2 (M+1).

(2) Synthesis of (1E,6E)-1-(1H-benzotriazol-5-yl)-7-[2-methoxy-4-(2-pyridylmethoxy)phenyl]hepta-1,6-diene-3,5-dione In a 20 mL reaction vessel were placed 44.3 mg (136 μmol) of 6-[2-methoxy-4-(2-pyridylmethoxy)phenyl]hex-5-ene-2,4-dione and 13.2 mg (0.190 mmol) of boron oxide and they were dissolved in 0.88 mL of ethyl acetate. To the mixture under stirring at 70° C., 20 mg (0.14 mmol) of 1H-benzotriazole-5-carboxaldehyde and 62 μL (0.27 mmol) of triisopropyl borate were sequentially added. After the mixture was stirred at the same temperature for 1 hour, a solution of 2.7 μL (27 μmol) of piperidine in ethyl acetate (0.135 mL) was added and the mixture was further stirred for 1 hour. To the reaction mixture was added a 1:1 solution (0.4 mL) of 1 N hydrochloric acid and saturated brine at room temperature and the mixture was stirred for 5 minutes to 1 hour (further, the mixture was neutralized with a saturated sodium bicarbonate aqueous solution as needed). The resulting organic phase was directly subjected to purification by silica gel column chromatography (hexane/ethyl acetate or methylene chloride/methanol) to give 5.9 mg (10% yield) of the title compound as an orange powder.

(3) Synthesis of 3-[(1E)-2-(1H-benzotriazol-5-yl)ethenyl]-5-[(1E)-2-[2-methoxy-4-(2-pyridylmethoxy)phenyl]ethenyl]-1H-pyrazole Synthesis was performed in the same manner as in Example 4 (4) except that 15 mg (33 μmol) of (1E,6E)-1-(1H-benzotriazol-5-yl)-7-[2-methoxy-4-(2-pyridylmethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 1.7 mg (11% yield) of the title compound as a pale yellowish white powder with the following properties.

melting point 113-120° C., MS (ESI+) m/z 451.2 (M+1).

Example 31

Synthesis of 3-[(1E)-2-(1H-benzimidazol-5-yl)ethenyl]-5-[(1E)-2-[2-methoxy-4-(2-pyridylmethoxy)phenyl]ethenyl]-1H-pyrazole

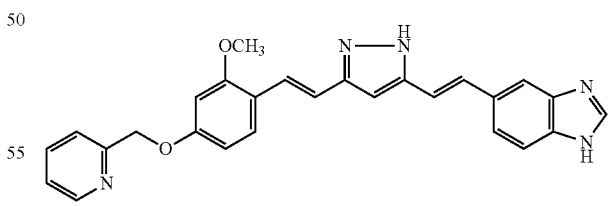

(1) Synthesis of (1E,6E)-1-(1H-benzimidazol-5-yl)-7-[2-methoxy-4-(2-pyridylmethoxy)phenyl]hepta-1,6-diene-3,5-dione Synthesis was performed in the same manner as in Example 30 (2) except that 20 mg (0.14 mmol) of 1H-benzimidazole-5-carboxaldehyde was used instead of 20 mg (0.14 mmol) of 1H-benzotriazole-5-carboxaldehyde to give 15.1 mg (24% yield) of the title compound as an orange powder.

(2) Synthesis of 3-[(1E)-2-(1H-benzimidazol-5-yl) ethenyl]-5-[(1E)-2-[2-methoxy-4-(2-pyridyl-methoxy)phenyl]ethenyl]-1H-pyrazole Synthesis was performed in the same manner as in Example 4 (4) except that 15 mg (33 μmol) of (1E,6E)-1-(1H-benzimidazol-5-yl)-7-[2-methoxy-4-(2-pyridylmethoxy) phenyl]hepta-1,6-diene-3,5-dione was used instead of 15 mg (35 μmol) of (1E,6E)-1-(1H-indol-5-yl)-7-[4-(2-pyridyl-methoxy)phenyl]hepta-1,6-diene-3,5-dione to give 4.8 mg (32% yield) of the title compound as a pale yellowish white powder with the following properties.

$^1$H NMR (δ, acetone-$d_6$): 3.90 (s, 3H), 5.22 (s, 2H), 6.65 (dd, J=2.3, 8.6 Hz, 1H), 6.71 (s, 1H), 6.74 (d, J=2.3 Hz, 1H), 7.06 (d, J=17 Hz, 1H), 7.13 (d, J=17 Hz, 1H), 7.28-7.4 (m, 2H), 7.39 (d, J=17 Hz, 1H), 7.45-7.75 (m, 5H), 7.82 (dt, J=1.8, 7.7 Hz, 1H), 8.15 (s, 1H), 8.58 (br d, J=5 Hz, 1H), 11.6 (br s, NH). melting point 135-142° C., MS (ESI+) m/z 450.3 (M+1).

Example 32

Synthesis of 3-[(1E)-2-[2-methoxy-4-(2-pyridyl-methoxy)phenyl]ethenyl]-5-[(1E)-2-(quinoxalin-6-yl)ethenyl]-1H-pyrazole

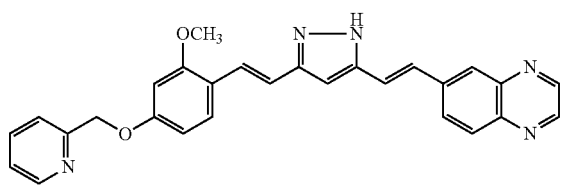 [SMILES: COc1cc(OCc2ccccn2)ccc1/C=C/c1cc(/C=C/c2ccc3nccnc3c2)[nH]n1]

(1) Synthesis of (1E,6E)-1-[2-methoxy-4-(2-pyridyl-methoxy)phenyl]-7-(quinoxalin-6-yl)hepta-1,6-diene-3,5-dione Synthesis was performed in the same manner as in Example 30 (2) except that 21 mg (0.14 mmol) of quinoxaline-6-carboxaldehyde was used instead of 20 mg (0.14 mmol) of 1H-benzotriazole-5-carboxaldehyde to give 19.4 mg (31% yield) of the title compound as an orange powder.

(2) Synthesis of 3-[(1E)-2-[2-methoxy-4-(2-pyridyl-methoxy)phenyl]ethenyl]-5-[(1E)-2-(quinoxalin-6-yl)ethenyl]-1H-pyrazole Synthesis was performed in the same manner as in Example 4 (4) except that 15 mg (32 μmol) of (1E,6E)-1-[2-methoxy-4-(2-pyridylmethoxy)phenyl]-7-(quinoxalin-6-yl) hepta-1,6-diene-3,5-dione was used instead of 15 mg (35 μmol) of (1E,6E)-1-(1H-indol-5-yl)-7-[4-(2-pyridyl-methoxy)phenyl]hepta-1,6-diene-3,5-dione to give 4.0 mg (27% yield) of the title compound as a yellowish white powder with the following properties.

$^1$H NMR (δ, DMSO-$d_6$): 3.86 (s, 3H), 5.22 (s, 2H), 6.65 (dd, J=2, 8 Hz, 1H), 6.74 (d, J=2 Hz, 1H), 6.79 (s, 1H), 6.99 (d, J=17 Hz, 1H), 7.29 (d, J=17 Hz, 1H), 7.30-7.46 (m, 3H), 7.50 (m, 1H), 7.54 (d, J=8 Hz, 1H), 7.85 (d, J=1.8, 7.7 Hz, 1H), 8.06 (d, J=9.1 Hz, 1H), 8.12 (br s, 1H), 8.18 (br s, 1H), 8.59 (br d, J=5 Hz, 1H), 8.88 (d, J=1.7 Hz, 1H), 8.93 (d, J=1.7 Hz, 1H). melting point 205-213° C., MS (ESI+) m/z 462.2 (M+1).

Example 33

Synthesis of 3-[(1E)-2-(benzofuran-2-yl)ethenyl]-5-[(1E)-2-[2-methoxy-4-(2-pyridylmethoxy)phenyl] ethenyl]-1H-pyrazole

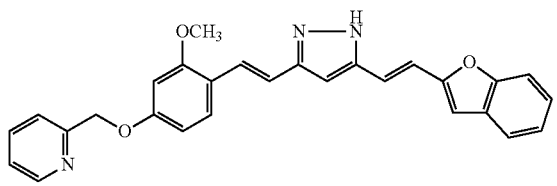 [SMILES: COc1cc(OCc2ccccn2)ccc1/C=C/c1cc(/C=C/c2cc3ccccc3o2)[nH]n1]

(1) Synthesis of (1E,6E)-1-(benzofuran-2-yl)-7-[2-methoxy-4-(2-pyridylmethoxy)phenyl]hepta-1,6-diene-3,5-dione Synthesis was performed using the same materials in the same relative quantities as in Example 30 (2) except that 186 μL (1.54 mmol) of benzofuran-2-carboxaldehyde was used instead of 20 mg (0.14 mmol) of 1H-benzotriazole-5-carboxaldehyde to give 169 mg (24% yield) of the title compound as a red powder with the following properties.

$^1$H NMR (δ, chloroform-d): 3.88 (s, 3H), 5.25 (s, 2H), 5.86 (s, 1H), 6.59-6.61 (m, 2H), 6.65 (d, J=16 Hz, 1H), 6.77 (d, J=15 Hz, 1H), 6.91 (s, 1H), 7.21-7.25 (m, 2H), 7.34 (m, 1H), 7.46-7.51 (m, 4H), 7.57 (d, J=7.2 Hz, 1H), 7.73 (dt, J=1.6, 7.7 Hz, 1H), 7.93 (d, J=16 Hz, 1H), 8.61 (m, 1H), 15.9 (br s, 1H). melting point 125.8-127.7° C., MS (EI) m/z 453 (M$^+$). EI-HRMS m/z calcd for $C_{32}H_{32}N_4O$ (M$^+$) 453.1576, found 453.1576.

(2) Synthesis of 3-[(1E)-2-(benzofuran-2-yl)ethe-nyl]-5-[(1E)-2-[2-methoxy-4-(2-pyridylmethoxy) phenyl]ethenyl]-1H-pyrazole Synthesis was performed using the same materials in the same relative quantities as in Example 4 (4) except that 100 mg (0.221 mmol) of (1E,6E)-1-(benzofuran-2-yl)-7-[2-methoxy-4-(2-pyridylmethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 21.0 mg (21% yield) of the title compound as a light brown powder with the following properties.

$^1$H NMR (δ, chloroform-d): 3.86 (s, 3H), 5.24 (s, 2H), 6.56-6.62 (m, 3H), 6.69 (s, 1H), 6.95 (d, J=17 Hz, 1H), 7.00 (d, J=16 Hz, 1H), 7.17-7.30 (m, 3H), 7.24 (d, J=16 Hz, 1H), 7.31 (d, J=17 Hz, 1H), 7.42-7.47 (m, 2H), 7.52 (d, J=11 Hz, 2H), 7.72 (dt, J=1.9, 7.7 Hz, 1H), 8.61 (m, 1H). melting point 199.4-200.9° C., MS (EI) m/z 449 (M$^+$). EI-HRMS m/z calcd for $C_{28}H_{23}N_3O_3$ (M$^+$) 449.1739, found 449.1743.

Example 34

Synthesis of 3-[(1E)-2-(benzothiophen-2-yl)ethenyl]-5-[(1E)-2-[2-methoxy-4-(2-pyridylmethoxy)phenyl]ethenyl]-1H-pyrazole

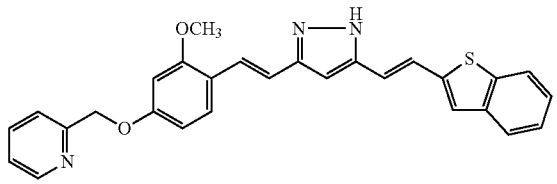

(1) Synthesis of (1E,6E)-1-(benzothiophen-2-yl)-7-[2-methoxy-4-(2-pyridylmethoxy)phenyl]hepta-1,6-diene-3,5-dione Synthesis was performed using the same materials in the same relative quantities as in Example 30 (2) except that 150 μL (0.923 mmol) of benzothiophene-2-carboxaldehyde was used instead of 20 mg (0.14 mmol) of 1H-benzotriazole-5-carboxaldehyde to give 97 mg (22% yield) of the title compound as a yellow powder with the following properties.

$^1$H NMR (δ, chloroform-d): 3.88 (s, 3H), 5.25 (s, 2H), 5.82 (s, 1H), 6.46 (d, J=15 Hz, 1H), 6.61-6.58 (m, 2H), 6.64 (d, J=16 Hz, 1H), 6.91 (s, 1H), 7.23-7.25 (m, 2H), 7.34-7.36 (m, 1H), 7.44 (s, 1H), 7.47-7.52 (m, 2H), 7.71-7.80 (m, 3H), 7.82 (d, J=15 Hz, 1H), 7.92 (d, J=16 Hz, 1H), 8.61 (m, 1H), 15.9 (m, 1H). melting point 187.7-188.4° C., MS (EI) m/z 469 (M$^+$). EI-HRMS m/z calcd for $C_{32}H_{32}N_4O$ (M$^+$) 469.1348, found 469.1351.

(2) Synthesis of 3-[(1E)-2-(benzothiophen-2-yl)ethenyl]-5-[(1E)-2-[2-methoxy-4-(2-pyridylmethoxy)phenyl]ethenyl]-1H-pyrazole Synthesis was performed using the same materials in the same relative quantities as in Example 4 (4) except that 40 mg (0.085 mmol) of (1E,6E)-1-(benzothiophen-2-yl)-7-[2-methoxy-4-(2-pyridylmethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 8.0 mg (20% yield) of the title compound as a pale yellowish white powder with the following properties.

$^1$H NMR (δ, DMSO-d$_6$): 3.86 (s, 3H), 5.22 (s, 2H), 6.63-6.77 (m, 3H), 6.86-7.01 (m, 2H), 7.23-7.37 (m, 4H), 7.42-7.56 (m, 4H), 7.77-7.93 (m, 2H), 7.85 (dt, J=1.9, 7.7 Hz, 1H), 8.59 (m, 1H), 13.0 (m, 1H). melting point 231.1-232.1° C., MS (EI) m/z 465 (M$^+$). EI-HRMS m/z calcd for $C_{28}H_{23}N_3O_2S$ (M$^+$) 465.1511, found 465.1509.

Example 35

Synthesis of 3-[(1E)-2-[2-methoxy-4-(2-pyridylmethoxy)phenyl]ethenyl]-5-[(1E)-2-(1-methyl-1H-indol-6-yl)ethenyl]-1H-pyrazole

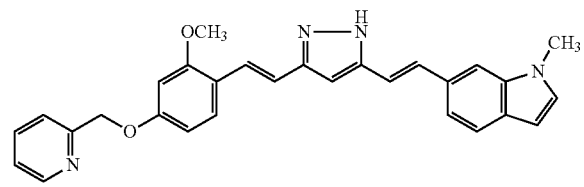 [SMILES: COc1cc(OCc2ccccn2)ccc1/C=C/c1cc(/C=C/c2ccc3ccn(C)c3c2)[nH]n1]

(1) Synthesis of (1E,6E)-1-[2-methoxy-4-(2-pyridylmethoxy)phenyl]-7-(1-methyl-1H-indol-6-yl)hepta-1,6-diene-3,5-dione Synthesis was performed using the same materials in the same relative quantities as in Example 30 (2) except that 391 mg (2.46 mmol) of 1-methyl-1H-indole-6-carboxaldehyde was used instead of 20 mg (0.14 mmol) of 1H-benzotriazole-5-carboxaldehyde to give 367 mg (32% yield) of the title compound as an orange powder with the following properties.

$^1$H NMR (δ, chloroform-d): 3.83 (s, 3H), 3.88 (s, 3H), 5.25 (s, 2H), 5.83 (s, 1H), 6.48 (d, J=3.1 Hz, 1H), 6.59-6.60 (m, 2H), 6.63 (d, J=16 Hz, 1H), 6.66 (d, J=16 Hz, 1H), 7.12 (d, J=3.1 Hz, 1H), 7.23-7.25 (m, 1H), 7.37 (dd, J=1.0, 8.2 Hz, 1H), 7.47-7.52 (m, 3H), 7.60 (d, J=8.2 Hz, 1H), 7.73 (dt, J=2.1, 7.7 Hz, 1H), 7.81 (d, J=16 Hz, 1H), 7.90 (d, J=16 Hz, 1H), 8.61 (m, 1H), 16.1 (br s, 1H). melting point 190.6-191.6° C., MS (EI) m/z 466 (M$^+$). EI-HRMS m/z calcd for $C_{32}H_{32}N_4O$ (M$^+$) 466.1893, found 466.1891.

(2) Synthesis of 3-[(1E)-2-[2-methoxy-4-(2-pyridylmethoxy)phenyl]ethenyl]-5-[(1E)-2-(1-methyl-1H-indol-6-yl)ethenyl]-1H-pyrazole Synthesis was performed using the same materials in the same relative quantities as in Example 4 (4) except that 130 mg (0.279 mmol) of (1E,6E)-1-[2-methoxy-4-(2-pyridylmethoxy)phenyl]-7-(1-methyl-1H-indol-6-yl)hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 48 mg (37% yield) of the title compound as a yellow powder with the following properties.

$^1$H NMR (δ, acetone-d$_6$): 3.86 (s, 3H), 3.91 (s, 3H), 5.23 (s, 2H), 6.42 (m, 1H), 6.66 (dd, J=2.6, 8.4 Hz, 1H), 6.69 (s, 1H), 6.75 (d, J=2.6 Hz, 1H), 7.07 (d, J=17 Hz, 1H), 7.15 (d, J=17 Hz, 1H), 7.23 (d, J=2.9 Hz, 1H), 7.30-7.37 (m, 3H), 7.39 (d, J=17 Hz, 1H), 7.52-7.58 (m, 4 H), 7.82 (dt, J=1.8, 7.7 Hz, 1H), 8.58 (m, 1H), 11.9 (br s, 1H). melting point 172.0-174.0° C., MS (EI) m/z 462 (M$^+$). EI-HRMS m/z calcd for $C_{29}H_{26}N_4O_2$ (M$^+$) 462.2056, found 462.2060.

Example 36

Synthesis of 3-[(1E)-2-(1H-indol-2-yl)ethenyl]-5-[(1E)-2-[2-methoxy-4-(2-pyridylmethoxy)phenyl]ethenyl]-1H-pyrazole

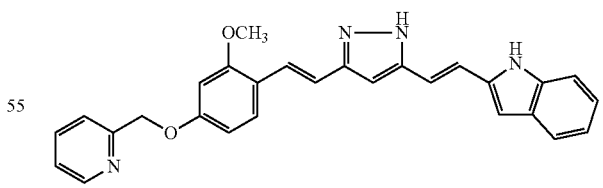

(1) Synthesis of (1E,6E)-1-(1H-indol-2-yl)-7-[2-methoxy-4-(2-pyridylmethoxy) phenyl]hepta-1,6-diene-3,5-dione Synthesis was performed using the same materials in the same relative quantities as in Example 30 (2) except that 220 mg (1.54 mmol) of 1H-indole-2-carboxaldehyde was used instead of 20 mg (0.14 mmol) of 1H-benzotriazole-5-carbaldehyde to give 64 mg (9.2% yield) of the title compound as an orange powder with the following properties.

¹H NMR (δ, chloroform-d): 3.87 (s, 3H), 5.25 (s, 2H), 5.79 (s, 1H), 6.40 (d, J=15 Hz, 1H), 6.57-6.61 (m, 2H), 6.62 (d, J=16 Hz, 1H), 6.83 (m, 1H), 7.12 (d, J=7.6 Hz, 1H), 7.23-7.27 (m, 2H), 7.35 (d, J=8.2 Hz, 1H), 7.47-7.52 (m, 2H), 7.60-7.65 (m, 2H), 7.92 (d, J=16 Hz, 1H), 8.29 (br s, 1H), 8.61 (m, 1H), 15.8 (s, 1H).

melting point 177.7-179.4° C., MS (EI) m/z 452 (M⁺). EI-HRMS m/z calcd for $C_{32}H_{32}N_4O$ (M⁺) 452.1736, found 452.1737.

(2) Synthesis of 3-[(1E)-2-(1H-indol-2-yl)ethenyl]-5-[(1E)-2-[2-methoxy-4-(2-pyridylmethoxy)phenyl]ethenyl]-1H-pyrazole Synthesis was performed using the same materials in the same relative quantities as in Example 4 (4) except that 100 mg (0.221 mmol) of (1E,6E)-1-(1H-indol-2-yl)-7-[2-methoxy-4-(2-pyridylmethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 49 mg (49% yield) of the title compound as a pale yellowish white powder with the following properties.

¹H NMR (δ, acetone-d₆): 3.91 (s, 3H), 5.23 (s, 2H), 6.59 (m, 1H), 6.66 (dd, J=2.6, 8.7 Hz, 1H), 6.69 (s, 1H), 6.75 (d, J=2.0 Hz, 1H), 6.99 (m, 1H), 7.06 (d, J=17 Hz, 1H), 7.10 (m, 1H), 7.11 (d, J=17 Hz, 1H) 7.24 (d, J=16 Hz, 1H), 7.30-7.37 (m, 2H), 7.39 (d, J=16 Hz, 1H), 7.51 (d, J=7.7 Hz, 1H), 7.52 (d, J=8.7 Hz, 1H), 7.57 (d, J=7.7 Hz, 1H), 7.82 (dt, J=2.0, 7.7 Hz, 1H), 8.59 (m, 1H), 10.5 (br s, 1H), 12.1 (br s, 1H). melting point 150.8-151.6° C., MS (EI) m/z 448 (M⁺). EI-HRMS m/z calcd for $C_{28}H_{24}N_4O_2$ (M⁺) 448.1899, found 448.1897.

Example 37

Synthesis of 3-[(1E)-2-(2-benzyloxy-4-diethylaminophenyl)ethenyl]-5-[(1E)-2-(1H-indol-6-yl)ethenyl]-1H-pyrazole

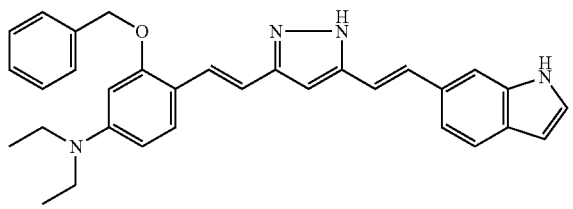 [SMILES: CCN(CC)c1ccc(/C=C/c2cc(/C=C/c3ccc4cc[nH]c4c3)[nH]n2)c(OCc2ccccc2)c1]

(1) Synthesis of (1E,6E)-1-(2-benzyloxy-4-diethylaminophenyl)-7-(1H-indol-6-yl)hepta-1,6-diene-3,5-dione Synthesis was performed using the same materials in the same relative quantities as in Example 16 (1) except that 411 mg (1.45 mmol) of 2-benzyloxy-4-diethylaminobenzaldehyde was used instead of 29 mg (0.14 mmol) of 4-(2-pyridylmethoxy)benzaldehyde to give 482 mg (74% yield) of the title compound as a black powder with the following properties.

¹H NMR (δ, acetone-d₆): 1.14 (t, J=7.2 Hz, 3H), 3.45 (q, J=7.2 Hz, 4H), 5.28 (s, 2H), 5.85 (s, 1H), 6.35-6.40 (m, 2H), 6.51 (m, 1H), 6.65 (d, J=16 Hz, 1H), 6.74 (d, J=16 Hz, 1H), 7.34-7.46 (m, 5H), 7.41 (d, J=8.7 Hz, 1H), 7.54-7.56 (m, 2H), 7.61 (d, J=8.2 Hz, 1H), 7.70 (s, 1H), 7.72 (d, J=15 Hz, 1H), 8.01 (d, J=16 Hz, 1H), 10.4 (br s, 1H), 16.7 (br s, 1H). melting point 160.1-162.9° C., MS (EI) m/z 492 (M⁺).

(2) Synthesis of 3-[(1E)-2-(2-benzyloxy-4-diethylaminophenyl)ethenyl]-5-[(1E)-2-(1H-indol-6-yl)ethenyl]-1H-pyrazole Synthesis was performed in the same manner as in Example 4 (4) except that 300 mg (0.609 mmol) of (1E,6E)-1-(2-benzyloxy-4-diethylaminophenyl)-7-(1H-indol-6-yl)hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 11.4 mg (3.83% yield) of the title compound as a light brown powder with the following properties.

¹H NMR (δ, acetone-d₆): 1.11 (t, J=7.2, 3H), 3.39 (q, J=7.2, 4H), 5.25 (s, 2H), 6.33-6.53 (m, 2H), 6.46 (m, 1H), 6.60 (s, 1H), 6.97 (d, J=17 Hz, 1H), 7.10 (d, J=16 Hz, 1H), 7.28 (d, J=16 Hz, 1H), 7.39-7.45 (m, 3H), 7.46 (d, J=17 Hz, 1H), 7.54-7.58 (m, 4H), 10.3 (s, 1H), 11.9 (br s, 1H). melting point 78.1-80.0° C., MS (EI) m/z 488 (M⁺). EI-HRMS m/z calcd for $C_{32}H_{32}N_4O$ (M⁺) 488.2576, found 488.2574.

Example 38

Synthesis of 3-[(1E)-2-(1H-indol-3-yl)ethenyl]-5-[(1E)-2-[2-methoxy-4-(2-pyridylmethoxy)phenyl]ethenyl]-1H-pyrazole

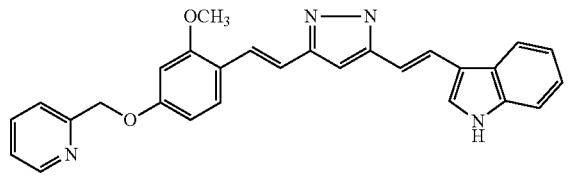 [SMILES: COc1cc(OCc2ccccn2)ccc1/C=C/c1cc(/C=C/c2c[nH]c3ccccc23)[nH]n1]

(1) Synthesis of (1E,6E)-1-(1H-indol-3-yl)-7-[2-methoxy-4-(2-pyridylmethoxy) phenyl]hepta-1,6-diene-3,5-dione Synthesis was performed using the same materials in the same relative quantities as in Example 30 (2) except that 40 mg (0.27 mmol) of 1H-indole-3-carboxaldehyde was used instead of 20 mg (0.14 mmol) of 1H-benzotriazole-5-carboxaldehyde to give 81.2 mg (67% yield) of the title compound as a brown powder.

(2) Synthesis of 3-[(1E)-2-(1H-indol-3-yl)ethenyl]-5-[(1E)-2-[2-methoxy-4-(2-pyridylmethoxy)phenyl]ethenyl]-1H-pyrazole Synthesis was performed in the same manner as in Example 4 (4) except that 15 mg (35 μmol) of (1E,6E)-1-(1H-indol-3-yl)-7-[2-methoxy-4-(2-pyridylmethoxy) phenyl]hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 4.8 mg (32% yield) of the title compound as a pale yellowish white powder with the following properties.

¹H NMR (δ, acetone-d₆): 3.90 (s, 3H), 5.22 (s, 2H), 6.64 (dd, J=2.4, 8.4 Hz, 1H), 6.65 (s, 1H), 6.73 (d, J=2.4 Hz, 1H), 7.05 (d, J=17 Hz, 1H), 7.09 (d, J=17 Hz, 1H), 7.11-7.19 (m, 2H), 7.31 (dd, J=5.1, 7.2 Hz, 1H), 7.37 (d, J=17 Hz, 1H), 7.43 (d, J=17 Hz, 1H), 7.45 (dd, J=1.4, 6.8 Hz, 1H), 7.53 (d, J=8.6

Hz, 1H), 7.56 (d, J=7.7 Hz, 1H), 7.59 (s, 1H), 7.82 (dt, J=1.8, 7.7 Hz, 1H), 7.97 (br d, J=7.2 Hz, 1H), 8.58 (br d, J=4 Hz, 1H), 10.5 (br s, NH). melting point 112-116° C., MS (ESI+) m/z 449.2 (M+1).

Example 39

Synthesis of 3-[(1E)-2-(1H-indol-4-yl)ethenyl]-5-[(1E)-2-[2-methoxy-4-(2-pyridylmethoxy)phenyl]ethenyl]-1H-pyrazole

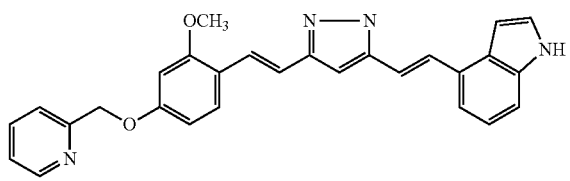 [SMILES: COc1cc(OCc2ccccn2)ccc1/C=C/c1cc(/C=C/c2cccc3[nH]ccc23)[nH]n1]

(1) Synthesis of (1E,6E)-1-(1H-indol-4-yl)-7-[2-methoxy-4-(2-pyridylmethoxy) phenyl]hepta-1,6-diene-3,5-dione Synthesis was performed using the same materials in the same relative quantities as in Example 30 (2) except that 40 mg (0.27 mmol) of 1H-indole-4-carboxaldehyde was used instead of 20 mg (0.14 mmol) of 1H-benzotriazole-5-carboxaldehyde to give 32.9 mg (27% yield) of the title compound as a brown powder.

(2) Synthesis of 3-[(1E)-2-(1H-indol-4-yl)ethenyl]-5-[(1E)-2-[2-methoxy-4-(2-pyridylmethoxy)phenyl]ethenyl]-1H-pyrazole Synthesis was performed in the same manner as in Example 4 (4) except that 15 mg (35 µmol) of (1E,6E)-1-(1H-indol-4-yl)-7-[2-methoxy-4-(2-pyridylmethoxy) phenyl]hepta-1,6-diene-3,5-dione was used instead of 15 mg (35 µmol) of (1E,6E)-1-(1H-indol-5-yl)-7-[4-(2-pyridylmethoxy) phenyl]hepta-1,6-diene-3,5-dione to give 5.8 mg (39% yield) of the title compound as a yellowish white powder with the following properties.
$^1$H NMR (δ, acetone-$d_6$): 3.91 (s, 3H), 5.22 (s, 2H), 6.65 (dd, J=2.4, 8.5 Hz, 1H), 6.74 (d, J=2.4 Hz, 1H), 6.78 (s, 1H), 6.88 (d, J=3 Hz, 1H), 7.07 (d, J=17 Hz, 1H), 7.12 (t, J=7.7 Hz, 1H), 7.29 (d, J=17 Hz, 1H), 7.29-7.44 (m, 5H), 7.53 (d, J=8.6 Hz, 1H), 7.56 (d, J=7.9 Hz, 1H), 7.64 (d, J=17 Hz, 1H), 7.82 (dt, J=1.7, 7.7 Hz, 1H), 8.58 (br d, J=5 Hz, 1H), 10.4 (br s, NH). melting point 108-113° C., MS (ESI+) m/z 449.1 (M+1).

Example 40

Synthesis of 3-[(1E)-2-(1H-indol-5-yl)ethenyl]-5-[(1E)-2-[2-methoxy-4-(2-pyridylmethoxy)phenyl]ethenyl]-1H-pyrazole

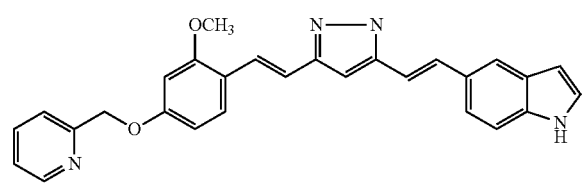 [SMILES: COc1cc(OCc2ccccn2)ccc1/C=C/c1cc(/C=C/c2ccc3[nH]ccc3c2)[nH]n1]

(1) Synthesis of (1E,6E)-1-(1H-indol-5-yl)-7-[2-methoxy-4-(2-pyridylmethoxy) phenyl]hepta-1,6-diene-3,5-dione Synthesis was performed using the same materials in the same relative quantities as in Example 30 (2) except that 40 mg (0.27 mmol) of 1H-indole-5-carboxaldehyde was used instead of 20 mg (0.14 mmol) of 1H-benzotriazole-5-carboxaldehyde to give 108 mg (89% yield) of the title compound as a yellow powder.

(2) Synthesis of 3-[(1E)-2-(1H-indol-5-yl)ethenyl]-5-[(1E)-2-[2-methoxy-4-(2-pyridylmethoxy)phenyl]ethenyl]-1H-pyrazole Synthesis was performed in the same manner as in Example 4 (4) except that 15 mg (35 µmol) of (1E,6E)-1-(1H-indol-5-yl)-7-[2-methoxy-4-(2-pyridylmethoxy) phenyl]hepta-1,6-diene-3,5-dione was used instead of 15 mg (35 µmol) of (1E,6E)-1-(1H-indol-5-yl)-7-[4-(2-pyridylmethoxy) phenyl]hepta-1,6-diene-3,5-dione to give 4.6 mg (31% yield) of the title compound as a pale yellowish white powder with the following properties.
$^1$H NMR (δ, acetone-$d_6$): 3.90 (s, 3H), 5.22 (s, 2H), 6.48 (d, J=3.0 Hz, 1H), 6.65 (dd, J=2.4, 8.6 Hz, 1H), 6.67 (s, 1H), 6.73 (d, J=2.4 Hz, 1H), 7.04 (d, J=17 Hz, 1H), 7.05 (d, J=17 Hz, 1H), 7.28-7.34 (m, 3H), 7.37 (d, J=17 Hz, 1H), 7.41 (m, 2H), 7.53 (d, J=8.6 Hz, 1H), 7.56 (d, J=7.8 Hz, 1H), 7.72 (s, 1H), 7.81 (dt, J=1.7, 7.7 Hz, 1H), 8.58 (br d, J=5 Hz, 1H), 10.3 (br s, NH). melting point 98-104° C., MS (ESI+) m/z 449.2 (M+1).

Example 41

Synthesis of 3-[(1E)-2-(1H-indol-7-yl)ethenyl]-5-[(1E)-2-[2-methoxy-4-(2-pyridylmethoxy)phenyl]ethenyl]-1H-pyrazole

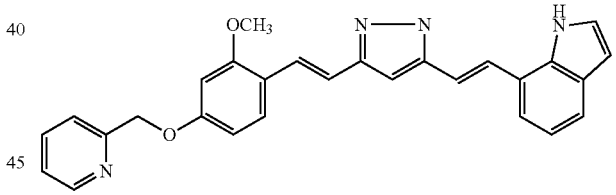

(1) Synthesis of (1E,6E)-1-(1H-indol-7-yl)-7-[2-methoxy-4-(2-pyridylmethoxy) phenyl]hepta-1,6-diene-3,5-dione Synthesis was performed in the same manner as in Example 30 (2) except that 20 mg (0.14 mmol) of 1H-indole-7-carboxaldehyde was used instead of 20 mg (0.14 mmol) of 1H-benzotriazole-5-carboxaldehyde to give 17.3 mg (28% yield) of the title compound as a brown powder.

(2) Synthesis of 3-[(1E)-2-(1H-indol-7-yl)ethenyl]-5-[(1E)-2-[2-methoxy-4-(2-pyridylmethoxy)phenyl]ethenyl]-1H-pyrazole Synthesis was performed in the same manner as in Example 4 (4) except that 15 mg (35 µmol) of (1E,6E)-1-(1H-indol-7-yl)-7-[2-methoxy-4-(2-pyridylmethoxy) phenyl]hepta-1,6-diene-3,5-dione was used instead of 15 mg (35 µmol) of (1E,6E)-1-(1H-indol-5-yl)-7-[4-(2-pyridylmethoxy) phenyl]hepta-1,6-diene-3,5-dione to give 6.1 mg (41% yield) of the title compound as a pale yellowish white powder with the following properties.

$^1$H NMR (δ, acetone-d$_6$): 3.91 (s, 3H), 5.22 (s, 2H), 6.51 (d, J=3.1 Hz, 1H), 6.65 (dd, J=2.4, 8.6 Hz, 1H), 6.74 (s, 1H), 6.74 (d, J=2.4 Hz, 1H), 7.05 (d, J=7.8 Hz, 1H), 7.06 (d, J=17 Hz, 1H), 7.23 (d, J=17 Hz, 1H), 7.31 (dd, J=5, 7 Hz, 1H), 7.38 (d, J=17 Hz, 1H), 7.38 (br d, J=3.1 Hz, 1H), 7.43 (d, J=7.3 Hz, 1H), 7.52 (d, J=7.7 Hz, 1H), 7.53 (d, J=8.5 Hz, 1H), 7.56 (d, J=7.9 Hz, 1H), 7.69 (d, J=17 Hz, 1H), 7.82 (dt, J=1.7, 7.7 Hz, 1H), 8.58 (br d, J=5 Hz, 1H), 10.6 (br s, NH). melting point 99-110° C., MS (ESI+) m/z 449.0 (M+1).

Example 42

Synthesis of 3-[(1E)-2-(1H-indol-3-yl)ethenyl]-5-[(1E)-2-[2-methoxy-4-(3-pyridylmethoxy)phenyl]ethenyl]-1H-pyrazole

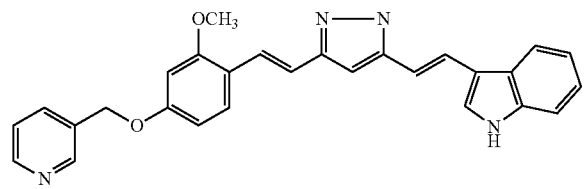 [SMILES: COc1cc(OCc2cccnc2)ccc1/C=C/c1cc(/C=C/c2c[nH]c3ccccc23)[nH]n1]

(1) Synthesis of (1E,6E)-1-(1H-indol-3-yl)-7-[2-methoxy-4-(3-pyridylmethoxy) phenyl]hepta-1,6-diene-3,5-dione Synthesis was performed in the same manner as in Example 10 (2) except that 33 mg (0.14 mmol) of 2-methoxy-4-(3-pyridylmethoxy)benzaldehyde was used instead of 29 mg (0.14 mmol) of 4-(2-pyridylmethoxy)benzaldehyde to give 20.7 mg (34% yield) of the title compound as an orange powder with the following properties.

(2) Synthesis of 3-[(1E)-2-(1H-indol-3-yl)ethenyl]-5-[(1E)-2-[2-methoxy-4-(3-pyridylmethoxy)phenyl]ethenyl]-1H-pyrazole Synthesis was performed in the same manner as in Example 4 (4) except that 15 mg (35 μmol) of (1E,6E)-1-(1H-indol-3-yl)-7-[2-methoxy-4-(3-pyridylmethoxy) phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 2.7 mg (18% yield) of the title compound as a pale yellowish white powder with the following properties.

$^1$H NMR (δ, acetone-d$_6$): 3.90 (s, 3H), 5.22 (s, 2H), 6.66 (s, 1H), 6.68 (dd, J=2.3, 8.6 Hz, 1H), 6.71 (d, J=2.3 Hz, 1H), 7.06 (d, J=17 Hz, 1H), 7.09 (d, J=17 Hz, 1H), 7.1-7.2 (m, 2H), 7.37 (d, J=17 Hz, 1H), 7.40 (m, 1H), 7.42 (d, J=17 Hz, 1H), 7.45 (dd, J=1.7, 5.5 Hz, 1H), 7.54 (d, J=8.5 Hz, 1H) 7.59 (s, 1H), 7.89 (br d, J=7.8 Hz, 1H), 7.97 (br d, J=6.8 Hz, 1H), 8.55 (dd, J=2.5, 4.8 Hz, 1H), 8.72 (d, J=1.7 Hz, 1H), 10.5 (br s, NH). melting point 129-137° C., MS (ESI+) m/z 449.1 (M+1).

Example 43

Synthesis of 3-[(1E)-2-(1H-indol-3-yl)ethenyl]-5-[(1E)-2-[2-methoxy-4-(4-pyridylmethoxy)phenyl]ethenyl]-1H-pyrazole

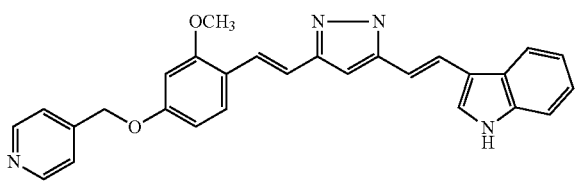 [SMILES: COc1cc(OCc2ccncc2)ccc1/C=C/c1cc(/C=C/c2c[nH]c3ccccc23)[nH]n1]

(1) Synthesis of (1E,6E)-1-(1H-indol-3-yl)-7-[2-methoxy-4-(4-pyridylmethoxy) phenyl]hepta-1,6-diene-3,5-dione Synthesis was performed in the same manner as in Example 10 (2) except that 33 mg (0.14 mmol) of 2-methoxy-4-(4-pyridylmethoxy)benzaldehyde was used instead of 29 mg (0.14 mmol) of 4-(2-pyridylmethoxy)benzaldehyde to give 61 mg (quantitative yield) of the title compound as an orange powder with the following properties.

(2) Synthesis of 3-[(1E)-2-(1H-indol-3-yl)ethenyl]-5-[(1E)-2-[2-methoxy-4-(4-pyridylmethoxy)phenyl]ethenyl]-1H-pyrazole Synthesis was performed in the same manner as in Example 4 (4) except that 15 mg (35 μmol) of (1E,6E)-1-(1H-indol-3-yl)-7-[2-methoxy-4-(4-pyridylmethoxy) phenyl]hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 3.4 mg (23% yield) of the title compound as a pale yellowish white powder with the following properties.

$^1$H NMR (δ, acetone-d$_6$): 3.90 (s, 3H), 5.24 (s, 2H), 6.64 (dd, J=2.3, 8.5 Hz, 1H), 6.65 (s, 1H), 6.73 (d, J=2.3 Hz, 1H), 7.05 (d, J=17 Hz, 1H), 7.09 (d, J=17 Hz, 1H), 7.1-7.2 (m, 2H), 7.37 (d, J=17 Hz, 1H), 7.43 (d, J=17 Hz, 1H), 7.43-7.46 (m, 3H), 7.54 (d, J=8.5 Hz, 1H), 7.59 (s, 1H), 7.97 (br d, J=7.2 Hz, 1H), 8.59 (dd, J=1.4, 4.4 Hz, 2H), 10.5 (br s, NH). melting point 128-139° C., MS (ESI+) m/z 449.2 (M+1).

Example 44

Synthesis of 3-[(1E)-2-(1H-indol-5-yl)ethenyl]-5-[(1E)-2-[2-methoxy-4-(3-pyridylmethoxy)phenyl]ethenyl]-1H-pyrazole

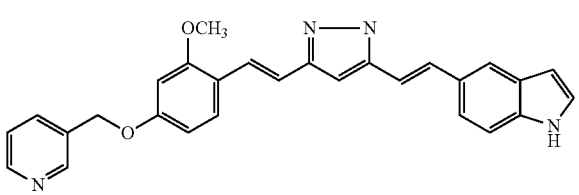 [SMILES: COc1cc(OCc2cccnc2)ccc1/C=C/c1cc(/C=C/c2ccc3[nH]ccc3c2)[nH]n1]

(1) Synthesis of (1E,6E)-1-(1H-indol-5-yl)-7-[2-methoxy-4-(3-pyridylmethoxy) phenyl]hepta-1,6-diene-3,5-dione Synthesis was performed in the same manner as in Example 4 (3) except that 33 mg (0.14 mmol) of 2-methoxy-4-(3-pyridylmethoxy)benzaldehyde was used instead of 29 mg (0.14 mmol) of 4-(2-pyridylmethoxy)benzaldehyde to give 32.4 mg (53% yield) of the title compound as a brown powder with the following properties.

(2) Synthesis of 3-[(1E)-2-(1H-indol-5-yl)ethenyl]-5-[(1E)-2-[2-methoxy-4-(3-pyridylmethoxy)phenyl]ethenyl]-1H-pyrazole Synthesis was performed in the same manner as in Example 4 (4) except that 15 mg (35 μmol) of (1E,6E)-1-(1H-indol-5-yl)-7-[2-methoxy-4-(3-pyridylmethoxy) phenyl]hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 2.8 mg (19% yield) of the title compound as a pale yellowish white powder with the following properties.
$^1$H NMR (δ, acetone-$d_6$): 3.90 (s, 3H), 5.22 (s, 2H), 6.48 (d, J=3.0 Hz, 1H), 6.67 (dd, J=2.4, 8.5 Hz, 1H), 6.68 (s, 1H), 6.71 (d, J=2.4 Hz, 1H), 7.05 (d, J=17 Hz, 1H), 7.06 (d, J=17 Hz, 1H), 7.28-7.34 (m, 3H), 7.38 (d, J=17 Hz, 1H), 7.38-7.42 (m, 2H), 7.54 (d, J=8.5 Hz, 1H), 7.72 (s, 1H), 7.89 (br d, J=7.9 Hz, 1H), 8.55 (dd, J=1.4, 4.7 Hz, 1H), 8.71 (br s, 1H), 10.3 (br s, NH). melting point 127-135° C., MS (ESI+) m/z 449.1 (M+1).

Example 45

Synthesis of 3-[(1E)-2-(1H-indol-5-yl)ethenyl]-5-[(1E)-2-[2-methoxy-4-(4-pyridylmethoxy)phenyl]ethenyl]-1H-pyrazole

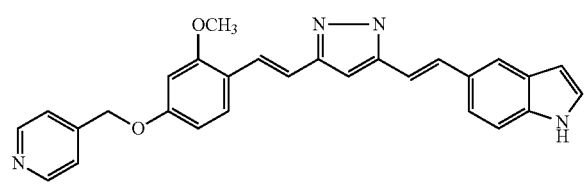 [SMILES: COc1cc(OCc2ccncc2)ccc1/C=C/c1cc(/C=C/c2ccc3[nH]ccc3c2)[nH]n1]

(1) Synthesis of (1E,6E)-1-(1H-indol-5-yl)-7-[2-methoxy-4-(4-pyridylmethoxy) phenyl]hepta-1,6-diene-3,5-dione Synthesis was performed in the same manner as in Example 4 (3) except that 33 mg (0.14 mmol) of 2-methoxy-4-(4-pyridylmethoxy)benzaldehyde was used instead of 29 mg (0.14 mmol) of 4-(2-pyridylmethoxy)benzaldehyde to give 30.4 mg (50% yield) of the title compound as an orange powder with the following properties.

(2) Synthesis of 3-[(1E)-2-(1H-indol-5-yl)ethenyl]-5-[(1E)-2-[2-methoxy-4-(4-pyridylmethoxy)phenyl]ethenyl]-1H-pyrazole Synthesis was performed in the same manner as in Example 4 (4) except that 15 mg (35 μmol) of (1E,6E)-1-(1H-indol-5-yl)-7-[2-methoxy-4-(4-pyridylmethoxy) phenyl]hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 2.9 mg (19% yield) of the title compound as a pale yellowish white powder with following properties.
$^1$H NMR (δ, acetone-$d_6$): 3.90 (s, 3H), 5.24 (s, 2H), 6.48 (d, J=2.7 Hz, 1H), 6.65 (dd, J=2.4, 8.5 Hz, 1H), 6.67 (s, 1H), 6.73 (d, J=2.4 Hz, 1H), 7.05 (d, J=17 Hz, 1H), 7.06 (d, J=17 Hz, 1H), 7.28-7.36 (m, 3H), 7.38-7.46 (m, 4H), 7.53 (d, J=8.5 Hz, 1H), 7.72 (s, 1H), 8.58 (br d, J=4 Hz, 2H), 10.3 (br s, NH). melting point 133-141° C., MS (ESI+) m/z 449.0 (M+1).

Example 46

Synthesis of 3-[(1E)-2-(1H-indol-6-yl)ethenyl]-5-[(1E)-2-[2-methoxy-4-(3-pyridylmethoxy)phenyl]ethenyl]-1H-pyrazole

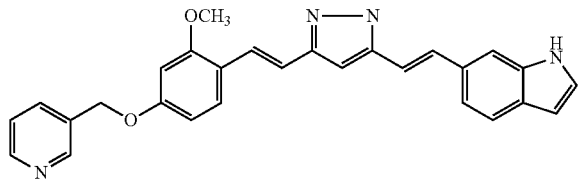 [SMILES: COc1cc(OCc2cccnc2)ccc1/C=C/c1cc(/C=C/c2ccc3cc[nH]c3c2)[nH]n1]

(1) Synthesis of (1E,6E)-1-(1H-indol-6-yl)-7-[2-methoxy-4-(3-pyridylmethoxy) phenyl]hepta-1,6-diene-3,5-dione Synthesis was performed in the same manner as in Example 16 (1) except that 33 mg (0.14 mmol) of 2-methoxy-4-(3-pyridylmethoxy)benzaldehyde was used instead of 29 mg (0.14 mmol) of 4-(2-pyridylmethoxy)benzaldehyde to give 31.0 mg (51% yield) of the title compound as a brown powder with the following properties.

(2) Synthesis of 3-[(1E)-2-(1H-indol-6-yl)ethenyl]-5-[(1E)-2-[2-methoxy-4-(3-pyridylmethoxy)phenyl]ethenyl]-1H-pyrazole Synthesis was performed in the same manner as in Example 4 (4) except that 15 mg (35 μmol) of (1E,6E)-1-(1H-indol-6-yl)-7-[2-methoxy-4-(3-pyridylmethoxy) phenyl]hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 5.0 mg (33% yield) of the title compound as a pale yellowish white powder with the following properties.
$^1$H NMR (δ, acetone-$d_6$): 3.90 (s, 3H), 5.22 (s, 2H), 6.45 (dd, J=0.7, 3.0 Hz, 1H), 6.67 (dd, J=2.4, 8.4 Hz, 1H), 6.69 (s, 1H), 6.72 (d, J=2.4 Hz, 1H), 7.06 (d, J=17 Hz, 1H), 7.09 (d, J=17 Hz, 1H), 7.30 (d, J=17 Hz, 1H), 7.31 (dd, J=1.3, 8.2 Hz, 1H), 7.34 (m, 1H), 7.38 (d, J=17 Hz, 1H), 7.40 (dd, J=4.8, 7.2 Hz, 1H), 7.54 (d, J=8.5 Hz, 1H), 7.55 (d, J=8.2 Hz, 1H), 7.57 (br s, 1H), 7.89 (br d, J=7.8 Hz, 1H), 8.55 (dd, J=1.5, 4.7 Hz, 1H), 8.72 (d, J=1.8 Hz, 1H), 10.3 (br s, NH). melting point 90-95° C., MS (ESI+) m/z 449.2 (M+1).

Example 47

Synthesis of 3-[(1E)-2-(1H-indol-6-yl)ethenyl]-5-[(1E)-2-[2-methoxy-4-(4-pyridylmethoxy)phenyl]ethenyl]-1H-pyrazole

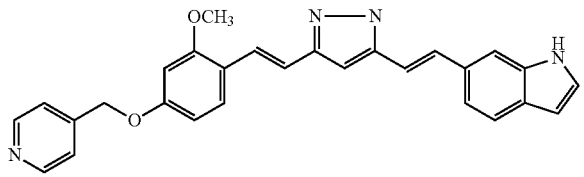 [SMILES: COc1cc(OCc2ccncc2)ccc1/C=C/c1cc(/C=C/c2ccc3cc[nH]c3c2)[nH]n1]

(1) Synthesis of (1E,6E)-1-(1H-indol-6-yl)-7-[2-methoxy-4-(4-pyridylmethoxy) phenyl]hepta-1,6-diene-3,5-dione Synthesis was performed in the same manner as in Example 16 (1) except that 33 mg (0.14 mmol) of 2-methoxy-4-(4-pyridylmethoxy)benzaldehyde was used instead of 29 mg (0.14 mmol) of 4-(2-pyridylmethoxy)benzaldehyde to give 42.0 mg (69% yield) of the title compound as an orange powder with the following properties.

(2) Synthesis of 3-[(1E)-2-(1H-indol-6-yl)ethenyl]-5-[(1E)-2-[2-methoxy-4-(4-pyridylmethoxy)phenyl]ethenyl]-1H-pyrazole Synthesis was performed in the same manner as in Example 4 (4) except that 15 mg (35 μmol) of (1E,6E)-1-(1H-indol-6-yl)-7-[2-methoxy-4-(4-pyridylmethoxy) phenyl]hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 5.0 mg (33% yield) of the title compound as a pale yellowish white powder with the following properties.

$^1$H NMR (δ, acetone-$d_6$): 3.90 (s, 3H), 5.24 (s, 2H), 6.45 (br d, J=3 Hz, 1H), 6.65 (dd, J=2.4, 8.6 Hz, 1H), 6.68 (s, 1H), 6.73 (d, J=2.4 Hz, 1H), 7.06 (d, J=17 Hz, 1H), 7.09 (d, J=17 Hz, 1H), 7.30 (d, J=17 Hz, 1H), 7.31 (dd, J=1.4, 8.2 Hz, 1H), 7.34 (m, 1H), 7.37 (d, J=17 Hz, 1H), 7.45 (br d, J=5 Hz, 2H), 7.53 (d, J=8 Hz, 1H), 7.55 (d, J=8 Hz, 1H), 7.57 (br s, 1H), 8.59 (dd, J=1.4, 4.5 Hz, 2H), 10.3 (br s, NH). melting point 103-118° C., MS (ESI+) m/z 449.2 (M+1).

Example 48

Synthesis of 3-[(1E)-2-(1H-indol-4-yl)ethenyl]-5-[(1E)-2-[2-methoxy-4-(3-pyridylmethoxy)phenyl]ethenyl]-1H-pyrazole

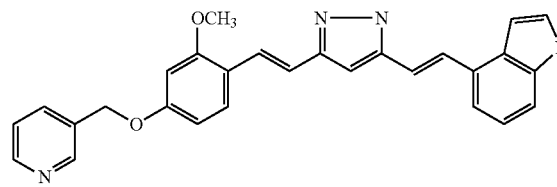

(1) Synthesis of (1E,6E)-1-(1H-indol-4-yl)-7-[2-methoxy-4-(3-pyridylmethoxy) phenyl]hepta-1,6-diene-3,5-dione In a 20 mL reaction vessel were placed 31.0 mg (136 μmol) of 6-(1H-indol-4-yl)hex-5-ene-2,4-dione and 13.2 mg (0.190 mmol) of boron oxide and they were dissolved in 0.88 mL of ethyl acetate. To the mixture under stirring at 70° C., 33 mg (0.14 mmol) of 2-methoxy-4-(3-pyridylmethoxy)benzaldehyde and 62 μL (0.27 mmol) of triisopropyl borate were sequentially added. After the mixture was stirred at the same temperature for 1 hour, a solution of 2.7 μL (27 μmol) of piperidine in ethyl acetate (0.135 mL) was added and the mixture was further stirred for 1 hour. To the reaction mixture was added a 1:1 solution (0.4 mL) of 1 N hydrochloric acid and saturated brine at room temperature and the mixture was stirred for 5 minutes to 1 hour (further, the mixture was neutralized with a saturated sodium bicarbonate aqueous solution as needed). The resulting organic phase was directly subjected to purification by silica gel column chromatography (hexane/ethyl acetate or methylene chloride/methanol) to give 42.8 mg (70% yield) of the title compound as an orange powder.

(2) Synthesis of 3-[(1E)-2-(1H-indol-4-yl)ethenyl]-5-[(1E)-2-[2-methoxy-4-(3-pyridylmethoxy)phenyl]ethenyl]-1H-pyrazole Synthesis was performed in the same manner as in Example 4 (4) except that 15 mg (35 μmol) of (1E,6E)-1-(1H-indol-4-yl)-7-[2-methoxy-4-(3-pyridylmethoxy) phenyl]hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 6.4 mg (43% yield) of the title compound as a pale yellowish white powder with the following properties.

$^1$H NMR (δ, acetone-$d_6$): 3.91 (s, 3H), 5.22 (s, 2H), 6.68 (dd, J=2.4, 8.4 Hz, 1H), 6.72 (d, J=2.4 Hz, 1H), 6.78 (s, 1H), 6.88 (br d, J=3 Hz, 1H), 7.08 (d, J=17 Hz, 1H), 7.13 (t, J=7.7 Hz, 1H), 7.29 (d, J=17 Hz, 1H), 7.32 (d, J=6.9 Hz, 1H), 7.36-7.42 (m, 4H), 7.55 (d, J=8.5 Hz, 1H), 7.64 (d, J=17 Hz, 1H), 7.89 (br d, J=7.8 Hz, 1H), 8.56 (dd, J=1.6, 4.7 Hz, 1H), 8.72 (d, J=1.8 Hz, 1H), 10.4 (br s, NH). melting point 109-114° C., MS (ESI+) m/z 449.1 (M+1).

Example 49

Synthesis of 3-[(1E)-2-(1H-indol-4-yl)ethenyl]-5-[(1E)-2-[2-methoxy-4-(4-pyridylmethoxy)phenyl]ethenyl]-1H-pyrazole

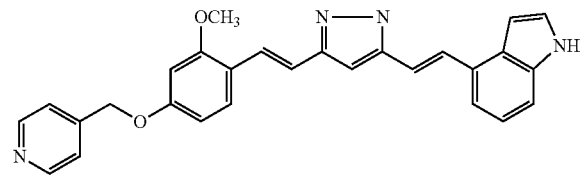 [SMILES: COc1cc(OCc2ccncc2)ccc1/C=C/c1cc(/C=C/c2cccc3[nH]ccc23)[nH]n1]

(1) Synthesis of (1E,6E)-1-(1H-indol-4-yl)-7-[2-methoxy-4-(4-pyridylmethoxy) phenyl]hepta-1,6-diene-3,5-dione Synthesis was performed in the same manner as in Example 49 (1) except that 33 mg (0.14 mmol) of 2-methoxy-4-(4-pyridylmethoxy)benzaldehyde was used instead of 33 mg (0.14 mmol) of 2-methoxy-4-(3-pyridylmethoxy)benzaldehyde to give 56.0 mg (92% yield) of the title compound as an orange powder with the following properties.

(2) Synthesis of 3-[(1E)-2-(1H-indol-4-yl)ethenyl]-5-[(1E)-2-[2-methoxy-4-(4-pyridylmethoxy)phenyl]ethenyl]-1H-pyrazole Synthesis was performed in the same manner as in Example 4 (4) except that 15 mg (35 μmol) of (1E,6E)-1-(1H-indol-4-yl)-7-[2-methoxy-4-(4-pyridylmethoxy) phenyl]hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 9.1 mg (61% yield) of the title compound as a pale yellowish white powder with the following properties.

$^1$H NMR (δ, acetone-$d_6$): 3.91 (s, 3H), 5.24 (s, 2H), 6.65 (dd, J=2.4, 8.5 Hz, 1H), 6.73 (d, J=2.4 Hz, 1H), 6.78 (s, 1H), 6.88 (d, J=3 Hz, 1H), 7.08 (d, J=17 Hz, 1H), 7.13 (t, J=7.7 Hz, 1H), 7.29 (d, J=17 Hz, 1H), 7.32-7.42 (m, 4H), 7.46 (br d, J=5 Hz, 2H), 7.54 (d, J=8.5 Hz, 1H), 7.64 (d, J=17 Hz, 1H), 8.59 (br d, J=5 Hz, 2H), 10.4 (br s, NH). melting point 207-215° C., MS (ESI+) m/z 449.1 (M+1).

Example 50

Synthesis of 3-[(1E)-2-(1H-indol-7-yl)ethenyl]-5-[(1E)-2-[2-methoxy-4-(3-pyridylmethoxy)phenyl]ethenyl]-1H-pyrazole

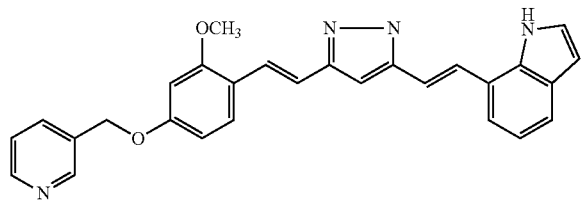 [SMILES: COc1cc(OCc2cccnc2)ccc1/C=C/c1cc(/C=C/c2cccc3cc[nH]c23)[nH]n1]

(1) Synthesis of (1E,6E)-1-(1H-indol-7-yl)-7-[2-methoxy-4-(3-pyridylmethoxy) phenyl]hepta-1,6-diene-3,5-dione In a 20 mL reaction vessel were placed 88 mg (0.27 mmol) of 6-[2-methoxy-4-(3-pyridylmethoxy)phenyl]hex-5-ene-2,4-dione and 26.4 mg (0.380 mmol) of boron oxide and they were dissolved in 1.76 mL of ethyl acetate. To the mixture under stirring at 70° C., 40 mg (0.27 mmol) of 1H-indole-7-carboxaldehyde and 124 µL (0.54 mmol) of triisopropyl borate were sequentially added. After the mixture was stirred at the same temperature for 1 hour, a solution of 5.4 µL (54 µmol) of piperidine in ethyl acetate (0.27 mL) was added and the mixture was further stirred for 1 hour. To the reaction mixture was added a 1:1 solution (0.8 mL) of 1 N hydrochloric acid and saturated brine at room temperature and the mixture was stirred for 5 minutes to 1 hour (further, the mixture was neutralized with a saturated sodium bicarbonate aqueous solution as needed). The resulting organic phase was directly subjected to purification by silica gel column chromatography (hexane/ethyl acetate or methylene chloride/methanol) to give 21.6 mg (18% yield) of the title compound as a yellow powder.

(2) Synthesis of 3-[(1E)-2-(1H-indol-7-yl)ethenyl]-5-[(1E)-2-[2-methoxy-4-(3-pyridylmethoxy)phenyl]ethenyl]-1H-pyrazole Synthesis was performed in the same manner as in Example 4 (4) except that 15 mg (35 µmol) of (1E,6E)-1-(1H-indol-7-yl)-7-[2-methoxy-4-(3-pyridylmethoxy) phenyl]hepta-1,6-diene-3,5-dione was used instead of 15 mg (35 µmol) of (1E,6E)-1-(1H-indol-5-yl)-7-[4-(2-pyridylmethoxy) phenyl]hepta-1,6-diene-3,5-dione to give 7.2 mg (48% yield) of the title compound as a yellowish white powder with the following properties.

$^1$H NMR (δ, acetone-$d_6$): 3.91 (s, 3H), 5.22 (s, 2H), 6.52 (d, J=3.2 Hz, 1H), 6.68 (dd, J=2.3, 8.5 Hz, 1H), 6.73 (d, J=2.3 Hz, 1H), 6.74 (s, 1H), 7.06 (t, J=7.7 Hz, 1H), 7.07 (d, J=17 Hz, 1H), 7.23 (d, J=17 Hz, 1H), 7.38 (d, J=17 Hz, 1H), 7.40 (m, 1H), 7.38 (br d, J=3.4 Hz, 1H), 7.43 (d, J=7.6 Hz, 1H), 7.53 (d, J=8 Hz, 1H), 7.55 (d, J=8.5 Hz, 1H), 7.70 (d, J=17 Hz, 1H), 7.89 (br d, J=7.8 Hz, 1H), 8.56 (br d, J=5 Hz, 1H), 8.71 (br s, 1H), 10.6 (br s, NH). melting point 122-129° C., MS (ESI+) m/z 449.1 (M+1).

Example 51

Synthesis of 3-[(1E)-2-(1H-indol-7-yl)ethenyl]-5-[(1E)-2-[2-methoxy-4-(4-pyridylmethoxy)phenyl]ethenyl]-1H-pyrazole

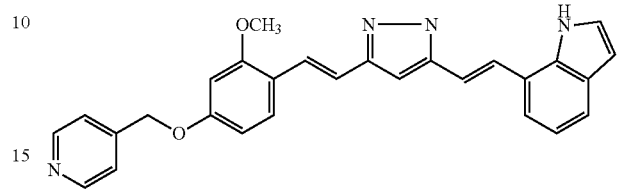

(1) Synthesis of (1E,6E)-1-(1H-indol-7-yl)-7-[2-methoxy-4-(4-pyridylmethoxy) phenyl]hepta-1,6-diene-3,5-dione In a 20 mL reaction vessel were placed 88 mg (0.27 mmol) of 6-[2-methoxy-4-(4-pyridylmethoxy)phenyl]hex-5-ene-2,4-dione and 26.4 mg (0.380 mmol) of boron oxide and they were dissolved in 1.76 mL of ethyl acetate. To the mixture under stirring at 70° C., 40 mg (0.27 mmol) of 1H-indole-7-carboxaldehyde and 124 µL (0.54 mmol) of triisopropyl borate were sequentially added. After the mixture was stirred at the same temperature for 1 hour, a solution of 5.4 µL (54 µmol) of piperidine in ethyl acetate (0.27 mL) was added and the mixture was further stirred for 1 hour. To the reaction mixture was added a 1:1 solution (0.8 mL) of 1 N hydrochloric acid and saturated brine at room temperature and the mixture was stirred for 5 minutes to 1 hour (further, the mixture was neutralized with a saturated sodium bicarbonate aqueous solution as needed). The resulting organic phase was directly subjected to purification by silica gel column chromatography (hexane/ethyl acetate or methylene chloride/methanol) to give 43.5 mg (36% yield) of the title compound as a yellow powder.

(2) Synthesis of 3-[(1E)-2-(1H-indol-7-yl)ethenyl]-5-[(1E)-2-[2-methoxy-4-(4-pyridylmethoxy)phenyl]ethenyl]-1H-pyrazole Synthesis was performed in the same manner as in Example 4 (4) except that 15 mg (35 µmol) of (1E,6E)-1-(1H-indol-7-yl)-7-[2-methoxy-4-(4-pyridylmethoxy) phenyl]hepta-1,6-diene-3,5-dione was used instead of 15 mg (35 µmol) of (1E,6E)-1-(1H-indol-5-yl)-7-[4-(2-pyridylmethoxy) phenyl]hepta-1,6-diene-3,5-dione to give 3.4 mg (23% yield) of the title compound as a pale yellowish white powder with the following properties.

$^1$H NMR (δ, acetone-$d_6$): 3.91 (s, 3H), 5.25 (s, 2H), 6.52 (br d, J=3.2 Hz, 1H), 6.65 (dd, J=2.4, 8.5 Hz, 1H), 6.73 (d, J=2.4 Hz, 1H), 6.74 (s, 1H), 7.06 (t, J=7.7 Hz, 1H), 7.06 (d, J=17 Hz, 1H), 7.23 (d, J=17 Hz, 1H), 7.38 (d, J=17 Hz, 1H), 7.38 (br d, J=3.2 Hz, 1H), 7.43 (d, J=7.3 Hz, 1H), 7.46 (br d, J=5.8 Hz, 2H), 7.52 (d, J=7.4 Hz, 1H), 7.54 (d, J=8.5 Hz, 1H), 7.70 (d, J=17 Hz, 1H), 8.59 (br d, J=5 Hz, 2H), 10.7 (br s, NH). melting point 201-206° C., MS (ESI+) m/z 449.2 (M+1).

Example 52

Synthesis of 3-[(1E)-2-(1H-indol-2-yl)ethenyl]-5-[(1E)-2-[2-methoxy-4-(3-pyridylmethoxy)phenyl]ethenyl]-1H-pyrazole

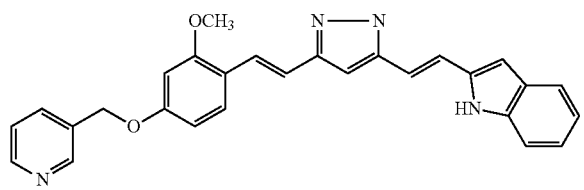 [SMILES: COc1cc(OCc2cccnc2)ccc1/C=C/c1cc(/C=C/c2cc3ccccc3[nH]2)[nH]n1]

(1) Synthesis of (1E,6E)-1-(1H-indol-2-yl)-7-[2-methoxy-4-(3-pyridylmethoxy) phenyl]hepta-1,6-diene-3,5-dione Synthesis was performed in the same manner as in Example 51 (1) except that 40 mg (0.27 mmol) of 1H-indole-2-carboxaldehyde was used instead of 40 mg (0.27 mmol) of 1H-indole-7-carboxaldehyde to give 44.4 mg (36% yield) of the title compound as a brown powder with the following properties.

(2) Synthesis of 3-[(1E)-2-(1H-indol-2-yl)ethenyl]-5-[(1E)-2-[2-methoxy-4-(3-pyridylmethoxy)phenyl]ethenyl]-1H-pyrazole Synthesis was performed in the same manner as in Example 4 (4) except that 15 mg (35 μmol) of (1E,6E)-1-(1H-indol-2-yl)-7-[2-methoxy-4-(3-pyridylmethoxy) phenyl]hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 6.3 mg (42% yield) of the title compound as a yellowish white powder with the following properties.

$^1$H NMR (δ, acetone-d$_6$): 3.90 (s, 3H), 5.22 (s, 2H), 6.58 (s, 1H), 6.68 (dd, J=2.3, 8.6 Hz, 1H), 6.69 (s, 1H), 6.72 (d, J=2.3 Hz, 1H), 6.98 (t, J=7 Hz, 1H), 7.04-7.14 (m, 3H), 7.24 (d, J=17 Hz, 1H), 7.34 (d, J=8.1 Hz, 1H), 7.38 (d, J=17 Hz, 1H), 7.40 (dd, J=5, 7 Hz, 1H), 7.50 (d, J=7.9 Hz, 1H), 7.53 (d, J=8.6 Hz, 1H), 7.89 (br d, J=7.8 Hz, 1H), 8.56 (dd, J=1.4, 4.7 Hz, 1H), 8.71 (d, J=1 Hz, 1H), 10.6 (br s, NH). melting point 126-138° C., MS (ESI+) m/z 449.1 (M+1).

Example 53

Synthesis of 3-[(1E)-2-(1H-indol-2-yl)ethenyl]-5-[(1E)-2-[2-methoxy-4-(4-pyridylmethoxy)phenyl]ethenyl]-1H-pyrazole

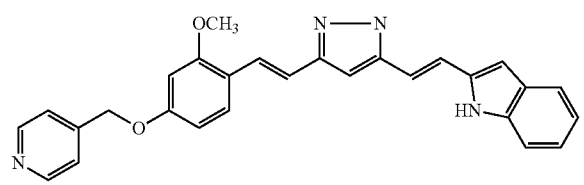 [SMILES: COc1cc(OCc2ccncc2)ccc1/C=C/c1cc(/C=C/c2cc3ccccc3[nH]2)[nH]n1]

(1) Synthesis of (1E,6E)-1-(1H-indol-2-yl)-7-[2-methoxy-4-(4-pyridylmethoxy) phenyl]hepta-1,6-diene-3,5-dione In a 20 mL reaction vessel were placed 31.0 mg (136 μmol) of 6-(1H-indol-2-yl)hex-5-ene-2,4-dione and 13.2 mg (0.190 mmol) of boron oxide and they were dissolved in 0.88 mL of ethyl acetate. To the mixture under stirring at 70° C., 33 mg (0.14 mmol) of 2-methoxy-4-(4-pyridylmethoxy)benzaldehyde and 62 μL (0.27 mmol) of triisopropyl borate were sequentially added. After the mixture was stirred at the same temperature for 1 hour, a solution of 2.7 μL (27 μmol) of piperidine in ethyl acetate (0.135 mL) was added and the mixture was further stirred for 1 hour. To the reaction mixture was added a 1:1 solution (0.4 mL) of 1 N hydrochloric acid and saturated brine at room temperature and the mixture was stirred for 5 minutes to 1 hour (further, the mixture was neutralized with a saturated sodium bicarbonate aqueous solution as needed). The resulting organic phase was directly subjected to purification by silica gel column chromatography (hexane/ethyl acetate or methylene chloride/methanol) to give 47.3 mg (78% yield) of the title compound as an orange powder.

(2) Synthesis of 3-[(1E)-2-(1H-indol-2-yl)ethenyl]-5-[(1E)-2-[2-methoxy-4-(4-pyridylmethoxy)phenyl]ethenyl]-1H-pyrazole Synthesis was performed in the same manner as in Example 4 (4) except that 15 mg (35 μmol) of (1E,6E)-1-(1H-indol-2-yl)-7-[2-methoxy-4-(4-pyridylmethoxy) phenyl]hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 2.8 mg (19% yield) of the title compound as a pale yellowish white powder with the following properties.

$^1$H NMR (δ, acetone-d$_6$): 3.90 (s, 3H), 5.24 (s, 2H), 6.58 (s, 1H), 6.65 (dd, J=2.4, 8.5 Hz, 1H), 6.69 (s, 1H), 6.73 (d, J=2.4 Hz, 1H), 6.98 (br t, J=7 Hz, 1H), 7.06 (d, J=17 Hz, 1H), 7.09 (m, 1H), 7.10 (d, J=17 Hz, 1H), 7.23 (d, J=17 Hz, 1H), 7.34 (d, J=8 Hz, 1H), 7.38 (d, J=17 Hz, 1H), 7.46 (br d, J=5 Hz, 2H), 7.48 (d, J=8 Hz, 1H), 7.52 (d, J=8.7 Hz, 1H), 8.58 (dd, J=1.4, 4.4 Hz, 2H), 10.5 (br s, NH). melting point 124-134° C., MS (ESI+) m/z 449.1 (M+1).

Example 54

Synthesis of 3-[(1E)-2-(2,4-dimethoxyphenyl)ethenyl]-5-[(1E)-2-(1H-indol-6-yl)ethenyl]-1H-pyrazole

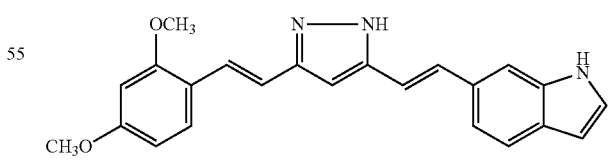

(1) Synthesis of (1E,6E)-1-(2,4-dimethoxyphenyl)-7-(1H-indol-6-yl)hepta-1,6-diene-3,5-dione Synthesis was performed in the same manner as in Example 16 (1) except that 21 mg (0.14 mmol) of 2,4-dimethoxybenzaldehyde was used instead of 29 mg (0.14 mmol) of 4-(2-pyridylmethoxy)benzaldehyde to give 43.6 mg (87% yield) of the title compound as an orange powder with the following properties.

(2) Synthesis of 3-[(1E)-2-(2,4-dimethoxyphenyl)ethenyl]-5-[(1E)-2-(1H-indol-6-yl)ethenyl]-1H-pyrazole Synthesis was performed in the same manner as in Example 4 (4) except that 15 mg (40 μmol) of (1E,6E)-1-(2,4-dimethoxyphenyl)-7-(1H-indol-6-yl)hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 8.6 mg (57% yield) of the title compound as a yellowish white powder with the following properties.

¹H NMR (δ, acetone-d₆): 3.82 (s, 3H), 3.89 (s, 3H), 6.45 (dd, J=1, 3 Hz, 1H), 6.56 (dd, J=2.3, 8.5 Hz, 1H), 6.58 (d, J=2.3 Hz, 1H), 6.67 (s, 1H), 7.04 (d, J=17 Hz, 1H), 7.09 (d, J=17 Hz, 1H), 7.30 (d, J=17 Hz, 1H), 7.30-7.35 (m, 2H), 7.37 (d, J=17 Hz, 1H), 7.52 (d, J=8.5 Hz, 1H), 7.55 (d, J=8.4 Hz, 1H), 7.57 (br s, 1H), 10.3 (br s, NH). melting point 121-133° C., MS (ESI+) m/z 372.2 (M+1).

Example 55

Synthesis of 3-[(1E)-2-[4-(acetylamino)phenyl]ethenyl]-5-[(1E)-2-(1H-indol-6-yl)ethenyl]-1H-pyrazole

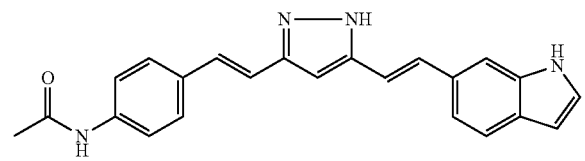 [SMILES: CC(=O)Nc1ccc(/C=C/c2cc(/C=C/c3ccc4cc[nH]c4c3)[nH]n2)cc1]

(1) Synthesis of (1E,6E)-1-[4-(acetylamino)phenyl]-7-(1H-indol-6-yl)hepta-1,6-diene-3,5-dione Synthesis was performed in the same manner as in Example 16 (1) except that 22 mg (0.14 mmol) of 4-(acetylamino)benzaldehyde was used instead of 29 mg (0.14 mmol) of 4-(2-pyridylmethoxy)benzaldehyde to give 40.6 mg (81% yield) of the title compound as a red powder with the following properties.

(2) Synthesis of 3-[(1E)-2-[4-(acetylamino)phenyl]ethenyl]-5-[(1E)-2-(1H-indol-6-yl)ethenyl]-1H-pyrazole Synthesis was performed in the same manner as in Example 4 (4) except that 15 mg (40 μmol) of (1E,6E)-1-[4-(acetylamino) phenyl]-7-(1H-indol-6-yl)hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 5.4 mg (36% yield) of the title compound as a pale yellowish white powder with the following properties.

¹H NMR (δ, acetone-d₆): 2.07 (s, 3H), 6.45 (dd, J=1, 3 Hz, 1H), 6.72 (s, 1H), 7.06 (d, J=17 Hz, 1H), 7.09 (d, J=17 Hz, 1H), 7.15 (d, J=17 Hz, 1H), 7.29 (d, J=17 Hz, 1H), 7.31 (dd, J=2, 8 Hz, 1H), 7.34 (d, J=3 Hz, 1H), 7.48 (d, J=8.6 Hz, 2H), 7.55 (d, J=8 Hz, 1H), 7.57 (br s, 1H), 7.66 (d, J=8.6 Hz, 2H), 10.3 (br s, NH). melting point>300° C., MS (ESI+) m/z 369.2 (M+1).

Example 56

Synthesis of 3-[(1E)-2-(1H-indol-6-yl)ethenyl]-5-[(1E)-2-(4-phenoxyphenyl)ethenyl]-1H-pyrazole

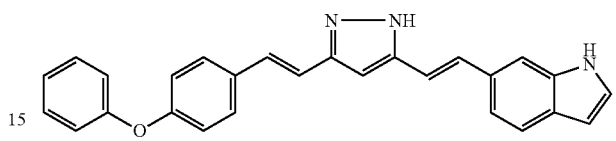

(1) Synthesis of (1E,6E)-1-(1H-indol-6-yl)-7-(4-phenoxyphenyl)hepta-1,6-diene-3,5-dione Synthesis was performed in the same manner as in Example 16 (1) except that 27 mg (0.14 mmol) of 4-phenoxybenzaldehyde was used instead of 29 mg (0.14 mmol) of 4-(2-pyridylmethoxy)benzaldehyde to give 40.1 mg (73% yield) of the title compound as a yellow powder with the following properties.

(2) Synthesis of 3-[(1E)-2-(1H-indol-6-yl)ethenyl]-5-[(1E)-2-(4-phenoxyphenyl)ethenyl]-1H-pyrazole Synthesis was performed in the same manner as in Example 4 (4) except that 15 mg (37 μmol) of (1E,6E)-1-(1H-indol-6-yl)-7-(4-phenoxyphenyl)hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 6.9 mg (46% yield) of the title compound as a pale yellowish white powder with the following properties.

¹H NMR (δ, acetone-d₆): 6.45 (br d, J=3 Hz, 1H), 6.74 (s, 1H), 7.01 (d, J=8.6 Hz, 2H), 7.04 (d, J=8 Hz, 2H), 7.09 (d, J=17 Hz, 1H), 7.09 (d, J=17 Hz, 1H), 7.15 (t, J=7.5 Hz, 1H), 7.20 (d, J=17 Hz, 1H), 7.30 (d, J=17 Hz, 1H), 7.31 (dd, J=1.2, 8.2 Hz, 1H), 7.34 (d, J=3.1 Hz, 1H), 7.40 (t, J=8 Hz, 2H), 7.55 (d, J=8 Hz, 1H), 7.57 (br s, 1H), 7.58 (d, J=9 Hz, 2H), 10.3 (br s, NH). melting point 175-182° C., MS (ESI+) m/z 404.2 (M+1).

Example 57

Synthesis of 3-[(1E)-2-(1H-indol-6-yl)ethenyl]-5-[(1E)-2-[4-(methanesulfonyl)phenyl]ethenyl]-1H-pyrazole

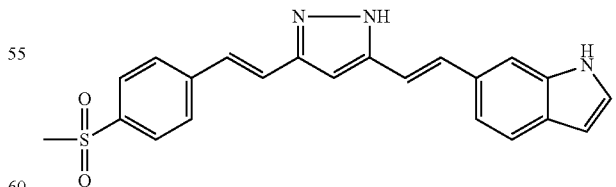

(1) Synthesis of (1E,6E)-1-(1H-indol-6-yl)-7-[4-(methanesulfonyl)phenyl]hepta-1,6-diene-3,5-dione Synthesis was performed in the same manner as in Example 16 (1) except that 25 mg (0.14 mmol) of 4-(methanesulfonyl)benzaldehyde was used instead of 29 mg (0.14 mmol) of 4-(2-pyridylmethoxy)benzaldehyde to give 14.4 mg (28% yield) of the title compound as a yellow powder with the following properties.

(2) Synthesis of 3-[(1E)-2-(1H-indol-6-yl)ethenyl]-5-[(1E)-2-[4-(methanesulfonyl)phenyl]ethenyl]-1H-pyrazole Synthesis was performed using the same materials in the same relative quantities as in Example 4 (4) except that 12 mg (31 µmol) of (1E,6E)-1-(1H-indol-6-yl)-7-[4-(methanesulfonyl)phenyl]hepta-1,6-diene-3,5-dione was used instead of 15 mg (35 µmol) of (1E,6E)-1-(1H-indol-5-yl)-7-[4-(2-pyridylmethoxy) phenyl]hepta-1,6-diene-3,5-dione to give 4.8 mg (40% yield) of the title compound as a pale yellowish white powder with the following properties.
$^1$H NMR (δ, acetone-$d_6$): 3.12 (s, 3H), 6.46 (br d, J=3 Hz, 1H), 6.82 (s, 1H), 7.11 (d, J=17 Hz, 1H), 7.30 (d, J=17 Hz, 1H), 7.30-7.36 (m, 3H), 7.38 (d, J=17 Hz, 1H), 7.56 (d, J=8 Hz, 1H), 7.58 (br s, 1H), 7.82 (d, J=8.4 Hz, 2H), 7.92 (d, J=8.4 Hz, 2H), 10.3 (br s, NH). melting point 260-268° C., MS (ESI+) m/z 390.2 (M+1).

Example 58

Synthesis of 3-[(1E)-2-(1H-indol-6-yl)ethenyl]-5-[(1E)-2-(5-methoxy-2-nitrophenyl)ethenyl]-1H-pyrazole

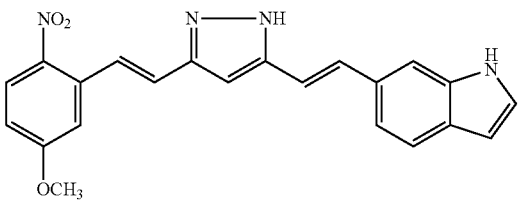

(1) Synthesis of (1E,6E)-1-(1H-indol-6-yl)-7-(5-methoxy-2-nitrophenyl) hepta-1,6-diene-3,5-dione Synthesis was performed in the same manner as in Example 16 (1) except that 25 mg (0.14 mmol) of 5-methoxy-2-nitrobenzaldehyde was used instead of 29 mg (0.14 mmol) of 4-(2-pyridylmethoxy)benzaldehyde to give 24.0 mg (46% yield) of the title compound as an orange powder with the following properties.

(2) Synthesis of 3-[(1E)-2-(1H-indol-6-yl)ethenyl]-5-[(1E)-2-(5-methoxy-2-nitrophenyl)ethenyl]-1H-pyrazole Synthesis was performed using the same materials in the same relative quantities as in Example 4 (4) except that 18 mg (47 µmol) of (1E,6E)-1-(1H-indol-6-yl)-7-(5-methoxy-2-nitrophenyl)hepta-1,6-diene-3,5-dione was used instead of 15 mg (35 µmol) of (1E,6E)-1-(1H-indol-5-yl)-7-[4-(2-pyridylmethoxy)phenyl]hepta-1,6-diene-3,5-dione to give 14.1 mg (78% yield) of the title compound as a yellow powder with the following properties.
$^1$H NMR (δ, acetone-$d_6$): 4.00 (s, 3H), 6.46 (br d, J=3 Hz, 1H), 6.81 (s, 1H), 7.04 (dd, J=2.8, 9.1 Hz, 1H), 7.11 (d, J=17 Hz, 1H), 7.21 (d, J=17 Hz, 1H), 7.32 (dd, J=1.4, 8 Hz, 1H), 7.33-7.38 (m, 3H), 7.56 (d, J=8.2 Hz, 1H), 7.58 (br s, 1H), 7.67 (d, J=17 Hz, 1H), 8.05 (d, J=9.1 Hz, 1H), 10.3 (br s, NH). melting point 104-109° C., MS (ESI) m/z 387.0 (M+1).

Example 59

Synthesis of 3-[(1E)-2-(1H-indol-6-yl)ethenyl]-5-[(1E)-2-[2-(3-pyridyl) phenyl]ethenyl]-1H-pyrazole

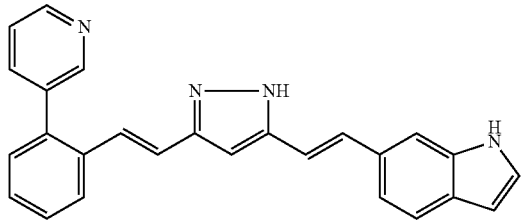 [SMILES: C(=C\c1cc(/C=C/c2ccccc2-c2cccnc2)n[nH]1)/c1ccc2cc[nH]c2c1]

(1) Synthesis of (1E,6E)-1-(1H-indol-6-yl)-7-[2-(3-pyridyl)phenyl]hepta-1,6-diene-3,5-dione Synthesis was performed in the same manner as in Example 16 (1) except that 25 mg (0.14 mmol) of 2-(3-pyridyl)benzaldehyde was used instead of 29 mg (0.14 mmol) of 4-(2-pyridylmethoxy)benzaldehyde to give 51.1 mg (96% yield) of the title compound as an orange powder with the following properties.

(2) Synthesis of 3-[(1E)-2-(1H-indol-6-yl)ethenyl]-5-[(1E)-2-[2-(3-pyridyl) phenyl]ethenyl]-1H-pyrazole Synthesis was performed using the same materials in the same relative quantities as in Example 4 (4) except that 20 mg (52 µmol) of (1E,6E)-1-(1H-indol-6-yl)-7-[2-(3-pyridyl)phenyl]hepta-1,6-diene-3,5-dione was used instead of 15 mg (35 µmol) of (1E,6E)-1-(1H-indol-5-yl)-7-[4-(2-pyridylmethoxy) phenyl]hepta-1,6-diene-3,5-dione to give 10.8 mg (54% yield) of the title compound as a yellowish white powder with the following properties.
$^1$H NMR (δ, acetone-$d_6$): 6.45 (dd, J=0.8, 3.1 Hz, 1H), 6.56 (s, 1H), 7.06 (d, J=17 Hz, 1H), 7.08 (d, J=17 Hz, 1H), 7.14 (d, J=17 Hz, 1H), 7.25 (d, J=17 Hz, 1H), 7.29 (dd, J=1.2, 8 Hz, 1H), 7.34 (d, J=3.1 Hz, 1H), 7.33-7.6 (m, 6H), 7.69 (m, 1H), 7.79 (ddd, J=1.8, 2.2, 7.9 Hz, 1H), 7.85 (br d, J=7.7 Hz, 1H), 8.61 (d, J=1.7 Hz, 1H), 10.3 (br s, NH). melting point 248-255° C., MS (ESI+) m/z 389.0 (M+1).

Example 60

Synthesis of 3-[(1E)-2-(2-bromo-5-hydroxy-4-methoxyphenyl)ethenyl]-5-[(1E)-2-(1H-indol-6-yl)ethenyl]-1H-pyrazole

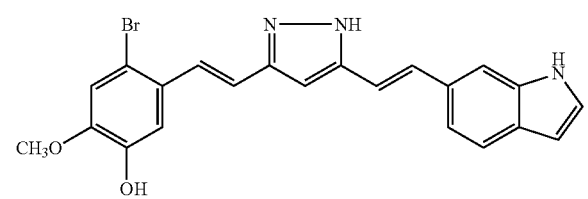

(1) Synthesis of (1E,6E)-1-(2-bromo-5-hydroxy-4-methoxyphenyl)-7-(1H-indol-6-yl)hepta-1,6-diene-3,5-dione Synthesis was performed in the same manner as in Example 16 (1) except that 31 mg (0.14 mmol) of 2-bromo-5-hydroxy-4-methoxybenzaldehyde was used instead of 29 mg (0.14 mmol) of 4-(2-pyridylmethoxy)benzaldehyde to give 20.7 mg (35% yield) of the title compound as a yellow powder with the following properties.

(2) Synthesis of 3-[(1E)-2-(2-bromo-5-hydroxy-4-methoxyphenyl)ethenyl]-5-[(1E)-2-(1H-indol-6-yl)ethenyl]-1H-pyrazole Synthesis was performed in the same manner as in Example 4 (4) except that 15 mg (34 μmol) of (1E,6E)-1-(2-bromo-5-hydroxy-4-methoxyphenyl)-7-(1H-indol-6-yl)hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 5.2 mg (35% yield) of the title compound as a pale yellowish white powder with the following properties.

$^1$H NMR (δ, acetone-$d_6$): 3.89 (s, 3H), 6.46 (br d, J=3 Hz, 1H), 6.75 (s, 1H), 6.94 (s, 1H), 6.99 (d, J=17 Hz, 1H), 7.10 (d, J=17 Hz, 1H), 7.14 (s, 1H), 7.29 (d, J=17 Hz, 1H), 7.32 (dd, J=1.2, 8 Hz, 1H), 7.35 (m, 1H), 7.37 (d, J=17 Hz, 1H), 7.56 (d, J=8.4 Hz, 1H), 7.58 (br s, 1H), 10.3 (br s, NH). melting point 137-142° C., MS (ESI+) m/z 435.9 (M+1).

Example 61

Synthesis of 3-[(1E)-2-(1H-indol-6-yl)ethenyl]-5-[(1E)-2-(4-phenylphenyl)ethenyl]-1H-pyrazole

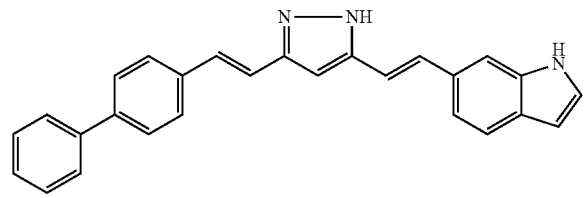 [SMILES: C(=C\c1cc(/C=C/c2ccc3cc[nH]c3c2)[nH]n1)/c1ccc(-c2ccccc2)cc1]

(1) Synthesis of (1E,6E)-1-(1H-indol-6-yl)-7-(4-phenylphenyl)hepta-1,6-diene-3,5-dione Synthesis was performed in the same manner as in Example 16 (1) except that 25 mg (0.14 mmol) of 4-phenylbenzaldehyde was used instead of 29 mg (0.14 mmol) of 4-(2-pyridylmethoxy)benzaldehyde to give 33.3 mg (64% yield) of the title compound as an orange powder with the following properties.

(2) Synthesis of 3-[(1E)-2-(1H-indol-6-yl)ethenyl]-5-[(1E)-2-(4-phenylphenyl)ethenyl]-1H-pyrazole Synthesis was performed using the same materials in the same relative quantities as in Example 4 (4) except that 20 mg (52 μmol) of (1E,6E)-1-(1H-indol-6-yl)-7-(4-phenylphenyl)hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 3.9 mg (20% yield) of the title compound as a pale yellowish white powder with the following properties.

$^1$H NMR (δ, acetone-$d_6$): 6.46 (dd, J=1, 3 Hz, 1H), 6.78 (s, 1H), 7.11 (d, J=17 Hz, 1H), 7.22 (d, J=17 Hz, 1H), 7.26 (d, J=17 Hz, 1H), 7.32 (d, J=17 Hz, 1H), 7.32 (dd, J=1.5, 8 Hz, 1H), 7.32-7.38 (m, 2H), 7.46 (dd, J=7.4, 7.8 Hz, 2H), 7.56 (d, J=8.4 Hz, 1H), 7.58 (br s, 1H), 7.65-7.7 (m, 6H), 10.3 (br s, NH). melting point 273-276° C., MS (ESI+) m/z 388.1 (M+1).

Example 62

Synthesis of 3-[(1E)-2-[2-bromo-4-(4-methylpiperazin-1-yl)phenyl]ethenyl]-5-[(1E)-2-(1H-indol-6-yl)ethenyl]-1H-pyrazole

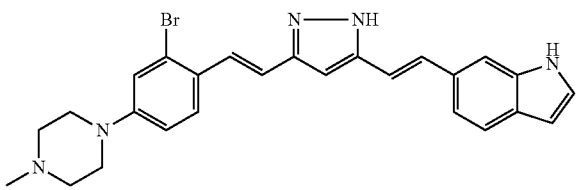 [SMILES: CN1CCN(c2ccc(/C=C/c3cc(/C=C/c4ccc5cc[nH]c5c4)[nH]n3)c(Br)c2)CC1]

(1) Synthesis of (1E,6E)-1-[2-bromo-4-(4-methylpiperazin-1-yl)phenyl]-7-(1H-indol-6-yl)hepta-1,6-diene-3,5-dione Synthesis was performed in the same manner as in Example 16 (1) except that 38 mg (0.14 mmol) of 2-bromo-4-(4-methylpiperazin-1-yl)benzaldehyde was used instead of 29 mg (0.14 mmol) of 4-(2-pyridylmethoxy)benzaldehyde to give 56.4 mg (86% yield) of the title compound as a brown powder with the following properties.

(2) Synthesis of 3-[(1E)-2-[2-bromo-4-(4-methylpiperazin-1-yl)phenyl]ethenyl]-5-[(1E)-2-(1H-indol-6-yl)ethenyl]-1H-pyrazole Synthesis was performed using the same materials in the same relative quantities as in Example 4 (4) except that 20 mg (41 μmol) of (1E,6E)-1-[2-bromo-4-(4-methylpiperazin-1-yl) phenyl]-7-(1H-indol-6-yl)hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 8.1 mg (41% yield) of the title compound as a yellowish white powder with the following properties.

$^1$H NMR (δ, acetone-$d_6$): 2.25 (s, 3H), 2.48 (t, J=5.0 Hz, 2H), 3.24 (t, J=5.0 Hz, 2H), 6.45 (dd, J=1, 3 Hz, 1H), 6.73 (s, 1H), 6.97 (d, J=17 Hz, 1H), 7.01 (dd, J=2.3, 8.8 Hz, 1H), 7.10 (d, J=17 Hz, 1H), 7.12 (d, J=2.3 Hz, 1H), 7.32 (d, J=17 Hz, 1H), 7.32 (dd, J=1.4, 8.4 Hz, 1H), 7.34 (m, 1H), 7.39 (d, J=17 Hz, 1H), 7.55 (d, J=8.3 Hz, 1H), 7.58 (br s, 1H), 7.66 (d, J=8.8 Hz, 1H), 10.3 (br s, NH). melting point 120-124° C., MS (ESI+) m/z 488.1 (M+1).

Example 63

Synthesis of 3-[(1E)-2-(4-benzyloxy-2-methoxyphenyl)ethenyl]-5-[(1E)-2-(1H-indol-6-yl)ethenyl]-1H-pyrazole

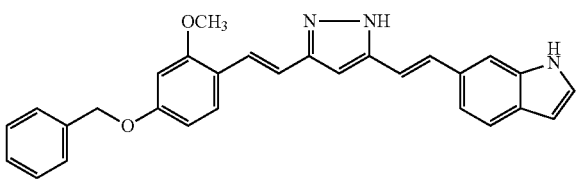 [SMILES: COc1cc(OCc2ccccc2)ccc1/C=C/c1cc(/C=C/c2ccc3cc[nH]c3c2)[nH]n1]

(1) Synthesis of (1E,6E)-1-(4-benzyloxy-2-methoxyphenyl)-7-(1H-indol-6-yl)hepta-1,6-diene-3,5-dione Synthesis was performed in the same manner as in Example 16 (1) except that 33 mg (0.14 mmol) of 4-benzyloxy-2-methoxybenzaldehyde was used instead of 29 mg (0.14 mmol) of 4-(2-pyridylmethoxy)benzaldehyde to give 59.2 mg (98% yield) of the title compound as a brown powder with the following properties.

(2) Synthesis of 3-[(1E)-2-(4-benzyloxy-2-methoxyphenyl) ethenyl]-5-[(1E)-2-(1H-indol-6-yl)ethenyl]-1H-pyrazole Synthesis was performed using the same materials in the same relative quantities as in Example 4 (4) except that 20 mg (45 µmol) of (1E,6E)-1-(4-benzyloxy-2-methoxyphenyl)-7-(1H-indol-6-yl)hepta-1,6-diene-3,5-dione was used instead of 15 mg (35 µmol) of (1E,6E)-1-(1H-indol-5-yl)-7-[4-(2-pyridylmethoxy)phenyl]hepta-1,6-diene-3,5-dione to give 10.2 mg (51% yield) of the title compound as a yellowish white powder with the following properties.

$^1$H NMR (δ, acetone-d$_6$): 3.89 (s, 3H), 5.15 (s, 2H), 6.45 (dd, J=1, 3 Hz, 1H), 6.64 (dd, J=2.4, 8.5 Hz, 1H), 6.68 (s, 1H), 6.69 (d, J=2.4 Hz, 1H), 7.05 (d, J=17 Hz, 1H), 7.09 (d, J=17 Hz, 1H), 7.30 (d, J=17 Hz, 1H), 7.31 (dd, J=1.4, 8 Hz, 1H), 7.32-7.36 (m, 3H), 7.40 (d, J=7.2, 7.5 Hz, 2H), 7.49 (d, J=7.0 Hz, 2H), 7.53 (d, J=8.5 Hz, 1H), 7.55 (d, J=8.3 Hz, 1H), 7.57 (br s, 1H), 10.3 (br s, NH). melting point 86-91° C., MS (ESI+) m/z 448.1 (M+1).

Example 64

Synthesis of 3-[(1E)-2-[4-(diphenylmethoxy)-2-methoxyphenyl]ethenyl]-5-[(1E)-2-(1H-indol-6-yl)ethenyl]-1H-pyrazole

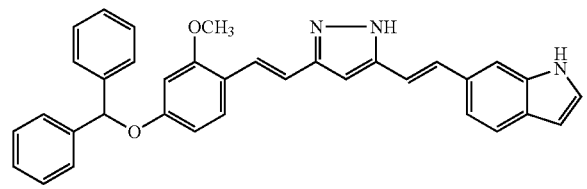 [SMILES: COc1cc(OC(c2ccccc2)c2ccccc2)ccc1/C=C/c1cc(/C=C/c2ccc3cc[nH]c3c2)[nH]n1]

(1) Synthesis of (1E,6E)-1-[4-(diphenylmethoxy)-2-methoxyphenyl]-7-(1H-indol-6-yl)hepta-1,6-diene-3,5-dione Synthesis was performed in the same manner as in Example 16 (1) except that 43 mg (0.14 mmol) of 4-(diphenylmethoxy)-2-methoxybenzaldehyde was used instead of 29 mg (0.14 mmol) of 4-(2-pyridylmethoxy)benzaldehyde to give 59.9 mg (85% yield) of the title compound as an orange powder with the following properties.

(2) Synthesis of 3-[(1E)-2-[4-(diphenylmethoxy)-2-methoxyphenyl]ethenyl]-5-[(1E)-2-(1H-indol-6-yl)ethenyl]-1H-pyrazole Synthesis was performed using the same materials in the same relative quantities as in Example 4 (4) except that 20 mg (38 µmol) of (1E,6E)-1-[4-(diphenylmethoxy)-2-methoxyphenyl]-7-(1H-indol-6-yl)hepta-1,6-diene-3,5-dione was used instead of 15 mg (35 µmol) of (1E,6E)-1-(1H-indol-5-yl)-7-[4-(2-pyridylmethoxy)phenyl]hepta-1,6-diene-3,5-dione to give 12.5 mg (63% yield) of the title compound as a yellowish white powder with the following properties.

$^1$H NMR (δ, acetone-d$_6$): 3.83 (s, 3H), 6.45 (br d, J=3 Hz, 1H), 6.52 (s, H), 6.61 (dd, J=2.3, 8.6 Hz, 1H), 6.65 (s, 1H), 6.73 (d, J=2.3 Hz, 1H), 7.00 (d, J=17 Hz, 1H), 7.07 (d, J=17 Hz, 1H), 7.24-7.38 (m, 10H), 7.43 (d, J=8.6 Hz, 1H), 7.53-7.57 (m, 5H), 7.57 (br s, 1H), 10.3 (br s, NH). melting point 114-119° C., MS (ESI+) m/z 524.2 (M+1).

Example 65

Synthesis of 3-[(1E)-2-(1H-indol-6-yl)ethenyl]-5-[(1E)-2-(4-isopropoxy-2-methoxyphenyl)ethenyl]-1H-pyrazole

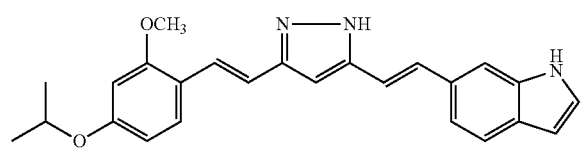 [SMILES: COc1cc(OC(C)C)ccc1/C=C/c1cc(/C=C/c2ccc3cc[nH]c3c2)[nH]n1]

(1) Synthesis of (1E,6E)-1-(1H-indol-6-yl)-7-(4-isopropoxy-2-methoxyphenyl) hepta-1,6-diene-3,5-dione Synthesis was performed in the same manner as in Example 16 (1) except that 26 mg (0.14 mmol) of 4-isopropoxy-2-methoxybenzaldehyde was used instead of 29 mg (0.14 mmol) of 4-(2-pyridylmethoxy)benzaldehyde to give 44.7 mg (83% yield) of the title compound as an orange powder with the following properties.

(2) Synthesis of 3-[(1E)-2-(1H-indol-6-yl)ethenyl]-5-[(1E)-2-(4-isopropoxy-2-methoxyphenyl)ethenyl]-1H-pyrazole Synthesis was performed using the same materials in the same relative quantities as in Example 4 (4) except that 20 mg (50 µmol) of (1E,6E)-1-(1H-indol-6-yl)-7-(4-isopropoxy-2-methoxyphenyl)hepta-1,6-diene-3,5-dione was used instead of 15 mg (35 µmol) of (1E,6E)-1-(1H-indol-5-yl)-7-[4-(2-pyridylmethoxy)phenyl]hepta-1,6-diene-3,5-dione to give 11.1 mg (56% yield) of the title compound as a yellowish white powder with the following properties.

$^1$H NMR (δ, acetone-d$_6$): 1.30 (d, J=6.0 Hz, 6H), 3.88 (s, 3H), 4.66 (tt, J=6.0, 6.0 Hz, 1H), 6.45 (dd, J=1, 3 Hz, 1H), 6.52-6.56 (m, 2H), 6.67 (s, 1H), 7.03 (d, J=17 Hz, 1H), 7.09 (d, J=17 Hz, 1H), 7.30 (d, J=17 Hz, 1H), 7.31 (dd, J=1.4, 8.2 Hz, 1H), 7.34 (m, 1H), 7.37 (d, J=17 Hz, 1H), 7.49 (m, 1H), 7.55 (d, J=8.4 Hz, 1H), 7.57 (br s, 1H), 10.3 (br s, NH). melting point 107-113° C., MS (ESI+) m/z 400.2 (M+1).

Example 66

Synthesis of 3-[(1E)-2-(1H-indol-6-yl)ethenyl]-5-[(1E)-2-[2-methoxy-4-(2-methoxyethoxy)phenyl]ethenyl]-1H-pyrazole

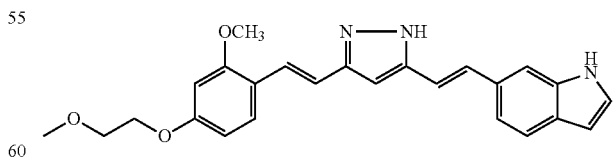

(1) Synthesis of (1E,6E)-1-(1H-indol-6-yl)-7-[2-methoxy-4-(2-methoxyethoxy) phenyl]hepta-1,6-diene-3,5-dione Synthesis was performed in the same manner as in Example 16 (1) except that 28 mg (0.14 mmol) of 2-methoxy- 4-(2-methoxyethoxy)benzaldehyde was used instead of 29 mg (0.14 mmol) of 4-(2-pyridylmethoxy)benzaldehyde to give 50.2 mg (90% yield) of the title compound as a brown powder with the following properties.

(2) Synthesis of 3-[(1E)-2-(1H-indol-6-yl)ethenyl]-5-[(1E)-2-[2-methoxy-4-(2-methoxyethoxy)phenyl]ethenyl]-1H-pyrazole Synthesis was performed using the same materials in the same relative quantities as in Example 4 (4) except that 20 mg (48 μmol) of (1E,6E)-1-(1H-indol-6-yl)-7-[2-methoxy-4-(2-methoxyethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 11.8 mg (59% yield) of the title compound as a yellowish white powder with the following properties.

$^1$H NMR (δ, acetone-$d_6$): 3.36 (s, 3H), 3.70 (t, J=4.7 Hz, 2H), 3.89 (s, 3H), 4.15 (t, J=4.7 Hz, 2H), 6.45 (dd, J=1, 3 Hz, 1H), 6.56 (d, J=2.3, 8.5 Hz, 1H), 6.59 (d, J=2.3 Hz, 1H), 6.67 (s, 1H), 7.04 (d, J=17 Hz, 1H), 7.09 (d, J=17 Hz, 1H), 7.30 (d, J=17 Hz, 1H), 7.31 (dd, J=1.4, 8.2 Hz, 1H), 7.34 (m, 1H), 7.37 (d, J=17 Hz, 1H), 7.51 (d, J=8.5 Hz, 1H), 7.55 (d, J=8.4 Hz, 1H), 7.57 (br s, 1H), 10.3 (br s, NH). melting point 90-96° C., MS (ESI+) m/z 416.1 (M+1).

(2) Synthesis of 3-[(1E)-2-(2-bromo-5-methoxyphenyl)ethenyl]-5-[(1E)-2-(1H-indol-6-yl)ethenyl]-1H-pyrazole Synthesis was performed using the same materials in the same relative quantities as in Example 4 (4) except that 20 mg (48 mmol) of (1E,6E)-1-(2-bromo-5-methoxyphenyl)-7-(1H-indol-6-yl)hepta-1,6-diene-3,5-dione was used instead of 15 mg (35 mmol) of (1E,6E)-1-(1H-indol-5-yl)-7-[4-(2-pyridylmethoxy)phenyl]hepta-1,6-diene-3,5-dione to give 9.0 mg (45% yield) of the title compound as a yellowish white powder with the following properties.

$^1$H NMR (δ, acetone-$d_6$): 3.87 (s, 3H), 6.46 (br d, J=3 Hz, 1H), 6.80 (s, 1H), 6.82 (dd, J=3.0, 8.8 Hz, 1H), 7.11 (d, J=17 Hz, 1H), 7.19 (d, J=17 Hz, 1H), 7.32 (dd, J=1.4, 8 Hz, 1H), 7.34 (d, J=17 Hz, 1H), 7.33-7.37 (m, 2H), 7.44 (d, J=17 Hz, 1H), 7.51 (d, J=8.8 Hz, 1H), 7.56 (d, J=8.3 Hz, 1H), 7.58 (br s, 1H), 10.3 (br s, NH). melting point 103-109° C., MS (ESI+) m/z 420.0 (M+1).

Example 68

Synthesis of 3-[(1E)-2-(1H-indol-6-yl)ethenyl]-5-[(1E)-2-[2-methoxy-4-(4-methoxybenzyloxy)phenyl]ethenyl]-1H-pyrazole

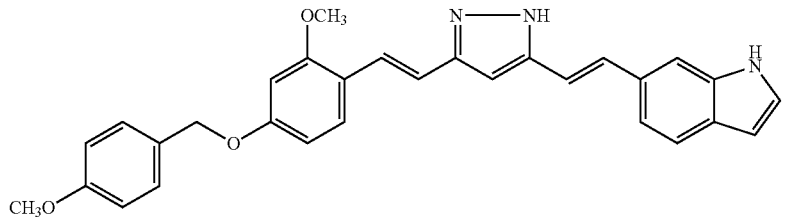

(1) Synthesis of (1E,6E)-1-(1H-indol-6-yl)-7-[2-methoxy-4-(4-methoxybenzyloxy)phenyl]hepta-1,6-diene-3,5-dione Synthesis was performed in the same manner as in Example 16 (1) except that 37 mg (0.14 mmol) of 2-methoxy-4-(4-methoxybenzyloxy)benzaldehyde was used instead of 29 mg (0.14 mmol) of 4-(2-pyridylmethoxy)benzaldehyde to give 20.1 mg (31% yield) of the title compound as an orange powder with following properties.

(2) Synthesis of 3-[(1E)-2-(1H-indol-6-yl)ethenyl]-5-[(1E)-2-[2-methoxy-4-(4-methoxybenzyloxy)phenyl]ethenyl]-1H-pyrazole Synthesis was performed using the same materials in the same relative quantities as in Example 4 (4) except that 18 mg (38 μmol) of (1E,6E)-1-(1H-indol-6-yl)-7-[2-methoxy-4-(4-methoxybenzyloxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 4.2 mg (23% yield) of the title compound as a white powder with the following properties.

$^1$H NMR (δ, acetone-$d_6$): 3.80 (s, 3H), 3.89 (s, 3H), 5.06 (s, 2H), 6.45 (dd, J=1, 3 Hz, 1H), 6.63 (dd, J=2.3, 8.4 Hz, 1H), 6.66 (d, J=2.3 Hz, 1H), 6.68 (s, 1H), 6.95 (d, J=8.8 Hz, 2H), 7.04 (d, J=17 Hz, 1H), 7.09 (d, J=17 Hz, 1H), 7.30 (d, J=17 Hz, 1H), 7.31 (dd, J=1.3, 8 Hz, 1H), 7.34 (m, 1H), 7.37 (d, J=17 Hz, 1H), 7.41 (d, J=8.8 Hz, 2H), 7.52 (d, J=8.3 Hz, 1H), 7.55 (d, J=8.3 Hz, 1H), 7.57 (br s, 1H), 10.3 (br s, NH). melting point 211-214° C., MS (ESI+) m/z 478.1 (M+1).

Example 67

Synthesis of 3-[(1E)-2-(2-bromo-5-methoxyphenyl)ethenyl]-5-[(1E)-2-(1H-indol-6-yl)ethenyl]-1H-pyrazole

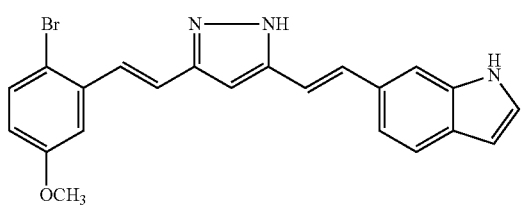 [SMILES: COc1ccc(Br)c(/C=C/c2cc(/C=C/c3ccc4cc[nH]c4c3)[nH]n2)c1]

(1) Synthesis of (1E,6E)-1-(2-bromo-5-methoxyphenyl)-7-(1H-indol-6-yl)hepta-1,6-diene-3,5-dione Synthesis was performed in the same manner as in Example 16 (1) except that 29 mg (0.14 mmol) of 2-bromo-5-methoxybenzaldehyde was used instead of 29 mg (0.14 mmol) of 4-(2-pyridylmethoxy)benzaldehyde to give 35.2 mg (62% yield) of the title compound as an orange powder with the following properties.

Example 69

Synthesis of 3-[(1E)-2-(quinolin-5-yl)ethenyl]-5-[(1E)-2-[2-methoxy-4-(2-pyridylmethoxy)phenyl]ethenyl]-1H-pyrazole

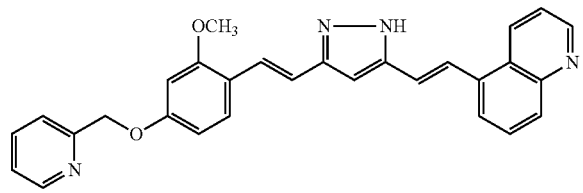 [SMILES: COc1cc(OCc2ccccn2)ccc1/C=C/c1cc(/C=C/c2cccc3ncccc23)[nH]n1]

(1) Synthesis of (1E,6E)-1-[2-methoxy-4-(2-pyridylmethoxy)phenyl]-7-(quinolin-5-yl)hepta-1,6-diene-3,5-dione Synthesis was performed using the same materials in the same relative quantities as in Example 30 (2) except that 40 mg (0.27 mmol) of quinoline-5-carboxaldehyde was used instead of 20 mg (0.14 mmol) of 1H-benzotriazole-5-carboxaldehyde to give 23.8 mg (19% yield) of the title compound as an orange powder.

(2) Synthesis of 3-[(1E)-2-[2-methoxy-4-(2-pyridylmethoxy)phenyl]ethenyl]-5-[(1E)-2-(quinolin-5-yl)ethenyl]-1H-pyrazole Synthesis was performed using the same materials in the same relative quantities as in Example 4 (4) except that 18 mg (39 μmol) of (1E,6E)-1-[2-methoxy-4-(2-pyridylmethoxy)phenyl]-7-(quinolin-5-yl)hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 4.6 mg (26% yield) of the title compound as a pale yellowish white powder with the following properties.

$^1$H NMR (δ, acetone-$d_6$): 3.91 (s, 3H), 5.22 (s, 2H), 6.66 (dd, J=2.4, 8.5 Hz, 1H), 6.75 (d, J=2.4 Hz, 1H), 6.91 (s, 1H), 7.08 (d, J=17 Hz, 1H), 7.28 (d, J=17 Hz, 1H), 7.32 (dd, J=5, 7 Hz, 1H), 7.41 (d, J=17 Hz, 1H), 7.52-7.58 (m, 3H), 7.77 (t, J=7.9 Hz, 1H), 7.82 (dt, J=1.8, 7.7 Hz, 1H), 7.96 (d, J=7.2 Hz, 1H), 8.00 (d, J=8.4 Hz, 1H), 8.05 (d, J=17 Hz, 1H), 8.58 (br d, J=5 Hz, 1H), 8.82 (d, J=8.5 Hz, 1H), 8.93 (dd, J=1.6, 4.0 Hz, 1H). melting point 107-120° C., MS (ESI+) m/z 461.2 (M+1).

Example 70

Synthesis of 3-[(1E)-2-(1-benzyl-1H-indol-6-yl)ethenyl]-5-[(1E)-2-[2-methoxy-4-(2-pyridylmethoxy)phenyl]ethenyl]-1H-pyrazole

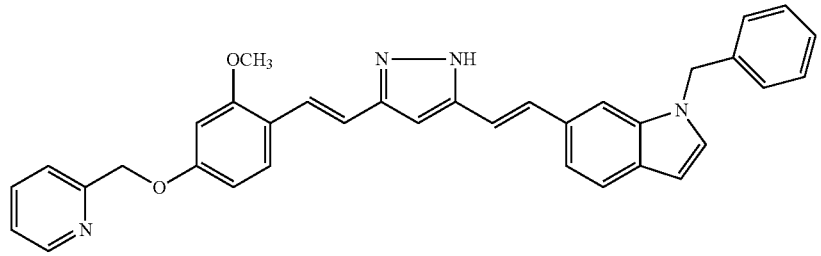 [SMILES: COc1cc(OCc2ccccn2)ccc1/C=C/c1cc(/C=C/c2ccc3ccn(Cc4ccccc4)c3c2)[nH]n1]

(1) Synthesis of (1E,6E)-1-(1-benzyl-1H-indol-6-yl)-7-[2-methoxy-4-(2-pyridylmethoxy)phenyl]hepta-1,6-diene-3,5-dione Synthesis was performed in the same manner as in Example 30 (2) except that 32 mg (0.14 mmol) of 1-benzyl-1H-indole-6-carboxaldehyde was used instead of 20 mg (0.14 mmol) of 1H-benzotriazole-5-carboxaldehyde to give 32.1 mg (44% yield) of the title compound as an orange powder.

(2) Synthesis of 3-[(1E)-2-(1-benzyl-1H-indol-6-yl)ethenyl]-5-[(1E)-2-[2-methoxy-4-(2-pyridylmethoxy)phenyl]ethenyl]-1H-pyrazole Synthesis was performed using the same materials in the same relative quantities as in Example 4 (4) except that 20 mg (37 μmol) of (1E,6E)-1-(1-benzyl-1H-indol-6-yl)-7-[2-methoxy-4-(2-pyridylmethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 8.4 mg (42% yield) of the title compound as a pale yellowish white powder with the following properties.

$^1$H NMR (δ, acetone-$d_6$): 3.89 (s, 3H), 5.21 (s, 2H), 5.49 (s, 2H), 6.50 (dd, J=1, 3 Hz, 1H), 6.65 (dd, J=2.4, 8.5 Hz, 1H), 6.66 (s, 1H), 6.73 (d, J=2.4 Hz, 1H), 7.04 (d, J=17 Hz, 1H), 7.09 (d, J=17 Hz, 1H), 7.21-7.28 (m, 4H), 7.28-7.34 (m, 4H), 7.36 (d, J=17 Hz, 1H), 7.40 (d, J=3.1 Hz, 1H), 7.52 (d, J=8.6 Hz, 1H), 7.56 (d, J=8 Hz, 1H), 7.56 (d, J=8.3 Hz, 1H), 7.58 (br s, 1H), 7.82 (dt, J=1.8, 7.7 Hz, 1H), 8.58 (br d, J=5 Hz, 1H). melting point 89-93° C., MS (ESI+) m/z 539.2 (M+1).

Example 71

Synthesis of 3-[(1E)-2-[2-bromo-4-(morpholin-4-yl)phenyl]ethenyl]-5-[(1E)-2-(1H-indol-6-yl)ethenyl]-1H-pyrazole

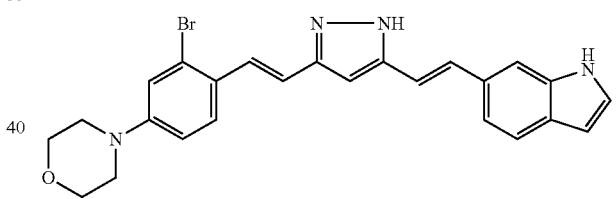

(1) Synthesis of (1E,6E)-1-[2-bromo-4-(morpholin-4-yl)phenyl]-7-(1H-indol-6-yl)hepta-1,6-diene-3,5-dione Synthesis was performed in the same manner as in Example 16 (1) except that 36 mg (0.14 mmol) of 2-bromo-4-(morpholin-4-yl)benzaldehyde was used instead of 29 mg (0.14 mmol) of 4-(2-pyridylmethoxy)benzaldehyde to give 62.6 mg (98% yield) of the title compound as an orange powder with the following properties.

(2) Synthesis of 3-[(1E)-2-[2-bromo-4-(morpholin-4-yl)phenyl]ethenyl]-5-[(1E)-2-(1H-indol-6-yl)ethenyl]-1H-pyrazole Synthesis was performed using the same materials in the same relative quantities as in Example 4 (4) except that 35 mg (74 μmol) of (1E,6E)-1-[2-bromo-4-(morpholin-4-yl)phenyl]-7-(1H-indol-6-yl) hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 16.4 mg (47% yield) of the title compound as a pale yellowish white powder with the following properties.
$^1$H NMR (δ, acetone-$d_6$): 3.20 (t, J=5 Hz, 2H), 3.77 (t, J=5 Hz, 2H), 6.46 (dd, J=1, 3 Hz, 1H), 6.74 (s, 1H), 6.99 (d, J=17 Hz, 1H), 7.00 (dd, J=2.5, 8.4 Hz, 1H), 7.10 (d, J=17 Hz, 1H), 7j 0.14 (d, J=2.5 Hz, 1H), 7.32 (d, J=17 Hz, 1H), 7.32 (dd, J=1.5, 8.4 Hz, 1H), 7.34 (m, 1H), 7.40 (d, J=17 Hz, 1H), 7.55 (d, J=8.3 Hz, 1H), 7.58 (br s, 1H), 7.67 (d, J=8.9 Hz, 1H), 10.3 (br s, NH). melting point 143-148° C., MS (ESI+) m/z 475.3 (M+1).

Example 72

Synthesis of 3-[(1E)-2-[2-bromo-4-(4-methyl-1,4-diazepan-1-yl)phenyl]ethenyl]-5-[(1E)-2-(1H-indol-6-yl)ethenyl]-1H-pyrazole

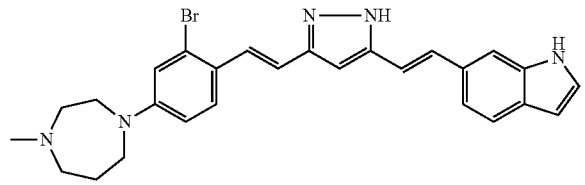 [SMILES: CN1CCCN(c2ccc(/C=C/c3cc(/C=C/c4ccc5cc[nH]c5c4)[nH]n3)c(Br)c2)CC1]

(1) Synthesis of (1E,6E)-1-[2-bromo-4-(4-methyl-1,4-diazepan-1-yl)phenyl]-7-(1H-indol-6-yl)hepta-1,6-diene-3,5-dione Synthesis was performed in the same manner as in Example 16 (1) except that 40 mg (0.14 mmol) of 2-bromo-4-(4-methyl-1,4-diazepan-1-yl)benzaldehyde was used instead of 29 mg (0.14 mmol) of 4-(2-pyridylmethoxy)benzaldehyde to give 59.3 mg (87% yield) of the title compound as a brown powder with the following properties.

(2) Synthesis of 3-[(1E)-2-[2-bromo-4-(4-methyl-1,4-diazepan-1-yl)phenyl]ethenyl]-5-[(1E)-2-(1H-indol-6-yl)ethenyl]-1H-pyrazole Synthesis was performed using the same materials in the same relative quantities as in Example 4 (4) except that 35 mg (70 μmol) of (1E,6E)-1-[2-bromo-4-(4-methyl-1,4-diazepan-1-yl) phenyl]-7-(1H-indol-6-yl)hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 7.0 mg (20% yield) of the title compound as a pale yellowish white powder with the following properties.
$^1$H NMR (δ, acetone-$d_6$): 1.96 (tt, J=5.6, 6.2 Hz, 2H), 2.30 (s, 3H), 2.50 (t, J=5.6 Hz, 2H), 2.66 (t, J=4.9 Hz, 2H), 3.50 (t, J=6.2 Hz, 2H), 3.58 (t, J=5.0 Hz, 2H), 6.45 (dd, J=1, 3 Hz, 1H), 6.70 (s, 1H), 6.79 (dd, J=2.5, 8.9 Hz, 1H), 6.90 (d, J=17 Hz, 1H), 6.91 (d, J=2.6 Hz, 1H), 7.09 (d, J=17 Hz, 1H), 7.31 (d, J=17 Hz, 1H), 7.32 (dd, J=1.3, 8 Hz, 1H), 7.34 (m, 1H), 7.39 (d, J=17 Hz, 1H), 7.55 (d, J=8.3 Hz, 1H), 7.57 (br s, 1H), 7.60 (d, J=8.9 Hz, 1H), 10.3 (br s, NH). melting point 132-136° C., MS (ESI+) m/z 502.2 (M+1).

Example 73

Synthesis of 3-[(1E)-2-(1-acetyl-1H-indol-6-yl)ethenyl]-5-[(1E)-2-[2-methoxy-4-(2-pyridylmethoxy)phenyl]ethenyl]-1H-pyrazole

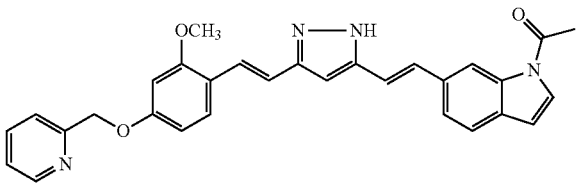 [SMILES: COc1cc(OCc2ccccn2)ccc1/C=C/c1cc(/C=C/c2ccc3ccn(C(C)=O)c3c2)[nH]n1]

(1) Synthesis of (1E,6E)-1-(1-acetyl-1H-indol-6-yl)-7-[2-methoxy-4-(2-pyridylmethoxy)phenyl]hepta-1,6-diene-3,5-dione Synthesis was performed using the same materials in the same relative quantities as in Example 30 (2) except that 40 mg (0.21 mmol) of 1-acetyl-1H-indole-6-carboxaldehyde was used instead of 20 mg (0.14 mmol) of 1H-benzotriazole-5-carboxaldehyde to give 25.0 mg (24% yield) of the title compound as an orange powder.

(2) Synthesis of 3-[(1E)-2-(1-acetyl-1H-indol-6-yl)ethenyl]-5-[(1E)-2-[2-methoxy-4-(2-pyridylmethoxy)phenyl]ethenyl]-1H-pyrazole Synthesis was performed using the same materials in the same relative quantities as in Example 4 (4) except that 20 mg (40 μmol) of (1E,6E)-1-(1-acetyl-1H-indol-6-yl)-7-[2-methoxy-4-(2-pyridylmethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 9.6 mg (48% yield) of the title compound as a pale yellowish white powder with the following properties.
$^1$H NMR (δ, acetone-$d_6$): 2.69 (s, 3H), 3.90 (s, 3H), 5.22 (s, 2H), 6.65 (dd, J=2.3, 8.5 Hz, 1H), 6.69 (dd, J=1, 3.8 Hz, 1H), 6.73 (d, J=2.3 Hz, 1H), 6.77 (s, 1H), 7.06 (d, J=17 Hz, 1H), 7.18 (d, J=17 Hz, 1H), 7.31 (dd, J=5, 7 Hz, 1H), 7.35 (d, J=17 Hz, 1H), 7.39 (d, J=17 Hz, 1H), 7.53 (d, J=8.6 Hz, 1H), 7.53-7.58 (m, 2H), 7.59 (d, J=8.3 Hz, 1H), 7.76 (d, J=3.8 Hz, 1H), 7.82 (dt, J=1.8, 7.7 Hz, 1H), 8.58 (br d, J=5 Hz, 1H), 8.60 (br s, 1H). melting point 182-187° C., MS (ESI+) m/z 491.3 (M+1).

Example 74

Synthesis of 3-[(1E)-2-(1-methanesulfonyl-1H-indol-6-yl)ethenyl]-5-[(1E)-2-[2-methoxy-4-(2-pyridylmethoxy)phenyl]ethenyl]-1H-pyrazole

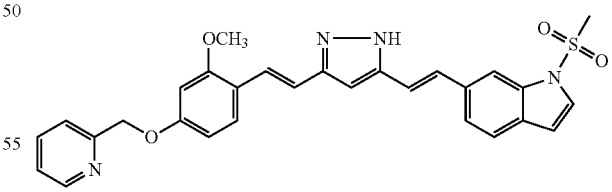

(1) Synthesis of (1E,6E)-1-(1-methanesulfonyl-1H-indol-6-yl)-7-[2-methoxy-4-(2-pyridylmethoxy)phenyl]hepta-1,6-diene-3,5-dione Synthesis was performed using the same materials in the same relative quantities as in Example 30 (2) except that 30 mg (0.13 mmol) of 1-methanesulfonyl-1H-indole-6-carboxaldehyde was used instead of 20 mg (0.14 mmol) of 1H-benzotriazole-5-carboxaldehyde to give 14.1 mg (20% yield) of the title compound as a yellow powder.

(2) Synthesis of 3-[(1E)-2-(1-methanesulfonyl-1H-indol-6-yl)ethenyl]-5-[(1E)-2-[2-methoxy-4-(2-pyridylmethoxy)phenyl]ethenyl]-1H-pyrazole Synthesis was performed using the same materials in the same relative quantities as in Example 4 (4) except that 12 mg (23 µmol) of (1E,6E)-1-(1-methanesulfonyl-1H-indol-6-yl)-7-[2-methoxy-4-(2-pyridylmethoxy)phenyl]hepta-1,6-diene-3,5-dione was used instead of 15 mg (35 µmol) of (1E,6E)-1-(1H-indol-5-yl)-7-[4-(2-pyridylmethoxy)phenyl]hepta-1,6-diene-3,5-dione to give 4.6 mg (38% yield) of the title compound as a white powder with the following properties.

$^1$H NMR (δ, acetone-$d_6$): 3.38 (s, 3H), 3.90 (s, 3H), 5.22 (s, 2H), 6.65 (dd, J=2.3, 8.5 Hz, 1H), 6.74 (d, J=2.3 Hz, 1H), 6.77 (s, 1H), 6.80 (dd, J=1, 3.7 Hz, 1H), 7.06 (d, J=17 Hz, 1H), 7.21 (d, J=17 Hz, 1H), 7.31 (dd, J=5, 7 Hz, 1H), 7.37 (d, J=17 Hz, 1H), 7.39 (d, J=17 Hz, 1H), 7.51-7.57 (m, 3H), 7.58 (d, J=1.3, 6.4 Hz, 1H), 7.66 (d, J=8.2 Hz, 1H), 7.82 (dt, J=1.7, 7.7 Hz, 1H), 8.04 (br s, 1H), 8.58 (br d, J=5 Hz, 1H). melting point 212-214° C., MS (ESI+) m/z 527.3 (M+1).

Example 75

Synthesis of 3-[(1E)-2-(7-aza-1H-indol-3-yl)ethenyl]-5-[(1E)-2-[2-methoxy-4-(2-pyridylmethoxy)phenyl]ethenyl]-1H-pyrazole

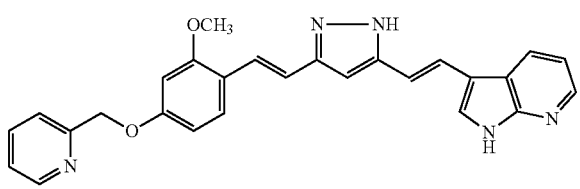

(1) Synthesis of (1E,6E)-1-(7-aza-1H-indol-3-yl)-7-[2-methoxy-4-(2-pyridylmethoxy)phenyl]hepta-1,6-diene-3,5-dione Synthesis was performed using the same materials in the same relative quantities as in Example 30 (2) except that 40 mg (0.27 mmol) of 7-aza-1H-indole-3-carboxaldehyde was used instead of 20 mg (0.14 mmol) of 1H-benzotriazole-5-carboxaldehyde to give 78.4 mg (63% yield) of the title compound as an orange powder.

(2) Synthesis of 3-[(1E)-2-(7-aza-1H-indol-3-yl)ethenyl]-5-[(1E)-2-[2-methoxy-4-(2-pyridylmethoxy)phenyl]ethenyl]-1H-pyrazole Synthesis was performed using the same materials in the same relative quantities as in Example 4 (4) except that 30 mg (66 µmol) of (1E,6E)-1-(7-aza-1H-indol-3-yl)-7-[2-methoxy-4-(2-pyridylmethoxy)phenyl]hepta-1,6-diene-3,5-dione was used instead of 15 mg (35 µmol) of (1E,6E)-1-(1H-indol-5-yl)-7-[4-(2-pyridylmethoxy)phenyl]hepta-1,6-diene-3,5-dione to give 18.0 mg (60% yield) of the title compound as a pale yellowish white powder with the following properties.

$^1$H NMR (δ, acetone-$d_6$): 3.90 (s, 3H), 5.22 (s, 2H), 6.65 (dd, J=2.3, 8 Hz, 1H), 6.66 (s, 1H), 6.73 (d, J=2.3 Hz, 1H), 7.05 (d, J=17 Hz, 1H), 7.11 (d, J=17 Hz, 1H), 7.16 (dd, J=4.7, 7.9 Hz, 1H), 7.31 (dd, J=5, 7 Hz, 1H), 7.37 (d, J=17 Hz, 1H), 7.39 (d, J=17 Hz, 1H), 7.53 (d, J=8.5 Hz, 1H), 7.56 (d, J=7.7 Hz, 1H), 7.71 (s, 1H), 7.82 (dt, J=1.7, 7.7 Hz, 1H), 8.28 (dd, J=1.5, 4.7 Hz, 1H), 8.35 (dd, J=1.5, 7.9 Hz, 1H), 8.58 (br d, J=5 Hz, 1H), 10.8 (br s, NH). melting point 219-223° C., MS (ESI+) m/z 450.2 (M+1).

Example 76

Synthesis of 3-[(1E)-2-[4-[2-(dimethylamino)ethoxy]-2-methoxyphenyl]ethenyl]-5-[(1E)-2-(1H-indol-6-yl)ethenyl]-1H-pyrazole

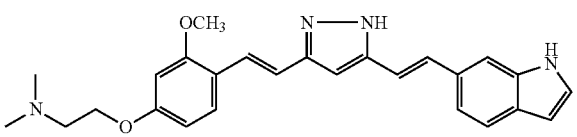 [SMILES: COc1cc(OCCN(C)C)ccc1/C=C/c1cc(/C=C/c2ccc3cc[nH]c3c2)[nH]n1]

(1) Synthesis of (1E,6E)-1-[4-[2-(dimethylamino)ethoxy]-2-methoxyphenyl]-7-(1H-indol-6-yl)hepta-1,6-diene-3,5-dione Synthesis was performed in the same manner as in Example 16 (1) except that 31 mg (0.14 mmol) of 4-[2-(dimethylamino)ethoxy]-2-methoxybenzaldehyde was used instead of 29 mg (0.14 mmol) of 4-(2-pyridylmethoxy)benzaldehyde to give 34.9 mg (59% yield) of the title compound as an orange powder with the following properties.

(2) Synthesis of 3-[(1E)-2-[4-[2-(dimethylamino)ethoxy]-2-methoxyphenyl]ethenyl]-5-[(1E)-2-(1H-indol-6-yl)ethenyl]-1H-pyrazole Synthesis was performed using the same materials in the same relative quantities as in Example 4 (4) except that 25 mg (58 µmol) of (1E,6E)-1-[4-[2-(dimethylamino)ethoxy]-2-methoxyphenyl]-7-(1H-indol-6-yl)hepta-1,6-diene-3,5-dione was used instead of 15 mg (35 µmol) of (1E,6E)-1-(1H-indol-5-yl)-7-[4-(2-pyridylmethoxy)phenyl]hepta-1,6-diene-3,5-dione to give 11.7 mg (47% yield) of the title compound as a yellowish white powder with the following properties.

$^1$H NMR (δ, acetone-$d_6$): 2.25 (s, 6H), 2.67 (br t, J=6 Hz, 1H), 3.89 (s, 3H), 4.11 (t, J=5.9 Hz, 1H), 5.22 (s, 2H), 6.45 (br d, J=3 Hz, 1H), 6.56 (dd, J=2.3, 8.5 Hz, 1H), 6.59 (d, J=2.3 Hz, 1H), 6.68 (s, 1H), 7.04 (d, J=17 Hz, 1H), 7.09 (d, J=17 Hz, 1H), 7.30 (d, J=17 Hz, 1H), 7.31 (dd, J=1.4, 8 Hz, 1H), 7.34 (m, 1H), 7.37 (d, J=17 Hz, 1H), 7.50 (d, J=8.5 Hz, 1H), 7.55 (d, J=8.5 Hz, 1H), 7.57 (br s, 1H), 10.3 (br s, NH). melting point 109-112° C., MS (ESI+) m/z 429.4 (M+1).

Example 77

Synthesis of 3-[(1E)-2-(1,3-benzodioxol-5-yl)ethenyl]-5-[(1E)-2-[2-methoxy-4-(2-pyridylmethoxy)phenyl]ethenyl]-1H-pyrazole

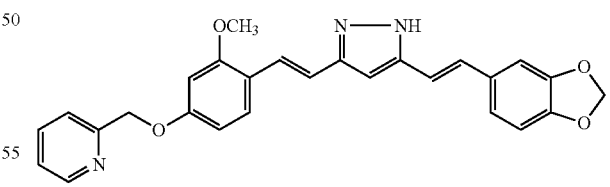

(1) Synthesis of (1E,6E)-1-(1,3-benzodioxol-5-yl)-7-[2-methoxy-4-(2-pyridylmethoxy)phenyl]hepta-1,6-diene-3,5-dione Synthesis was performed using the same materials in the same relative quantities as in Example 30 (2) except that 40 mg (0.27 mmol) of 1,3-benzodioxole-5-carboxaldehyde was used instead of 20 mg (0.14 mmol) of 1H-benzotriazole-5-carboxaldehyde to give 23.8 mg (20% yield) of the title compound as a brown powder.

(2) Synthesis of 3-[(1E)-2-(1,3-benzodioxol-5-yl)ethenyl]-5-[(1E)-2-[2-methoxy-4-(2-pyridylmethoxy)phenyl]ethenyl]-1H-pyrazole Synthesis was performed using the same materials in the same relative quantities as in Example 4 (4) except that 20 mg (44 μmol) of (1E,6E)-1-(1,3-benzodioxol-5-yl)-7-[2-methoxy-4-(2-pyridylmethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 3.6 mg (18% yield) of the title compound as a yellowish white powder with the following properties.

$^1$H NMR (δ, acetone-$d_6$): 3.90 (s, 3H), 5.22 (s, 2H), 6.01 (s, 2H), 6.64 (dd, J=2.4, 8.6 Hz, 1H), 6.65 (s, 1H), 6.73 (d, J=2.4 Hz, 1H), 6.80 (d, J=8.0 Hz, 1H), 6.99 (d, J=17 Hz, 1H), 7.00 (dd, J=1.6, 8.0 Hz, 1H), 7.04 (d, J=17 Hz, 1H), 7.14 (d, J=17 Hz, 1H), 7.15 (d, J=1.6 Hz, 1H), 7.31 (dd, J=5, 7 Hz, 1H), 7.36 (d, J=17 Hz, 1H), 7.51 (d, J=8.6 Hz, 1H), 7.56 (br d, J=8.2 Hz, 1H), 7.82 (dt, J=1.7, 7.7 Hz, 1H), 8.58 (br d, J=5 Hz, 1H). melting point 218-220° C., MS (ESI+) m/z 454.3 (M+1).

Example 78

Synthesis of 3-[(1E)-2-(1H-indol-6-yl)ethenyl]-5-[(1E)-2-(4-isopropylphenyl)ethenyl]-1H-pyrazole

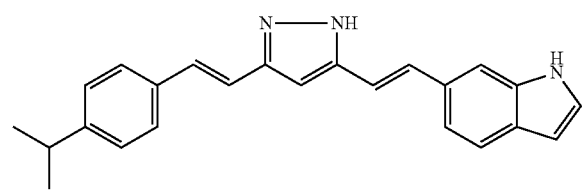 [SMILES: CC(C)c1ccc(/C=C/c2cc(/C=C/c3ccc4cc[nH]c4c3)[nH]n2)cc1]

(1) Synthesis of (1E,6E)-1-(1H-indol-6-yl)-7-(4-isopropylphenyl)hepta-1,6-diene-3,5-dione Synthesis was performed using the same materials in the same relative quantities as in Example 16 (1) except that 20 mg (0.14 mmol) of 4-isopropylbenzaldehyde was used instead of 29 mg (0.14 mmol) of 4-(2-pyridylmethoxy)benzaldehyde to give 27.9 mg (57% yield) of the title compound as a yellow powder with the following properties.

(2) Synthesis of 3-[(1E)-2-(1H-indol-6-yl)ethenyl]-5-[(1E)-2-(4-isopropylphenyl)ethenyl]-1H-pyrazole Synthesis was performed using the same materials in the same relative quantities as in Example 4 (4) except that 30 mg (84 μmol) of (1E,6E)-1-(1H-indol-6-yl)-7-(4-isopropylphenyl)hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 22.2 mg (74% yield) of the title compound as a yellowish white powder with the following properties.

$^1$H NMR (δ, acetone-$d_6$): 1.23 (d, J=6.9 Hz, 6H), 2.90 (tt, J=6.9, 6.9 Hz, 1H), 6.46 (dd, J=1, 3 Hz, 1H), 6.74 (s, 1H), 7.10 (d, J=17 Hz, 1H), 7.11 (d, J=17 Hz, 1H), 7.18 (d, J=17 Hz, 1H), 7.25 (d, J=8.2 Hz, 2H), 7.30 (d, J=17 Hz, 1H), 7.31 (dd, J=1.4, 8 Hz, 1H), 7.34 (m, 1H), 7.48 (d, J=8.2 Hz, 2H), 7.56 (d, J=8.6 Hz, 1H), 7.57 (br s, 1H), 10.3 (br s, NH). melting point 208-212° C., MS (ESI+) m/z 354.2 (M+1).

Example 79

Synthesis of 3-[(1E)-2-[2-methoxy-4-(2-pyridylmethoxy)phenyl]ethenyl]-5-[(1E)-2-(4-nitro-1H-indol-6-yl)ethenyl]-1H-pyrazole

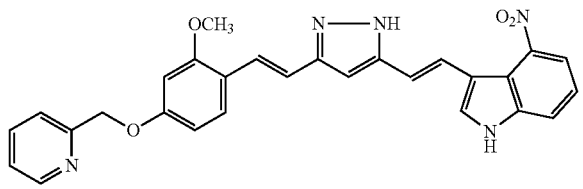 [SMILES: COc1cc(OCc2ccccn2)ccc1/C=C/c1cc(/C=C/c2c[nH]c3cccc([N+](=O)[O-])c23)[nH]n1]

(1) Synthesis of (1E,6E)-1-[2-methoxy-4-(2-pyridylmethoxy)phenyl]-7-(4-nitro-1H-indol-6-yl)hepta-1,6-diene-3,5-dione Synthesis was performed using the same materials in the same relative quantities as in Example 30 (2) except that 52 mg (0.27 mmol) of 4-nitro-1H-indole-6-carboxaldehyde was used instead of 20 mg (0.14 mmol) of 1H-benzotriazole-5-carboxaldehyde to give 20.6 mg (15% yield) of the title compound as a yellow powder.

(2) Synthesis of 3-[(1E)-2-[2-methoxy-4-(2-pyridylmethoxy)phenyl]ethenyl]-5-[(1E)-2-(4-nitro-1H-indol-6-yl)ethenyl]-1H-pyrazole Synthesis was performed using the same materials in the same relative quantities as in Example 4 (4) except that 15 mg (30 μmol) of (1E,6E)-1-[2-methoxy-4-(2-pyridylmethoxy)phenyl]-7-(4-nitro-1H-indol-6-yl)hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 7.8 mg (52% yield) of the title compound as an orange powder with the following properties.

$^1$H NMR (δ, acetone-$d_6$): 3.90 (s, 3H), 5.22 (s, 2H), 6.62 (s, 1H), 6.64 (dd, J=2.3, 8.6 Hz, 1H), 6.73 (d, J=2.3 Hz, 1H), 6.81 (d, J=17 Hz, 1H), 7.07 (d, J=17 Hz, 1H), 7.31 (dd, J=7.9, 8.0 Hz, 1H), 7.32 (m, 1H), 7.38 (d, J=17 Hz, 1H), 7.49 (d, J=17 Hz, 1H), 7.53 (d, J=8.6 Hz, 1H), 7.56 (br d, J=7.8 Hz, 1H), 7.81 (dt, J=1.7, 7.7 Hz, 1H), 7.81 (dd, J=0.7, 7.9 Hz, 1H), 7.81 (dd, J=0.7, 8.0 Hz, 1H), 8.02 (s, 1H), 8.58 (br d, J=5 Hz, 1H), 11.3 (br s, NH). melting point 125-131° C., MS (ESI+) m/z 494.3 (M+1).

Example 80

Synthesis of 3-[(1E)-2-[4-(cyclohexylmethoxy)-2-methoxyphenyl]ethenyl]-5-[(1E)-2-(1H-indol-6-yl)ethenyl]-1H-pyrazole

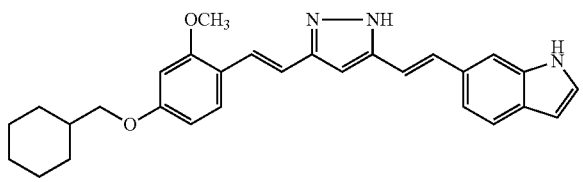 [SMILES: COc1cc(OCC2CCCCC2)ccc1/C=C/c1cc(/C=C/c2ccc3cc[nH]c3c2)[nH]n1]

(1) Synthesis of (1E,6E)-1-[4-(cyclohexylmethoxy)-2-methoxyphenyl]-7-(1H-indol-6-yl)hepta-1,6-diene-3,5-dione Synthesis was performed using the same materials in the same relative quantities as in Example 16 (1) except that 67 mg (0.27 mmol) of 4-(cyclohexylmethoxy)-2-methoxybenzaldehyde was used instead of 29 mg (0.14 mmol) of 4-(2-pyridylmethoxy)benzaldehyde to give 84.1 mg (70% yield) of the title compound as an orange powder with the following properties.

(2) Synthesis of 3-[(1E)-2-[4-(cyclohexylmethoxy)-2-methoxyphenyl]ethenyl]-5-[(1E)-2-(1H-indol-6-yl)ethenyl]-1H-pyrazole Synthesis was performed using the same materials in the same relative quantities as in Example 4 (4) except that 30 mg (66 µmol) of (1E,6E)-1-[4-(cyclohexylmethoxy)-2-methoxyphenyl]-7-(1H-indol-6-yl)hepta-1,6-diene-3,5-dione was used instead of 15 mg (35 µmol) of (1E,6E)-1-(1H-indol-5-yl)-7-[4-(2-pyridylmethoxy)phenyl]hepta-1,6-diene-3,5-dione to give 7.0 mg (23% yield) of the title compound as a pale yellowish white powder with the following properties.
¹H NMR (δ, acetone-d₆): 1.02-1.38 (m, 6H), 1.64-1.92 (m, 5H), 3.83 (d, J=6.3 Hz, 2H), 3.90 (s, 3H), 6.45 (br d, J=3 Hz, 1H), 6.54 (dd, J=2.3, 8.5 Hz, 1H), 6.58 (d, J=2.3 Hz, 1H), 6.67 (s, 1H), 7.03 (d, J=17 Hz, 1H), 7.09 (d, J=17 Hz, 1H), 7.30 (d, J=17 Hz, 1H), 7.31 (dd, J=1.4, 8.2 Hz, 1H), 7.34 (m, 1H), 7.37 (d, J=17 Hz, 1H), 7.50 (d, J=8.5 Hz, 1H), 7.55 (d, J=8.3 Hz, 1H), 7.57 (br s, 1H), 10.3 (br s, NH). melting point 104-108° C., MS (ESI+) m/z 454.4 (M+1).

Example 81

Synthesis of 3-[(1E)-2-(1H-indol-6-yl)ethenyl]-5-[(1E)-2-[2-methoxy-4-[2-(pyrrol-1-yl)ethoxy]phenyl]ethenyl]-1H-pyrazole

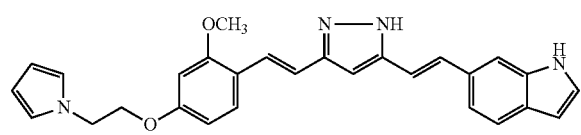 [SMILES: COc1cc(OCCn2cccc2)ccc1/C=C/c1cc(/C=C/c2ccc3cc[nH]c3c2)[nH]n1]

(1) Synthesis of (1E,6E)-1-(1H-indol-6-yl)-7-[2-methoxy-4-[2-(pyrrol-1-yl) ethoxy]phenyl]hepta-1,6-diene-3,5-dione Synthesis was performed using the same materials in the same relative quantities as in Example 16 (1) except that 66 mg (0.27 mmol) of 2-methoxy-4-[2-(pyrrol-1-yl)ethoxy]benzaldehyde was used instead of 29 mg (0.14 mmol) of 4-(2-pyridylmethoxy)benzaldehyde to give 60.5 mg (50% yield) of the title compound as an orange powder with the following properties.

(2) Synthesis of 3-[(1E)-2-(1H-indol-6-yl)ethenyl]-5-[(1E)-2-[2-methoxy-4-[2-(pyrrol-1-yl)ethoxy]phenyl]ethenyl]-1H-pyrazole Synthesis was performed using the same materials in the same relative quantities as in Example 4 (4) except that 30 mg (66 µmol) of (1E,6E)-1-(1H-indol-6-yl)-7-[2-methoxy-4-[2-(pyrrol-1-yl)ethoxy]phenyl]hepta-1,6-diene-3,5-dione was used instead of 15 mg (35 µmol) of (1E,6E)-1-(1H-indol-5-yl)-7-[4-(2-pyridylmethoxy)phenyl]hepta-1,6-diene-3,5-dione to give 14.7 mg (49% yield) of the title compound as a pale yellowish white powder with the following properties.
¹H NMR (δ, acetone-d₆): 3.88 (s, 3H), 4.31 (m, 4H), 6.01 (t, J=2.1 Hz, 2H), 6.45 (dd, J=1, 3 Hz, 1H), 6.55 (dd, J=2.3, 8.5 Hz, 1H), 6.58 (d, J=2.3 Hz, 1H), 6.67 (s, 1H), 6.80 (t, J=2.1 Hz, 2H), 7.04 (d, J=17 Hz, 1H), 7.08 (d, J=17 Hz, 1H), 7.30 (d, J=17 Hz, 1H), 7.31 (dd, J=1.4, 8 Hz, 1H), 7.34 (m, 1H), 7.36 (d, J=17 Hz, 1H), 7.50 (d, J=8.5 Hz, 1H), 7.55 (d, J=8.4 Hz, 1H), 7.57 (br s, NH). melting point 102-110° C., MS (ESI+) m/z 451.4 (M+1).

Example 82

Synthesis of 3-[(1E)-2-(1H-indol-6-yl)ethenyl]-5-[(1E)-2-[2-methoxy-4-(1,3-thiazol-2-ylmethoxy)phenyl]ethenyl]-1H-pyrazole

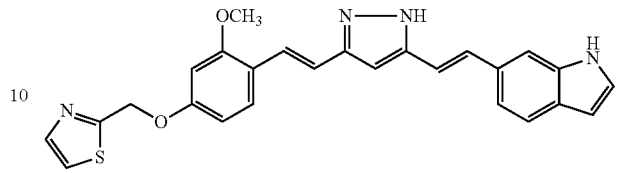

(1) Synthesis of (1E,6E)-1-(1H-indol-6-yl)-7-[2-methoxy-4-(1,3-thiazol-2-ylmethoxy)phenyl]hepta-1,6-diene-3,5-dione Synthesis was performed using the same materials in the same relative quantities as in Example 16 (1) except that 71 mg (0.2 mmol) of 2-methoxy-4-(1,3-thiazol-2-ylmethoxy)benzaldehyde was used instead of 29 mg (0.14 mmol) of 4-(2-pyridylmethoxy)benzaldehyde to give 52.6 mg (43% yield) of the title compound as an orange powder with the following properties.

(2) Synthesis of 3-[(1E)-2-(1H-indol-6-yl)ethenyl]-5-[(1E)-2-[2-methoxy-4-(1,3-thiazol-2-ylmethoxy)phenyl]ethenyl]-1H-pyrazole Synthesis was performed using the same materials in the same relative quantities as in Example 4 (4) except that 30 mg (66 µmol) of (1E,6E)-1-(1H-indol-6-yl)-7-[2-methoxy-4-(1,3-thiazol-2-ylmethoxy)phenyl]hepta-1,6-diene-3,5-dione was used instead of 15 mg (35 µmol) of (1E,6E)-1-(1H-indol-5-yl)-7-[4-(2-pyridylmethoxy)phenyl]hepta-1,6-diene-3,5-dione to give 17.4 mg (58% yield) of the title compound as a yellowish white powder with the following properties.
¹H NMR (δ, acetone-d₆): 3.91 (s, 3H), 5.29 (s, 2H), 6.45 (br d, J=3 Hz, 1H), 6.68 (s, 1H), 6.68 (dd, J=2.4, 8.4 Hz, 1H), 6.73 (d, J=2.4 Hz, 1H), 7.06 (d, J=17 Hz, 1H), 7.09 (d, J=17 Hz, 1H), 7.30 (d, J=17 Hz, 1H), 7.31 (dd, J=1.4, 8 Hz, 1H), 7.34 (m, 1H), 7.38 (d, J=17 Hz, 1H), 7.53 (d, J=8.4 Hz, 1H), 7.55 (d, J=8.1 Hz, 1H), 7.57 (br s, 1H), 7.69 (br d, J=2.0 Hz, 1H), 9.03 (d, J=2.0 Hz, 1H), 10.3 (br s, NH). melting point 229-237° C., MS (ESI+) m/z 455.3 (M+1).

Example 83

Synthesis of 3-[(1E)-2-(1,4-benzodioxan-6-yl)ethenyl]-5-[(1E)-2-[2-methoxy-4-(2-pyridylmethoxy)phenyl]ethenyl]-1H-pyrazole

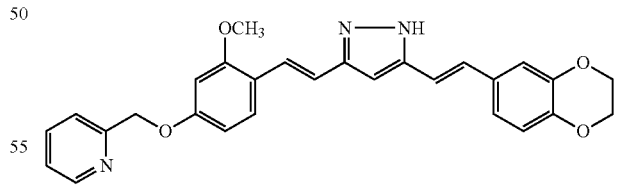

(1) Synthesis of (1E,6E)-1-(1,4-benzodioxan-6-yl)-7-[2-methoxy-4-(2-pyridylmethoxy)phenyl]hepta-1,6-diene-3,5-dione Synthesis was performed using the same materials in the same relative quantities as in Example 30 (2) except that 44 mg (0.27 mmol) of 1,4-benzodioxane-6-carboxaldehyde was used instead of 20 mg (0.14 mmol) of 1H-benzotriazole-5-carboxaldehyde to give 25.0 mg (20% yield) of the title compound as an orange powder.

(2) Synthesis of 3-[(1E)-2-(1,4-benzodioxan-6-yl)ethenyl]-5-[(1E)-2-[2-methoxy-4-(2-pyridylmethoxy)phenyl]ethenyl]-1H-pyrazole Synthesis was performed using the same materials in the same relative quantities as in Example 4 (4) except that 20 mg (42 μmol) of (1E,6E)-1-(1,4-benzodioxan-6-yl)-7-[2-methoxy-4-(2-pyridylmethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 7.7 mg (39% yield) of the title compound as a pale yellowish white powder with the following properties.

$^1$H NMR (δ, acetone-$d_6$): 3.89 (s, 3H), 4.27 (s, 4H), 5.22 (s, 2H), 6.64 (dd, J=2.4, 8.5 Hz, 1H), 6.65 (s, 1H), 6.73 (d, J=2.4 Hz, 1H), 6.81 (d, J=8.8 Hz, 1H), 6.97 (d, J=17 Hz, 1H), 7.00-7.05 (m, 2H), 7.04 (d, J=17 Hz, 1H), 7.09 (d, J=17 Hz, 1H), 7.31 (dd, J=5, 7 Hz, 1H), 7.36 (d, J=17 Hz, 1H), 7.51 (d, J=8.5 Hz, 1H), 7.56 (br d, J=8 Hz, 1H), 7.81 (dt, J=1.7, 7.7 Hz, 1H), 8.58 (br d, J=5 Hz, 1H). melting point 153-155° C., MS (ESI+) m/z 468.3 (M+1).

Example 84

Synthesis of 3-[(1E)-2-[2-bromo-5-(2-pyridylmethoxy)phenyl]ethenyl]-5-[(1E)-2-(1H-indol-6-yl)ethenyl]-1H-pyrazole

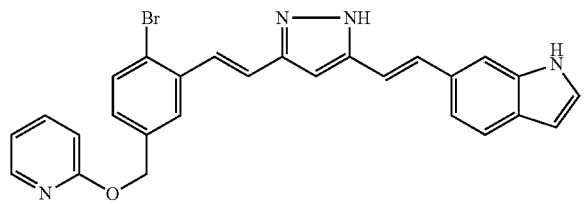 [SMILES: Brc1ccc(COc2ccccn2)cc1/C=C/c1cc(/C=C/c2ccc3cc[nH]c3c2)[nH]n1]

(1) Synthesis of (1E,6E)-1-[2-bromo-5-(2-pyridylmethoxy)phenyl]-7-(1H-indol-6-yl)hepta-1,6-diene-3,5-dione Synthesis was performed using the same materials in the same relative quantities as in Example 16 (1) except that 78 mg (0.27 mmol) of 2-bromo-5-(2-pyridylmethoxy)benzaldehyde was used instead of 29 mg (0.14 mmol) of 4-(2-pyridylmethoxy)benzaldehyde to give 28.1 mg (21% yield) of the title compound as a brown powder with the following properties.

(2) Synthesis of 3-[(1E)-2-[2-bromo-5-(2-pyridylmethoxy)phenyl]ethenyl]-5-[(1E)-2-(1H-indol-6-yl)ethenyl]-1H-pyrazole Synthesis was performed using the same materials in the same relative quantities as in Example 4 (4) except that 20 mg (40 mmol) of (1E,6E)-1-[2-bromo-5-(2-pyridylmethoxy)phenyl]-7-(1H-indol-6-yl)hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 3.4 mg (17% yield) of the title compound as a pale yellowish white powder with the following properties.

$^1$H NMR (δ, acetone-$d_6$): 5.28 (s, 2H), 6.46 (br d, J=3 Hz, 1H), 6.80 (s, 1H), 6.93 (dd, J=3.0, 8.8 Hz, 1H), 7.11 (d, J=17 Hz, 1H), 7.20 (d, J=17 Hz, 1H), 7.29-7.38 (m, 4H), 7.44 (d, J=17 Hz, 1H), 7.50 (d, J=3.0 Hz, 1H), 7.53 (d, J=8.8 Hz, 1H), 7.56 (d, J=8.9 Hz, 1H), 7.58 (br s, 1H), 7.59 (br d, J=8 Hz, 1H), 7.83 (dt, J=1.7, 7.7 Hz, 1H), 8.58 (br d, J=5 Hz, 1H), 10.3 (br s, NH). melting point 100-106° C., MS (ESI+) m/z 497.3 (M+1).

Example 85

Synthesis of 3-[(1E)-2-(1H-indol-6-yl)ethenyl]-5-[(1E)-2-[2-methoxy-4-(2-tetrahydrofuranylmethoxy)phenyl]ethenyl]-1-phenyl-1H-pyrazole and 5-[(1E)-2-(1H-indol-6-yl)ethenyl]-3-[(1E)-2-[2-methoxy-4-(2-tetrahydrofuranylmethoxy)phenyl]ethenyl]-1-phenyl-1H-pyrazole

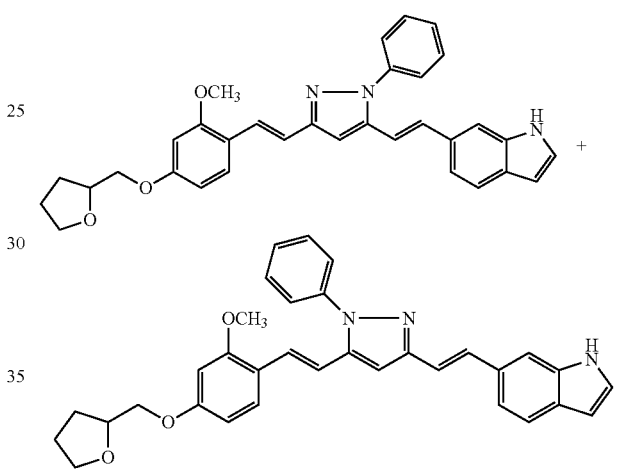

In 0.22 mL of toluene and 11 μL of trifluoroacetic acid, 10 mg (22 mmol) of (1E,6E)-1-(1H-indol-6-yl)-7-[2-methoxy-4-(2-tetrahydrofuranylmethoxy)phenyl]hepta-1,6-diene-3,5-dione was dissolved. To this solution was added 7.3 mg (66 mmol) of phenylhydrazine at room temperature and the mixture was stirred at 100° C. for 1 hour. The reaction mixture was diluted with ethyl acetate, washed with a saturated sodium bicarbonate aqueous solution and then with saturated brine, and dried over magnesium sulfate. After filtration, the solvent was evaporated under reduced pressure. The residue was purified by silica gel column chromatography (hexane/ethyl acetate or methylene chloride/methanol). The resulting solid was washed with an organic solvent to give 3.1 mg (27% yield) of the title compound as a pale yellowish white powder with the following properties.

$^1$H NMR (δ, acetone-$d_6$): 1.7-2.0 (m, 4H), 3.71 (m, 1H), 3.83 (m, 1H), 3.88 (s, 3H×0.5), 3.91 (s, 3H×0.5), 3.99 (d, J=5.3 Hz, 1H×0.5), 4.00 (d, J=5.3 Hz, 1H×0.5), 4.2 (m, 1H), 6.45 (m, 1H), 6.53 (dd, J=2, 8 Hz, 1H×0.5), 6.58 (dd, J=2.4, 8.5 Hz, 1H×0.5), 6.61 (d, J=3 Hz, 1H×0.5), 6.62 (d, J=3 Hz, 1H×0.5), 6.97 (d, J=17 Hz, 1H×0.5), 7.00 (d, J=17 Hz, 1H×0.5), 7.01 (s, 1H), 7.08 (d, J=17 Hz, 1H×0.5), 7.12 (d, J=17 Hz, 1H×0.5), 7.23 (dd, J=2, 8.2 Hz, 1H×0.5), 7.32-7.62 (m, 11H+1H×0.5), 10.3 (br s, NH). melting point 90-95° C., MS (ESI+) m/z 518.2 (M+1).

Example 86

Synthesis of 3-[(1E)-2-(1H-indol-6-yl)ethenyl]-5-[(1E)-2-[2-methoxy-4-(2-pyridylmethoxy)phenyl]ethenyl]-1-phenyl-1H-pyrazole and 5-[(1E)-2-(1H-indol-6-yl)ethenyl]-3-[(1E)-2-[2-methoxy-4-(2-pyridylmethoxy)phenyl]ethenyl]-1-phenyl-1H-pyrazole

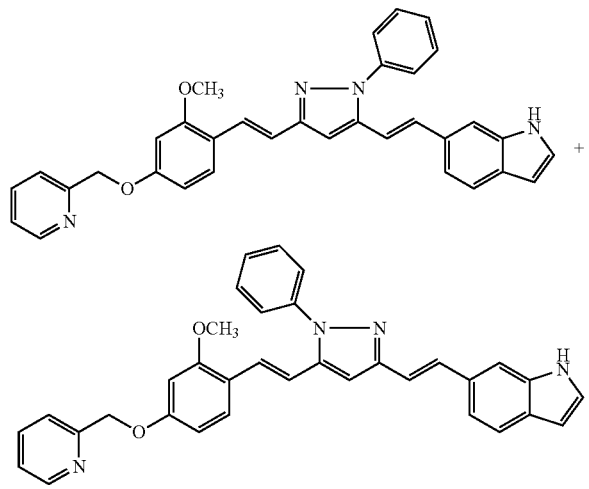

Synthesis was performed using the same materials in the same relative quantities as in Example 85 except that 10 mg (22 µmol) of (1E,6E)-1-(1H-indol-6-yl)-7-[2-methoxy-4-(2-pyridylmethoxy)phenyl]hepta-1,6-diene-3,5-dione was used instead of 10 mg (22 µmol) of (1E,6E)-1-(1H-indol-6-yl)-7-[2-methoxy-4-(2-tetrahydrofuranylmethoxy)phenyl]hepta-1,6-diene-3,5-dione to give 7.7 mg (66% yield) of the title compound as a pale yellowish white powder with following properties.

$^1$H NMR (δ, acetone-$d_6$): 3.88 (s, 3H×0.5), 3.92 (s, 3H×0.5), 5.21 (s, 2H×0.5), 5.23 (s, 2H×0.5), 6.46 (br d, J=3 Hz, 1H), 6.62 (dd, J=2.5, 8.7 Hz, 1H×0.5), 6.66 (dd, J=2.5, 8.7 Hz, 1H×0.5), 6.73 (d, J=3 Hz, 1H×0.5), 6.74 (d, J=3 Hz, 1H×0.5), 6.95 (d, J=17 Hz, 1H×0.5), 7.01 (br s, 1H), 7.02 (d, J=17 Hz, 1H×0.5), 7.09 (d, J=17 Hz, 1H×0.5), 7.13 (d, J=17 Hz, 1H×0.5), 7.23 (dd, J=2, 8 Hz, 1H×0.5), 7.26-7.63 (m, 13H+1H×0.5), 7.82 (m, 1H), 8.57 (m, 1H), 10.3 (br s, NH). melting point 96-104° C., MS (ESI+) m/z 525.0 (M+1).

Example 87

Synthesis of 3-[(1E)-2-(1H-indol-6-yl)ethenyl]-5-[(1E)-2-[2-methoxy-4-(2-tetrahydrofuranylmethoxy)phenyl]ethenyl]-1-nitrophenyl-1H-pyrazole and 5-[(1E)-2-(1H-indol-6-yl)ethenyl]-3-[(1E)-2-[2-methoxy-4-(2-tetrahydrofuranylmethoxy)phenyl]ethenyl]-1-nitrophenyl-1H-pyrazole

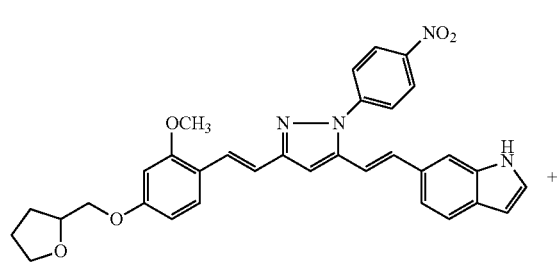

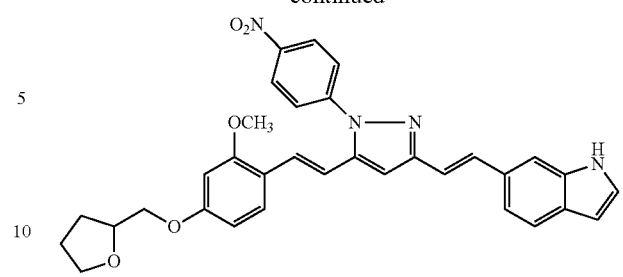

In 0.44 mL of toluene and 22 µL of trifluoroacetic acid, 20 mg (45 µmol) of (1E,6E)-1-(1H-indol-6-yl)-7-[2-methoxy-4-(2-tetrahydrofuranylmethoxy)phenyl]hepta-1,6-diene-3,5-dione was dissolved. To this solution was added 21 mg (0.14 mmol) of 4-nitrophenylhydrazine at room temperature and the mixture was stirred at 80° C. for 1 hour. The reaction mixture was diluted with ethyl acetate, washed with a saturated sodium bicarbonate aqueous solution and then with saturated brine, and dried over magnesium sulfate. After filtration, the solvent was evaporated under reduced pressure. The residue was purified by silica gel column chromatography (hexane/ethyl acetate or methylene chloride/methanol). The resulting solid was washed with an organic solvent to give 5.7 mg (23% yield) of the title compound as a yellow powder with the following properties.

$^1$H NMR (δ, acetone-$d_6$): 1.7-2.0 (m, 4H), 3.73 (m, 1H), 3.85 (m, 1H), 3.93 (s, 3H×0.5), 3.94 (s, 3H×0.5), 4.02 (d, J=5 Hz, 1H×0.5), 4.03 (d, J=5 Hz, 1H×0.5), 4.2 (m, 1H), 6.49 (m, 1H), 6.57 (dd, J=2.4, 8.5 Hz, 1H×0.5), 6.60 (dd, J=2.4, 8.5 Hz, 1H×0.5), 6.65 (d, J=2.5 Hz, 1H×0.5), 6.66 (d, J=2.5 Hz, 1H×0.5), 7.10 (d, J=17 Hz, 1H×0.5), 7.11 (d, J=17 Hz, 1H×0.5), 7.12 (s, 1H), 7.16 (d, J=17 Hz, 1H×0.5), 7.17 (d, J=17 Hz, 1H×0.5), 7.34 (dd, J=1.4, 8.4 Hz, 1H×0.5), 7.39 (m, 1H), 7.41 (dd, J=1.4, 8.4 Hz, 1H×0.5), 7.45-7.61 (m, 4H), 7.65 (br s, 1H×0.5), 7.66 (br s, 1H×0.5), 7.94 (br d, J=9.2 Hz, 2H×0.5), 7.95 (br d, J=9.2 Hz, 2H×0.5), 8.47 (br d, J=9.2 Hz, 2H×0.5), 8.48 (br d, J=9.2 Hz, 2H×0.5), 10.4 (br s, NH). melting point 94-101° C., MS (ESI+) m/z 563.2 (M+1).

Example 88

Synthesis of 3-[(1E)-2-(1H-indol-6-yl)ethenyl]-5-[(1E)-2-[2-methoxy-4-(2-pyridylmethoxy)phenyl]ethenyl]-1-nitrophenyl-1H-pyrazole and 5-[(1E)-2-(1H-indol-6-yl)ethenyl]-3-[(1E)-2-[2-methoxy-4-(2-pyridylmethoxy)phenyl]ethenyl]-1-nitrophenyl-1H-pyrazole

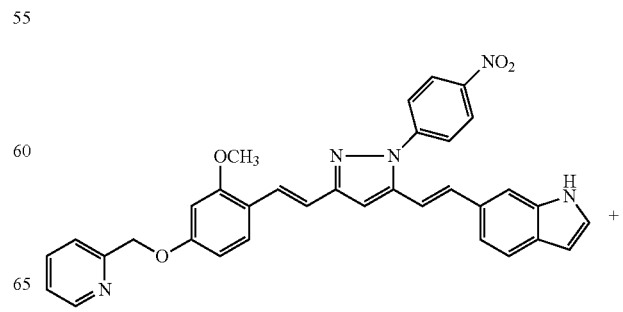

89

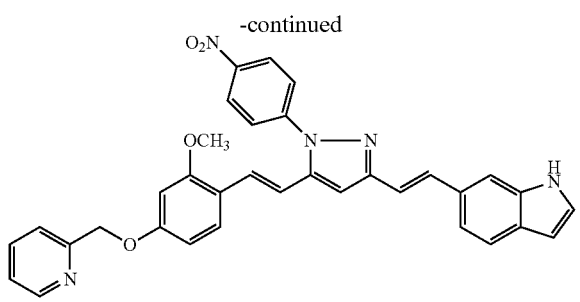

-continued

Synthesis was performed using the same materials in the same relative quantities as in Example 87 except that 20 mg (44 μmol) of (1E,6E)-1-(1H-indol-6-yl)-7-[2-methoxy-4-(2-pyridylmethoxy)phenyl]hepta-1,6-diene-3,5-dione was used instead of 20 mg (45 μmol) of (1E,6E)-1-(1H-indol-6-yl)-7-[2-methoxy-4-(2-tetrahydrofuranylmethoxy)phenyl]hepta-1,6-diene-3,5-dione to give 20.5 mg (81% yield) of the title compound as a yellow powder with the following properties.

$^1$H NMR (δ, acetone-$d_6$): 3.93 (s, 3H×0.5), 3.94 (s, 3H×0.5), 5.25 (s, 2H), 6.49 (m, 1H), 6.66 (dd, J=2.4, 9 Hz, 1H×0.5), 6.69 (dd, J=2.4, 9 Hz, 1H×0.5), 6.77 (d, J=2.5 Hz, 1H×0.5), 6.78 (d, J=2.5 Hz, 1H×0.5), 7.10 (d, J=17 Hz, 1H×0.5), 7.12 (d, J=17 Hz, 1H×0.5), 7.13 (br s, 1H), 7.16 (d, J=17 Hz, 1H×0.5), 7.17 (d, J=17 Hz, 1H×0.5), 7.30-7.42 (m, 3H), 7.45-7.54 (m, 2H), 7.54-7.67 (m, 3H), 7.65 (br s, 1H×0.5), 7.66 (br s, 1H×0.5), 7.83 (dt, J=1.7, 7.8 Hz, 1H×0.5), 7.84 (dt, J=1.7, 7.8 Hz, 1H×0.5), 7.94 (br d, J=9.2 Hz, 2H×0.5), 7.95 (br d, J=9.2 Hz, 2H×0.5), 8.46 (br d, J=9.2 Hz, 2H×0.5), 8.48 (br d, J=9.2 Hz, 2H×0.5), 8.60 (br d, J=6 Hz, 1H), 10.4 (br s, NH). melting point 107-112° C., MS (ESI+) m/z 570.2 (M+1).

Example 89

Synthesis of 3-[(1E)-2-(1H-indol-6-yl)ethenyl]-5-[(1E)-2-[2-methoxy-4-(2-pyridylmethoxy)phenyl]ethenyl]-1-methyl-1H-pyrazole and 5-[(1E)-2-(1H-indol-6-yl)ethenyl]-3-[(1E)-2-[2-methoxy-4-(2-pyridylmethoxy)phenyl]ethenyl]-1-methyl-1H-pyrazole

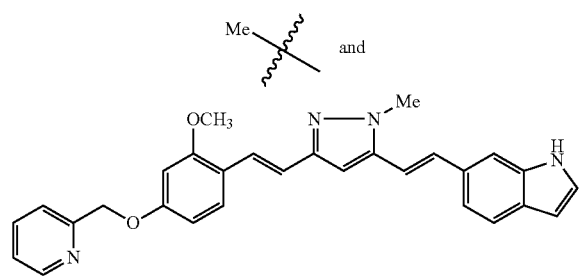

In 0.22 mL of acetic acid was dissolved 20 mg (44 μmol) of (1E,6E)-1-(1H-indol-6-yl)-7-[2-methoxy-4-(2-pyridylmethoxy)phenyl]hepta-1,6-diene-3,5-dione. To this solution was added 7.0 μL (0.13 mmol) of methylhydrazine at room temperature and the mixture was stirred at 80° C. for 1 hour. The reaction mixture was diluted with ethyl acetate, washed with a saturated sodium bicarbonate aqueous solution and then with saturated brine, and dried over magnesium sulfate. After filtration, the solvent was evaporated under reduced pressure. The residue was purified by silica gel column chromatography (hexane/ethyl acetate or methylene chloride/methanol). The resulting solid was washed with an organic solvent to give 2.1 mg (10% yield) of the title compound as a yellow powder with the following properties.

$^1$H NMR (δ, acetone-$d_6$): 3.80 (s, 3H×0.5), 3.90 (s, 3H×0.5), 3.92 (s, 3H×0.5), 3.93 (s, 3H×0.5), 5.22 (s, 2H×0.5), 5.23 (s, 2H×0.5), 6.44 (dd, J=1, 3 Hz, 1H×0.5), 6.46 (dd, J=1, 3 Hz, 1H×0.5), 6.64 (dd, J=2.3, 9 Hz, 1H×0.5), 6.65 (dd, J=2.3, 9 Hz, 1H×0.5), 6.72 (d, J=2.4 Hz, 1H×0.5), 6.74 (br s, 1H+1H×0.5), 6.98 (d, J=17 Hz, 1H×0.5), 7.02 (d, J=17 Hz, 1H×0.5), 7.09 (d, J=17 Hz, 1H×0.5), 7.12 (d, J=17 Hz, 1H×0.5), 7.26 (d, J=17 Hz, 1H×0.5), 7.27-7.37 (m, 4H), 7.40 (dd, J=1.3, 8.4 Hz, 1H×0.5), 7.51-7.60 (m, 3H), 7.63 (br s, 1H), 7.81 (dt, J=1.8, 7.7 Hz, 1H×0.5), 7.82 (dt, J=1.8, 7.7 Hz, 1H×0.5), 8.58 (br d, J=5 Hz, 1H), 10.28 (br s, NH×0.5), 10.33 (br s, NH×0.5). melting point 80-85° C., MS (ESI+) m/z 463.1 (M+1).

Example 90

Synthesis of 1-tert-butyl-3-[(1E)-2-(1H-indol-6-yl)ethenyl]-5-[(1E)-2-[2-methoxy-4-(2-pyridylmethoxy)phenyl]ethenyl]-1H-pyrazole and 1-tert-butyl-5-[(1E)-2-(1H-indol-6-yl)ethenyl]-3-[(1E)-2-[2-methoxy-4-(2-pyridylmethoxy)phenyl]ethenyl]-1H-pyrazole

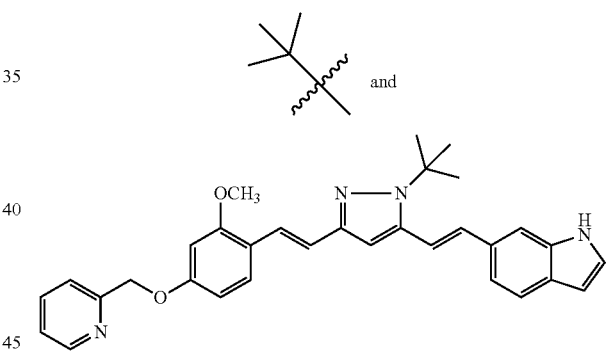

Synthesis was performed in the same manner as in Example 89 except that 16 mg (0.13 mmol) of tert-butylhydrazine was used instead of 7.0 μL (0.13 mmol) of methylhydrazine (the reaction duration was 14 hours) to give 2.5 mg (11% yield) of the title compound as a pale yellowish white powder with the following properties.

$^1$H NMR (δ, acetone-$d_6$): 1.69 (s, 9H×0.5), 1.71 (s, 9H×0.5), 3.90 (s, 3H×0.5), 3.93 (s, 3H×0.5), 5.22 (s, 2H×0.5), 5.23 (s, 2H×0.5), 6.44 (dd, J=1, 3 Hz, 1H×0.5), 6.46 (dd, J=1, 3 Hz, 1H×0.5), 6.64 (dd, J=2.5, 9 Hz, 1H×0.5), 6.65 (dd, J=2.5, 9 Hz, 1H×0.5), 6.72 (d, J=2.5 Hz, 1H×0.5), 6.761 (d, J=2.5 Hz, 1H×0.5), 6.764 (br s, 1H), 6.99 (d, J=17 Hz, 1H×0.5), 7.04 (d, J=17 Hz, 1H×0.5), 7.17 (d, J=17 Hz, 1H×0.5), 7.22 (d, J=17 Hz, 1H×0.5), 7.26-7.38 (m, 4H+1H×0.5), 7.44 (d, J=17 Hz, 1H×0.5), 7.52-7.58 (m, 3H), 7.62 (br s, 1H), 7.81 (dt, J=1.8, 7.7 Hz, 1H×0.5), 7.82 (dt, J=1.8, 7.7 Hz, 1H×0.5), 8.58 (br d, J=5 Hz, 1H), 10.25 (br s, NH×0.5), 10.31 (br s, NH×0.5). melting point 76-84° C., MS (ESI+) m/z 505.3 (M+1).

Example 91

Synthesis of 1-hydroxyethyl-3-[(1E)-2-(1H-indol-6-yl)ethenyl]-5-[(1E)-2-[2-methoxy-4-(2-pyridylmethoxy)phenyl]ethenyl]-1H-pyrazole and 1-hydroxyethyl-5-[(1E)-2-(1H-indol-6-yl)ethenyl]-3-[(1E)-2-[2-methoxy-4-(2-pyridylmethoxy)phenyl]ethenyl]-1H-pyrazole

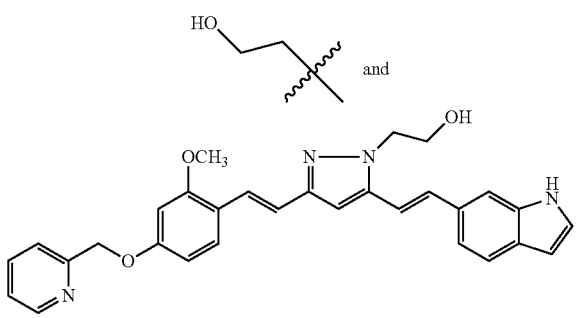

Synthesis was performed in the same manner as in Example 89 except that 9.0 µL (0.13 mmol) of 2-hydroxyethylhydrazine was used instead of 7.0 µL (0.13 mmol) of methylhydrazine (the reaction duration was 2 hours) to give 10.2 mg (47% yield) of the title compound as a pale yellowish white powder with the following properties.

$^1$H NMR (δ, acetone-$d_6$): 3.88-3.94 (m, 2H), 3.90 (s, 3H×0.5), 3.91 (s, 3H×0.5), 4.31 (d, J=5.6 Hz, 2H×0.5), 4.34 (d, J=5.6 Hz, 2H×0.5), 5.22 (s, 2H×0.5), 5.23 (s, 2H×0.5), 6.45 (dd, J=1, 3 Hz, 1H×0.5), 6.46 (dd, J=1, 3 Hz, 1H×0.5), 6.64 (dd, J=2.5, 9 Hz, 1H×0.5), 6.66 (dd, J=2.5, 9 Hz, 1H×0.5), 6.73 (d, J=2.5 Hz, 1H×0.5), 6.74 (d, J=2.5 Hz, 1H×0.5), 6.76 (br s, 1H), 7.00 (d, J=17 Hz, 1H×0.5), 7.05 (d, J=17 Hz, 1H×0.5), 7.16 (d, J=17 Hz, 1H×0.5), 7.20 (d, J=17 Hz, 1H×0.5), 7.28 (d, J=17 Hz, 1H×0.5), 7.27-7.40 (m, 4H+1H×0.5), 7.52-7.59 (m, 3H), 7.60 (d, J=8.7 Hz, 1H×0.5), 7.62 (br s, 1H×0.5), 7.82 (br dt, J=2, 8 Hz, 1H), 8.58 (br d, J=5 Hz, 1H), 10.29 (br s, NH×0.5), 10.33 (br s, NH×0.5). melting point 94-97° C., MS (ESI+) m/z 493 (M+1).

Example 92

Synthesis of 1-benzyl-3-[(1E)-2-(1H-indol-6-yl)ethenyl]-5-[(1E)-2-[2-methoxy-4-(2-pyridylmethoxy)phenyl]ethenyl]-1H-pyrazole and 1-benzyl-5-[(1E)-2-(1H-indol-6-yl)ethenyl]-3-[(1E)-2-[2-methoxy-4-(2-pyridylmethoxy)phenyl]ethenyl]-1H-pyrazole

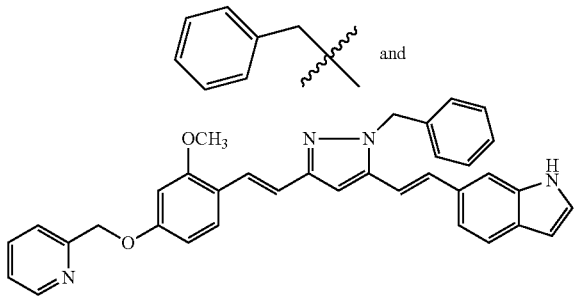

Synthesis was performed in the same manner as in Example 89 except that 21 mg (0.13 mmol) of benzylhydrazine was used instead of 7.0 µL (0.13 mmol) of methylhydrazine (the reaction duration was 10 hours) to give 11.2 mg (47% yield) of the title compound as a pale yellowish white powder with the following properties.

$^1$H NMR (δ, acetone-$d_6$): 3.88 (s, 3H×0.5), 3.90 (s, 3H×0.5), 5.21 (s, 2H×0.5), 5.22 (s, 2H×0.5), 5.50 (s, 2H×0.5), 5.54 (s, 2H×0.5), 6.44 (m, 1H), 6.61 (dd, J=2.3, 8.6 Hz, 1H×0.5), 6.64 (dd, J=2.4, 8.6 Hz, 1H×0.5), 6.72 (d, J=2.4 Hz, 1H×0.5), 6.73 (d, J=2.4 Hz, 1H×0.5), 6.84 (br s, 1H), 7.03 (d, J=17 Hz, 1H×0.5), 7.07 (d, J=17 Hz, 1H×0.5), 7.12 (d, J=17 Hz, 1H×0.5), 7.14 (d, J=17 Hz, 1H×0.5), 7.22-7.35 (m, 9H+1H×0.5), 7.39 (d, J=17 Hz, 1H×0.5), 7.47 (d, J=8.7 Hz, 1H×0.5), 7.51-7.57 (m, 2H+1H×0.5), 7.57 (br s, 1H×0.5), 7.58 (br s, 1H×0.5), 7.81 (dt, J=1.8, 7.7 Hz, 1H×0.5), 7.82 (dt, J=1.8, 7.7 Hz, 1H×0.5), 8.57 (m, 1H), 10.29 (br s, NH×0.5), 10.32 (br s, NH×0.5). melting point 80-86° C., MS (ESI+) m/z 539.2 (M+1).

Example 93

Synthesis of 1-cyclohexyl-3-[(1E)-2-(1H-indol-6-yl)ethenyl]-5-[(1E)-2-[2-methoxy-4-(2-pyridylmethoxy)phenyl]ethenyl]-1H-pyrazole and 1-cyclohexyl-5-[(1E)-2-(1H-indol-6-yl)ethenyl]-3-[(1E)-2-[2-methoxy-4-(2-pyridylmethoxy)phenyl]ethenyl]-1H-pyrazole

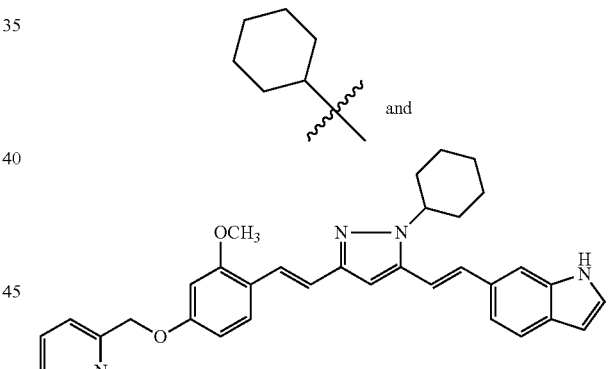

Synthesis was performed in the same manner as in Example 89 except that 20 mg (0.13 mmol) of cyclohexylhydrazine was used instead of 7.0 µL (0.13 mmol) of methylhydrazine (the reaction duration was 12 hours) to give 3.6 mg (15% yield) of the title compound as a pale yellowish white powder with the following properties.

$^1$H NMR (δ, acetone-$d_6$): 1.2-2.0 (m, 10H), 3.90 (s, 3H×0.5), 3.92 (s, 3H×0.5), 4.43 (m, 1H), 5.22 (s, 2H×0.5), 5.23 (s, 2H×0.5), 6.44 (br d, J=3 Hz, 1H×0.5), 6.46 (br d, J=3 Hz, 1H×0.5), 6.65 (br dd, J=2, 9 Hz, 1H), 6.72 (d, J=2.4 Hz, 1H×0.5), 6.74 (br s, 1H), 6.75 (d, J=2.4 Hz, 1H×0.5), 7.02 (d, J=17 Hz, 1H×0.5), 7.06 (d, J=17 Hz, 1H×0.5), 7.16 (d, J=17 Hz, 1H×0.5), 7.20 (d, J=17 Hz, 1H×0.5), 7.25 (d, J=17 Hz, 1H×0.5), 7.27-7.38 (m, 4H), 7.40 (dd, J=1.3, 8.4 Hz, 1H×0.5), 7.52-7.58 (m, 3H), 7.60 (d, J=8.7 Hz, 1H×0.5), 7.61 (br s, 1H×0.5), 7.81 (br dt, J=2, 8 Hz, 1H), 8.58 (br d, J=4 Hz, 1H), 10.29 (br s, NH×0.5), 10.32 (br s, NH×0.5). melting point 101-115° C., MS (ESI+) m/z 531.3 (M+1).

Example 94

Synthesis of 3-[(1E)-2-(1H-indol-6-yl)ethenyl]-5-[(1E)-2-[2-methoxy-4-(2-pyridylmethoxy)phenyl]ethenyl]-1-(2-pyridyl)-1H-pyrazole and 5-[(1E)-2-(1H-indol-6-yl)ethenyl]-3-[(1E)-2-[2-methoxy-4-(2-pyridylmethoxy)phenyl]ethenyl]-1-(2-pyridyl)-1H-pyrazole

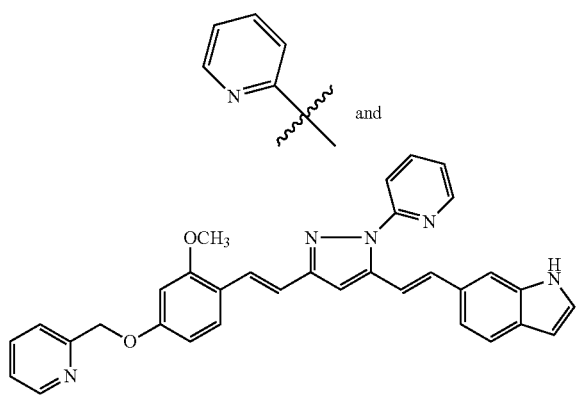

Synthesis was performed in the same manner as in Example 89 except that 15 mg (0.13 mmol) of 2-pyridylhydrazine was used instead of 7.0 μL (0.13 mmol) of methylhydrazine to give 18.2 mg (78% yield) of the title compound as a pale yellowish white powder with the following properties.

$^1$H NMR (δ, acetone-$d_6$): 3.92 (s, 3H×0.5), 3.93 (s, 3H×0.5), 5.23 (s, 2H×0.5), 5.24 (s, 2H×0.5), 6.47 (br d, J=3 Hz, 1H), 6.66 (dd, J=2.5, 8.5 Hz, 1H×0.5), 6.67 (dd, J=2.3, 8.5 Hz, 1H×0.5), 6.75 (d, J=2 Hz, 1H×0.5), 6.76 (d, J=2 Hz, 1H×0.5), 7.11 (d, J=17 Hz, 1H×0.5), 7.102 (br s, 1H×0.5), 7.106 (br s, 1H×0.5), 7.14 (d, J=17 Hz, 1H×0.5), 7.30-7.61 (m, 9H), 7.63 (br s, 1H×0.5), 7.64 (br s, 1H×0.5), 7.818 (dt, J=1.8, 7.7 Hz, 1H×0.5), 7.822 (dt, J=1.8, 7.7 Hz, 1H×0.5), 7.94-8.02 (m, 2H), 8.12 (d, J=17 Hz, 1H×0.5), 8.16 (d, J=17 Hz, 1H×0.5), 8.52-8.60 (m, 2H), 10.3 (br s, NH). melting point 91-97° C., MS (ESI+) m/z 526.2 (M+1).

Example 95

Synthesis of 3-[(1E)-2-(1H-indol-6-yl)ethenyl]-1-(4-methoxyphenyl)-5-[(1E)-2-[2-methoxy-4-(2-pyridylmethoxy)phenyl]ethenyl]-1H-pyrazole and 5-[(1E)-2-(1H-indol-6-yl)ethenyl]-1-(4-methoxyphenyl)-3-[(1E)-2-[2-methoxy-4-(2-pyridylmethoxy)phenyl]ethenyl]-1H-pyrazole

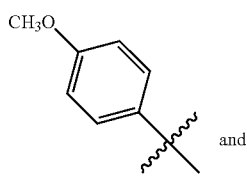

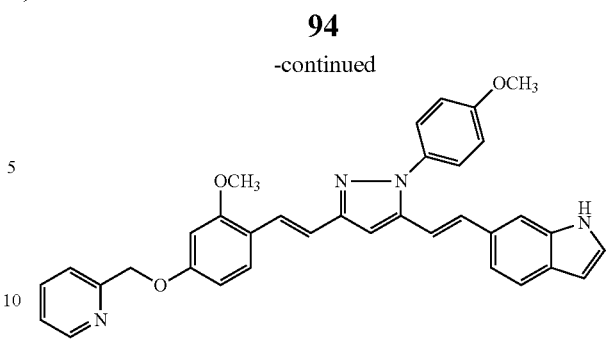

Synthesis was performed in the same manner as in Example 89 except that 23 mg (0.13 mmol) of 4-methoxyphenylhydrazine was used instead of 7.0 μL (0.13 mmol) of methylhydrazine to give 7.9 mg (32% yield) of the title compound as a pale yellowish white powder with the following properties.

$^1$H NMR (δ, acetone-$d_6$): 3.878 (s, 3H×0.5), 3.883 (s, 3H×0.5), 3.90 (s, 3H×0.5), 3.91 (s, 3H×0.5), 5.21 (s, 2H×0.5), 5.23 (s, 2H×0.5), 6.45 (m, 1H), 6.61 (dd, J=2.4, 8.5 Hz, 1H×0.5), 6.66 (dd, J=2.4, 8.5 Hz, 1H×0.5), 6.73 (d, J=3 Hz, 1H×0.5), 6.74 (d, J=3 Hz, 1H×0.5), 6.88 (d, J=17 Hz, 1H×0.5), 6.94 (d, J=17 Hz, 1H×0.5), 6.97 (br s, 1H), 7.07 (d, J=17 Hz, 1H×0.5), 7.08-7.14 (m, 2H+1H×0.5), 7.21 (dd, J=1.4, 8.4 Hz, 1H×0.5), 7.28-7.60 (m, 10H), 7.61 (br s, 1H×0.5), 7.81 (dt, J=1.7, 7.8 Hz, 1H×0.5), 7.82 (dt, J=1.8, 7.8 Hz, 1H×0.5), 8.57 (m, 1H), 10.3 (br s, NH). melting point 92-99° C., MS (ESI+) m/z 555.1 (M+1).

Example 96

Synthesis of 3-[(1E)-2-(1H-indol-6-yl)ethenyl]-5-[(1E)-2-[2-methoxy-4-(2-pyridylmethoxy)phenyl]ethenyl]-1-(2-methylphenyl)-1H-pyrazole and 5-[(1E)-2-(1H-indol-6-yl)ethenyl]-3-[(1E)-2-[2-methoxy-4-(2-pyridylmethoxy)phenyl]ethenyl]-1-(2-methylphenyl)-1H-pyrazole

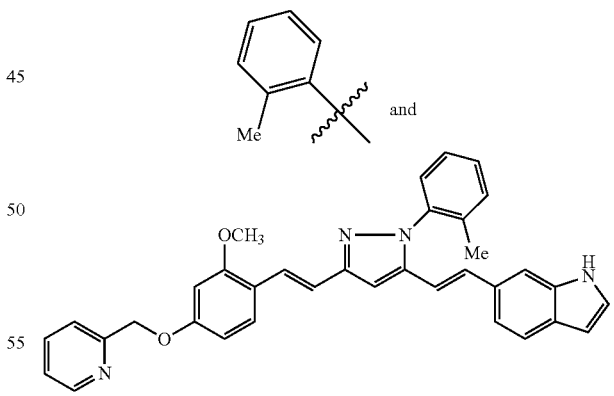

Synthesis was performed in the same manner as in Example 89 except that 21 mg (0.13 mmol) of 2-methylphenylhydrazine was used instead of 7.0 μL (0.13 mmol) of methylhydrazine to give 21.4 mg (74% yield) of the title compound as a pale yellowish white powder with the following properties.

$^1$H NMR (δ, acetone-$d_6$): 2.04 (s, 3H×0.5), 2.10 (s, 3H×0.5), 3.81 (s, 3H×0.5), 3.91 (s, 3H×0.5), 5.18 (s, 2H×0.5), 5.22 (s, 2H×0.5), 6.43 (br d, J=3 Hz, 1H×0.5), 6.45 (br d, J=3

Hz, 1H×0.5), 6.56 (d, J=17 Hz, 1H×0.5), 6.57 (dd, J=2.4, 8.3 Hz, 1H×0.5), 6.60 (d, J=17 Hz, 1H×0.5), 6.66 (dd, J=2.4, 8.6 Hz, 1H×0.5), 6.69 (d, J=2.4 Hz, 1H×0.5), 6.74 (d, J=2.3 Hz, 1H×0.5), 6.99 (br s, 1H), 7.01 (d, J=7.4 Hz, 1H×0.5), 7.08 (d, J=17 Hz, 1H×0.5), 7.11 (d, J=7.4 Hz, 1H×0.5), 7.12 (d, J=17 Hz, 1H×0.5), 7.26-7.61 (m, 12H), 7.79 (dt, J=1.7, 7.8 Hz, 1H×0.5), 7.82 (dt, J=1.7, 7.8 Hz, 1H×0.5), 8.56 (br d, J=5 Hz, 1H×0.5), 8.57 (br d, J=5 Hz, 1H×0.5), 10.27 (br s, NH×0.5), 10.31 (br s, NH×0.5). melting point 94-100° C., MS (ESI+) m/z 539.3 (M+1).

Example 97

Synthesis of 3-[(1E)-2-[4-diethylamino-2-[2-(1-piperidyl)ethoxy]phenyl]ethenyl]-5-[(1E)-2-(1H-indol-6-yl)ethenyl]-1H-pyrazole

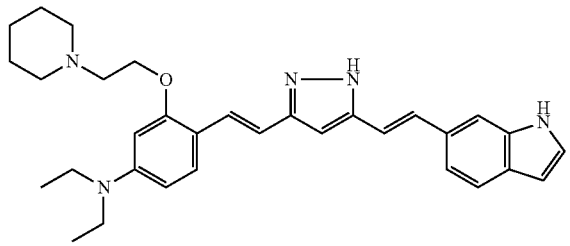 [SMILES: CCN(CC)c1ccc(/C=C/c2cc(/C=C/c3ccc4cc[nH]c4c3)[nH]n2)c(OCCN2CCCCC2)c1]

(1) Synthesis of 4-diethylamino-2-[2-(1-piperidyl)ethoxy]benzaldehyde

In 90 mL of acetonitrile was dissolved 2.8 g (14.6 mmol) of 4-diethylaminosalicylaldehyde. To this solution were added 14.3 g (43.8 mmol) of cesium carbonate and 2.8 g (15.3 mmol) of 1-(2-chloroethyl)piperidine hydrochloride at room temperature and the mixture was stirred at 80° C. for 4 hours. Water (150 mL) was added to the resulting reaction mixture and extraction with ethyl acetate (100 mL×3) was performed. The combined organic layer was dried over anhydrous sodium sulfate. After filtration, the solvent was evaporated under reduced pressure to quantitatively give 4.5 g of the title compound.
$^1$H NMR (δ, chloroform-d): 1.21 (t, J=7.1 Hz, 6H), 1.43-1.48 (m, 2H), 1.59-1.64 (m, 4H), 2.52-2.58 (m, 4H), 2.83-2.86 (m, 2H), 3.39-3.44 (m, 4H), 4.17-4.21 (m, 2H), 6.04 (d, J=2.3 Hz, 1H), 6.28 (dd, J=1.7 Hz, 9.0 Hz, 1H), 7.71 (d, J=9.2 Hz, 1H), 10.16 (s, 1H). melting point 70-72° C., MS (EI) m/z 304 (M+).

(2) Synthesis of (1E,6E)-1-[4-diethylamino-2-[2-(1-piperidyl)ethoxy]phenyl]-7-(1H-indol-6-yl)hepta-1,6-diene-3,5-dione Synthesis was performed using the same materials in the same relative quantities as in Example 1 (2) except that 295 mg (0.97 mmol) of 4-diethylamino-2-[2-(1-piperidyl)ethoxy]benzaldehyde was used instead of 20 mg (85 µmol) of 2-methoxy-4-(2-tetrahydrofuranylmethoxy)benzaldehyde to give 140 mg (31% yield) of the title compound.
$^1$H NMR (δ, DMSO-$d_6$): 1.14 (t, J=7.1 Hz, 6H), 1.37-1.46 (m, 2H), 1.51-1.57 (m, 4H), 2.48-2.51 (m, 4H, overlapped DMSO), 2.73-2.76 (m, 2H), 3.40-3.45 (m, 4H), 4.15-4.18 (m, 2H), 5.95 (s, 1H), 6.22 (d, J=2.6 Hz, 1H), 6.33 (dd, J=2.0 Hz, 9.0 Hz, 1H), 6.46-6.48 (m, 1H), 6.65 (d, J=15.4 Hz, 1H), 6.79 (d, J=16.0 Hz, 1H), 7.37-7.40 (m, 1H), 7.45-7.48 (m, 2H), 7.58 (d, J=8.4 Hz, 1H), 7.65-7.69 (m, 2H), 7.79 (d, J=16.1 Hz, 1H), 11.31 (s, 1H), 16.61 (br s, 1H). MS (EI) m/z 513 (M+).

(3) Synthesis of 3-[(1E)-2-[4-diethylamino-2-[2-(1-piperidyl)ethoxy]phenyl]ethenyl]-5-[(1E)-2-(1H-indol-6-yl)ethenyl]-1H-pyrazole Synthesis was performed using the same materials in the same relative quantities as in Example 4 (4) except that 400 mg (0.78 mmol) of (1E,6E)-1-[4-diethylamino-2-[2-(1-piperidyl)ethoxy]phenyl]-7-(1H-indol-6-yl)hepta-1,6-diene-3,5-dione was used instead of 15 mg (35 µmol) of (1E,6E)-1-(1H-indol-5-yl)-7-[4-(2-pyridylmethoxy)phenyl]hepta-1,6-diene-3,5-dione to give 196 mg (49% yield) of the title compound.
$^1$H NMR (δ, DMSO-$d_6$): 1.12 (t, J=7.1 Hz, 6H), 1.37-1.44 (m, 2H), 1.52-1.58 (m, 4H), 2.52-2.59 (m, 4H), 2.76-2.82 (m, 2H), 3.35-3.40 (m, 4H), 4.12-4.16 (m, 2H), 6.24 (d, J=2.6 Hz, 1H), 6.30 (dd, J=2.3 Hz, 8.7 Hz, 1H), 6.42 (s, 1H), 6.57 (s, 1H), 6.85 (d, J=16.7 Hz, 1H), 7.00 (d, J=16.6 Hz, 1H), 7.18-7.28 (m, 3H), 7.31-7.37 (m, 2H), 7.48-7.54 (m, 2H), 11.10 (s, 1H), 12.68 (br s, 1H). melting point 102-104° C., MS (EI) m/z 509 (M+).

Example 98

Synthesis of 3-[(1E)-2-[4-diethylamino-2-(2-morpholinoethoxy)phenyl]ethenyl]-5-[(1E)-2-(1H-indol-6-yl)ethenyl]-1H-pyrazole

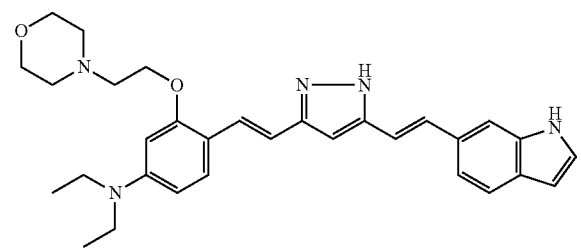 [SMILES: CCN(CC)c1ccc(/C=C/c2cc(/C=C/c3ccc4cc[nH]c4c3)[nH]n2)c(OCCN2CCOCC2)c1]

(1) Synthesis of 4-diethylamino-2-(2-morpholinoethoxy)benzaldehyde

Synthesis was performed using the same materials in the same relative quantities as in Example 97 (1) except that 5.1 g (27.2 mmol) of 1-(2-chloroethyl)morpholine hydrochloride was used instead of 2.8 g (15.3 mmol) of 1-(2-chloroethyl)piperidine hydrochloride to give 7.0 g (89% yield) of the title compound.
$^1$H NMR (δ, chloroform-d): 1.22 (t, J=7.4 Hz, 6H), 2.58-2.63 (m, 4H), 2.85-2.88 (m, 2H), 3.39-3.45 (m, 4H), 3.71-3.75 (m, 4H), 4.18-4.21 (m, 2H), 6.03 (d, J=2.3 Hz, 1H), 6.30 (dd, J=1.8 Hz, 8.7 Hz, 1H), 7.71 (d, J=9.2 Hz, 1H), 10.15 (s, 1H). melting point 107-109° C., MS (EI) m/z 306 (M+).

(2) Synthesis of (1E,6E)-1-[4-diethylamino-2-(2-morpholinoethoxy)phenyl]-7-(1H-indol-6-yl)hepta-1,6-diene-3,5-dione Synthesis was performed using the same materials in the same relative quantities as in Example 1 (2) except that 1.5 g (4.8 mmol) of 4-diethylamino-2-(2-morpholinoethoxy)benzaldehyde was used instead of 20 mg (85 μmol) of 2-methoxy-4-(2-tetrahydrofuranylmethoxy)benzaldehyde to give 1.2 g (53% yield) of the title compound.

$^1$H NMR (δ, DMSO-d$_6$): 1.14 (t, J=6.8 Hz, 6H), 2.52-2.55 (m, 4H), 2.77-2.81 (m, 2H), 3.40-3.45 (m, 4H), 3.60-3.63 (m, 4H), 4.18-4.21 (m, 2H), 5.95 (s, 1H), 6.23 (d, J=2.6 Hz, 1H), 6.34 (dd, J=2.0 Hz, 9.0 Hz, 1H), 6.46-6.48 (m, 1H), 6.66 (d, J=15.3 Hz, 1H), 6.80 (d, J=16.0 Hz, 1H), 7.38-7.41 (m, 1H), 7.44-7.49 (m, 2H), 7.58 (d, J=8.4 Hz, 1H), 7.65-7.70 (m, 2H), 7.80 (d, J=16.1 Hz, 1H), 11.31 (s, 1H), 16.62 (br s, 1H). MS (EI) m/z 515 (M+).

(3) Synthesis of 3-[(1E)-2-[4-diethylamino-2-(2-morpholinoethoxy)phenyl]ethenyl]-5-[(1E)-2-(1H-indol-6-yl)ethenyl]-1H-pyrazole Synthesis was performed using the same materials in the same relative quantities as in Example 4 (4) except that 712 mg (1.38 mmol) of (1E,6E)-1-[4-diethylamino-2-(2-morpholinoethoxy) phenyl]-7-(1H-indol-6-yl)hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 446 mg (63% yield) of the title compound.

$^1$H NMR (δ, DMSO-d$_6$): 1.12 (t, J=7.1 Hz, 6H), 2.53-2.58 (m, 4H), 2.78-2.83 (m, 2H), 3.34-3.40 (m, 4H), 3.60-3.63 (m, 4H), 4.14-4.18 (m, 2H), 6.25 (d, J=1.9 Hz, 1H), 6.30 (dd, J=2.0 Hz, 9.0 Hz, 1H), 6.42 (s, 1H), 6.57 (s, 1H), 6.87 (d, J=16.7 Hz, 1H), 7.00 (d, J=16.7 Hz, 1H), 7.18-7.28 (m, 3H), 7.31-7.36 (m, 2H), 7.49-7.54 (m, 2H), 11.10 (s, 1H), 12.69 (br s, 1H). melting point 96-99° C., MS (EI) m/z 511 (M+).

Example 99

Synthesis of 3-[(1E)-2-(5-fluoro-1H-indol-3-yl)ethenyl]-5-[(1E)-2-[2-methoxy-4-(2-pyridylmethoxy)phenyl]ethenyl]-1H-pyrazole

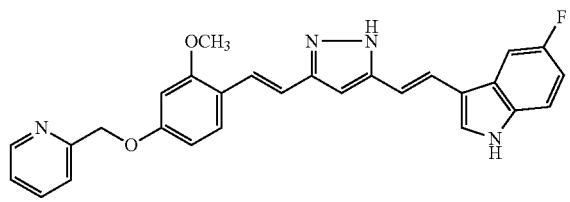 [SMILES: COc1cc(OCc2ccccn2)ccc1/C=C/c1cc(/C=C/c2c[nH]c3ccc(F)cc23)[nH]n1]

(1) Synthesis of (1E,6E)-1-(5-fluoro-1H-indol-3-yl)-7-[2-methoxy-4-(2-pyridylmethoxy)phenyl]hepta-1,6-diene-3,5-dione Synthesis was performed using the same materials in the same relative quantities as in Example 30 (2) except that 111 mg (0.68 mmol) of 5-fluoro-1H-indole-3-carbaldehyde was used instead of 20 mg (0.14 mmol) of 1H-benzotriazole-5-carboxaldehyde to give 57 mg (20% yield) of the title compound.

$^1$H NMR (δ, DMSO-d$_6$): 3.89 (s, 3H), 5.26 (s, 2H), 6.11 (s, 1H), 6.69-6.78 (m, 4H), 7.05-7.10 (m, 1H), 7.35-7.38 (m, 1H), 7.46-7.50 (m, 1H), 7.55 (d, J=7.7 Hz, 1H), 7.65 (d, J=9.0 Hz, 1H), 7.75 (d, J=15.4 Hz, 1H), 7.80-7.88 (m, 3H), 8.02 (s, 1H), 8.59-8.60 (m, 1H), 11.89 (s, 1H), 16.50 (br s, 1H). melting point 183-186° C., MS (EI) m/z 470 (M+).

(2) Synthesis of 3-[(1E)-2-(5-fluoro-1H-indol-3-yl)ethenyl]-5-[(1E)-2-[2-methoxy-4-(2-pyridylmethoxy)phenyl]ethenyl]-1H-pyrazole Synthesis was performed using the same materials in the same relative quantities as in Example 4 (4) except that 40 mg (85 μmol) of (1E,6E)-1-(5-fluoro-1H-indol-3-yl)-7-[2-methoxy-4-(2-pyridylmethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 20 mg (50% yield) of the title compound.

$^1$H NMR (δ, DMSO-d$_6$): 3.86 (s, 3H), 5.23 (s, 2H), 6.61-6.67 (m, 2H), 6.74 (s, 1H), 6.90 (d, J=16.7 Hz, 1H), 6.93-7.06 (m, 2H), 7.18-7.37 (m, 3H), 7.38-7.44 (m, 1H), 7.47-7.56 (m, 2H), 7.60-7.64 (m, 1H), 7.69-7.71 (m, 1H), 7.85 (dt, J=1.9, 7.7 Hz, 1H), 8.58-8.60 (m, 1H), 11.30-11.47 (m, 1H), 12.55-12.75 (m, 1H). melting point 209-213° C., MS (EI) m/z 466 (M+).

Example 100

Synthesis of 3-[(1E)-2-(5-methoxy-1H-indol-3-yl)ethenyl]-5-[(1E)-2-[2-methoxy-4-(2-pyridylmethoxy)phenyl]ethenyl]-1H-pyrazole

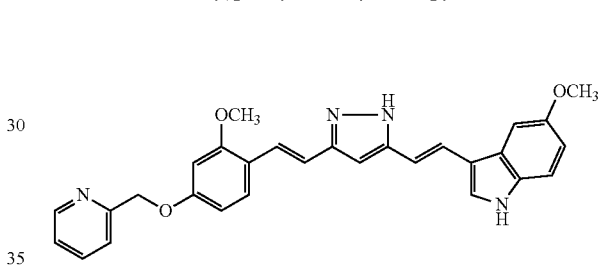

(1) Synthesis of (1E,6E)-1-(5-methoxy-1H-indol-3-yl)-7-[2-methoxy-4-(2-pyridylmethoxy)phenyl]hepta-1,6-diene-3,5-dione Synthesis was performed using the same materials in the same relative quantities as in Example 30 (2) except that 119 mg (0.68 mmol) of 5-methoxy-1H-indole-3-carbaldehyde was used instead of 20 mg (0.14 mmol) of 1H-benzotriazole-5-carboxaldehyde to give 142 mg (48% yield) of the title compound.

$^1$H NMR (δ, DMSO-d$_6$): 3.86 (s, 3H), 3.89 (s, 3H), 5.26 (s, 2H), 6.08 (s, 1H), 6.67-6.71 (m, 2H), 6.73-6.78 (m, 2H), 6.87 (dd, J=2.3 Hz, 8.7 Hz, 1H), 7.35-7.38 (m, 2H), 7.42 (d, J=2.6 Hz, 1H), 7.55 (d, J=7.7 Hz, 1H), 7.64 (d, J=8.4 Hz, 1H), 7.74 (d, J=16.1 Hz, 1H), 7.85 (dt, J=1.9 Hz, 7.7 Hz, 1H), 7.88-7.93 (m, 2H), 8.59-8.60 (m, 1H), 11.70 (s, 1H), 16.58 (br s, 1H). MS (EI) m/z 482 (M+).

(2) Synthesis of 3-[(1E)-2-(5-methoxy-1H-indol-3-yl)ethenyl]-5-[(1E)-2-[2-methoxy-4-(2-pyridylmethoxy)phenyl]ethenyl]-1H-pyrazole Synthesis was performed using the same materials in the same relative quantities as in Example 4 (4) except that 40 mg (83 μmol) of (1E,6E)-1-(5-methoxy-1H-indol-3-yl)-7-[2-methoxy-4-(2-pyridylmethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 22 mg (55% yield) of the title compound.

$^1$H NMR (δ, DMSO-d$_6$): 3.84 (s, 3H), 3.86 (s, 3H), 5.22 (s, 2H), 6.61-6.68 (m, 2H), 6.73 (s, 1H), 6.78-6.90 (m, 2H), 6.97 (d, J=16.7 Hz, 1H), 7.20-7.72 (m, 8H), 7.85 (dt, J=1.9, 7.7 Hz, 1H), 8.58-8.60 (m, 1H), 11.07-11.24 (m, 1H), 12.63-12.72 (m, 1H). melting point 189-195° C., MS (EI) m/z 478 (M+).

Example 101

Synthesis of 3-[(1E)-2-(5-benzyloxy-1H-indol-3-yl)ethenyl]-5-[(1E)-2-[2-methoxy-4-(2-pyridylmethoxy)phenyl]ethenyl]-1H-pyrazole

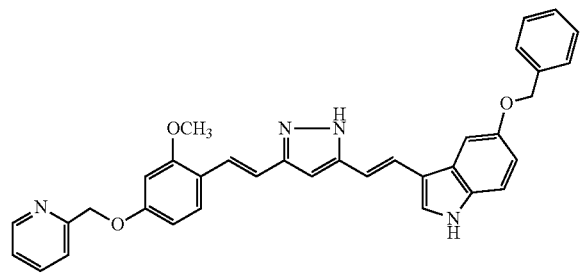 [SMILES: COc1cc(OCc2ccccn2)ccc1/C=C/c1cc(/C=C/c2c[nH]c3ccc(OCc4ccccc4)cc23)[nH]n1]

(1) Synthesis of (1E,6E)-1-(5-benzyloxy-1H-indol-3-yl)-7-[2-methoxy-4-(2-pyridylmethoxy)phenyl]hepta-1,6-diene-3,5-dione Synthesis was performed using the same materials in the same relative quantities as in Example 30 (2) except that 170 mg (0.67 mmol) of 5-benzyloxyindole-3-carboxaldehyde was used instead of 20 mg (0.14 mmol) of 1H-benzotriazole-5-carboxaldehyde to give 94 mg (27% yield) of the title compound.

$^1$H NMR (δ, DMSO-d$_6$): 3.88 (s, 3H), 5.21 (s, 2H), 5.26 (s, 2H), 6.07 (s, 1H), 6.66 (d, J=16.0 Hz, 1H), 6.70 (dd, J=2.2 Hz, 8.7 Hz, 1H), 6.73-6.78 (m, 2H), 6.95 (dd, J=2.0 Hz, 9.0 Hz, 1H), 7.32-7.44 (m, 5H), 7.52-7.55 (m, 4H), 7.64 (d, J=9.0 Hz, 1H), 7.74 (d, J=16.1 Hz, 1H), 7.83-7.92 (m, 3H), 8.58-8.60 (m, 1H), 11.71 (s, 1H), 16.58 (br s, 1H). MS (EI) m/z 558 (M+).

(2) Synthesis of 3-[(1E)-2-(5-benzyloxy-1H-indol-3-yl)ethenyl]-5-[(1E)-2-[2-methoxy-4-(2-pyridylmethoxy)phenyl]ethenyl]-1H-pyrazole Synthesis was performed using the same materials in the same relative quantities as in Example 4 (4) except that 100 mg (0.18 mmol) of (1E,6E)-1-(5-benzyloxy-1H-indol-3-yl)-7-[2-methoxy-4-(2-pyridylmethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 42 mg (43% yield) of the title compound.

$^1$H NMR (δ, DMSO-d$_6$): 3.86 (s, 3H), 5.17 (s, 2H), 5.22 (s, 2H), 6.61-6.68 (m, 2H), 6.73 (s, 1H), 6.84-6.92 (m, 2H), 6.98 (d, J=16.0 Hz, 1H), 7.21-7.37 (m, 5H), 7.39-7.43 (m, 2H), 7.46-7.72 (m, 6H), 7.84 (dt, J=1.9, 7.7 Hz, 1H), 8.59-8.60 (m, 1H), 11.10-11.26 (m, 1H), 12.63-12.72 (m, 1H). MS (EI) m/z 554 (M+).

Example 102

Synthesis of 5-[(1E)-2-(1H-indol-6-yl)ethenyl]-3-[(1E)-2-[4-(4-methylpiperazin-1-yl)phenyl]ethenyl]-1H-pyrazole

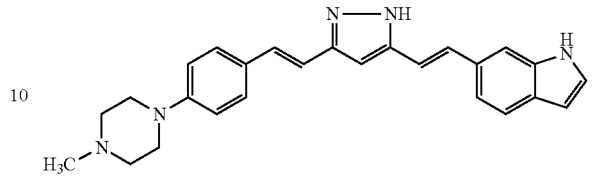

(1) Synthesis of (1E,6E)-1-(1H-indol-6-yl)-7-[4-(4-methylpiperazin-1-yl) phenyl]hepta-1,6-diene-3,5-dione Synthesis was performed in the same manner as in Example 1 (2) except that 0.45 g (2.2 mmol) of 4-(4-methylpiperazin-1-yl)benzaldehyde was used instead of 20 mg (85 μmol) of 2-methoxy-4-(2-tetrahydrofuranylmethoxy)benzaldehyde to give 0.47 g (52% yield) of the title compound with the following properties.

$^1$H NMR (δ, DMSO-d$_6$): 2.22 (s, 3H), 2.42-2.45 (m, 4H), 3.25-3.33 (m, 4H, overlapped H2O), 6.09 (s, 1H), 6.46-6.49 (m, 1H), 6.68 (d, 1H, J=16.0 Hz), 6.82 (d, 1H, J=16.0 Hz), 6.97 (d, 2H, J=9.0 Hz), 7.41 (dd, 1H, J=1.3 Hz, 8.4 Hz), 7.46-7.48 (m, 1H), 7.52-7.60 (m, 4H), 7.68-7.76 (m, 2H), 11.33 (s, 1H), 15.7-17.1 (br, 1H). melting point 65-77° C., MS (EI) m/z 413 (M+).

(2) Synthesis of 5-[(1E)-2-(1H-indol-6-yl)ethenyl]-3-[(1E)-2-[4-(4-methylpiperazin-1-yl)phenyl]ethenyl]-1H-pyrazole Synthesis was performed in the same manner as in Example 1 (3) except that 0.45 g (1.09 mmol) of (1E,6E)-1-(1H-indol-6-yl)-7-[4-(4-methylpiperazin-1-yl) phenyl]hepta-1,6-diene-3,5-dione was used instead of 400 mg (0.898 mmol) of (1E,6E)-1-(1H-indol-6-yl)-7-[2-methoxy-4-(2-tetrahydrofuranylmethoxy)phenyl]hepta-1,6-diene-3,5-dione to give 175 mg (39% yield) of the title compound with the following properties.

$^1$H NMR (δ, DMSO-d$_6$): 2.22 (s, 3H), 2.43-2.47 (m, 4H), 3.15-3.21 (m, 4H), 6.42 (s, 1H), 6.67 (s, 1H), 6.81-7.13 (m, 5H), 7.16-7.31 (m, 2H), 7.32-7.43 (m, 3H), 7.49-7.57 (m, 1H), 7.50 (s, 1H), 11.10 and 11.12 (each s, total 1H), 12.78 and 12.79 (each s, total 1H). melting point 192-198° C., MS (EI) m/z 409 (M+).

Example 103

Synthesis of 5-[(1E)-2-(1H-indol-6-yl)ethenyl]-3-[(1E)-2-(4-morpholinophenyl)ethenyl]-1H-pyrazole

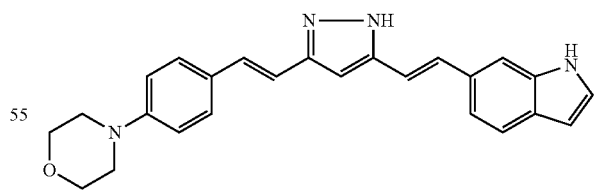

(1) Synthesis of (1E,6E)-1-(1H-indol-6-yl)-7-(4-morpholinophenyl)hepta-1,6-diene-3,5-dione Synthesis was performed in the same manner as in Example 1 (2) except that 0.42 g (2.2 mmol) of 4-morpholinobenzaldehyde was used instead of 20 mg (85 μmol) of 2-methoxy-4-(2-tetrahydrofuranylmethoxy)benzaldehyde to give 0.60 g (68% yield) of the title compound with the following properties.

¹H NMR (δ, DMSO-d₆): 3.22-3.28 (m, 4H), 3.72-3.76 (m, 4H), 6.10 (s, 1H), 6.47-6.49 (m, 1H), 6.70 (d, 1H, J=16.0 Hz), 6.83 (d, 1H, J=16.0 Hz), 6.98 (d, 2H, J=9.0 Hz), 7.41 (dd, 1H, J=1.3 Hz, 8.4 Hz), 7.45-7.48 (m, 1H), 7.53-7.61 (m, 4H), 7.69-7.71 (m, 1H), 7.73 (d, 1H, J=16.0 Hz), 11.34 (s, 1H), 15.82-17.02 (br, 1H). melting point 93-97° C., MS (EI) m/z 400 (M⁺).

(2) Synthesis of 5-[(1E)-2-(1H-indol-6-yl)ethenyl]-3-[(1E)-2-(4-morpholinophenyl)ethenyl]-1H-pyrazole Synthesis was performed in the same manner as in Example 1 (3) except that 0.50 g (1.25 mmol) of (1E,6E)-1-(1H-indol-6-yl)-7-(4-morpholinophenyl)hepta-1,6-diene-3,5-dione was used instead of 400 mg (0.898 mmol) of (1E,6E)-1-(1H-indol-6-yl)-7-[2-methoxy-4-(2-tetrahydrofuranylmethoxy)phenyl]hepta-1,6-diene-3,5-dione to give 0.26 g (53% yield) of the title compound with the following properties.

¹H NMR (δ, DMSO-d₆): 3.12-3.17 (m, 4H), 3.72-3.76 (m, 4H), 6.42 (s, 1H), 6.68 (s, 1H), 6.83-7.13 (m, 3H), 6.94 (d, 2H, J=7.7 Hz), 7.17-7.39 (m, 3H), 7.42 (d, 2H, J=7.7 Hz), 7.49-7.56 (m, 1H), 7.51 (s, 1H), 11.05-11.17 (m, 1H), 12.80 (s, 1H). melting point 236-238° C., MS (EI) m/z 396 (M⁺).

Example 104

Synthesis of 3-[(1E)-2-(4-diethylamino-2-methoxyphenyl)ethenyl]-5-[(1E)-2-(1H-indol-6-yl)ethenyl]-1H-pyrazole

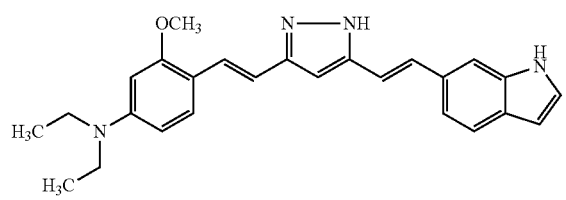 [SMILES: CCN(CC)c1ccc(/C=C/c2cc(/C=C/c3ccc4cc[nH]c4c3)[nH]n2)c(OC)c1]

(1) Synthesis of (1E,6E)-1-(4-diethylamino-2-methoxyphenyl)-7-(1H-indol-6-yl)hepta-1,6-diene-3,5-dione Synthesis was performed in the same manner as in Example 1 (2) except that 0.46 g (2.2 mol) of 4-(diethylamino)-2-methoxybenzaldehyde was used instead of 20 mg (85 μmol) of 2-methoxy-4-(2-tetrahydrofuranylmethoxy)benzaldehyde to give 0.68 g (75% yield) of the title compound with the following properties.

¹H NMR (δ, DMSO-d₆): 1.14 (t, 6H, J=7.1 Hz), 3.40-3.46 (m, 4H), 3.88 (s, 3H), 5.99 (s, 1H), 6.20 (d, 1H, J=1.9 Hz), 6.34 (dd, 1H, J=2.6 Hz, 9.0 Hz), 6.46-6.48 (m, 1H), 6.58 (d, 1H, J=16.0 Hz), 6.81 (d, 1H, J=16.0 Hz), 7.39 (dd, 1H, J=1.3 Hz, 8.3 Hz), 7.44-7.47 (m, 1H), 7.50 (d, 1H, J=9.0 Hz), 7.58 (d, 1H, J=8.3 Hz), 7.66-7.68 (m, 1H), 7.68 (d, 1H, J=16.0 Hz), 7.81 (d, 1H, J=16.0 Hz), 11.31 (s, 1H), 16.00-17.20 (br, 1H). melting point 61-65° C., MS (EI) m/z 416 (M⁺).

(2) Synthesis of 3-[(1E)-2-(4-diethylamino-2-methoxyphenyl)ethenyl]-5-[(1E)-2-(1H-indol-6-yl)ethenyl]-1H-pyrazole Synthesis was performed in the same manner as in Example 1 (3) except that 0.59 g (1.42 mmol) of (1E,6E)-1-(4-diethylamino-2-methoxyphenyl)-7-(1H-indol-6-yl)hepta-1,6-diene-3,5-dione was used instead of 400 mg (0.898 mmol) of (1E,6E)-1-(1H-indol-6-yl)-7-[2-methoxy-4-(2-tetrahydrofuranylmethoxy)phenyl]hepta-1,6-diene-3,5-dione to give 55 mg (9.4% yield) of the title compound with the following properties.

¹H NMR (δ, DMSO-d₆): 1.12 (t, 6H, J=7.1 Hz), 3.38 (q, 4H, J=7.1 Hz), 3.85 (s, 3H), 6.23 (br s, 1H), 6.27-6.33 (m, 1H), 6.40-6.43 (m, 1H), 6.62 (s, 1H), 6.82 (d, 1H, J=16.7 Hz), 6.99 (d, 1H, J=16.1 Hz), 7.19-7.28 (m, 3H), 7.32-7.38 (m, 2H), 7.49-7.51 (m, 1H), 7.52 (d, 1H, J=8.4 Hz), 11.10 (s, 1H), 12.27-13.07 (br, 1H). melting point 104-108° C., MS (EI) m/z 412 (M⁺).

Example 105

Synthesis of 3-[(1E)-2-(4-dimethylaminophenyl)ethenyl]-5-[(1E)-2-(1H-indol-6-yl)ethenyl]-1H-pyrazole

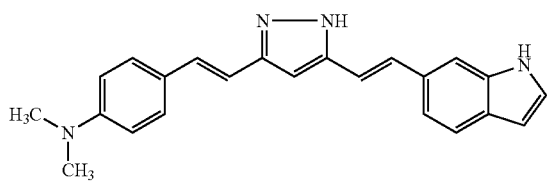 [SMILES: CN(C)c1ccc(/C=C/c2cc(/C=C/c3ccc4cc[nH]c4c3)[nH]n2)cc1]

(1) Synthesis of (1E,6E)-1-(4-dimethylaminophenyl)-7-(1H-indol-6-yl)hepta-1,6-diene-3,5-dione Synthesis was performed in the same manner as in Example 1 (2) except that 0.33 g (2.2 mol) of 4-dimethylaminobenzaldehyde was used instead of 20 mg (85 μmol) of 2-methoxy-4-(2-tetrahydrofuranylmethoxy)benzaldehyde to give 0.63 g (36% yield) of the title compound with the following properties.

¹H NMR (δ, DMSO-d₆): 3.00 (s, 6H), 6.07 (s, 1H), 6.47-6.48 (m, 1H), 6.62 (d, 1H, J=16.0 Hz), 6.74 (d, 2H, J=9.0 Hz), 6.81 (d, 1H, J=16.0 Hz), 7.40 (dd, 1H, J=1.3 Hz, 8.3 Hz), 7.45-7.48 (m, 1H), 7.55 (d, 2H, J=9.0 Hz), 7.56 (d, 1H, J=16.0 Hz), 7.58 (d, 1H, J=8.3 Hz), 7.68-7.70 (m, 1H), 7.71 (d, 1H, J=16.0 Hz), 11.33 (s, 1H), 15.70-17.20 (br, 1H). melting point 112-119° C., MS (EI) m/z 358 (M⁺).

(2) Synthesis of 3-[(1E)-2-(4-dimethylaminophenyl)ethenyl]-5-[(1E)-2-(1H-indol-6-yl)ethenyl]-1H-pyrazole Synthesis was performed in the same manner as in Example 1 (3) except that 243 mg (0.68 mmol) of (1E,6E)-1-(4-dimethylaminophenyl)-7-(1H-indol-6-yl)hepta-1,6-diene-3,5-dione was used instead of 400 mg (0.898 mmol) of (1E,6E)-1-(1H-indol-6-yl)-7-[2-methoxy-4-(2-tetrahydrofuranylmethoxy)phenyl]hepta-1,6-diene-3,5-dione to give 66 mg (28% yield) of the title compound with the following properties.

¹H NMR (δ, DMSO-d₆): 2.93 (s, 6H), 6.42 (s, 1H), 6.66 (s, 1H), 6.73 (d, 2H, J=8.3 Hz), 6.75-6.91 (m, 1H), 6.94-7.10 (m, 2H), 7.14-7.31 (m, 2H), 7.32-7.41 (m, 1H), 7.38 (d, 2H, J=8.3 Hz), 7.49-7.51 (m, 1H), 7.53 (d, 1H, J=7.1 Hz), 11.04-11.07 (m, 1H), 12.68-12.80 (m, 1H). melting point 224-227° C., MS (EI) m/z 354 (M⁺).

Example 106

Synthesis of 3-[(1E)-2-(4-diethylaminophenyl)ethenyl]-5-[(1E)-2-(1H-indol-6-yl)ethenyl]-1H-pyrazole

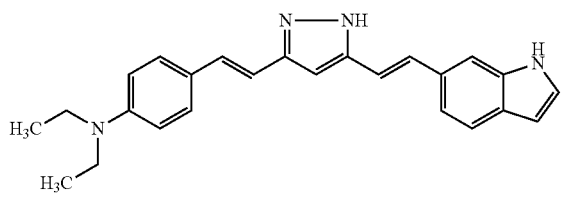 [SMILES: CCN(CC)c1ccc(/C=C/c2cc(/C=C/c3ccc4cc[nH]c4c3)[nH]n2)cc1]

(1) Synthesis of (1E,6E)-1-(4-diethylaminophenyl)-7-(1H-indol-6-yl)hepta-1,6-diene-3,5-dione Synthesis was performed in the same manner as in Example 1 (2) except that 0.39 g (2.2 mol) of 4-diethylaminobenzaldehyde was used instead of 20 mg (85 μmol) of 2-methoxy-4-(2-tetrahydrofuranylmethoxy)benzaldehyde to give 0.63 g (37% yield) of the title compound with the following properties.
$^1$H NMR (δ, DMSO-$d_6$): 1.12 (t, 6H, J=7.1 Hz), 3.41 (q, 4H, J=7.1 Hz), 6.06 (s, 1H), 6.46-6.49 (m, 1H), 6.57 (d, 1H, J=16.0 Hz), 6.70 (d, 2H, J=9.0 Hz), 6.81 (d, 1H, J=16.0 Hz), 7.40 (d, 1H, J=8.3 Hz), 7.45-7.47 (m, 1H), 7.51 (d, 2H, J=9.0 Hz), 7.54 (d, 1H, J=16.0 Hz), 7.58 (d, 1H, J=8.3 Hz), 7.68-7.73 (m, 2H), 11.33 (s, 1H), 15.68-17.27 (br, 1H). melting point 110-118° C., MS (EI) m/z 386 (M$^+$).

(2) Synthesis of 3-[(1E)-2-(4-diethylaminophenyl)ethenyl]-5-[(1E)-2-(1H-indol-6-yl)ethenyl]-1H-pyrazole Synthesis was performed in the same manner as in Example 1 (3) except that 264 mg (0.68 mmol) of (1E,6E)-1-(4-diethylaminophenyl)-7-(1H-indol-6-yl)hepta-1,6-diene-3,5-dione was used instead of 400 mg (0.898 mmol) of (1E,6E)-1-(1H-indol-6-yl)-7-[2-methoxy-4-(2-tetrahydrofuranylmethoxy)phenyl]hepta-1,6-diene-3,5-dione to give 112 mg (43% yield) of the title compound with the following properties.
$^1$H NMR (δ, DMSO-$d_6$): 1.10 (t, 6H, J=7.1 Hz), 3.36 (q, 4H, J=7.1 Hz), 6.42 (s, 1H), 6.65 (s, 1H), 6.66 (d, 2H, J=8.3 Hz), 6.71-6.88 (m, 1H), 6.93-7.09 (m, 2H), 7.15-7.30 (m, 1H), 7.27 (d, 1H, J=8.3 Hz), 7.32-7.38 (m, 3H), 7.50 (s, 1H), 7.53 (d, 1H, J=8.3 Hz), 11.10 (s, 1H), 12.72 (s, 1H). melting point 201-204° C., MS (EI) m/z 382 (M$^+$).

Example 107

Synthesis of 5-[(1E)-2-(1H-indol-6-yl)ethenyl]-3-[(1E)-2-[4-(1-piperidinyl)phenyl]ethenyl]-1H-pyrazole

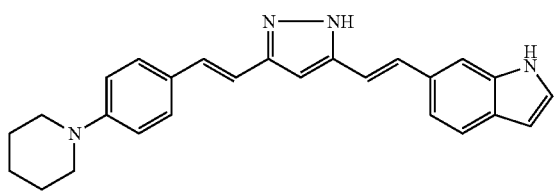 [SMILES: C(=C\c1cc(/C=C/c2ccc3cc[nH]c3c2)[nH]n1)/c1ccc(N2CCCCC2)cc1]

(1) Synthesis of (1E,6E)-1-(1H-indol-6-yl)-7-[4-(1-piperidinyl)phenyl]hepta-1,6-diene-3,5-dione Synthesis was performed in the same manner as in Example 1 (2) except that 0.42 g (2.2 mol) of 4-(1-piperidinyl)benzaldehyde was used instead of 20 mg (85 μmol) of 2-methoxy-4-(2-tetrahydrofuranylmethoxy)benzaldehyde to give 0.65 g (74% yield) of the title compound with the following properties.
$^1$H NMR (δ, DMSO-$d_6$): 1.56-1.62 (m, 6H), 3.23-3.34 (m, 4H, overlapped H2O), 6.08 (s, 1H), 6.47-6.49 (m, 1H), 6.65 (d, 1H, J=16.0 Hz), 6.82 (d, 1H, J=16.0 Hz), 6.94 (d, 2H, J=9.0 Hz), 7.41 (dd, 1H, J=1.3 Hz, 8.4 Hz), 7.46-7.48 (m, 1H), 7.52-7.60 (m, 4H), 7.68-7.71 (m, 1H), 7.73 (d, 1H, J=16.0 Hz), 11.33 (s, 1H), 15.94-17.05 (br, 1H). melting point 91-96° C., MS (EI) m/z 398 (M$^+$).

(2) Synthesis of 5-[(1E)-2-(1H-indol-6-yl)ethenyl]-3-[(1E)-2-[4-(1-piperidinyl)phenyl]ethenyl]-1H-pyrazole Synthesis was performed in the same manner as in Example 1 (3) except that 580 mg (1.46 mmol) of (1E,6E)-1-(1H-indol-6-yl)-7-[4-(1-piperidinyl)phenyl]hepta-1,6-diene-3,5-dione was used instead of 400 mg (0.898 mmol) of (1E,6E)-1-(1H-indol-6-yl)-7-[2-methoxy-4-(2-tetrahydrofuranylmethoxy)phenyl]hepta-1,6-diene-3,5-dione to give 144 mg (25% yield) of the title compound with the following properties.
$^1$H NMR (δ, DMSO-$d_6$): 1.52-1.58 (m, 2H), 1.58-1.64 (m, 4H), 3.16-3.22 (m, 4H), 6.40-6.44 (m, 1H), 6.67 (s, 1H), 6.79-7.10 (m, 3H), 6.92 (d, 2H, J=9.0 Hz), 7.16-7.30 (m, 1H), 7.26 (d, 1H, J=7.7 Hz), 7.31-7.41 (m, 3H), 7.49-7.51 (m, 1H), 7.53 (d, 1H, J=7.7 Hz), 11.10 (s, 1H), 12.77 (s, 1H). melting point 189-191° C., MS (EI) m/z 394 (M$^+$).

Example 108

Synthesis of 3-[(1E)-2-[4-diethylamino-2-(2-pyridylmethoxy)phenyl]ethenyl]-5-[(1E)-2-(1H-indol-6-yl)ethenyl]-1H-pyrazole

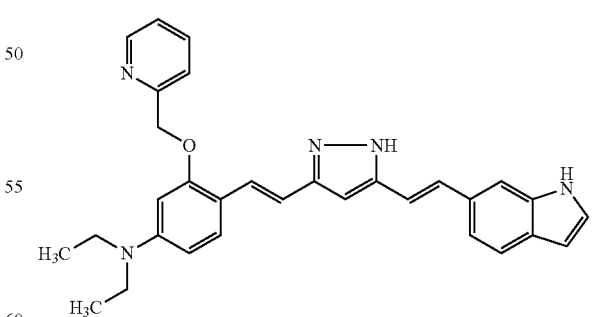

(1) Synthesis of 4-diethylamino-2-(2-pyridylmethoxy)benzaldehyde

Synthesis was performed using the same materials in the same relative quantities as in Example 97 (1) except that 1.8 g (10.9 mmol) of 2-chloromethylpyridine hydrochloride was used instead of 2.8 g (15.3 mmol) of 1-(2-chloroethyl)piperidine hydrochloride to quantitatively give 2.9 g of the title compound.

$^1$H NMR (δ, chloroform-d): 1.16 (t, J=7.1 Hz, 6H), 3.36-3.41 (m, 4H), 5.38 (s, 2H), 6.13 (d, J=2.3 Hz, 1H), 6.31 (dd, J=2.1 Hz, 9.0 Hz, 1H), 7.30-7.33 (m, 1H), 7.70-7.74 (m, 2H), 7.81-7.85 (m, 1H), 8.59-8.61 (m, 1H), 10.26 (s, 1H). melting point 78-81° C., MS (EI) m/z 284 (M+).

(2) Synthesis of (1E,6E)-1-[4-diethylamino-2-(2-pyridylmethoxy)phenyl]-7-(1H-indol-6-yl)hepta-1,6-diene-3,5-dione Synthesis was performed in the same manner as in Example 1 (2) except that 0.39 g (1.4 mmol) of 4-diethylamino-2-(2-pyridylmethoxy)benzaldehyde was used instead of 20 mg (85 µmol) of 2-methoxy-4-(2-tetrahydrofuranylmethoxy)benzaldehyde to give 0.68 g (90% yield) of the title compound with the following properties.

$^1$H NMR (δ, DMSO-d$_6$): 1.05 (t, 6H, J=7.1 Hz), 3.36 (q, 4H, J=7.1 Hz), 5.33 (s, 2H), 5.96 (s, 1H), 6.25 (d, 1H, J=2.6 Hz), 6.34 (dd, 1H, J=2.6 Hz, 9.0 Hz), 6.46-6.48 (m, 1H), 6.66 (d, 1H, J=16.0 Hz), 6.81 (d, 1H, J=16.0 Hz), 7.35-7.39 (m, 1H), 7.40 (dd, 1H, J=1.3 Hz, 8.3 Hz), 7.44-7.47 (m, 1H), 7.51-7.55 (m, 2H), 7.58 (d, 1H, J=8.3 Hz), 7.66-7.71 (m, 2H), 7.86-7.93 (m, 2H), 8.60-8.63 (m, 1H), 11.32 (s, 1H), 16.00-17.20 (br, 1H). melting point 92-96° C., MS (EI) m/z 493 (M$^+$).

(3) Synthesis of 3-[(1E)-2-[4-diethylamino-2-(2-pyridylmethoxy)phenyl]ethenyl]-5-[(1E)-2-(1H-indol-6-yl)ethenyl]-1H-pyrazole Synthesis was performed in the same manner as in Example 1 (3) except that 280 mg (0.57 mmol) of (1E,6E)-1-[4-diethylamino-2-(2-pyridylmethoxy)phenyl]-7-(1H-indol-6-yl) hepta-1,6-diene-3,5-dione was used instead of 400 mg (0.898 mmol) of (1E,6E)-1-(1H-indol-6-yl)-7-[2-methoxy-4-(2-tetrahydrofuranylmethoxy)phenyl]hepta-1,6-diene-3,5-dione to give 24 mg (8.6% yield) of the title compound with the following properties.

$^1$H NMR (δ, DMSO-d$_6$): 1.03 (t, 6H, J=7.7 Hz), 3.30 (t, 4H, J=7.7 Hz), 5.29 (s, 2H), 6.23-6.26 (m, 1H), 6.27-6.32 (m, 1H), 6.41-6.43 (m, 1H), 6.61 (s, 1H), 6.87 (d, 1H, J=16.7 Hz), 7.00 (d, 1H, J=16.7 Hz), 7.20-7.41 (m, 6H), 7.48-7.52 (m, 1H), 7.52 (d, 1H, J=8.4 Hz), 7.55-7.59 (m, 1H), 7.87 (dt, 1H, J=1.9 Hz, 7.7 Hz), 8.58-8.62 (m, 1H), 11.10 (s, 1H), 12.33-13.13 (br, 1H). MS (EI) m/z 489 (M$^+$).

Example 109

Synthesis of 3-[(1E)-2-[2-methoxy-4-(2-pyridylmethoxy)phenyl]ethenyl]-5-[(1E)-2-phenylethenyl]-1H-pyrazole

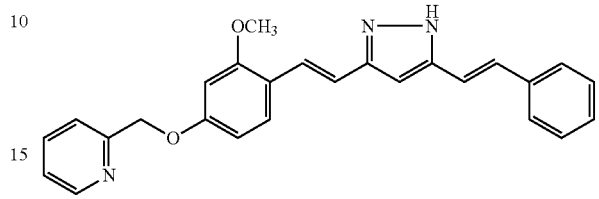

(1) Synthesis of (1E,6E)-1-[2-methoxy-4-(2-pyridylmethoxy) phenyl]-7-phenylhepta-1,6-diene-3,5-dione Synthesis was performed in the same manner as in Example 30 (2) except that 15 mg (0.14 mmol) of benzaldehyde was used instead of 20 mg (0.14 mmol) of 1H-benzotriazole-5-carboxaldehyde to give 3.9 mg (7% yield) of the title compound.

(2) Synthesis of 3-[(1E)-2-[2-methoxy-4-(2-pyridylmethoxy)phenyl]ethenyl]-5-[(1E)-2-phenylethenyl]-1H-pyrazole Synthesis was performed in the same manner as in Example 4 (4) except that 13 mg (31 µmol) of (1E,6E)-1-[2-methoxy-4-(2-pyridylmethoxy)phenyl]-7-phenylhepta-1,6-diene-3,5-dione was used instead of 15 mg (35 µmol) of (1E,6E)-1-(1H-indol-5-yl)-7-[4-(2-pyridylmethoxy)phenyl] hepta-1,6-diene-3,5-dione to give 8.6 mg (67% yield) of the title compound as a pale yellowish white powder with the following properties.

$^1$H NMR (δ, acetone-d$_6$): 5.22 (s, 2H), 6.65 (dd, J=2.4, 8.5 Hz, 1H), 6.71 (s, 1H), 6.74 (d, J=2.4 Hz, 1H), 7.06 (d, J=17 Hz, 1H), 7.15 (d, J=17 Hz, 1H), 7.23 (d, J=17 Hz, 1H), 7.22-7.42 (m, 5H), 7.53 (d, J=8.5 Hz, 1H), 7.54-7.59 (m, 2H), 7.82 (dt, J=1.7, 7.7 Hz, 1H), 8.58 (br d, J=5 Hz, 1H). melting point 143-146° C., MS (ESI+) m/z 410 2 (M+1).

Example 110

Synthesis of 3,5-bis[(1E)-2-[2-methoxy-4-(2-pyridylmethoxy)phenyl]ethenyl]-1H-pyrazole

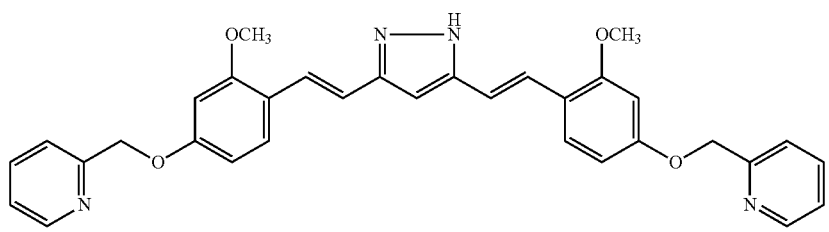 [SMILES: COc1cc(OCc2ccccn2)ccc1/C=C/c1cc(/C=C/c2ccc(OCc3ccccn3)cc2OC)[nH]n1]

An amount of 149 mg of (1E,6E)-1,7-bis[2-methoxy-4-(2-pyridylmethoxy)phenyl]hepta-1,6-diene-3,5-dione was obtained as a by-product in Example 30 (1).

Synthesis was then performed in the same manner as in Example 4 (4) except that 27.5 mg (50.0 μmol) of (1E,6E)-1,7-bis[2-methoxy-4-(2-pyridylmethoxy)phenyl]hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 3.0 mg (13% yield) of the title compound as a pale yellowish white powder with the following properties.

$^1$H NMR (δ, acetone-$d_6$): 5.22 (s, 4H), 6.63 (s, 1H), 6.68 (dd, J=2.4, 8.3 Hz, 2H), 6.73 (d, J=2.4 Hz, 2H), 7.05 (d, J=17 Hz, 2H), 7.31 (m, 2H), 7.37 (d, J=17 Hz, 2H), 7.53 (d, J=8.3 Hz, 2H), 7.56 (m, 2H), 7.82 (dt, J=1.7, 7.7 Hz, 2H), 8.58 (br d, J=5 Hz, 2H). melting point 195-197° C., MS (ESI+) m/z 547.3 (M+1).

Example 111

Synthesis of 3-[(1E)-2-[2-methoxy-4-(2-pyridylmethoxy)phenyl]ethenyl]-5-[(1E)-2-(3-amino-4-hydroxy-phenyl)ethenyl]-1H-pyrazole

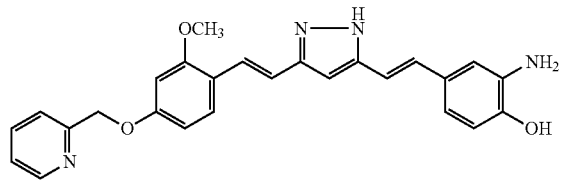 [SMILES: COc1cc(OCc2ccccn2)ccc1/C=C/c1cc(/C=C/c2ccc(O)c(N)c2)[nH]n1]

(1) Synthesis of (1E,6E)-1-(benzoxazol-5-yl)-7-(1H-indol-6-yl)hepta-1,6-diene-3,5-dione Synthesis was performed using the same materials in the same relative quantities as in Example 16 (1) except that 40 mg (0.27 mmol) of benzoxazole-5-carboxaldehyde was used instead of 29 mg (0.14 mmol) of 4-(2-pyridylmethoxy)benzaldehyde to give 10.1 mg (8% yield) of the title compound as an orange powder with the following properties.

(2) Synthesis of 3-[(1E)-2-(3-amino-4-hydroxyphenyl)ethenyl]-5-[(1E)-2-(1H-indol-6-yl)ethenyl]-1H-pyrazole Synthesis was performed using the same materials in the same relative quantities as in Example 4 (4) except that 8.0 mg (18 μmol) of (1E,6E)-1-(benzoxazol-5-yl)-7-(1H-indol-6-yl) hepta-1,6-diene-3,5-dione was used instead of 15 mg (35 μmol) of (1E,6E)-1-(1H-indol-5-yl)-7-[4-(2-pyridylmethoxy) phenyl]hepta-1,6-diene-3,5-dione to give 3.4 mg (44% yield) of the title compound as a white powder with the following properties.

$^1$H NMR (δ, acetone-$d_6$): 3.89 (s, 3H), 5.21 (s, 2H), 6.61 (s, 1H), 6.64 (dd, J=2.2, 8.5 Hz, 1H), 6.66 (dd, J=1.7, 8 Hz, 1H), 6.71 (d, J=8 Hz, 1H), 6.73 (d, J=2 Hz, 1H), 6.85 (d, J=17 Hz, 1H), 6.94 (d, J=1.8 Hz, 1H), 7.02 (d, J=17 Hz, 1H), 7.03 (d, J=17 Hz, 1H), 7.31 (dd, J=5, 7 Hz, 1H), 7.35 (d, J=17 Hz, 1H), 7.51 (d, J=8.5 Hz, 1H), 7.56 (br d, J=7.8 Hz, 1H), 7.81 (dt, J=1.7, 7.7 Hz, 1H), 8.58 (br d, J=5 Hz, 1H). melting point 123-126° C., MS (ESI+) m/z 441.3 (M+1).

Example 112

Synthesis of 3,5-bis[(1E)-2-(1H-indol-6-yl)ethenyl]-1H-pyrazole

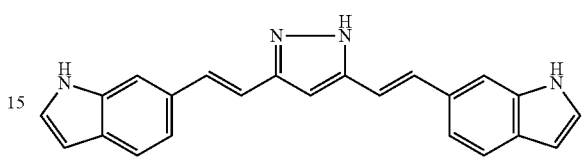

Synthesis was performed in the same manner as in Example 4 (4) except that 17.7 mg (50.0 μmol) of (1E,6E)-1,7-bis(1H-indol-6-yl)hepta-1,6-diene-3,5-dione was used instead of 15 mg (35 μmol) of (1E,6E)-1-(1H-indol-5-yl)-7-[4-(2-pyridylmethoxy)phenyl]hepta-1,6-diene-3,5-dione to give 9.2 mg (53% yield) of the title compound as a brown powder with the following properties.

$^1$H NMR (δ, acetone-$d_6$): 6.46 (dd, J=0.9, 3.1 Hz, 2H), 6.74 (s, 1H), 7.10 (d, J=17 Hz, 2H), 7.30 (d, J=17 Hz, 2H), 7.32 (d, J=1.6, 8.4 Hz, 2H), 7.35 (d, J=3.1 Hz, 2H), 7.56 (d, J=8 Hz, 2H), 7.57 (br s, 2H), 10.3 (br s, 2NH). melting point 289-291° C., MS (ESI+) m/z 351.1 (M+1).

Pharmacological Test Example 1: Determination of Tau Aggregation Inhibitory Activity A recombinant three-repeat microtubule-binding domain (3R-MBD) of tau protein was expressed in *E. coli* and was purified and used for the experiment. The purified tau solution was diluted with a 50 mM Tris-HCl buffer (pH 7.6) to a final concentration of 10 μM. The test compounds were prepared using dimethylsulfoxide (DMSO) at 20-fold of their final concentrations and added to the plate so that the DMSO concentration would be 5%. Heparin was added to the plate so that the final concentration would be 10 μM and the plate was left to stand at 37° C. for 16 hours. Thioflavin T was added to the plate so that the concentration would be 10 μM and the fluorescence intensity was measured with a fluorescence plate reader (PerkinElmer, Inc.) (excitation wavelength: 440 nm; emission wavelength: 480 nm).

The final concentration of each compound at the time of measurement was set at 0.1, 0.3, 1, 3, and 10 μM. The sample to which only DMSO was added was used as a negative control and its fluorescence intensity was taken as 0% inhibitory activity. The inhibitory activity of each compound was determined as 50% inhibitory concentration ($IC_{50}$). The test results are shown in Table 1. The inhibitory activities at 1 μM of the compounds of Example 109, Example 110, and Example 112 were 0%, 0%, and 24%, respectively.

Some of the samples that were left to stand for 16 hours after the addition of heparin were observed with an electron microscope. The samples were placed on a grid and washed with distilled water. A 1 mM phosphotungstic acid aqueous solution was added to the samples. The samples were washed, dried overnight, and observed. The results are shown in FIG. 1. The samples to which the compound of Example 2 was added showed less tau aggregate formation and greater tau aggregation inhibitory activities than the sample to which only DMSO was added.

Pharmacological Test Example 2: Determination of β-Secretase Inhibitory Activity The β-secretase inhibitory activity was measured with BACE-1 FRET assay Kit (Invitrogen). The test compounds were prepared using DMSO at 30-fold of their final concentrations and dissolved so that the DMSO concentration would be 10%. To each of the solutions, an equal volume of a recombinant human β-secretase (1 U/mL) dissolved in the assay buffer and an equal volume of fluorescent substrate peptide (2.5 nM) were added and the solutions were left to stand for 1 hour. The fluorescence intensity was measured with a fluorescence plate reader (excitation wavelength: 545 nm; emission wavelength: 590 nm).

The final concentration of each compound at the time of measurement was set at 0.1, 0.3, 1, 3, and 10 μM, at 0.3, 1, 3, 10, and 30 μM, or at 1, 3, 10, 30, and 100 μM. The sample to which only DMSO was added was used as a negative control and its fluorescence intensity was taken as 0% inhibitory activity for the determination of the 50% inhibitory concentration ($IC_{50}$) of each compound. The fluorescent substrate peptide had the amino acid sequence of Ser-Glu-Val-Asn-Leu-Asp-Ala-Glu-Lys-Arg, in which the Ser residue at position 1 was labeled with a fluorescent donor (Cy3) and the Lys at position 9 was labeled with a fluorescence quencher (Cy5Q). The 50% inhibitory concentration ($IC_{50}$) of each compound was calculated. The test results are shown in Table 1. The inhibitory activities at 1 μM of the compounds of Example 109, Example 110, and Example 112 were 12%, 12%, and 30%, respectively.

Pharmacological test example 3: Determination of Aβ aggregation inhibitory activity Aβ 1-42 (Peptide Institute, Inc.) was dissolved in 0.3% ammonia water so that the concentration would be 0.5 mM and then diluted with PBS to 20 μM. The test compounds were prepared using DMSO at 100-fold of their final concentrations and adjusted so that the DMSO concentration would be 2%. The Aβ solution and each of the test compound solutions were mixed at an equivalent ratio and the mixtures were incubated at 37° C. for 24 hours. To each of the mixtures, an equal volume of a thioflavin T solution adjusted with a 100 mM Tris-glycine buffer (pH 8.5) to 6 μM was added. The fluorescence intensity was measured with a fluorescence plate reader (excitation wavelength: 440 nm; emission wavelength: 480 nm).

The final concentration of each compound at the time of measurement was set at 0.1, 0.3, 1, 3, and 10 μM. The sample to which only DMSO was added was used as a negative control and its fluorescence intensity was taken as 0% inhibitory activity. With the use of the fluorescence intensity of the control taken as 0% inhibitory activity, the 50% inhibitory concentration ($IC_{50}$) of each compound was calculated. The test results are shown in Table 1. The inhibitory activity at 3 μM of the compound of Example 112 was 17%.

TABLE 1

| Compound No. | $IC_{50}$ (μM) | | |
|---|---|---|---|
| | Test example 1 | Test example 2 | Test example 3 |
| Example 1 | 1.49 | 2.85 | 3.00 |
| Example 2 | 0.92 | 3.00 | 1.50 |
| Example 3 | — | 2.90 | 1.60 |
| Example 27 | 1.28 | 1.04 | 7.53 |
| Example 31 | 1.57 | 0.69 | 6.88 |
| Example 35 | — | — | 0.91 |
| Example 36 | — | — | 2.90 |
| Example 37 | — | — | 0.40 |
| Example 58 | 3.84 | 1.11 | 2.17 |
| Example 63 | 1.37 | 4.39 | >10 |
| Example 72 | 1.46 | 0.22 | 2.45 |
| Example 77 | 1.26 | 13.70 | >10 |
| Example 79 | 1.10 | 0.85 | 0.58 |
| Example 82 | 1.04 | 3.99 | 4.43 |
| Example 83 | 0.85 | 22.65 | >10 |
| Example 98 | 1.29 | 1.25 | 3.27 |
| Example 102 | 1.46 | 1.06 | 4.33 |
| Example 110 | — | — | 1.90 |
| Example 111 | 1.46 | 2.89 | 5.05 |
| Example 112 | — | — | 2.8 |
| Curcumin | 1.5 | 6.9 | 1.7 |

As shown above, the compounds with the structure represented by the general formula (I) exhibited significantly excellent effects in terms of at least one of an inhibitory activity against tau protein aggregation, a β-secretase inhibitory activity, and an Aβ aggregation inhibitory activity, as compared with curcumin etc., which lack a pyrazole ring. Therefore, this structure is considered to be closely related to the inhibitory activity against tau protein aggregation.

Pharmacological test example 4: Evaluation of in vivo pharmacokinetics

To SD rats (male, 7 weeks old), the test compound was orally administered (p. o.) at an amount of 50 mg/kg bw or intravenously administered (i.v.) at an amount of 1 mg/kg bw and the concentrations in the blood and brain were measured up to 3 hours. The administration vehicle was an 80% PEG 400 aqueous solution. The blood was collected under isoflurane inhalational anesthesia and the brain was harvested after the rats were sacrificed. The plasma was separated from the blood. The brain was homogenized after addition of a three-fold volume of PBS and then methanol was added thereto. Thus the prepared test samples were subjected to measurement. The measurement was performed by LC-MS/MS (Applied Biosystems and Waters).

Figure 2:
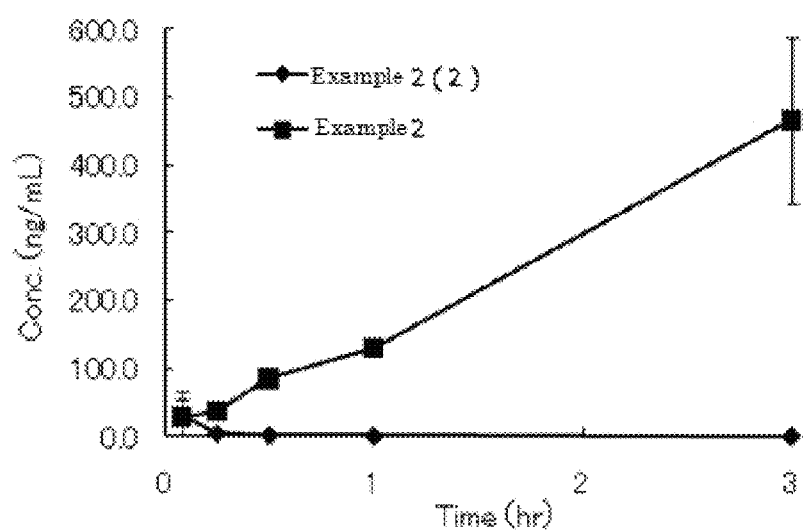
FIG. 2 shows a chart showing the blood concentration changes of the compounds of Example 2 and Example 2 (2) after oral administration thereof.

The blood concentration changes of the compounds of Example 2 and Example 2 (2) ((1E,6E)-1-(1H-indol-6-yl)-7-[2-methoxy-4-(2-pyridylmethoxy)phenyl]hepta-1,6-diene-3,5-dione) after oral administration (p.o.) thereof are shown in FIG. 2. The brain concentration changes of the compounds after intravenous administration (i.v.) and oral administration (p.o.) thereof are shown in Table 2. The compound of Example 2 showed higher blood and brain concentrations than the compound of Example 2 (2).

TABLE 2

| | i.v. 5 min | i.v. 180 min | p.o. 60 min | p.o. 180 min | |
|---|---|---|---|---|---|
| Example 2 (2) | 5.15 ± 3.34 | 0.93 ± 0.67 | 0 | 18.04 ± 30.79 | |
| Example 2 | 48.66 | 17.46 | 8.54 ± 2.93 | 68.93 ± 39.38 | (ng/mL) |

Pharmacological test example 5: Determination of Aβ aggregation inhibitory activity and Aβ production inhibitory activity in mice with oral administration To APPswe/PS1dE9 Tg mice (male, 10 to 12 months old, n=8 to 10), the compound of Example 2 was orally administered and the concentration of Aβ in the brain was measured. The administration vehicle was an 80% PEG 400 aqueous solution. The dose volume was 10 mL/kg bw/day and the dose was adjusted to be 25 mg/kg bw/day or 50 mg/kg bw/day. To Vehicle group, 10 mL/kg bw/day of an 80% PEG 400 aqueous solution was administered. Administration was performed with an oral feeding tube (Fuchigami Kikai Company) by gavage and continued for four weeks. After termination of the administration, the mice were sacrificed under pentobarbital anesthesia and the brain was harvested. The brain was homogenized after addition of a 10-fold volume of a phosphoric acid buffer (pH 7.4) and the homogenate was centrifuged at 4° C., 16,000 g for 1 hour. The centrifugal supernatant was used as a soluble protein sample. The pellet was resuspended in 70% formic acid, neutralized with a 20-fold volume of a 0.9 M Tris buffer (pH 12.0) and used as an insoluble protein sample. For Aβ measurement, β-amyloid (1-42) ELISA Kit (Wako Pure Chemical Industries Co., Ltd.) was used. To a primary antibody-immobilized plate were added the samples diluted with a standard dilution solution and a standard curve dilution series each in an amount of 100 µL, and the plate was left to stand at 4° C. overnight. After the plate was washed with a washing buffer 5 times, 100 µL of a HRP-labeled secondary antibody solution was added and the plate was left to stand at 4° C. for 1 hour. After the plate was washed with a washing buffer 5 times again, a TMB solution was added to allow a chromogenic reaction to proceed for 20 minutes. An amount of 100 µL of a reaction stop solution was added to stop the chromogenic reaction and the absorbance was measured at 450 nm with a microplate reader (Bio-Rad). The Aβ concentration was determined from the standard curve produced from the measured values of the standard curve dilution series.

Figure 3:
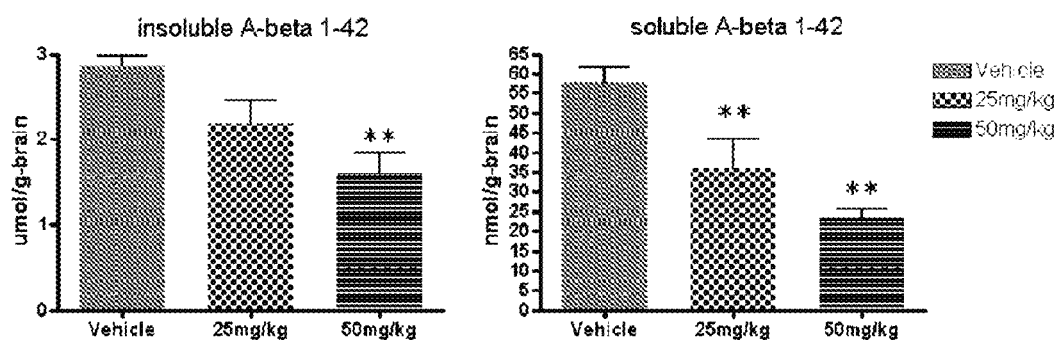
FIG. 3 shows charts showing insoluble and soluble Aβ 1-42 amounts in the brain of mice to which the compound of Example 2 was administered. The left figure shows the insoluble Aβ 1-42 amount, and the right figure shows the soluble Aβ 1-42 amount.

The test results are shown in FIG. 3. It was observed that the amounts of the insoluble and soluble Aβ 1-42 in the brain decreased in a dose-dependent manner in the group to which the compound of Example 2 was administered (the values in the charts are mean±SEM, ** p<0.01, and One way ANOVA was used for the test of significance).

Pharmacological test example 6: Determination of tau aggregation inhibitory activity in mice with oral administration To tau N279K Tg mice (male, 8 months old, n=8), the compound of Example 2 was orally administered and the tau concentration in the brain was measured. The administration vehicle was an 80% PEG 400 aqueous solution. The dose volume was 10 mL/kg bw/day and the dose was adjusted to be 10, 20, or 40 mg/kg bw/day. To Vehicle group, 10 mL/kg bw/day of an 80% PEG 400 aqueous solution was administered. To Positive control compound group, methylene blue (MB) adjusted to be 40 mg/kg bw/day was administered. Administration was performed with an oral feeding tube (Fuchigami Kikai Company) by gavage and continued for four weeks. After termination of the administration, the mice were sacrificed under pentobarbital anesthesia and the brain was harvested. The brain was homogenized after addition of a 5-fold volume of a high salt buffer (0.8 M NaCl, 1 mM EGTA, 10 mM Tris-HCl, 10% sucrose). Sarcosyl was added to the homogenate so that the sarcosyl concentration would be 1%, and the homogenate was incubated at 37° C. for 1 hour and centrifuged at 4° C., 100,000 g for 1 hour. The pellet was resuspended in an extraction buffer (4 M guanidine, 50 mM Tris-HCl), diluted with a 50 mM Tris-HCl buffer, and used as a sarcosyl-insoluble protein sample. For tau measurement, human tau ELISA Kit (Invitrogen) was used. To a primary antibody-immobilized plate were added the samples diluted with a standard dilution solution and a standard curve dilution series each in an amount of 100 µL, and the plate was left to stand at 4° C. overnight. After the plate was washed with a washing buffer, 100 µL of a secondary antibody solution was added and the plate was left to stand at 4° C. for 1 hour. After the plate was washed again, a HRP-labeled anti-IgG antibody solution was added and the plate was left to stand for 30 minutes. After the plate was washed again, a TMB solution was added to allow a chromogenic reaction to proceed for 20 minutes. An amount of 100 µL of a reaction stop solution was added to stop the chromogenic reaction and the absorbance was measured at 450 nm with a microplate reader. The tau concentration was determined from the standard curve produced from the measured values of the standard curve dilution series.

Figure 4:
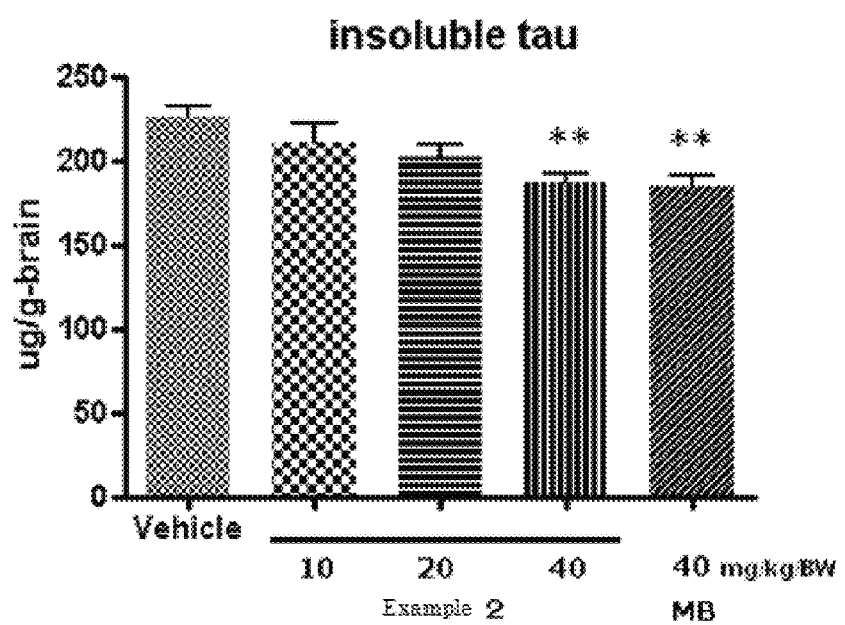
FIG. 4 shows a chart showing insoluble tau amount in the brain of mice to which the compound of Example 2 was administered.

The test results on the insoluble tau amount in the mouse brain are shown in FIG. 4. It was observed that the amount of the sarcosyl-insoluble tau in the brain decreased in a dose-dependent manner in the group to which the compound of Example 2 was administered (the values in the chart are mean±SEM, ** p<0.01, and One way ANOVA was used for the test of significance).

INDUSTRIAL APPLICABILITY

The compound of the present invention is useful as a prophylactic agent, a therapeutic agent, and the like for Alzheimer's disease and therefore the present invention can be applied to industrial fields such as pharmaceutical industry.

The invention claimed is:
1. A compound represented by the following general formula (I):

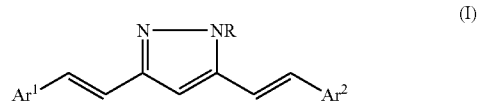

[wherein R represents hydrogen, a chain or cyclic hydrocarbon group optionally having a substituent, or a heterocyclic group optionally having a substituent; and
Ar$^1$ represents a phenyl group having a C$_{1-3}$ alkyloxy group substituted with a heterocycloalkyl group optionally having a substituent, a phenyl group having a C$_{1-3}$ alkyloxy group substituted with a cycloalkyl group optionally having a substituent, a phenyl group having a C$_{1-3}$ alkyloxy group substituted with a heteroaryl group optionally having a substituent, a phenyl group having a C$_{1-3}$ alkyloxy group substituted with an aryl group optionally having a substituent, a phenyl group having a C$_{1-3}$ alkyloxy group substituted with a dialkylamino group optionally having a substituent, a phenyl group having a C$_{1-3}$ alkyloxy group substituted with an alkyloxy group optionally having a substituent, or a phenyl group having a C$_{1-3}$ alkyloxy group substituted with an alkyl group optionally having a substituent and Ar$^2$, which is identical to or different from Ar$^1$ and each represents a homocyclic or heterocyclic group optionally having a substituent;
or a salt thereof.
2. The compound or a salt thereof according to claim 1, wherein R in the general formula (I) is hydrogen.

3. The compound or a salt thereof according to claim 1, wherein $Ar^1$ in the general formula (I) is a phenyl group having a tetrahydrofuran-3-ylmethoxy group, a tetrahydrofuran-2-ylmethoxy group, a 2-(piperidin-1-yl)ethoxy group, a 2-(4-methylpiperazino)ethoxy group, a 2-(4-benzylpiperazino)ethoxy group, a 2-morpholinoethoxy group, a 2-pyrrolidinoethoxy group, a β-D-glucopyranosyloxy group, a 2-[4-(tert-butoxycarbonyl)piperazin-1-yl]ethoxy group, a 2-[4-(methylsulfonyl)piperazin-1-yl]ethoxy group, or a 2-[4-(2-hydroxyethyl)piperazin-1-yl]ethoxy group.

4. The compound or a salt thereof according to claim 1, wherein $Ar^1$ in the general formula (I) is a 2-methoxy-4-(tetrahydrofuran-3-ylmethoxy)phenyl group, a 2-methoxy-4-(tetrahydrofuran-2-ylmethoxy)phenyl group, a 2-methoxy-4-[2-(piperidin-1-yl)ethoxy]phenyl group, a 2-methoxy-4-[2-(4-methylpiperazino)ethoxy]phenyl group, a 2-methoxy-4-(2-morpholinoethoxy)phenyl group, a 4-(β-D-glucopyranosyl)oxy-2-methoxyphenyl group, a 4-(tetrahydrofuran-3-ylmethoxy)phenyl group, a 4-(tetrahydrofuran-2-ylmethoxy)phenyl group, a 3-methoxy-4-(tetrahydrofuran-3-ylmethoxy)phenyl group, a 3-methoxy-4-(tetrahydrofuran-2-ylmethoxy)phenyl group, a 2-[2-(4-benzylpiperazino)ethoxy]-4-methoxyphenyl group, a 4-diethylamino-2-(2-morpholinoethoxy)phenyl group, a 4-dimethylamino-2-(2-morpholinoethoxy)phenyl group, a 4-diethylamino-2-(2-morpholinoethoxy)phenyl group, a 4-diethylamino-2-(2-pyrrolidinoethoxy)phenyl group, or a 4-diethylamino-2[2-(piperidin-1-yl)ethoxy]phenyl group.

5. The compound or a salt thereof according to claim 1, wherein $Ar^1$ in the general formula (I) is a phenyl group having a pyridin-2ylmethoxy group, a pyridin-3-ylmethoxy group, a pyridin-4-ylmethoxy group, or a 1-pyrrolylmethoxy group.

6. The compound or a salt thereof according to claim 1, wherein $Ar^1$ in the general formula (I) is a 4-(pyridin-2-ylmethoxy)phenyl group, a 2-methoxy-4-(pyridin-2-ylmethoxy)phenyl group, a 2-[2-(piperidin-1-yl)ethoxy]-4-(pyridin-2-ylmethoxy)phenyl group, a 2-(2-morpholinoethoxy)-4-(pyridin-2-ylmethoxy)phenyl group, a 2-(2-pyrrolidinoethoxy)-4-(pyridin-2-ylmethoxy)phenyl group, a 2-[2-(4-methylpiperazino)ethoxy]-4-(pyridin-2-ylmethoxy)phenyl group, a 3-methoxy-4-(pyridin-2-ylmethoxy)phenyl group, a 2-hydroxy-4-(pyridin-2-ylmethoxy)phenyl group, a 3-(pyridin-2-ylmethoxy)phenyl group, a 2-methoxy-3-(pyridin-2-ylmethoxy)phenyl group, a 4-methoxy-3-(pyridin-2-ylmethoxy)phenyl group, a 3-methoxy-5-(pyridin-2-ylmethoxy)phenyl group, a 2-methoxy-5-(pyridin-2-ylmethoxy)phenyl group, a 2-(pyridin-2-ylmethoxy)phenyl group, a 4-methoxy-2-(pyridin-2-ylmethoxy)phenyl group, a 5-methoxy-2-(pyridin-2-ylmethoxy)phenyl group, a 2-nitro-5-(pyridin-3-ylmethoxy)phenyl group, a 4-diethylamino-2-(pyridin-3-ylmethoxy)phenyl group, or a 2-methoxy-2-(1-pyrrolylmethoxy)phenyl group.

7. The compound or a salt thereof according to claim 1, wherein $Ar^2$ in the general formula (I) is a bicyclic homocyclic or heterocyclic group optionally having a substituent.

8. The compound or a salt thereof according to claim 1, wherein $Ar^2$ in the general formula (I) is a bicyclic heterocyclic group optionally having a substituent.

9. The compound or a salt thereof according to claim 8, wherein $Ar^2$ in the general formula (I) is an indol-2-yl group, an indol-3-yl group, an indol-4-yl group, an indol-5-yl group, an indol-6-yl group, an indol-7-yl group, a benzotriazol-5-yl group, a benzimidazol-5-yl group, a quinoxalin-6-yl group, a benzofuran-2-yl group, a benzothiophen-2-yl group, a 1H-indazol-5-yl group, a 7-azaindol-3-yl group, a quinolin-2-yl group, a quinolin-5-yl group, a quinolin-8-yl group, a 1,4-benzodioxan-6-yl group, a 1,3-benzodioxol-5-yl group, a chromon-3-yl group, a coumarin-6-yl group, a 7-methoxycoumarin-4-yl group, or a 4-methoxycoumarin-6-yl group.

10. The compound or a salt thereof according to claim 8, wherein $Ar^2$ in the general formula (I) is a bicyclic heterocyclic group having a methyl group, an ethyl group, a benzyl group, an acetyl group, a benzoyl group, a tert-butoxycarbonyl group, a methylsulfonyl group, a p-toluenesulfonyl group, a hydroxy group, or a nitro group.

11. The compound or a salt thereof according to claim 8, wherein $Ar^2$ in the general formula (I) is a 1-methylindol-6-yl group, a 1-methylindol-2-yl group, a 1-methylindol-3-yl group, a 1-ethylindol-6-yl group, a 1-benzylindol-3-yl group, a 1-benzylindol-6-yl group, a 1-acetylindol-3-yl group, a 1-acetylindol-6-yl group, a 1-benzoylindol-3-yl group, a 1-tert-butoxycarbonylindol-5-yl group, a 1-methylsulfonylindol-3-yl group, a 1-methylsulfonylindol-6-yl group, a 1-p-toluenesulfonylindol-3-yl group, a 1-p-toluenesulfonylindol-6-yl group, a 4-hydroxyindol-3-yl group, or a 4-nitroindol-3-yl group.

12. A tau aggregation inhibitor comprising the compound or a salt thereof according to claim 1 as an active ingredient.

13. A β-secretase inhibitor comprising the compound or a salt thereof according to claim 1 as an active ingredient.

14. An amyloid β-protein aggregation inhibitor comprising the compound or a salt thereof according to claim 1 as an active ingredient.

15. A pharmaceutical composition comprising the compound or a salt thereof according to claim 1 as an active ingredient.

16. A method for treating a disease in which tau, β-secretase, or amyloid β-protein is involved, wherein the disease is Alzheimer's disease, comprising a step of administering an effective amount of pharmaceutical composition according to claim 15.

17. An oral or parenteral preparation comprising the compound or a salt thereof according to claim 1 and one or more pharmacologically acceptable carriers.

* * * * *